(12) United States Patent
Miyake et al.

(10) Patent No.: US 11,871,656 B2
(45) Date of Patent: ***Jan. 9, 2024

(54) ORGANIC ELECTROLUMINESCENCE DEVICE AND MONOAMINE COMPOUND FOR ORGANIC ELECTROLUMINESCENCE DEVICE

(71) Applicant: SAMSUNG DISPLAY CO., LTD., Yongin-si (KR)

(72) Inventors: Hideo Miyake, Yokohama (JP); Masatsugu Ueno, Yokohama (JP); Xiulan Jin, Yokohama (JP); Ichinori Takada, Yokohama (JP); Takuya Uno, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 409 days.

This patent is subject to a terminal disclaimer.

(21) Appl. No.: 16/256,225

(22) Filed: Jan. 24, 2019

(65) Prior Publication Data
US 2019/0237668 A1 Aug. 1, 2019

(30) Foreign Application Priority Data

Jan. 26, 2018 (KR) .................... 10-2018-0009993
Nov. 23, 2018 (KR) .................... 10-2018-0146236

(51) Int. Cl.
*H10K 85/60* (2023.01)
*C07C 211/58* (2006.01)
(Continued)

(52) U.S. Cl.
CPC .......... *H10K 85/633* (2023.02); *C07C 211/54* (2013.01); *C07C 211/56* (2013.01);
(Continued)

(58) Field of Classification Search
CPC ............... H01L 51/006; H01L 51/0058; H01L 51/0061; H01L 51/0067; H01L 51/5012;
(Continued)

(56) References Cited

U.S. PATENT DOCUMENTS 4,720,432 A 1/1988 VanSlyke et al.
5,061,569 A 10/1991 VanSlyke et al.
(Continued)

FOREIGN PATENT DOCUMENTS

CN 102596907 B 12/2014
CN 106008424 A 10/2016
(Continued)

OTHER PUBLICATIONS

Journal of Materials Chemistry C, (2018), vol. 6, pp. 8280-8325 (Year: 2018).*
(Continued)

*Primary Examiner* — Dawn L Garrett
(74) *Attorney, Agent, or Firm* — Lewis Roca Rothgerber Christie LLP

(57) ABSTRACT

An organic electroluminescence device includes a first electrode, a hole transport region on the first electrode, an emission layer on the hole transport region, an electron transport region on the emission layer, and a second electrode on the electron transport region. The hole transport region includes a monoamine compound represented by the following Formula 1:

(Continued)

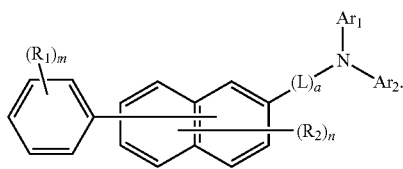

[Formula 1]

18 Claims, 2 Drawing Sheets

(51) Int. Cl.
| | | |
|---|---|---|
| C07C 211/61 | (2006.01) | |
| H05B 33/22 | (2006.01) | |
| C07D 333/76 | (2006.01) | |
| C07D 407/12 | (2006.01) | |
| C07C 211/56 | (2006.01) | |
| C07D 409/12 | (2006.01) | |
| C07D 307/91 | (2006.01) | |
| C07D 209/82 | (2006.01) | |
| C07C 211/54 | (2006.01) | |
| H10K 50/11 | (2023.01) | |
| H10K 50/18 | (2023.01) | |
| C07C 211/60 | (2006.01) | |
| H10K 50/15 | (2023.01) | |
| H10K 50/16 | (2023.01) | |

(52) U.S. Cl.
CPC .......... *C07C 211/58* (2013.01); *C07C 211/60* (2013.01); *C07C 211/61* (2013.01); *C07D 209/82* (2013.01); *C07D 307/91* (2013.01); *C07D 333/76* (2013.01); *C07D 407/12* (2013.01); *C07D 409/12* (2013.01); *H05B 33/22* (2013.01); *H10K 50/11* (2023.02); *H10K 50/18* (2023.02); *H10K 85/626* (2023.02); *H10K 85/636* (2023.02); *H10K 85/654* (2023.02); *H10K 85/6572* (2023.02); *H10K 85/6574* (2023.02); *H10K 85/6576* (2023.02); *C07C 2602/26* (2017.05); *C07C 2603/16* (2017.05); *C07C 2603/26* (2017.05); *C07C 2603/74* (2017.05); *C07C 2603/97* (2017.05); *H10K 50/15* (2023.02); *H10K 50/156* (2023.02); *H10K 50/16* (2023.02)

(58) Field of Classification Search
CPC ............. H01L 51/5096; H01L 51/0072; H01L 51/0073; H01L 51/0074; H01L 51/5056; H01L 51/5064; H01L 51/5072; H01L 51/0056; H01L 51/0052; H05B 33/22; C07D 333/76; C07D 407/12; C07D 211/56; C07D 409/12; C07D 307/91; C07D 209/82; C07D 213/38; C07C 211/54; C07C 211/60; C07C 211/58; C07C 211/61; C07C 2603/74; C07C 2603/16; C07C 2603/97; C07C 2602/26; C07C 2603/26; C07C 211/57; C07C 213/38; C07C 211/56; C09K 11/06; C09K 2211/1088; C09K 2211/1092; C09K 2211/1029; C09K 2211/1007; C09K 2211/1011; H10K 85/633; H10K 50/11; H10K 50/18; H10K 85/626; H10K 85/636; H10K 85/654; H10K 85/6572; H10K 85/6574; H10K 85/6576; H10K 50/15; H10K 50/156; H10K 50/16; H10K 85/615; H10K 85/624

See application file for complete search history.

(56) References Cited

U.S. PATENT DOCUMENTS

| | | |
|---|---|---|
| 6,242,115 B1 | 6/2001 | Thomson et al. |
| 7,507,485 B2 | 3/2009 | Oh et al. |
| 8,129,038 B2 | 3/2012 | Yabunouchi et al. |
| 8,889,268 B2 | 11/2014 | Takada et al. |
| 9,139,522 B2 | 9/2015 | Yabunouchi et al. |
| 9,278,926 B2 | 3/2016 | Kato |
| 9,525,141 B2 | 12/2016 | Kim et al. |
| 9,590,186 B2 | 3/2017 | Itoi et al. |
| 9,842,995 B2 | 12/2017 | Jung et al. |
| 9,972,787 B2 | 5/2018 | Miyake et al. |
| 10,014,477 B2 | 7/2018 | Kato et al. |
| 10,211,406 B2 | 2/2019 | Hwang et al. |
| 10,333,075 B2 | 6/2019 | Miyake et al. |
| 10,941,108 B2 | 3/2021 | Jeong et al. |
| 11,196,008 B2 | 12/2021 | Park et al. |
| 2002/0094452 A1* | 7/2002 | Ueda ............... H05B 33/14 428/917 |
| 2008/0241591 A1 | 10/2008 | Kawamura et al. |
| 2009/0230852 A1 | 9/2009 | Lee et al. |
| 2011/0031877 A1 | 2/2011 | Takada et al. |
| 2012/0199820 A1 | 8/2012 | Ito et al. |
| 2014/0367649 A1 | 12/2014 | Cho et al. |
| 2014/0374711 A1* | 12/2014 | Cho ............... H01L 51/0067 257/40 |
| 2015/0179940 A1* | 6/2015 | Mujica-Fernaud .. C07D 405/04 548/440 |
| 2015/0243891 A1 | 8/2015 | Kato et al. |
| 2016/0093810 A1 | 3/2016 | Miyake et al. |
| 2016/0163982 A1 | 6/2016 | Ishihara et al. |
| 2016/0293843 A1 | 10/2016 | Itoi |
| 2016/0365517 A1 | 12/2016 | Mun et al. |
| 2016/0372665 A1 | 12/2016 | Takada |
| 2016/0372666 A1* | 12/2016 | Ryu ............... C07D 409/12 |
| 2016/0372677 A1 | 12/2016 | Miyake |
| 2017/0125677 A1 | 5/2017 | Kim et al. |
| 2017/0125689 A1 | 5/2017 | Lee et al. |
| 2018/0083197 A1 | 3/2018 | Park et al. |
| 2018/0182961 A1 | 6/2018 | Kawakami et al. |
| 2018/0226585 A1 | 8/2018 | Park et al. |
| 2018/0269401 A1* | 9/2018 | Cha ............... C07D 209/88 |
| 2018/0331290 A1 | 11/2018 | Miyake et al. |
| 2019/0039996 A1* | 2/2019 | Takada ............... H01L 51/0073 |
| 2019/0055187 A1 | 2/2019 | Kim et al. |
| 2019/0140177 A1* | 5/2019 | Lee ............... C07C 211/61 |
| 2019/0237668 A1 | 8/2019 | Miyake et al. |

FOREIGN PATENT DOCUMENTS

| | | |
|---|---|---|
| CN | 106831313 A | 6/2017 |
| CN | 106083606 B | 6/2018 |
| CN | 109749735 A | 5/2019 |
| CN | 111315717 A | 6/2020 |
| JP | 5-303221 A | 11/1993 |
| JP | 6-314594 A | 11/1994 |
| JP | 8-291115 A | 11/1996 |
| JP | 11-144873 A | 5/1999 |
| JP | 2000-302756 A | 10/2000 |
| JP | 2000-309566 A | 11/2000 |
| JP | 2003-201472 A | 7/2003 |
| JP | 2006-151979 A | 6/2006 |
| JP | 2009-029726 A | 2/2009 |
| JP | 2009-267255 A | 11/2009 |
| JP | 2009-283899 A | 12/2009 |
| JP | 2010-186983 A | 8/2010 |
| JP | 5739815 B2 | 6/2015 |
| JP | 2016-66723 A | 4/2016 |
| JP | 5919427 B2 | 5/2016 |
| JP | 6085354 B2 | 2/2017 |
| JP | 2018065806 A * | 4/2018 |
| KR | 10-2013-0101726 A | 9/2013 |

(56) References Cited

FOREIGN PATENT DOCUMENTS

| | | |
|---|---|---|
| KR | 10-1373587 B1 | 3/2014 |
| KR | 10-2014-0043224 A | 4/2014 |
| KR | 10-2015-0006374 A | 1/2015 |
| KR | 10-2015-006374 A | 1/2015 |
| KR | 10-2015-0024735 A | 3/2015 |
| KR | 10-1530266 B1 | 6/2015 |
| KR | 10-1580074 B1 | 12/2015 |
| KR | 10-2016-0054855 A | 5/2016 |
| KR | 10-2016-0059609 A | 5/2016 |
| KR | 2016-0054866 A | 5/2016 |
| KR | 10-2016-0061571 A | 6/2016 |
| KR | 10-1638072 B1 | 7/2016 |
| KR | 10-1639867 B1 | 7/2016 |
| KR | 10-2016-0113783 A | 10/2016 |
| KR | 10-2016-0120609 A | 10/2016 |
| KR | 10-2016-0132344 A | 11/2016 |
| KR | 10-2016-0149977 A | 12/2016 |
| KR | 10-2016-0149987 A | 12/2016 |
| KR | 10-2017-0011947 A | 2/2017 |
| KR | 10-1730275 B1 | 4/2017 |
| KR | 10-2017-0061727 A | 6/2017 |
| KR | 10-2017-0094665 A | 8/2017 |
| KR | 10-2017-0094708 A | 8/2017 |
| KR | 10-2017-0127099 A | 11/2017 |
| KR | 10-2018-0078177 A | 7/2018 |
| KR | 10-1881645 B1 | 7/2018 |
| KR | 10-2018-0124728 | 11/2018 |
| KR | 10-2019-0020275 A | 2/2019 |
| KR | 10-2019-0050525 A | 5/2019 |
| KR | 10-2019-0052505 A | 5/2019 |
| KR | 10-2019-0091410 A | 8/2019 |
| WO | WO 2010/044130 A1 | 4/2010 |
| WO | WO 2011/163610 A2 | 12/2011 |
| WO | WO 2012/018120 A1 | 2/2012 |
| WO | WO 2012/091471 A2 | 7/2012 |
| WO | WO 2012/148127 A2 | 11/2012 |
| WO | WO 2013/002514 A2 | 1/2013 |
| WO | WO 2014/034795 A1 | 3/2014 |
| WO | WO 2015/130069 A1 | 9/2015 |
| WO | WO 2015/194791 A2 | 12/2015 |
| WO | WO 2016/178544 A2 | 11/2016 |
| WO | WO 2016/208862 A1 | 12/2016 |
| WO | WO 2017/014357 A1 | 1/2017 |
| WO | WO 2017/100967 A1 | 6/2017 |
| WO | WO 2017/116167 A1 | 7/2017 |
| WO | WO 2007/125714 A1 | 11/2017 |
| WO | 2018/038544 A1 | 3/2018 |
| WO | WO 2019088517 A1 * | 5/2019 |

OTHER PUBLICATIONS

Journal of Power Sources, vol. 425, (2019), pp. 87-93 (Year: 2019).*

Machine translation of JP 2018-065806 A (publication date Apr. 2018). (Year: 2018).*

Machine translation of WO 2019/088517 A1 (publication date May 2019). (Year: 2019).*

Tong et al., Synthetic Metals, 147 (2004), pp. 199-203. (Year: 2004).*

Hwang, Seok-Hwan, et al. "Improved performance of organic light-emitting diodes using advanced hole-transporting materials." Synthetic metals 159.23-24 (2009): 2578-2583. (Year: 2009).*

Subramanian, V., & Rajakumar, B. (2019). Excited state C—N bond dissociation and cyclization of tri-aryl amine-based OLED materials: a theoretical investigation. Physical Chemistry Chemical Physics, 21(1), 438-447. (Year: 2019).*

Machine English translation of Ham et al. (WO 2016/178544 A2). Feb. 16, 2021.

U.S. Office Action dated Feb. 22, 2021, issued in U.S. Appl. No. 16/254,777 (11 pages).

Extended European Search Report for corresponding European Patent Application No. 19153702.6, dated May 7, 2019, 9 pages.

U.S. Office Action dated Nov. 17, 2021, issued in U.S. Appl. No. 16/590,214 (10 pages).

Machine translation of WO 2018/038544, translation generated Jun. 2022, 84 pages. (Year: 2022).

US Office Action dated Jul. 13, 2022, issued in U.S. Appl. No. 16/590,214 (10 pages).

US Office Action dated Jul. 27, 2022, issued in U.S. Appl. No. 16/842,556 (16 pages).

U.S. Advisory Action dated May 26, 2022, issued in U.S. Appl. No. 16/590,214 (4 pages).

U.S. Notice of Allowance dated Jun. 17, 2022, issued in U.S. Appl. No. 16/254,777 (8 pages).

Advisory Action for U.S. Appl. No. 16/254,777 dated Oct. 8, 2021, 3 pages.

Notice of Allowance for U.S. Appl. No. 16/254,777 dated Mar. 2, 2022, 8 pages.

Office Action for U.S. Appl. No. 16/254,777 dated Jul. 23, 2021, 12 pages.

Office Action for U.S. Appl. No. 16/254,777 dated Oct. 29, 2021, 9 pages.

Office Action for U.S. Appl. No. 16/590,214 dated Mar. 18, 2022, 10 pages.

US Office Action dated Oct. 24, 2022, issued in U.S. Appl. No. 16/590,214 (8 pages).

US Office Action dated Nov. 4, 2022, issued in U.S. Appl. No. 16/254,777 (6 pages).

Chinese Office Action dated Oct. 13, 2022, issued in corresponding Chinese Patent Application No. 201910069905.7 (10 pages).

US Final Office Action dated Feb. 1, 2023, issued in U.S. Appl. No. 16/842,556 (16 pages).

US Notice of Allowance dated Feb. 10, 2023, issued in U.S. Appl. No. 16/590,214 (7 pages).

US Non-Final Office Action dated Feb. 17, 2023, issued in U.S. Appl. No. 17/947,056 (6 pages).

Notice of Allowance for U.S. Appl. No. 16/254,777 dated Apr. 4, 2023, 8 pages.

Notice of Allowance for U.S. Appl. No. 16/590,214 dated Jun. 5, 2023, 6 pages.

Notice of Allowance for U.S. Appl. No. 17/947,056 dated Jun. 6, 2023, 8 pages.

Office Action for CN Patent Application No. 201910073655.4 dated Jun. 14, 2023, 7 pages.

Office Action for U.S. Appl. No. 16/842,556 dated Aug. 29, 2023, 23 pages.

\* cited by examiner

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

Korean Patent Application No. 10-2018-0009993, filed on Jan. 26, 2018, and Korean Patent Application No. 10-2018-0146236, filed on Nov. 23, 2018, in the Korean Intellectual Property Office, and entitled: "Organic Electroluminescence Device and Monoamine Compound for Organic Electroluminescence Device," is incorporated by reference herein in its entirety.

BACKGROUND

1. Field

Embodiments relate to an organic electroluminescence device and a monoamine compound for an organic electroluminescence device.

2. Description of the Related Art

Development on an organic electroluminescence display as an image display is being actively conducted. An organic electroluminescence display is different from a liquid crystal display and is so called a self-luminescent display which accomplishes display by recombining holes and electrons injected from a first electrode and a second electrode in an emission layer and emitting light from a luminescent material which includes an organic compound in the emission layer.

SUMMARY

Embodiments are directed to an organic electroluminescence device including a first electrode, a hole transport region on the first electrode, an emission layer on the hole transport region, an electron transport region on the emission layer and a second electrode on the electron transport region, in which the hole transport region includes a monoamine compound represented by the following Formula 1.

[Formula 1]

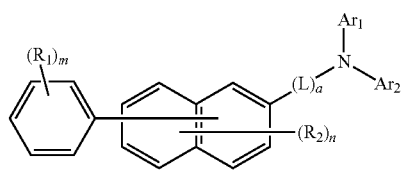

In Formula 1, $Ar_1$ and $Ar_2$ may each independently be a substituted or unsubstituted alkyl group having 1 to 10 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 2 to 30 ring carbon atoms, L may be a substituted or unsubstituted arylene group having 6 to 30 ring carbon atoms, or a substituted or unsubstituted heteroarylene group having 2 to 30 ring carbon atoms, $R_1$ may be a hydrogen atom, a deuterium atom, a halogen atom, a substituted or unsubstituted alkyl group having 1 to 20 carbon atoms, a substituted or unsubstituted cycloalkyl group having 3 to 20 ring carbon atoms, or a substituted or unsubstituted aryl group having 6 to 30 ring carbon atoms, $R_2$ may be a hydrogen atom, a deuterium atom, a halogen atom, a substituted or unsubstituted alkyl group having 1 to 20 carbon atoms, or a substituted or unsubstituted cycloalkyl group having 3 to 20 ring carbon atoms, a may be an integer of 0 to 3, m may be an integer of 0 to 1, n may be an integer of 0 to 6, and when any one of $Ar_1$ and $Ar_2$ is 3-dibenzofuranyl, the other may not be 9-phenanthryl.

The hole transport region may have a plurality of layers, and a layer of the plurality of layers contacting the emission layer may include the monoamine compound according to an example embodiment.

The hole transport region may include a hole injection layer on the first electrode, a hole transport layer on the hole injection layer, and an electron blocking layer on the hole transport layer, and the electron blocking layer may include the monoamine compound according to an example embodiment.

The electron transport region may include a hole blocking layer on the emission layer, an electron transport layer on the hole blocking layer, and an electron injection layer on the electron transport layer.

Formula 1 may be represented by any one of the following Formulae 2 to 8.

[Formula 2]

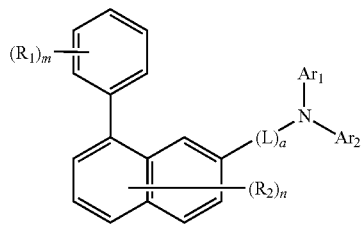

[Formula 3]

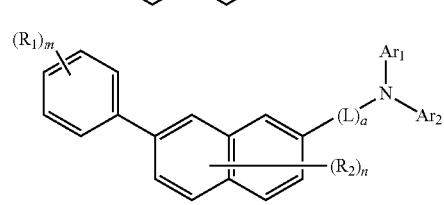

[Formula 4]

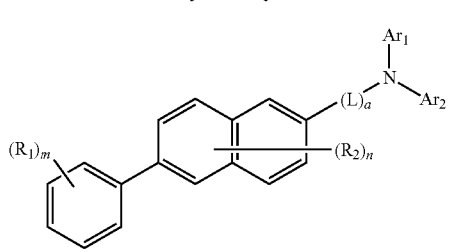

[Formula 5]

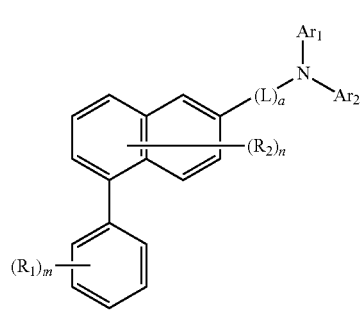

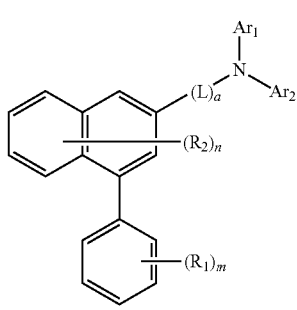

[Formula 6]

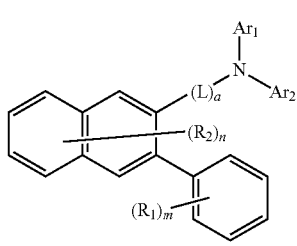

[Formula 7]

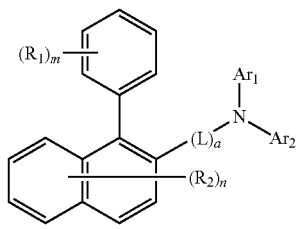

[Formula 8]

In Formulae 2 to 8, $Ar_1$, $Ar_2$, L, $R_1$, $R_2$, a, m, and n are the same as defined in Formula 1.

L may be a substituted or unsubstituted arylene group having 6 to 12 ring carbon atoms.

L may be a substituted or unsubstituted phenylene group.

$Ar_1$ and $Ar_2$ may be each independently a substituted or unsubstituted aryl group having 6 to 12 ring carbon atoms.

$Ar_1$ and $Ar_2$ may be each independently a substituted or unsubstituted phenyl group, a substituted or unsubstituted biphenyl group, a substituted or unsubstituted naphthyl group, or a substituted or unsubstituted fluorenyl group.

$Ar_1$ and $Ar_2$ may be each independently a substituted or unsubstituted heteroaryl group having 5 to 12 ring carbon atoms.

$Ar_1$ and $Ar_2$ may be each independently a substituted or unsubstituted dibenzofuran group, a substituted or unsubstituted dibenzothiophene group, or a substituted or unsubstituted carbazole group.

Embodiments are also directed to a monoamine compound represented by the above Formula 1.

BRIEF DESCRIPTION OF THE DRAWINGS

Features will become apparent to those of skill in the art by describing in detail example embodiments with reference to the attached drawings in which.

DETAILED DESCRIPTION

Figure 1:
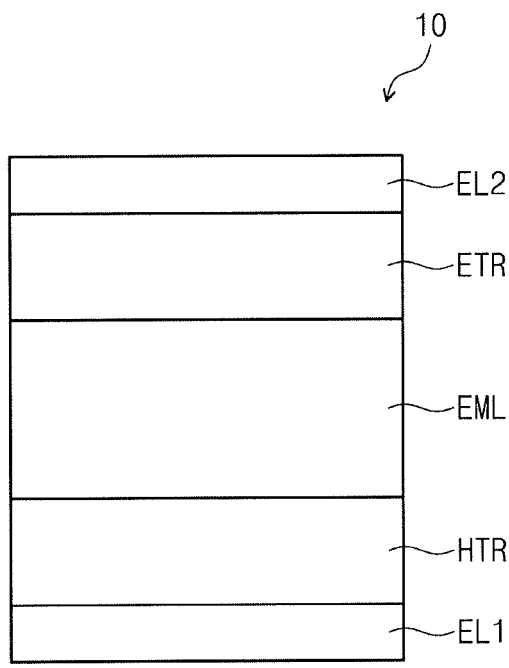
FIG. 1 illustrates a schematic cross-sectional view of an organic electroluminescence device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprise" or "have," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the other hand, when a layer, a film, a region, a plate, etc. is referred to as being "under" another part, it can be "directly under" the other part, or intervening layers may also be present.

First, an organic electroluminescence device according to an example embodiment will be explained referring to FIGS. 1 to 3.

FIG. 1 is a schematic cross-sectional view illustrating an organic electroluminescence device according to an example embodiment. FIG. 2 is a schematic cross-sectional view illustrating an organic electroluminescence device according to an example embodiment. FIG. 3 is a schematic cross-sectional view illustrating an organic electroluminescence device according to an example embodiment.

Figure 2:
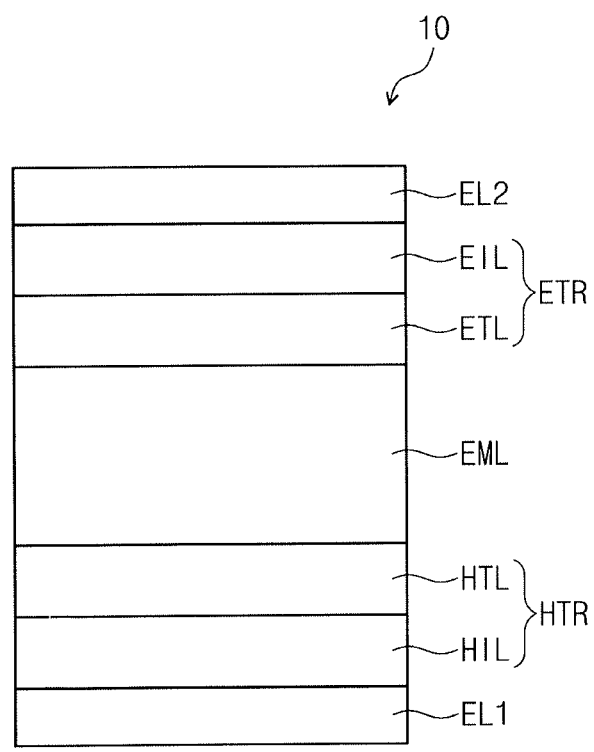
FIG. 2 illustrates a schematic cross-sectional view of an organic electroluminescence device according to an example embodiment.
Figure 3:
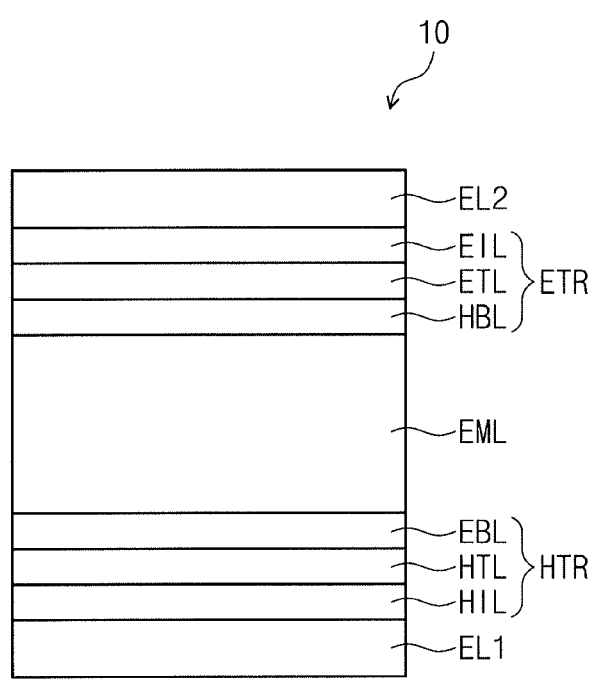
FIG. 3 illustrates a schematic cross-sectional view of an organic electroluminescence device according to an example embodiment.

Referring to FIGS. 1 to 3, an organic electroluminescence device 10 according to an example embodiment includes a first electrode EL1, a hole transport region HTR, an emission layer EML, an electron transport region ETR, and a second electrode EL2.

The hole transport region HTR includes the monoamine compound according to an example embodiment. Hereinafter, the monoamine compound according to an example embodiment will be specifically explained, and then each layer of the organic electroluminescence device 10 will be explained.

In the present disclosure, "substituted or unsubstituted" may mean unsubstituted or substituted with at least one substituent selected from the group of deuterium, halogen, cyano, nitro, silyl, boron, phosphine, alkyl, alkenyl, aryl and heterocyclic group. In addition, each of the substituent described above may be substituted or unsubstituted. For example, biphenyl may be interpreted as aryl, or phenyl substituted with phenyl.

In the present disclosure, examples of a halogen atom are a fluorine atom, a chlorine atom, a bromine atom, and an iodine atom.

In the present disclosure, the alkyl group may have a linear, branched or cyclic form. The carbon number of the alkyl group may be 1 to 30, 1 to 20, 1 to 10, or 1 to 4. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 30, 6 to 20, or 6 to 12. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc.

In the present disclosure, the fluorenyl group may be substituted, and two substituents may be combined with each other to form a spiro structure. Examples of the substituted fluorenyl group may include the following groups:

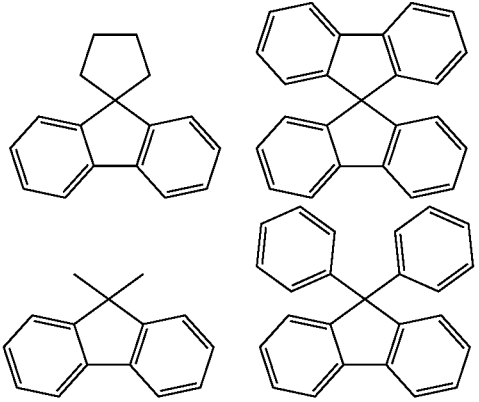

In the present disclosure, the heteroaryl group may be heteroaryl including at least one of O, N, P, Si, or S as a heteroatom. When the heteroaryl group includes two heteroatoms, the two heteroatoms may be the same or different from each other. The carbon number of the heteroaryl group for forming a ring may be 2 to 30, or 5 to 12. The heteroaryl group may be monocyclic heteroaryl or polycyclic heteroaryl. Polycyclic heteroaryl may have bicyclic or tricyclic structure, for example. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-aryl carbazole, N-heteroaryl carbazole, N-alkyl carbazole, benzoxazole, benzoimidazole, benzothiazole, benzocarbazole, benzothiophene, dibenzothiophene, thienothiophene, benzofuran, phenanthroline, thiazole, isoxazole, oxadiazole, thiadiazole, phenothiazine, dibenzosilole, dibenzofuran, etc.

In the present disclosure, the silyl group may include alkyl silyl and aryl silyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc.

In the present disclosure, the boron group may include alkyl boron and aryl boron. Examples of the boron group may include trimethyl boron, triethyl boron, t-butyl dimethyl boron, triphenyl boron, diphenyl boron, phenyl boron, etc.

In the present disclosure, the alkenyl group may be linear or branched. The carbon number is not specifically limited, and may be 2 to 30, 2 to 20, or 2 to 10. Examples of the alkenyl group may include vinyl, 1-butenyl, 1-pentenyl, 1,3-butadienyl aryl, styrenyl, styrylvinyl, etc.

The above explanation on the aryl group may be applied to the arylene group, except that the arylene group is divalent.

The above explanation on the heteroaryl group may be applied to the heteroarylene group, except that the heteroarylene group is divalent.

A monoamine compound according to an example embodiment is represented by the following Formula 1.

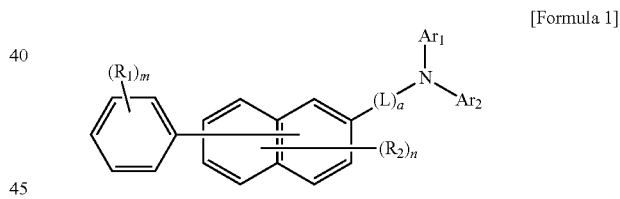

[Formula 1]

According to the present example embodiment, in Formula 1, $Ar_1$ and $Ar_2$ may each independently be a substituted or unsubstituted alkyl group having 1 to 10 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 2 to 30 ring carbon atoms.

In Formula 1, L may be a substituted or unsubstituted arylene group having 6 to 30 ring carbon atoms, or a substituted or unsubstituted heteroarylene group having 2 to 30 ring carbon atoms.

In Formula 1, $R_1$ may be a hydrogen atom, a deuterium atom, a halogen atom, a substituted or unsubstituted alkyl group having 1 to 20 carbon atoms, a substituted or unsubstituted cycloalkyl group having 3 to 20 ring carbon atoms, or a substituted or unsubstituted aryl group having 6 to 30 ring carbon atoms.

In Formula 1, $R_2$ may be a hydrogen atom, a deuterium atom, a halogen atom, a substituted or unsubstituted alkyl group having 1 to 20 carbon atoms, or a substituted or unsubstituted cycloalkyl group having 3 to 20 ring carbon atoms.

In an example embodiment, $R_2$ may be neither an aryl group nor a heteroaryl group. In a compound of Formula 1 in which $R_2$ is an aryl group or a heteroaryl group, the naphthalene structure may have a largely distributed HOMO (highest occupied molecular orbital) energy level and the amine group may not maintain the property of extending device life due to the relatively decreased electron density, thereby decreasing life of the organic electroluminescence device including the compound. When $R_2$ is referred to as being neither an aryl group nor a heteroaryl group, it may include both the case where $R_2$ is neither an aryl group nor a heteroaryl group and the case where $R_2$ is substituted with neither an aryl group nor a heteroaryl group.

In Formula 1, a may be an integer of 0 to 3. In case a is an integer of 2 or more, a plurality of L may be the same or different from each other.

In Formula 1, m may be an integer of 0 to 1.

In Formula 1, n may be an integer of 0 to 6. In case n is an integer of 2 or more, a plurality of $R_2$ may be the same or different from each other.

In Formula 1, in case any one of $Ar_1$ and $Ar_2$ is 3-dibenzofuranyl, the other may not be 9-phenanthryl. For example, when $Ar_1$ is 3-dibenzofuranyl, $Ar_2$ is not 9-phenanthryl, and when $Ar_2$ is 3-dibenzofuranyl, $Ar_1$ is not 9-phenanthryl. Furthermore, the compound of Formula 1, where the nitrogen atom is substituted with both of 3-dibenzofuranyl and 9-phenanthryl, is excluded. A compound of Formula 1 in which the nitrogen atom is substituted with both of 3-dibenzofuranyl and 9-phenanthryl may have a strong molecular stacking and increased deposition temperature, which may result in thermal decomposition and thereby degrade the quality of organic electroluminescence device including the compound.

In an embodiment, Formula 1 may be represented by any one of the following Formulae 2 to 8.

[Formula 2]

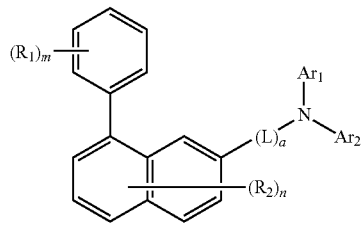

[Formula 3]

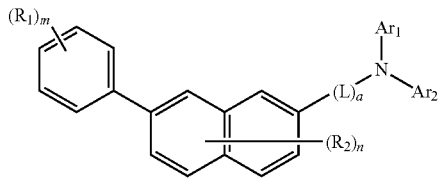

[Formula 4]

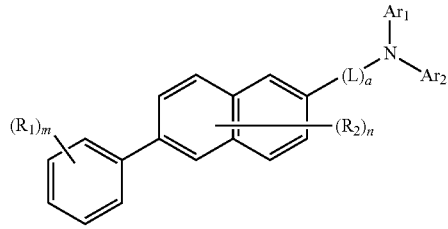

[Formula 5]

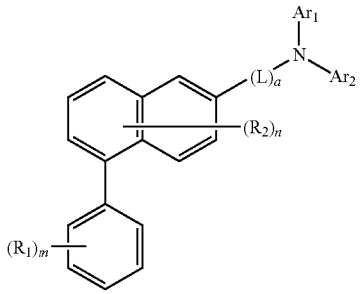

[Formula 6]

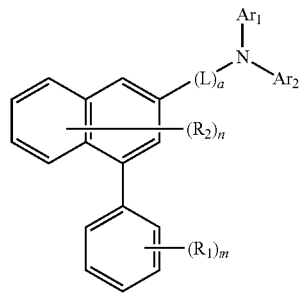

[Formula 7]

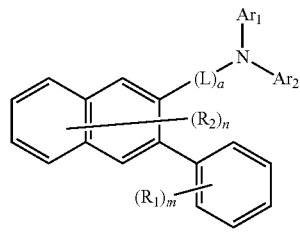

[Formula 8]

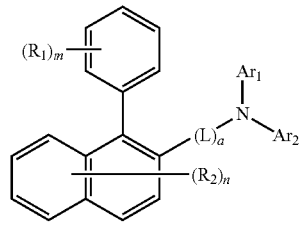

In Formulae 2 to 8, $Ar_1$, $Ar_2$, L, $R_1$, $R_2$, a, m, and n are the same as defined in Formula 1.

In Formula 1, m may be 1, and L may be a substituted or unsubstituted arylene group having 6 to 12 ring carbon atoms. For example, L may be a substituted or unsubstituted phenylene group.

In Formula 1, $Ar_1$ and $Ar_2$ may be each independently a substituted or unsubstituted aryl group having 6 to 12 ring carbon atoms. For example, $Ar_1$ and $Ar_2$ may be each independently a substituted or unsubstituted phenyl group, a substituted or unsubstituted biphenyl group, a substituted or unsubstituted naphthyl group, or a substituted or unsubstituted fluorenyl group.

In Formula 1, $Ar_1$ and $Ar_2$ may be each independently a substituted or unsubstituted heteroaryl group having 5 to 12 ring carbon atoms. For example, Ar and $Ar_2$ may be each independently a substituted or unsubstituted dibenzofuran group, a substituted or unsubstituted dibenzothiophene group, or a substituted or unsubstituted carbazole group.

In Formula 1, $R_2$ may be a hydrogen atom or a deuterium atom.

The monoamine compound represented by Formula 1 according to an example embodiment may be any one selected from the group of compounds represented in the following Compound Groups 1 to 7.
[Compound Group 1]
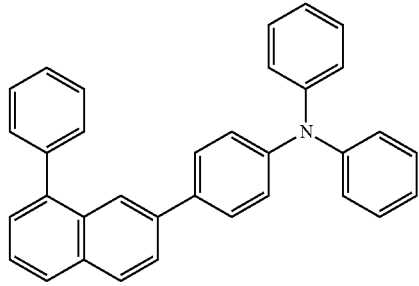
A1
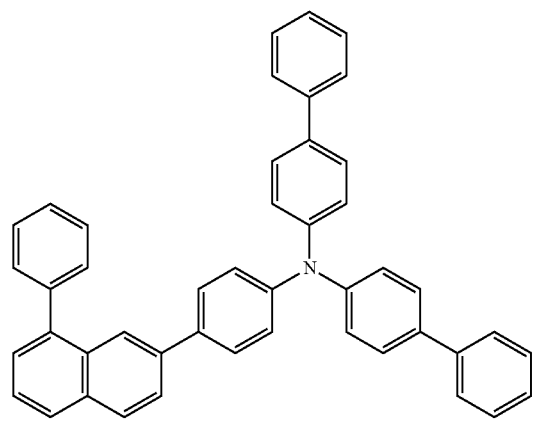
A2
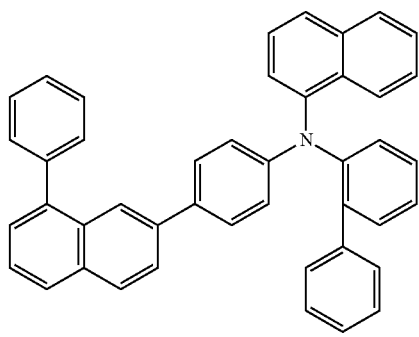
A3
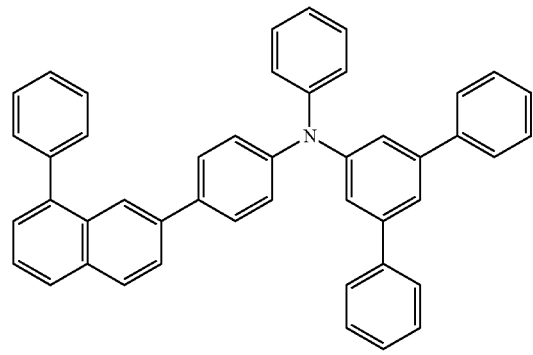
A4
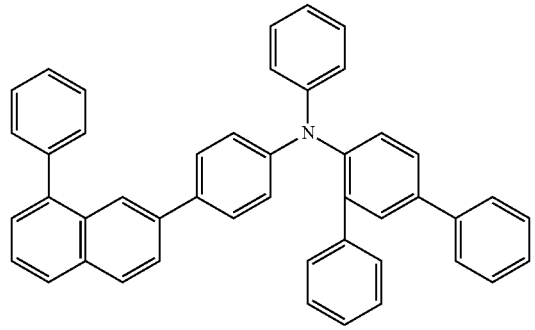
A5
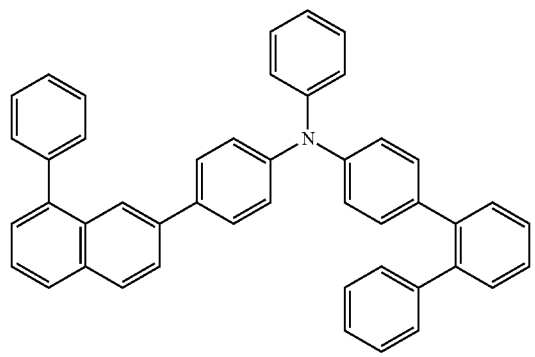
A6
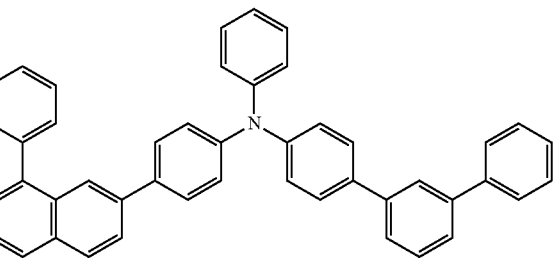
A7
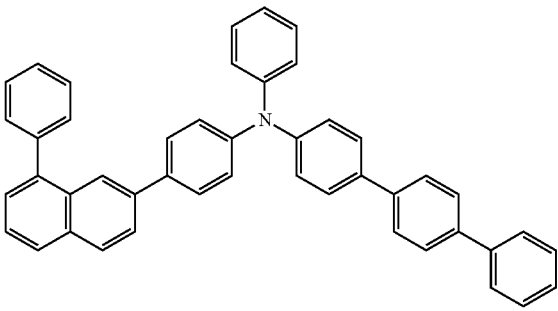
A8

A9
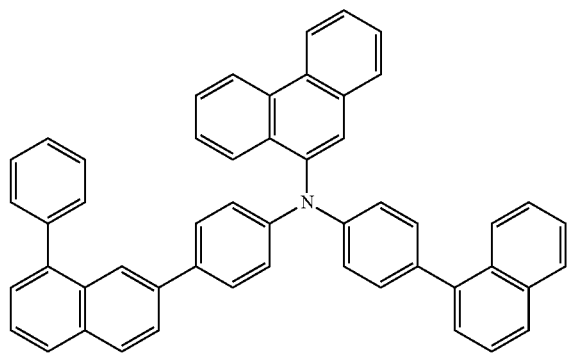
A10
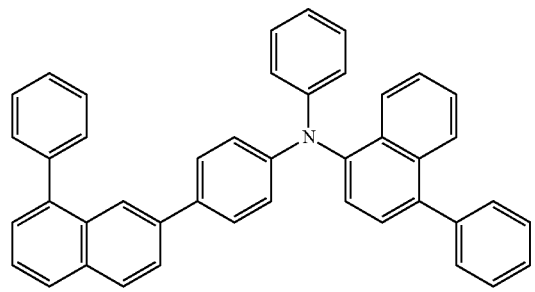
A11
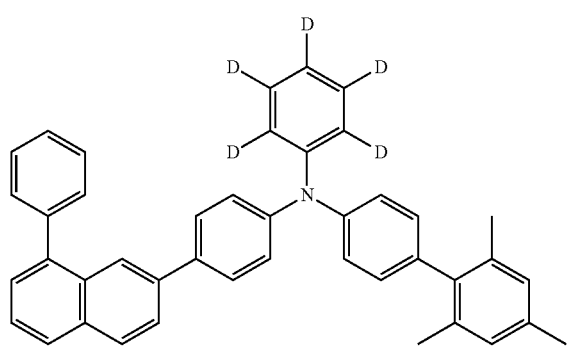
A12
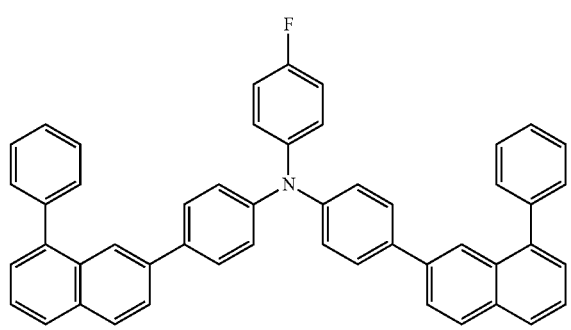
A13
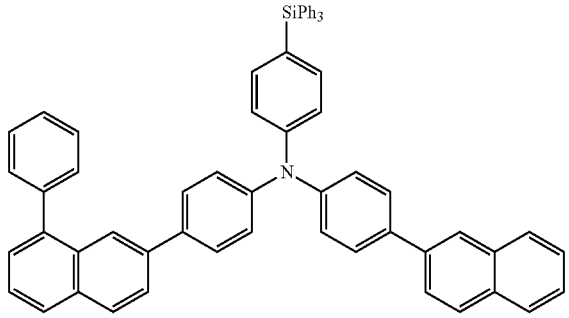
A14
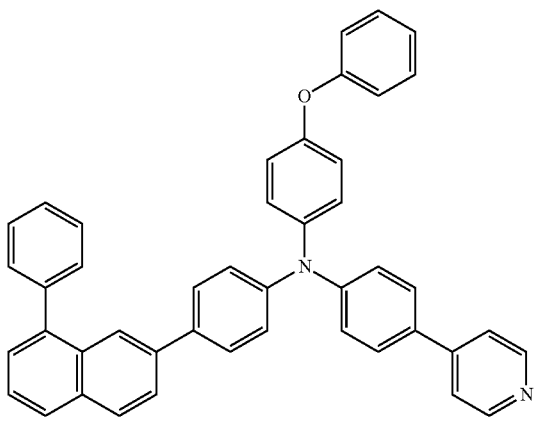
A15
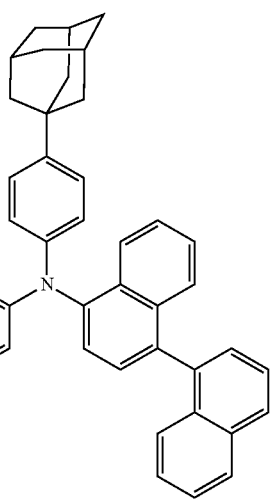

A16
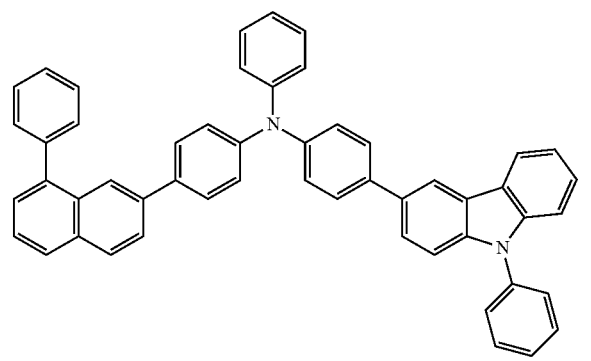
A20
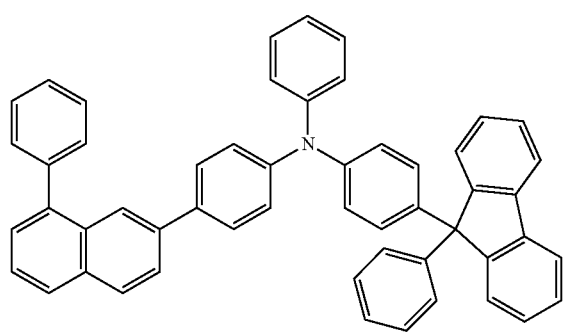
A17
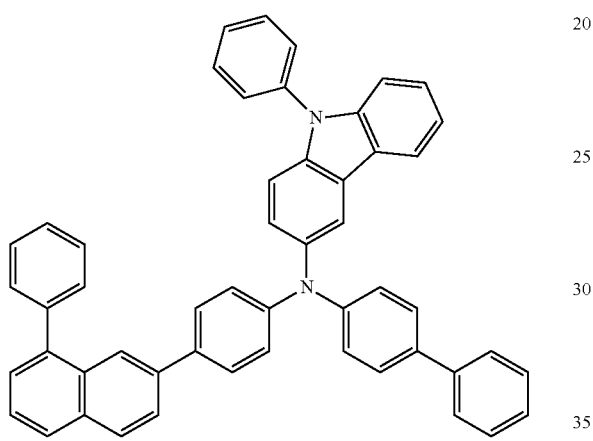
A21
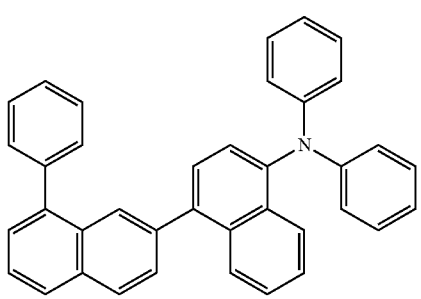
A18
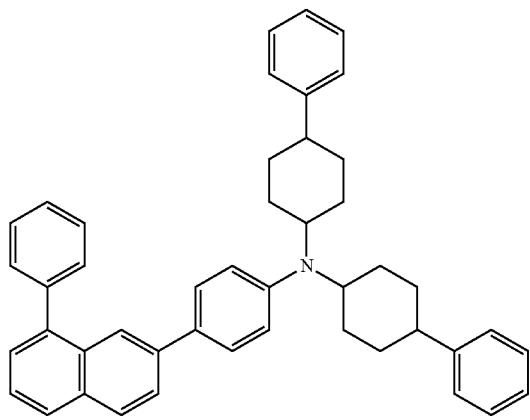
A22
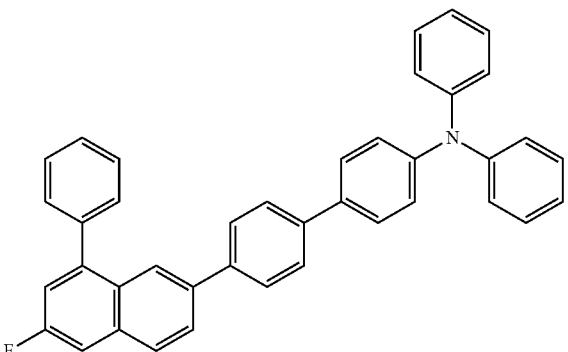
A19
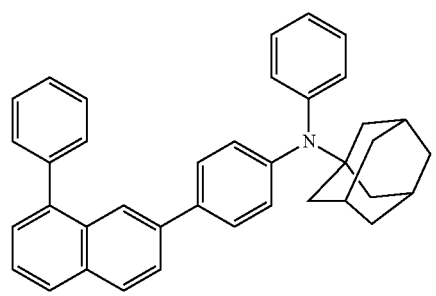
A23
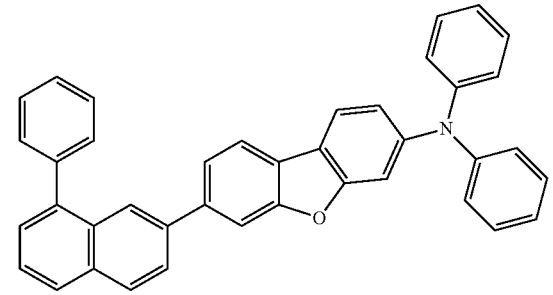

-continued
A24
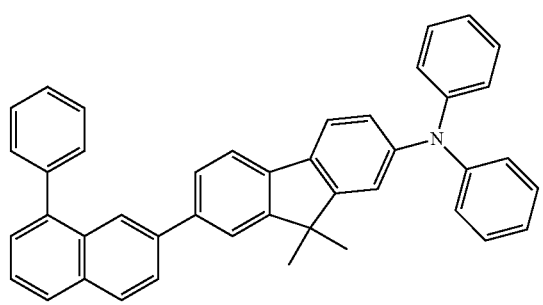
A25
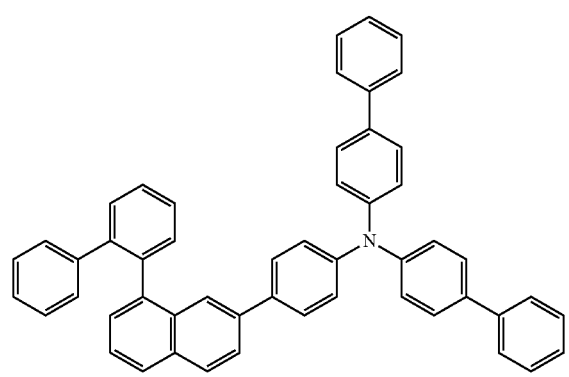
A26
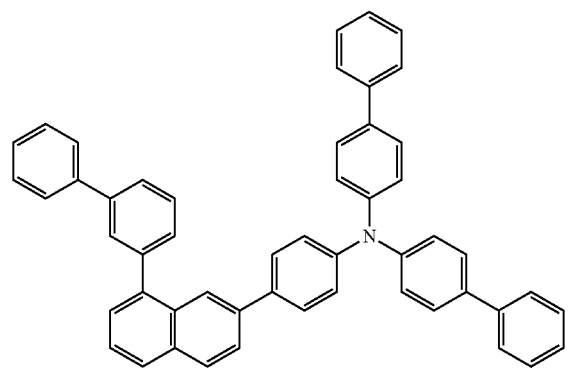
A27
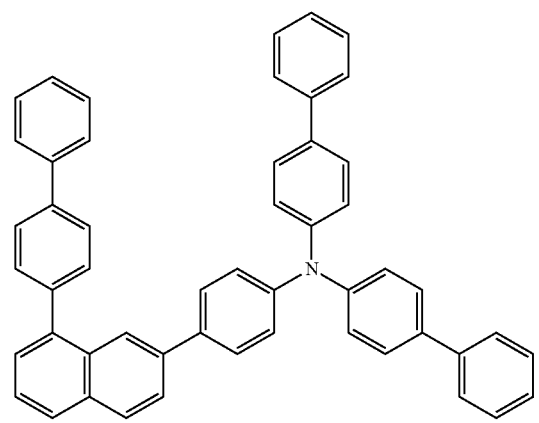
-continued
A28
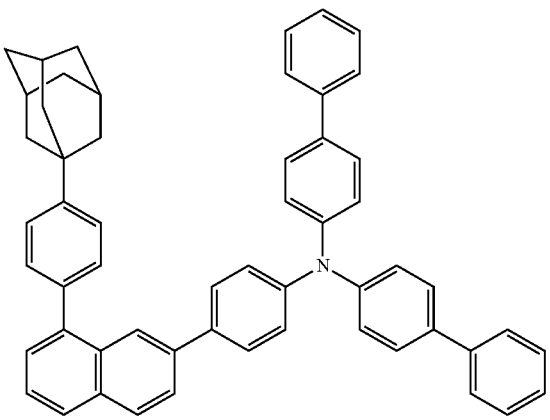
A29
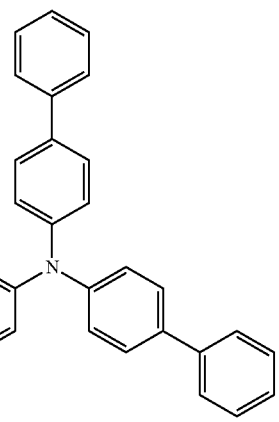
A30
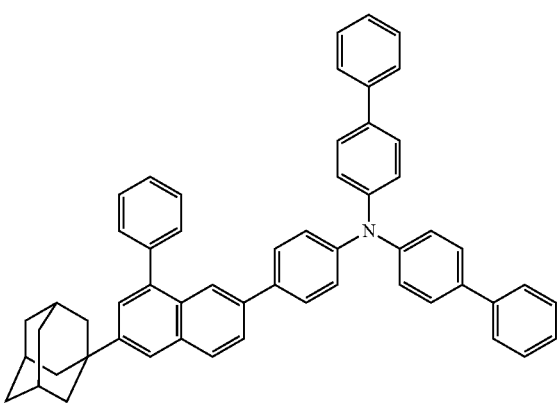

A31
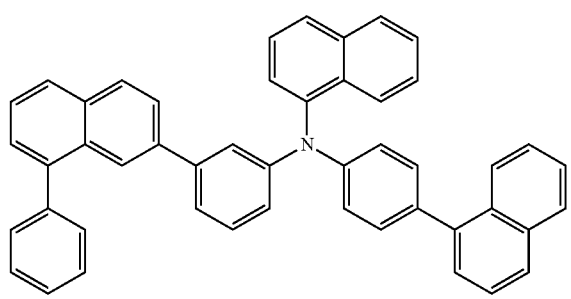
A32
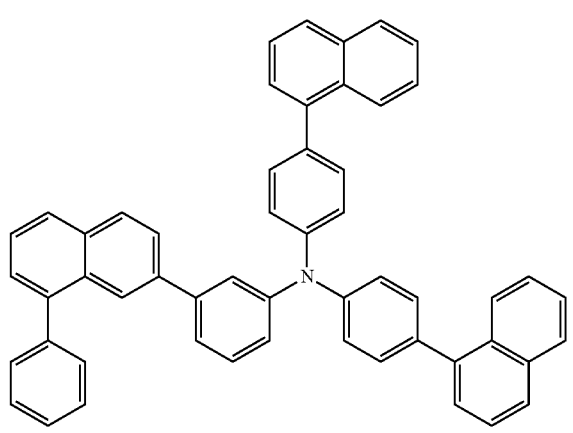
A33
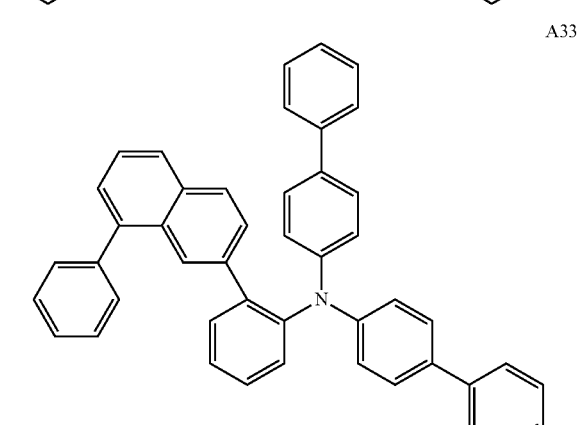
A34
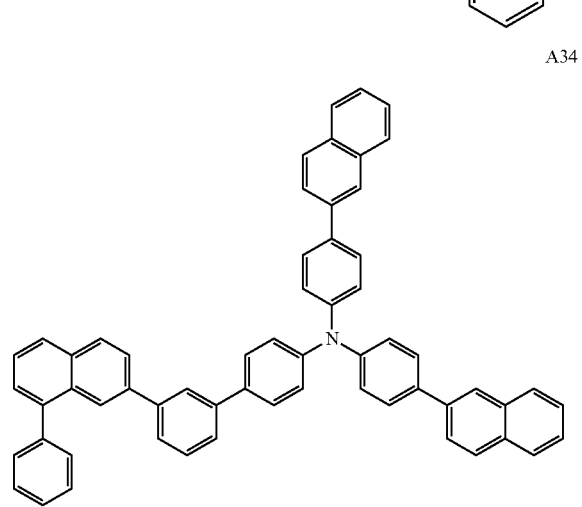
A35
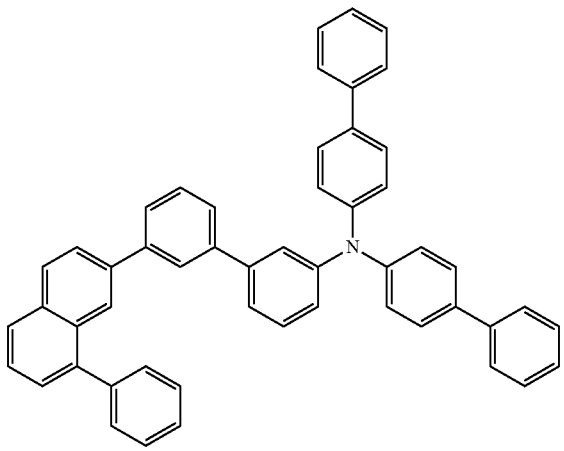
A36
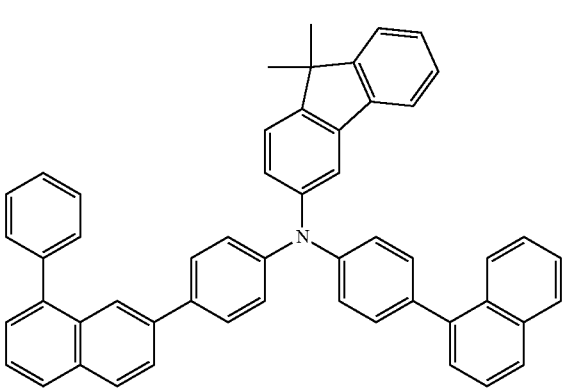
A37
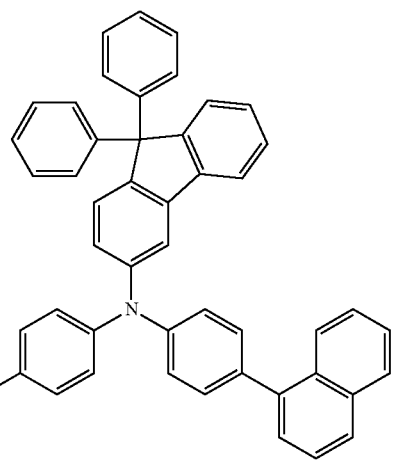

A38
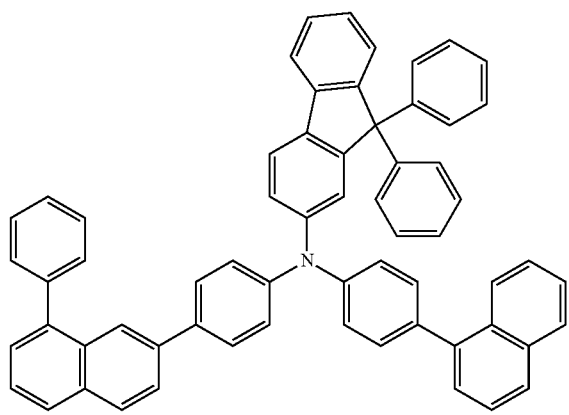
A39
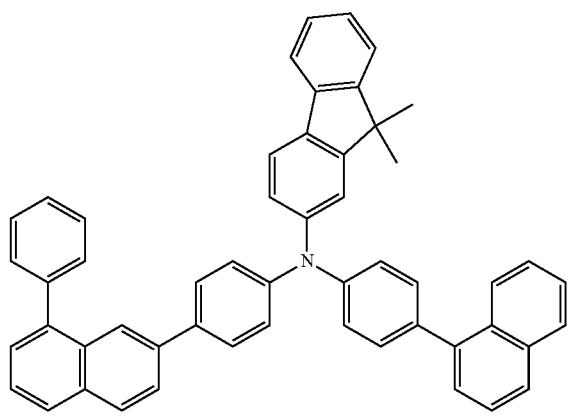
A40
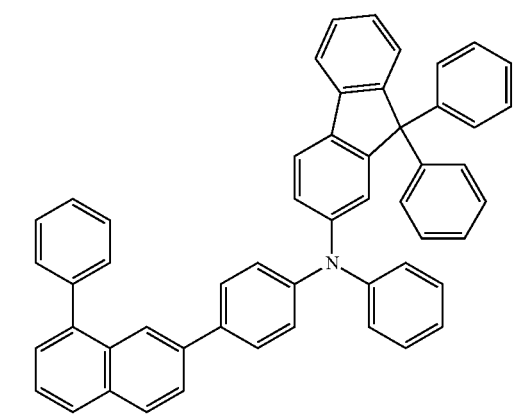
A41
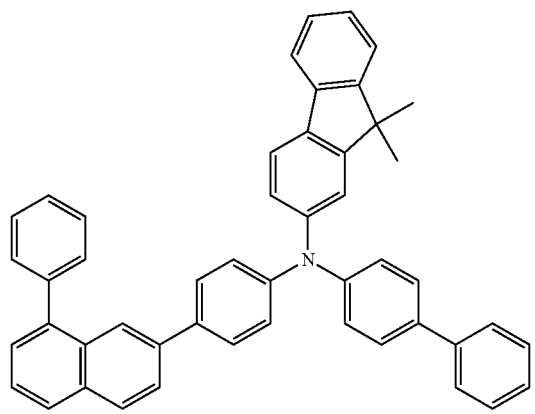
A42
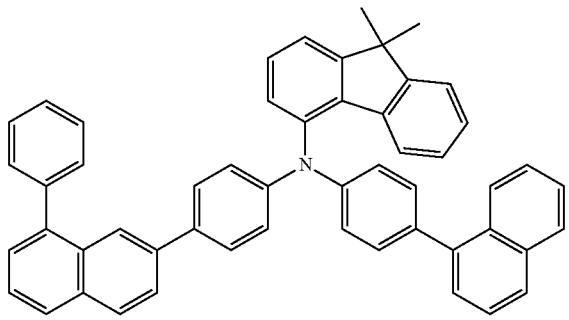
A43
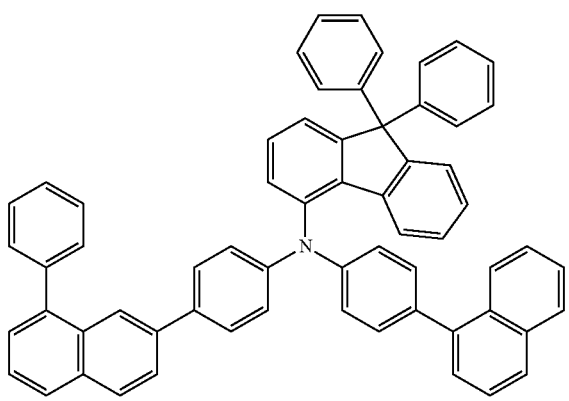
A44
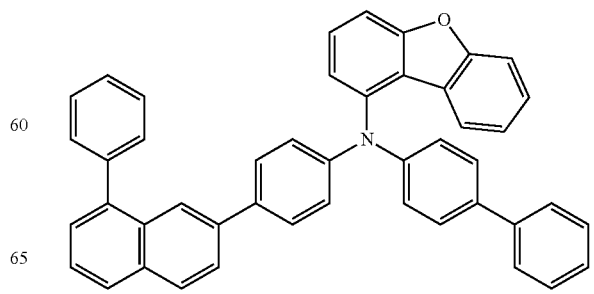

A45
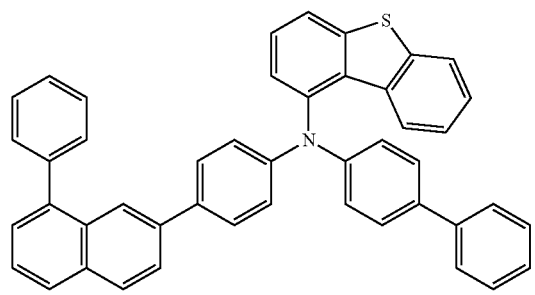
A46
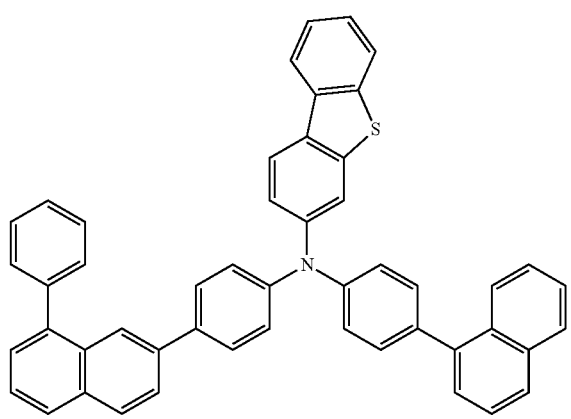
A47
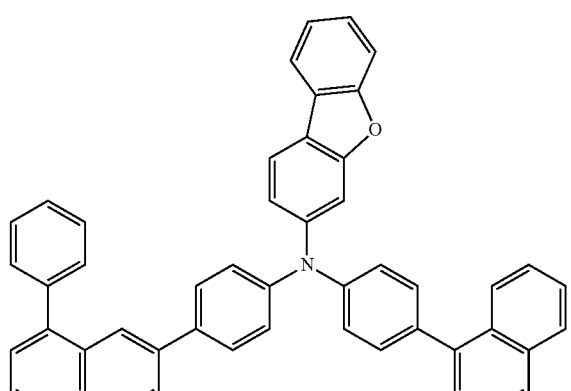
A48
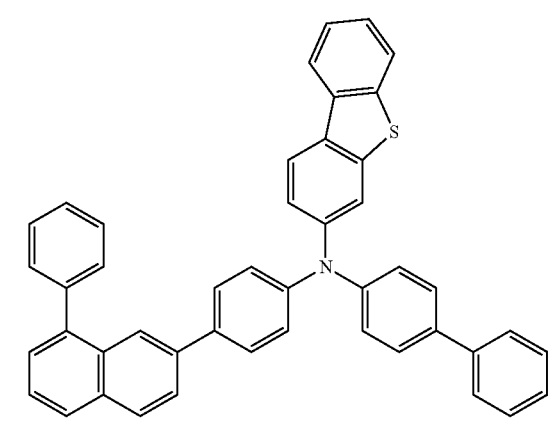
A49
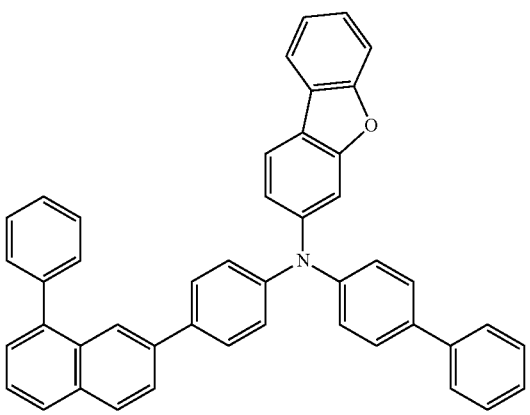
A50
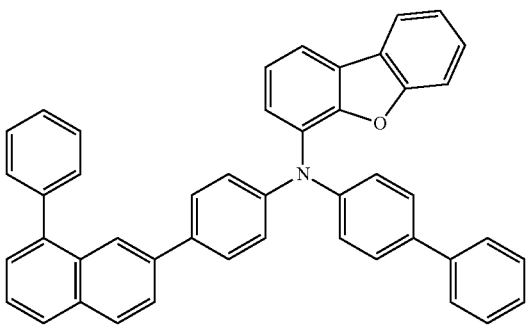
A51
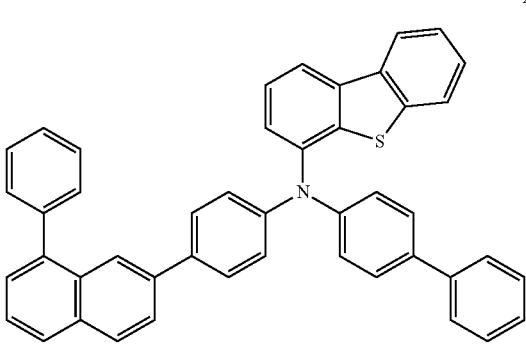
A52
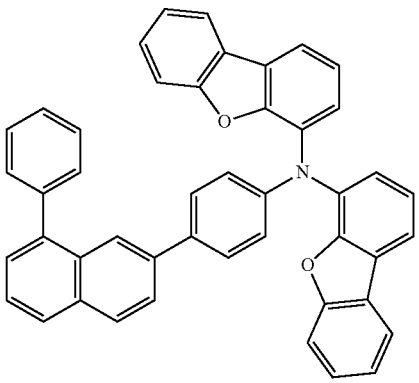

-continued
A53
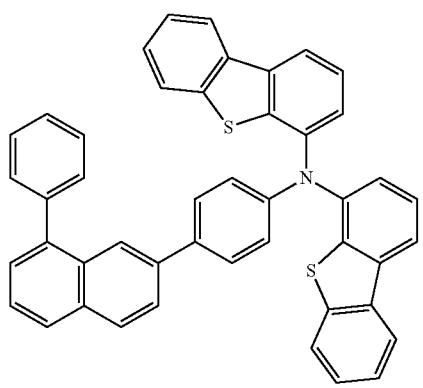
A54
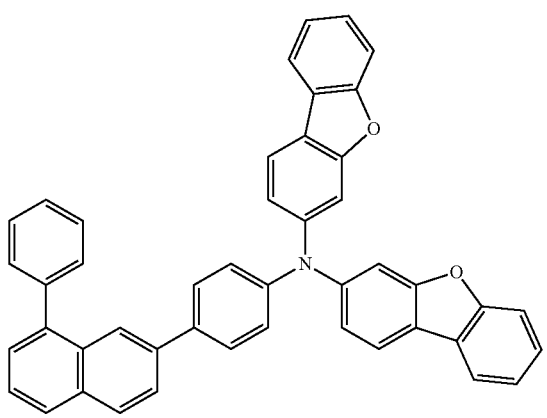
A55
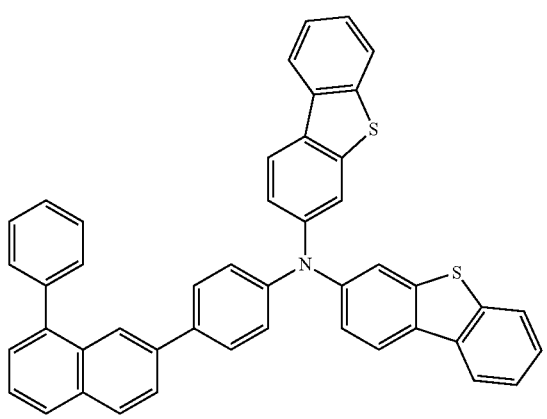
-continued
A56
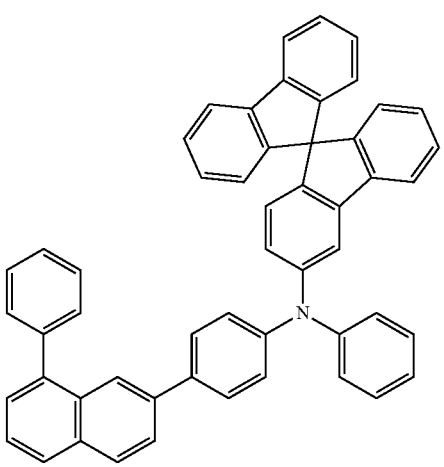
A57
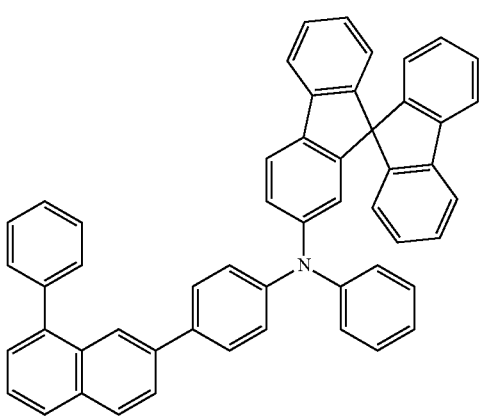
A58
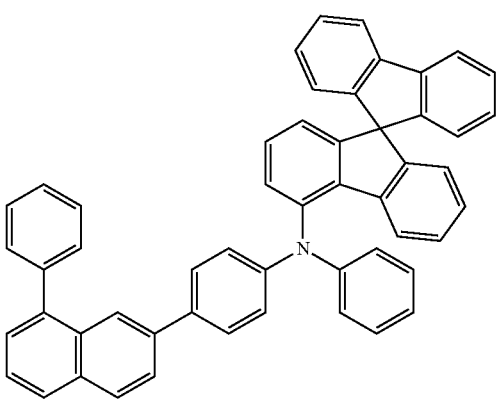

A59
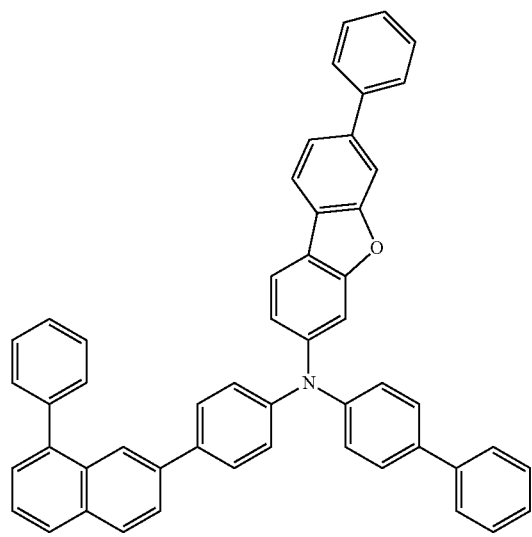
A60
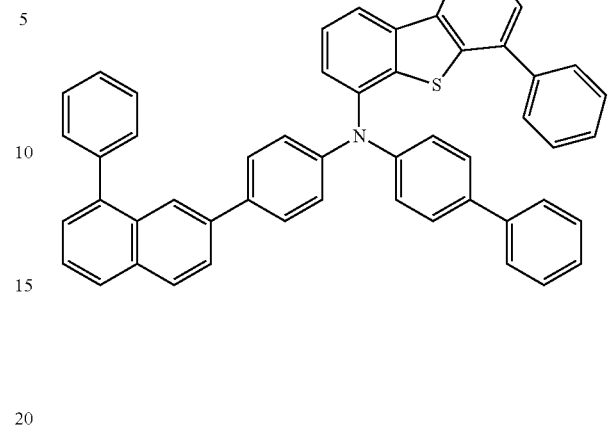
[Compound Group 2]
B1
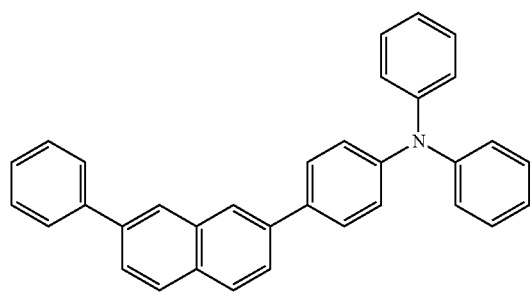
B2
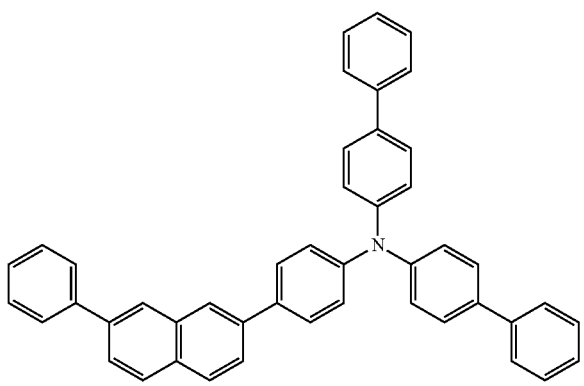
B3
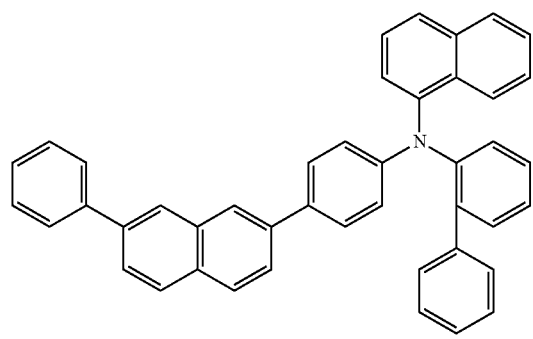
B4
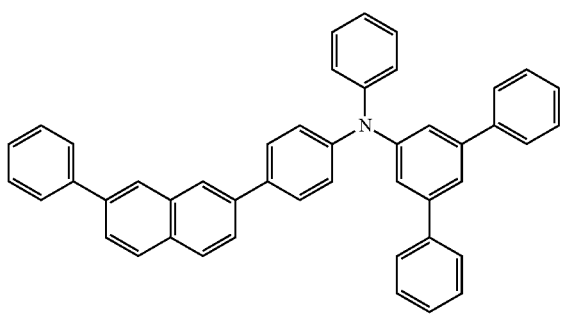

-continued
B5
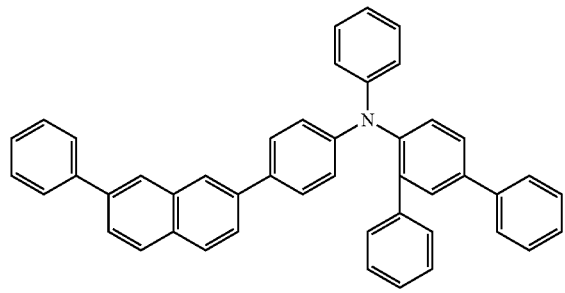
B6
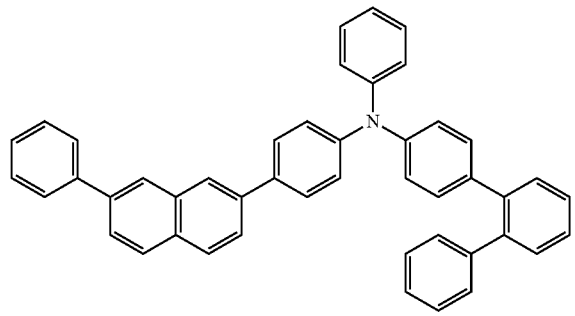
B7
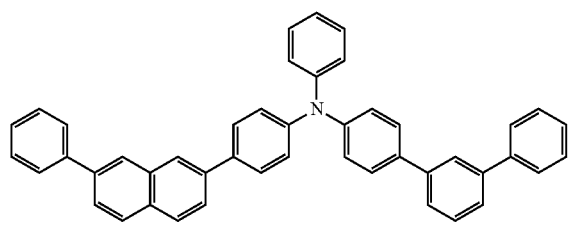
B8
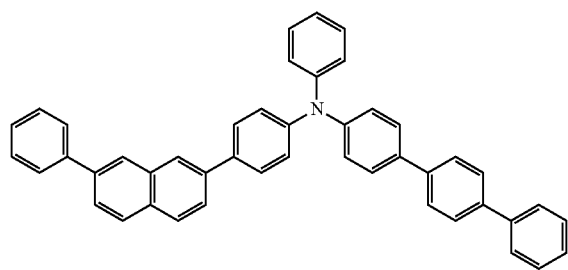
B9
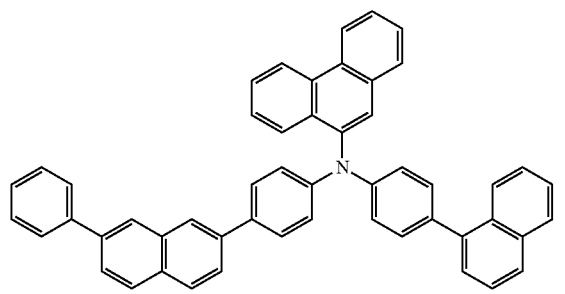
B10
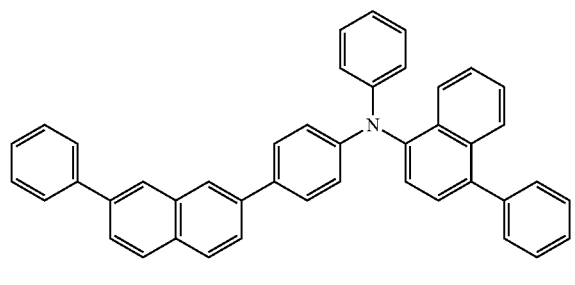
B11
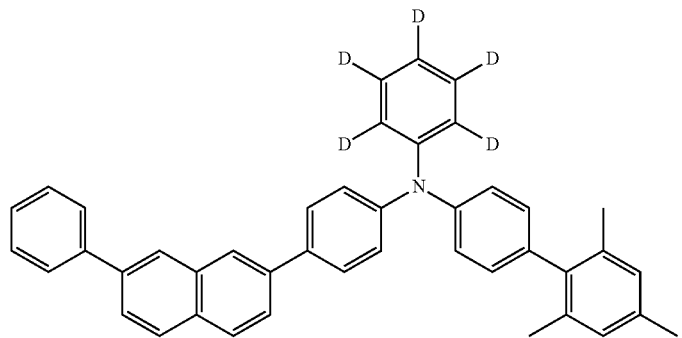
B12
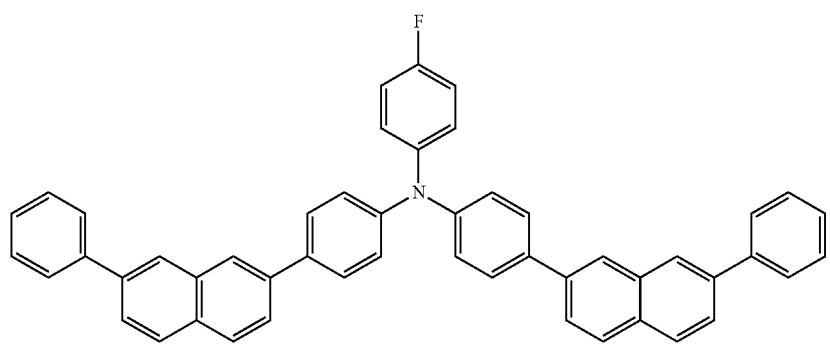

-continued
B13
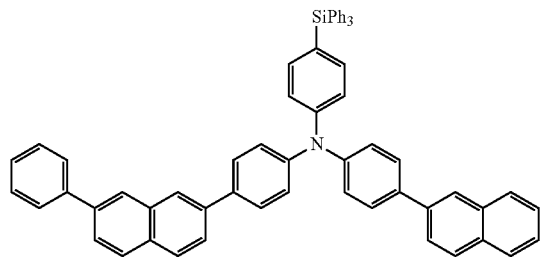
B14
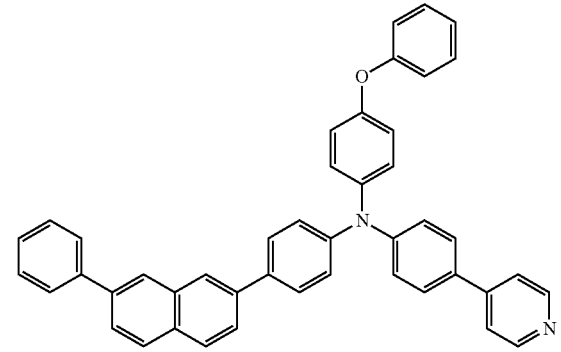
B15
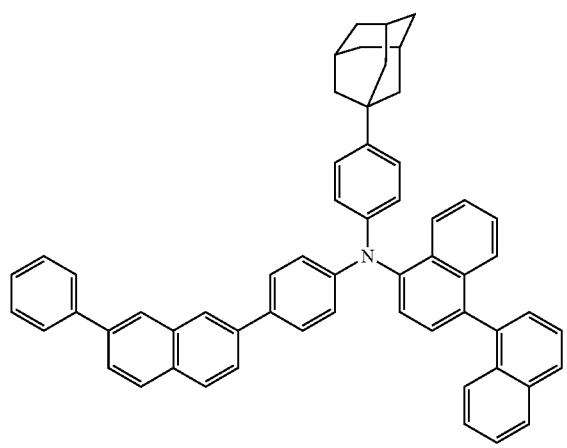
B16
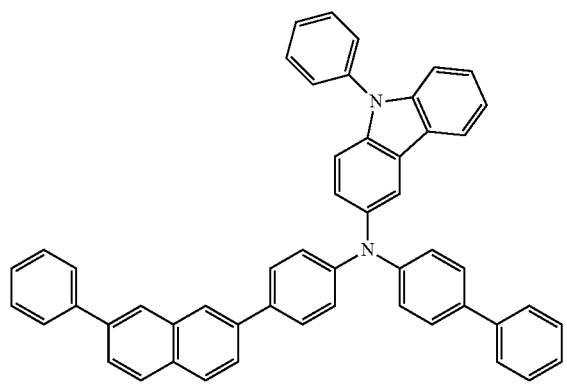
B17
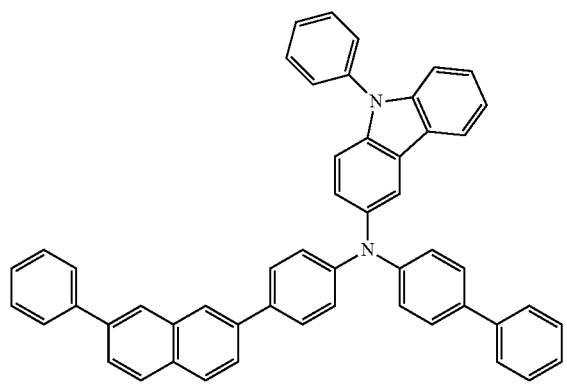
B18
B19
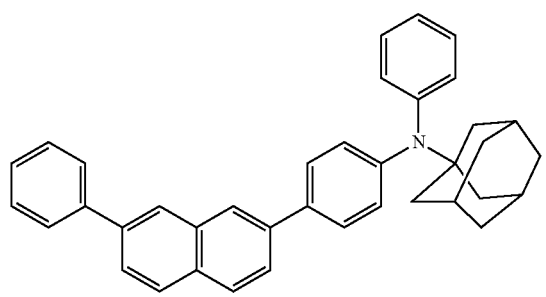
B20
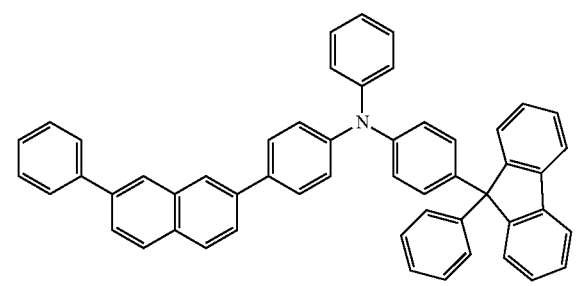

-continued
B21
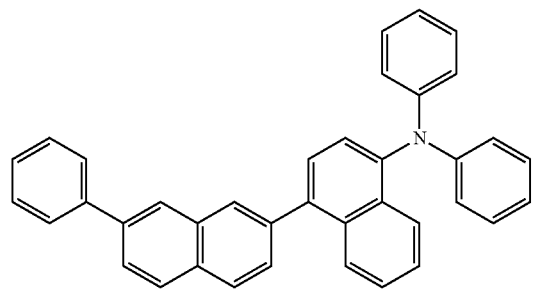
B22
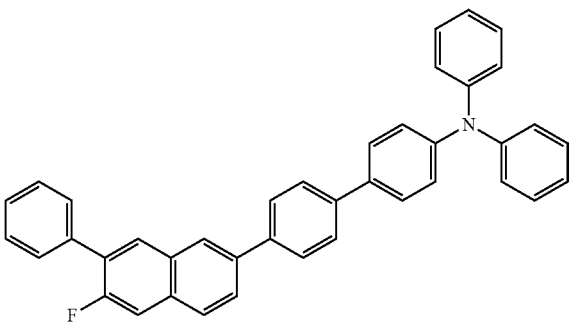
B23
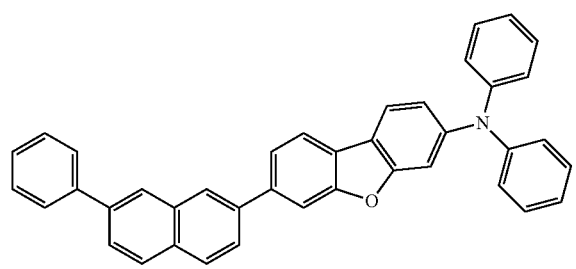
B24
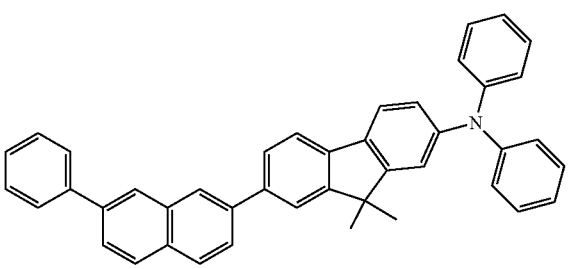
B25
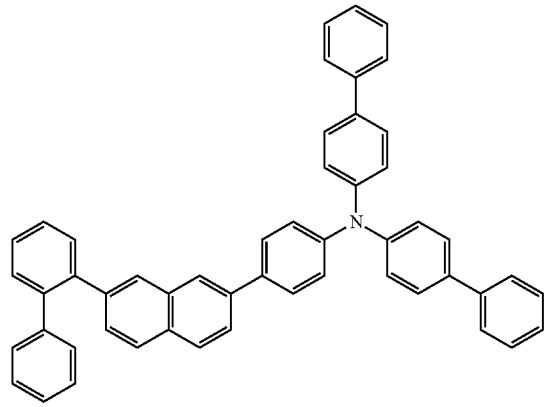
B26
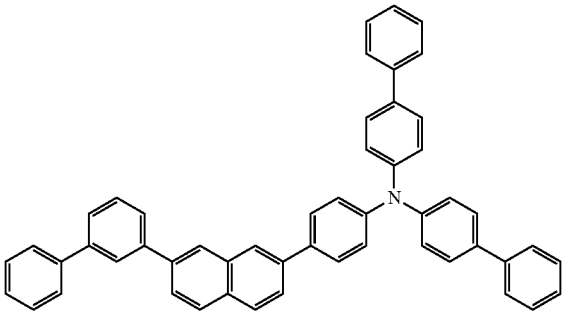
B27
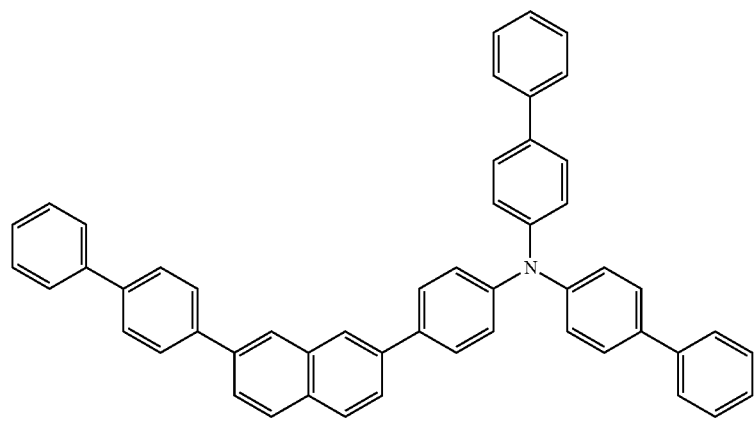

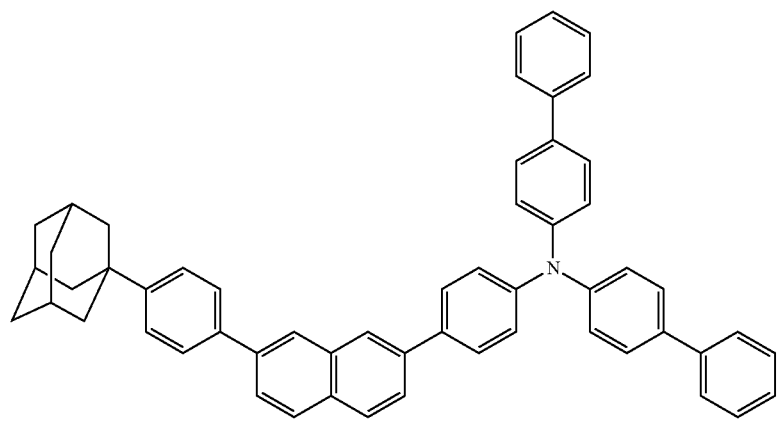
B28
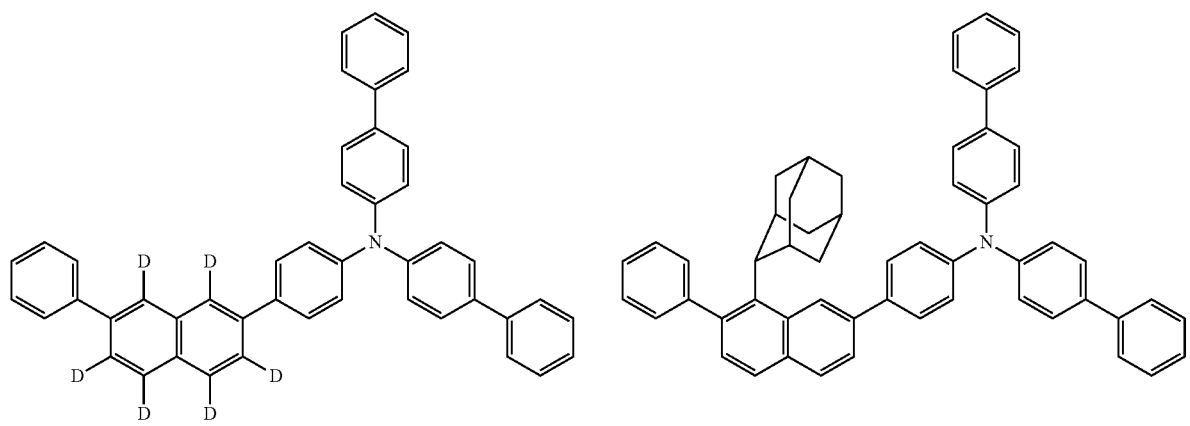
B29　　B30
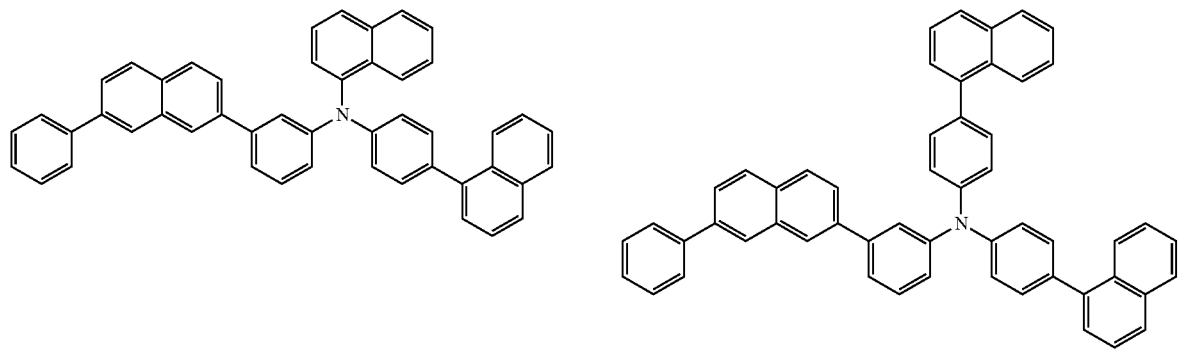
B31　　B32
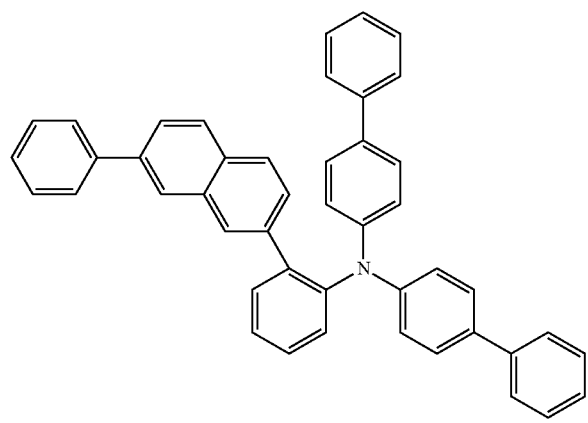
B33

-continued
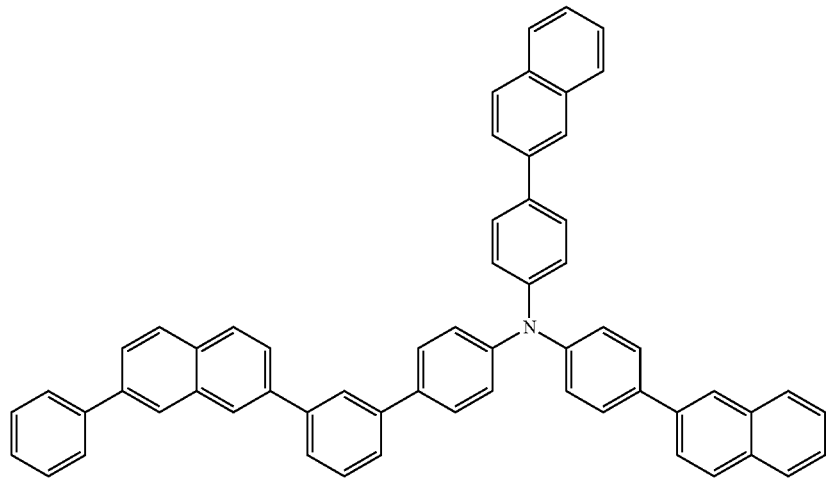
B34
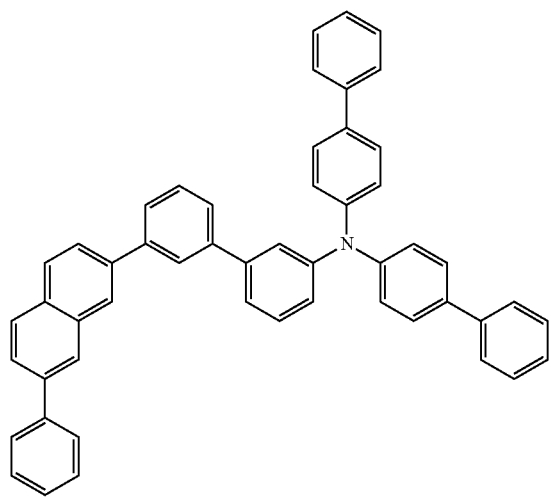
B35
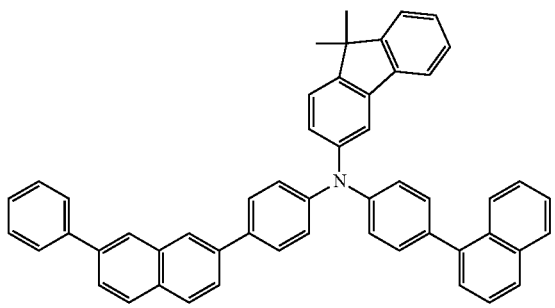
B36
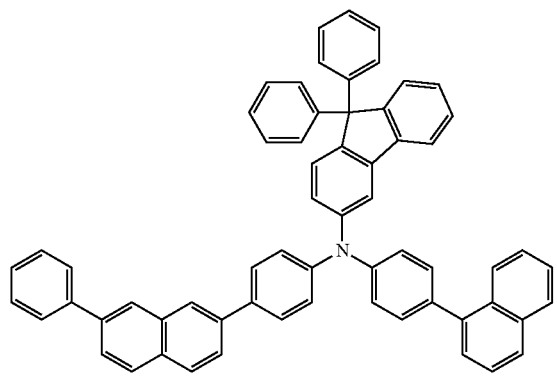
B37
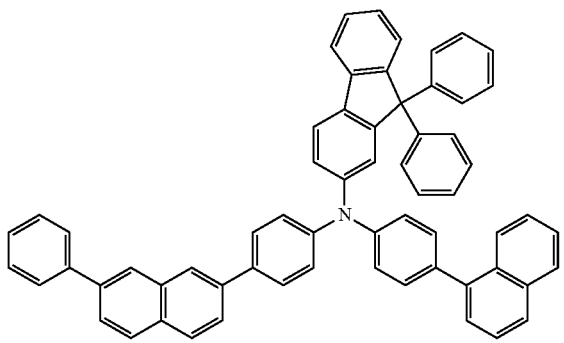
B38

-continued
B39
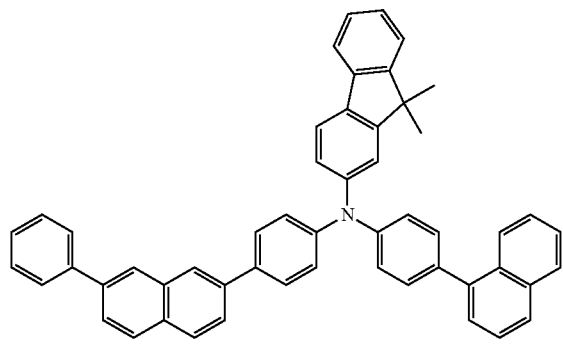
B40
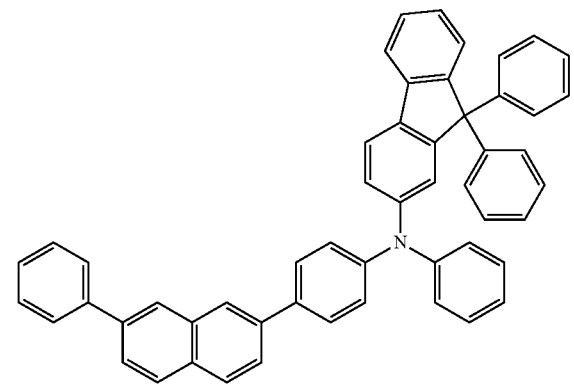
B41
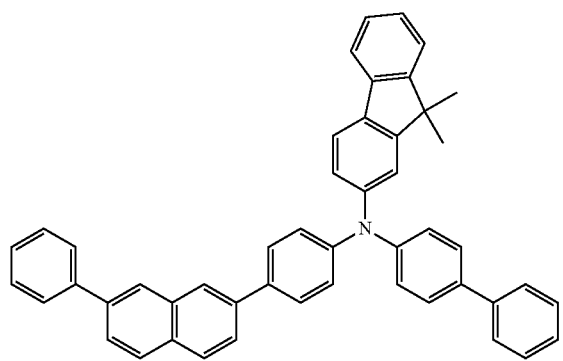
B42
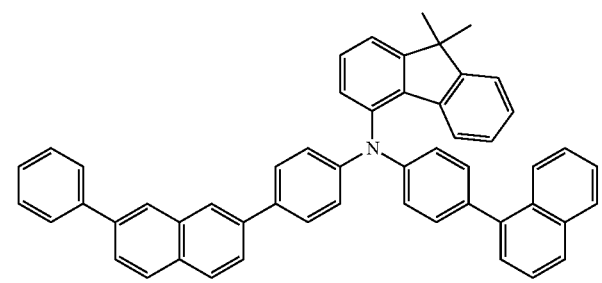
B43
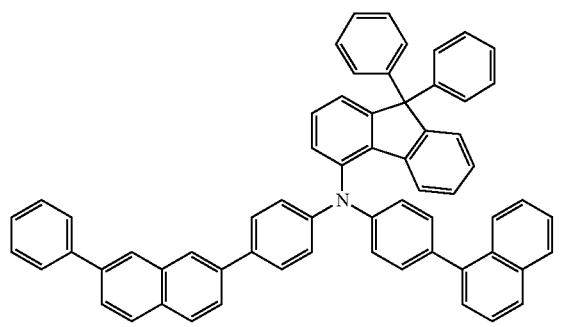
B44
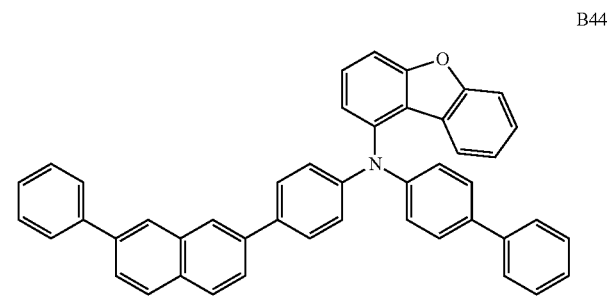
B45
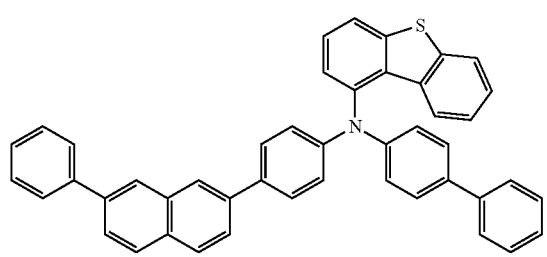
B46
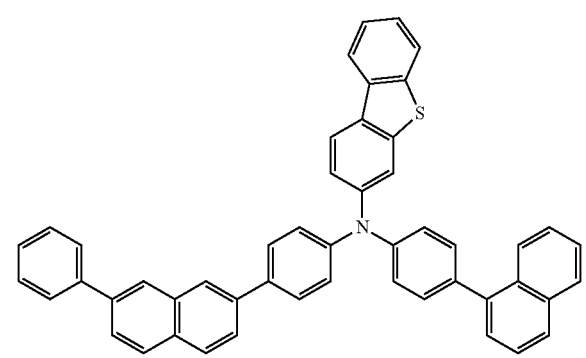

-continued
B47
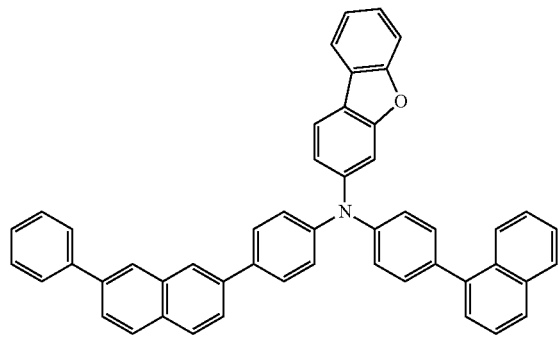
B48
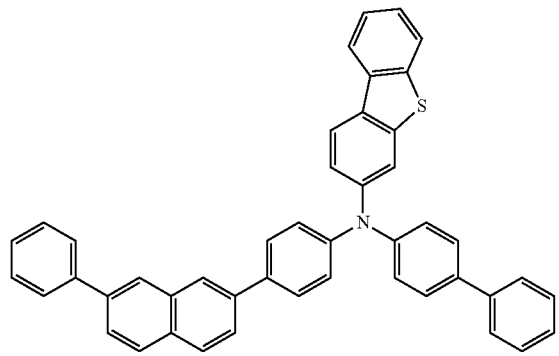
B49
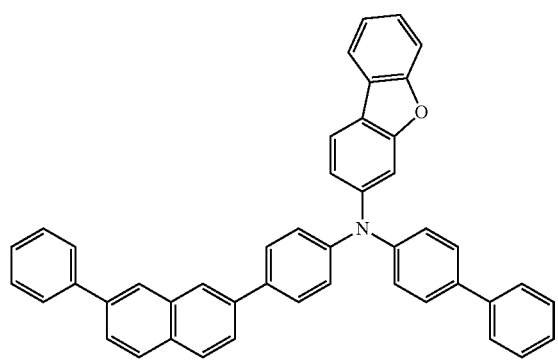
B50
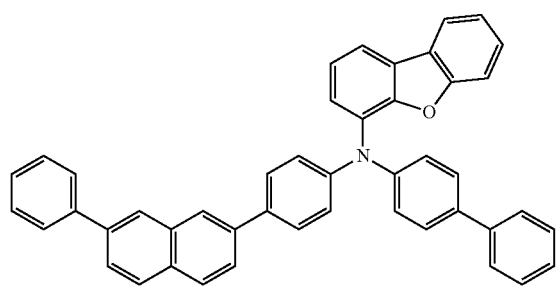
B51
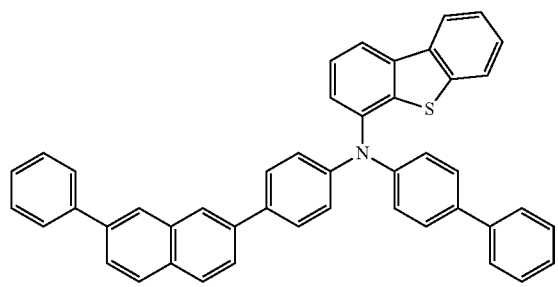
B52
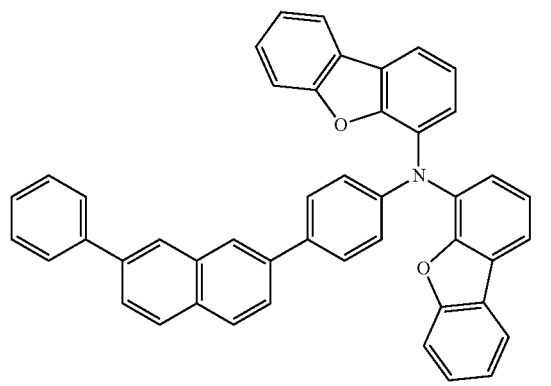
B53
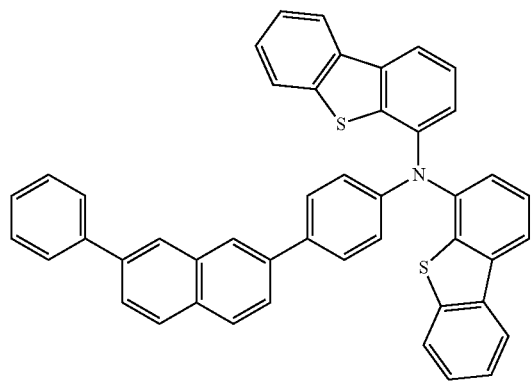
B54
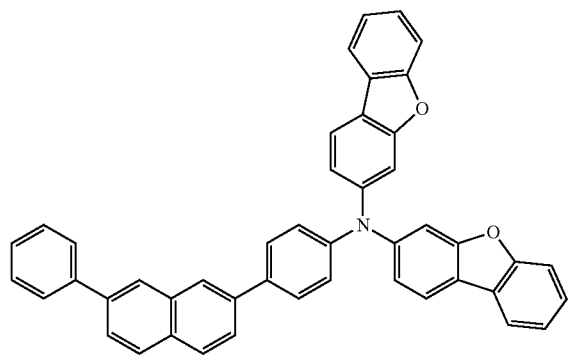

-continued
B55
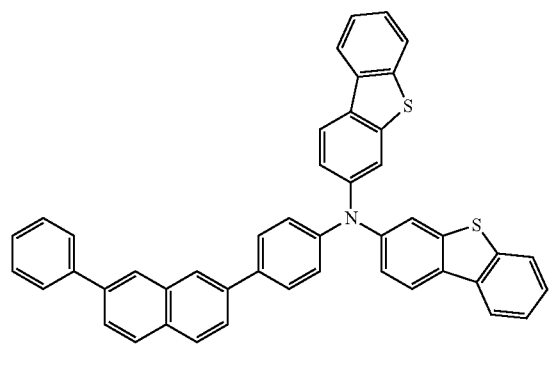
B56
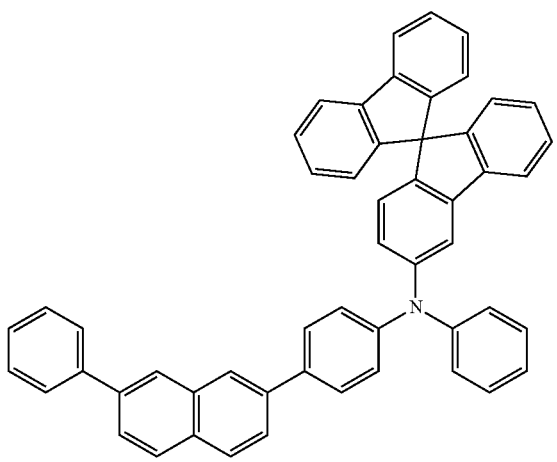
B57
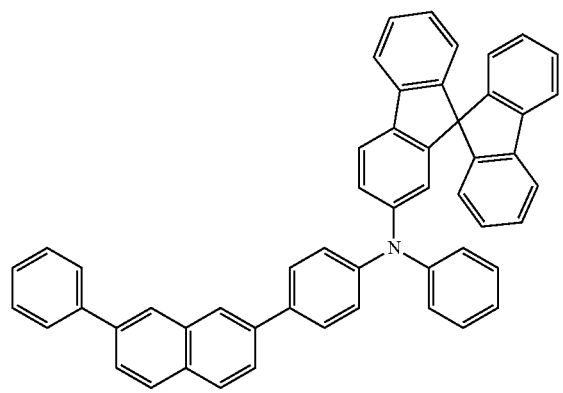
B58
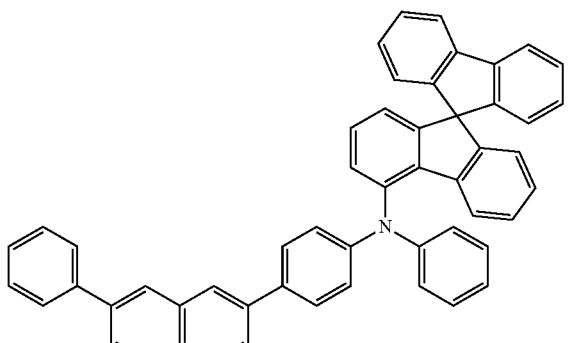
B59
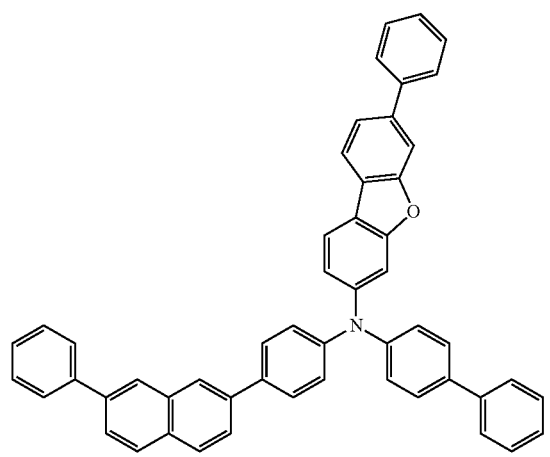
B60
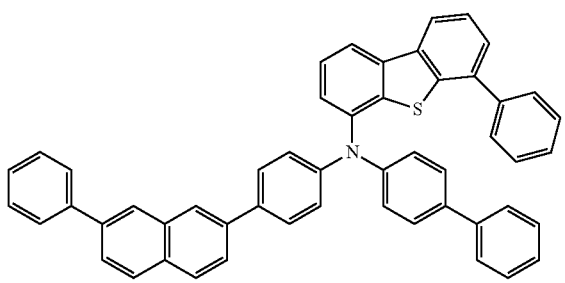

[Compound Group 3]
C1
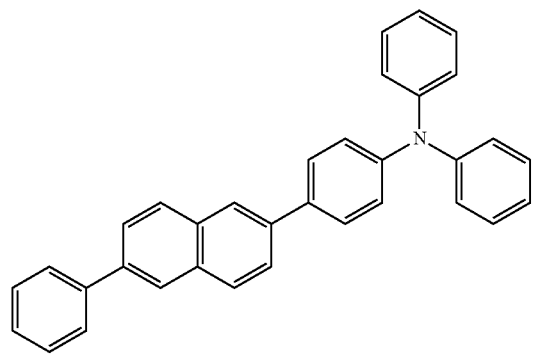
C2
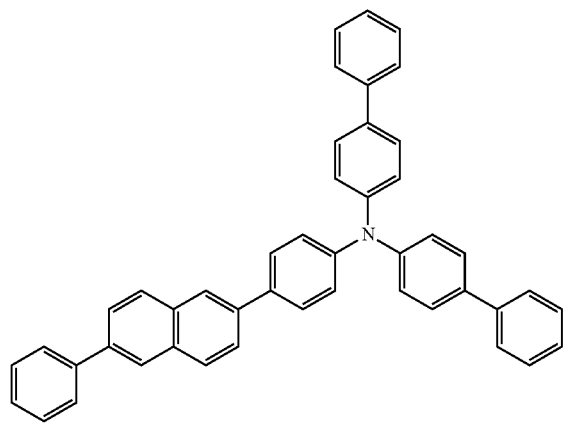
C3
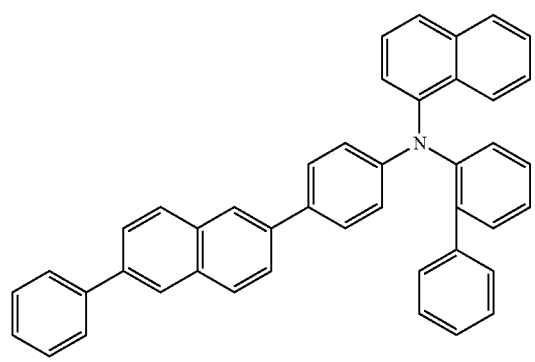
C4
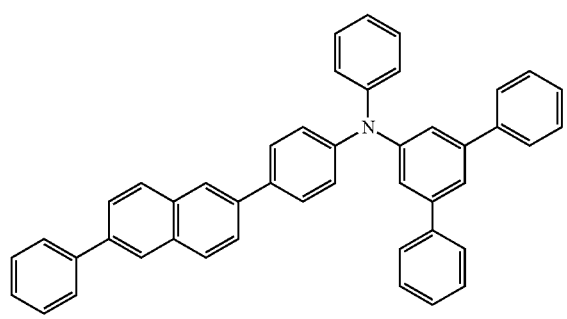
C5
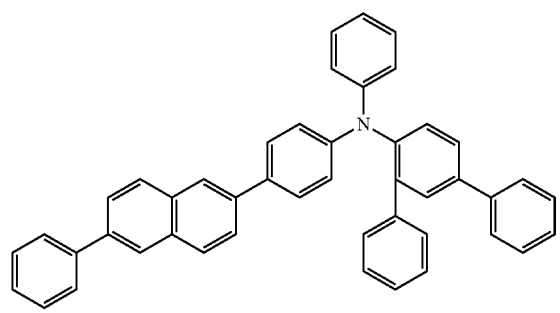
C6
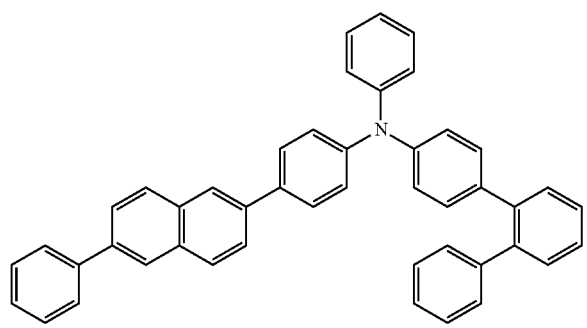
C7
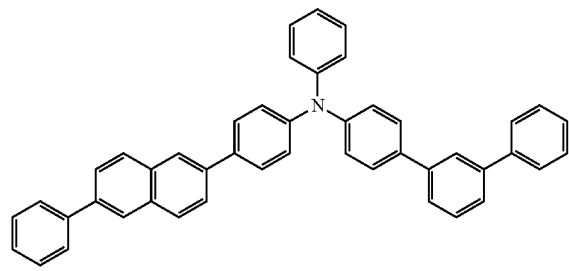
C8
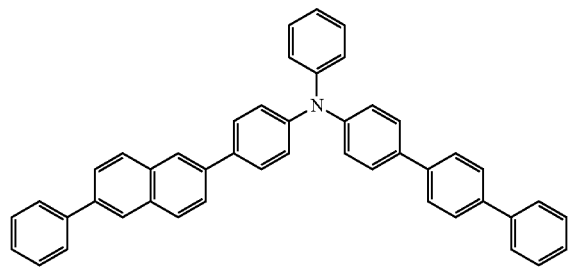

-continued
C9
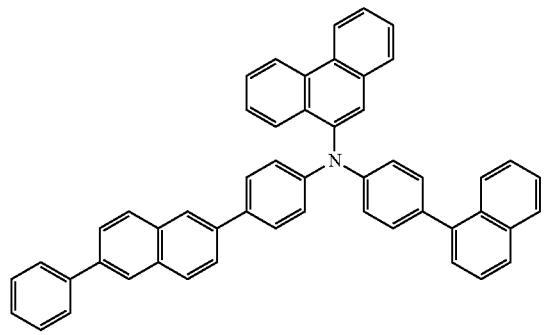
C10
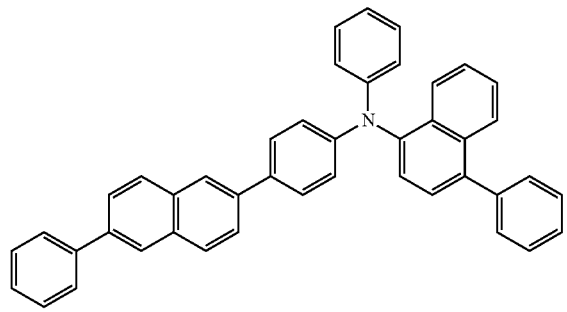
C11
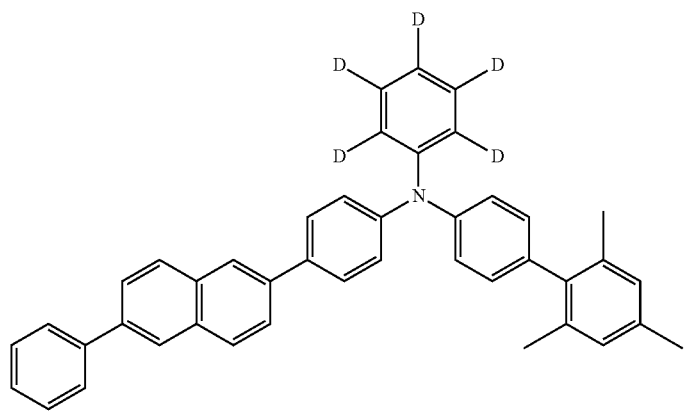
C12
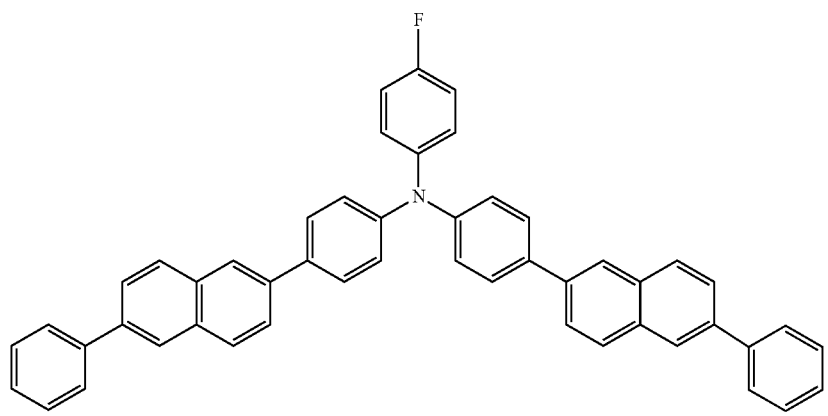
C13
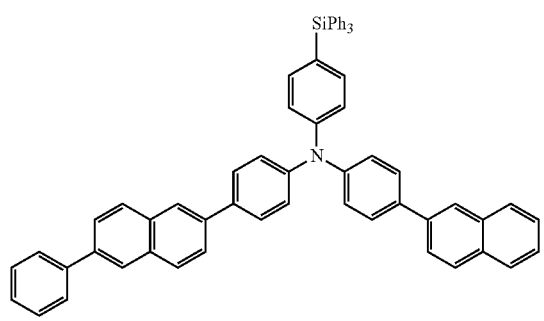
C14
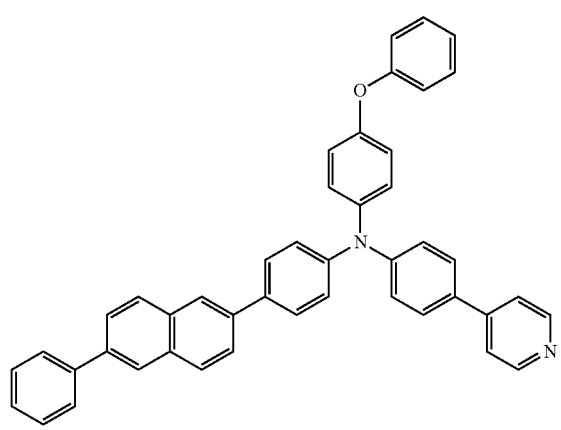

-continued
C15
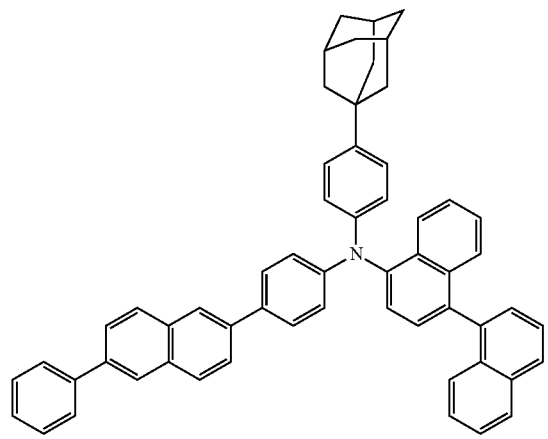
C16
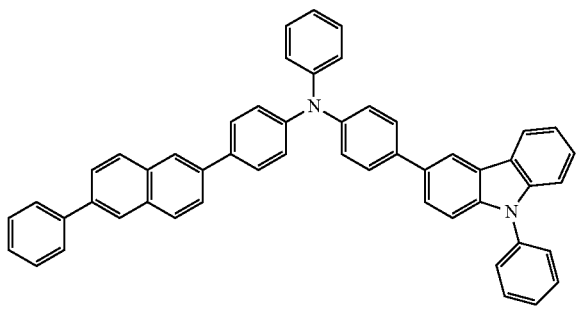
C17
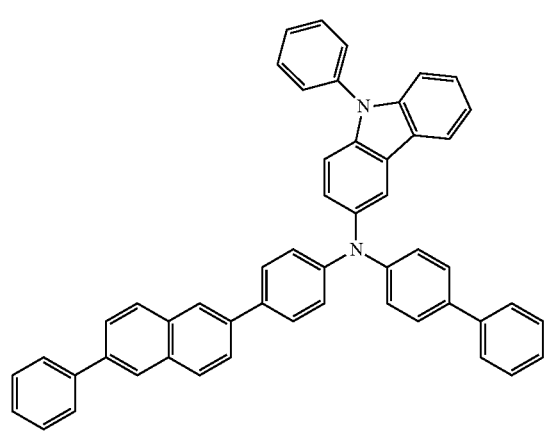
C18
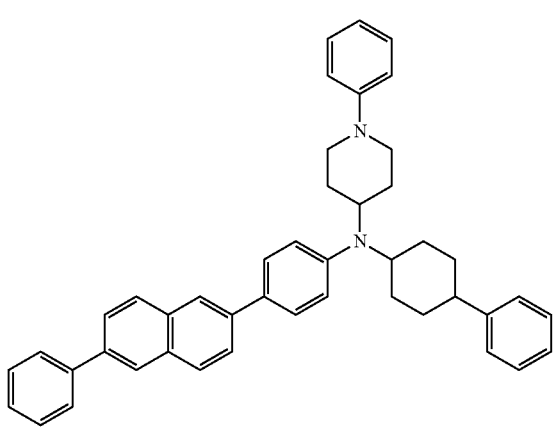
C19
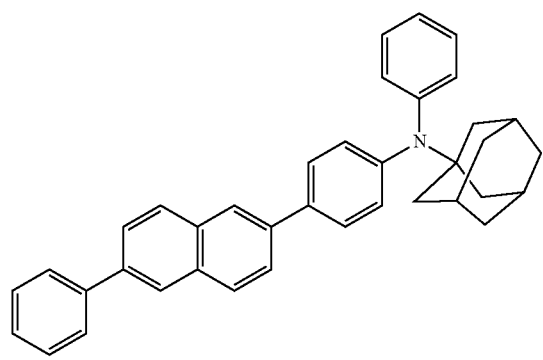
C20
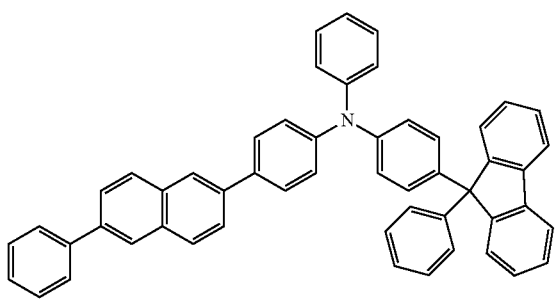
C21
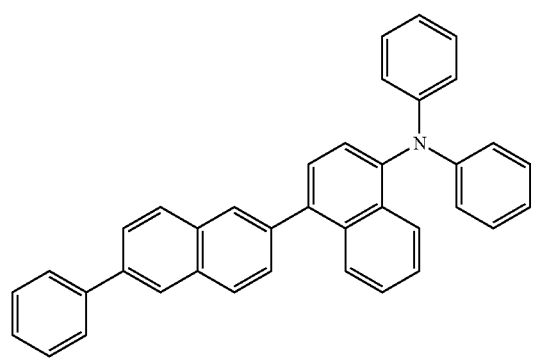
C22
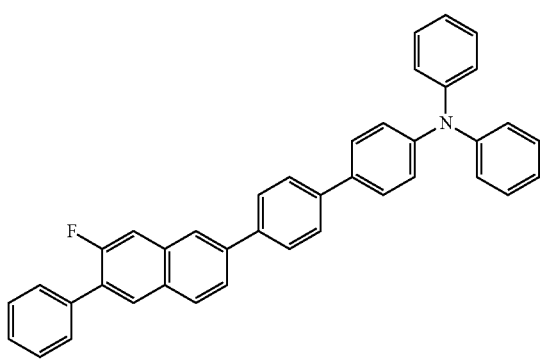

-continued
C23
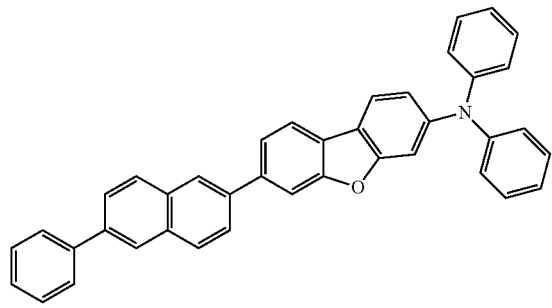
C24
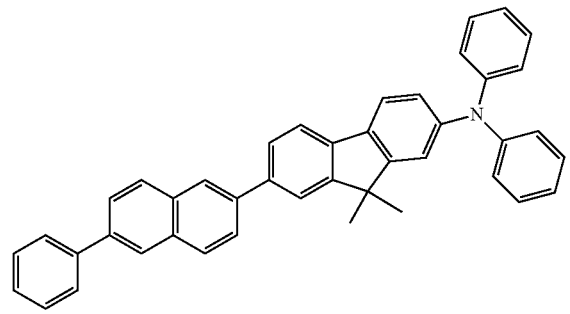
C25
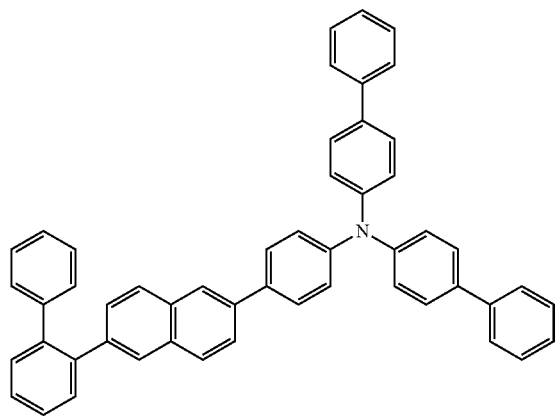
C26
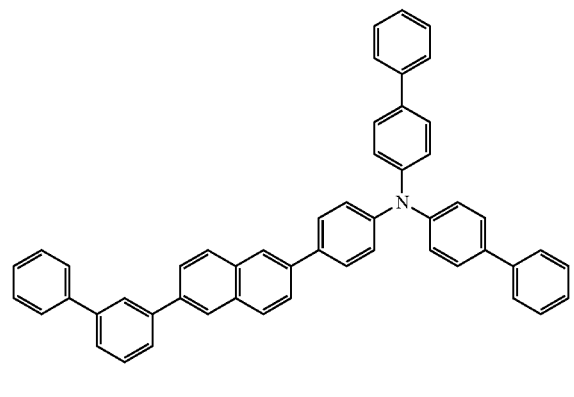
C27
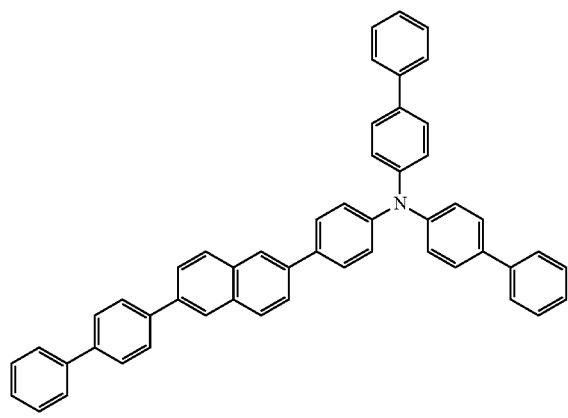
C28
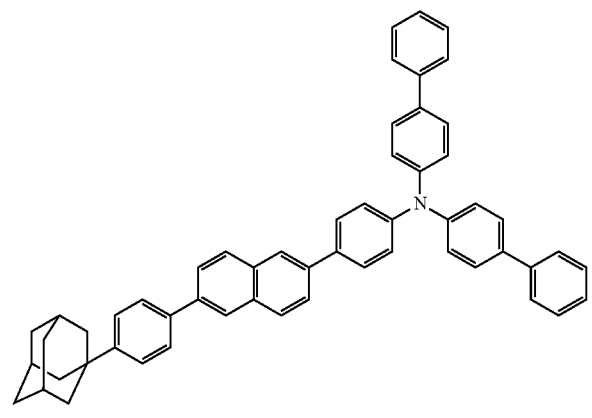
C29
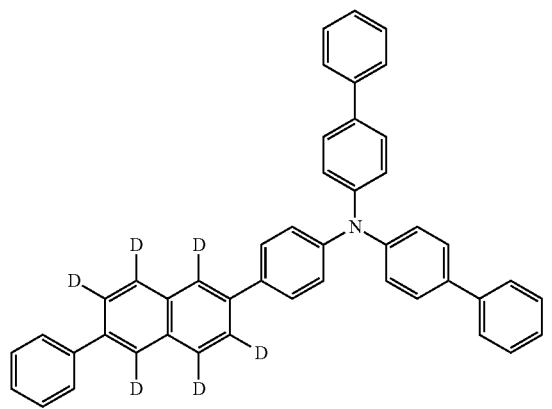
C30
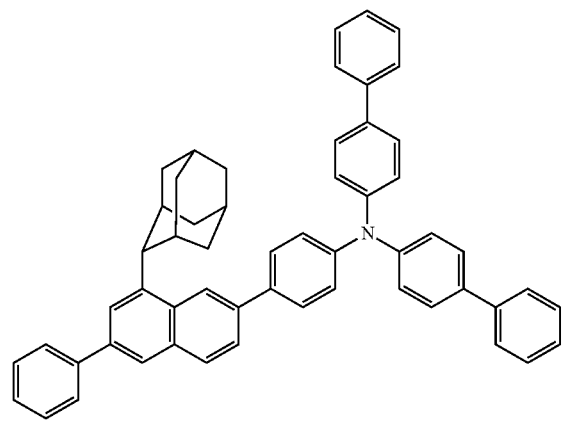

-continued
C31
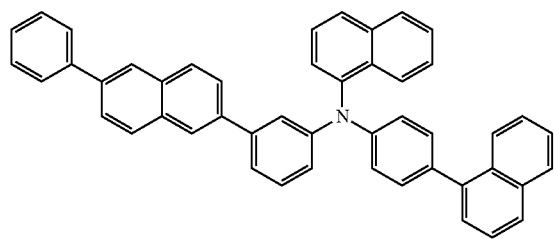
C32
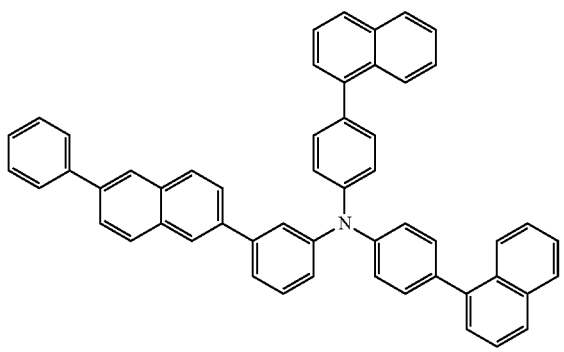
C33
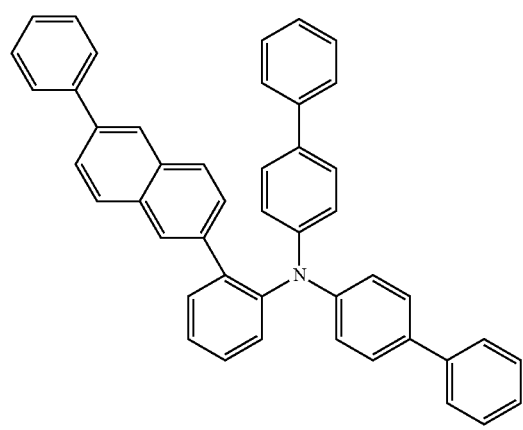
C34
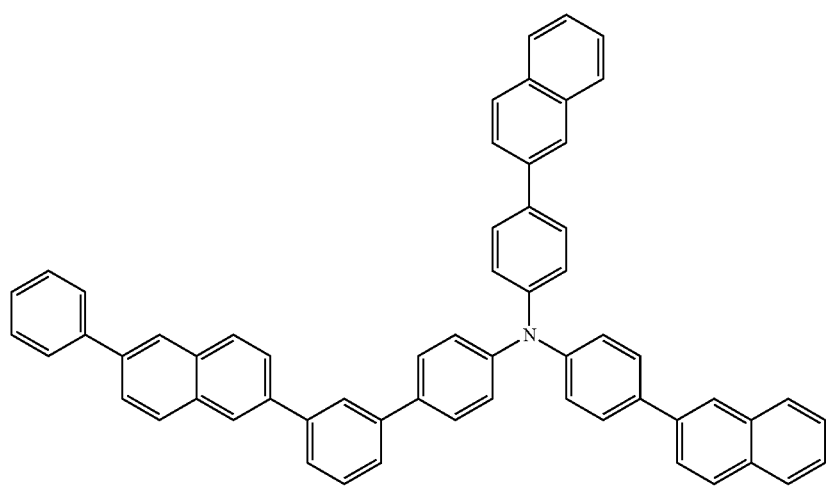

-continued
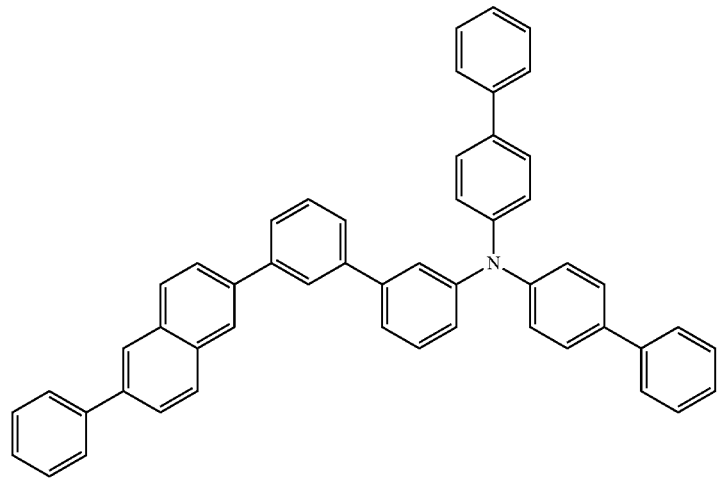
C35
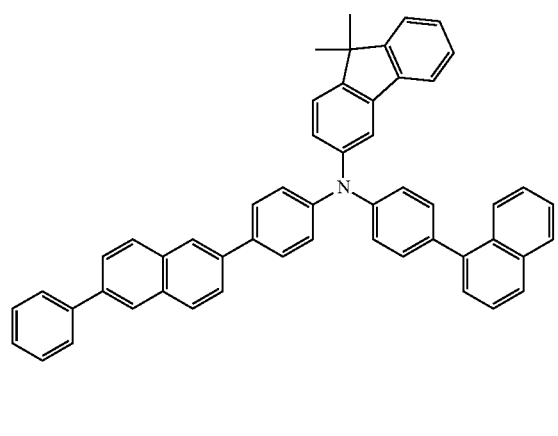
C36
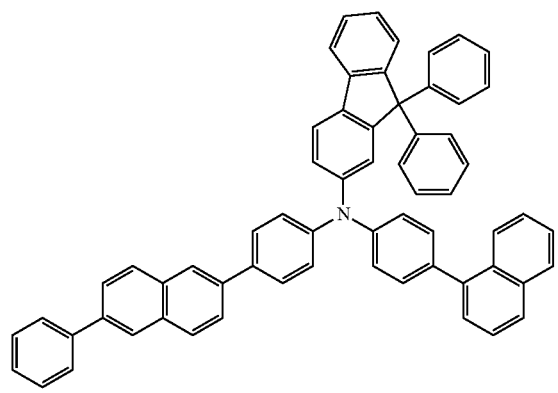
C38
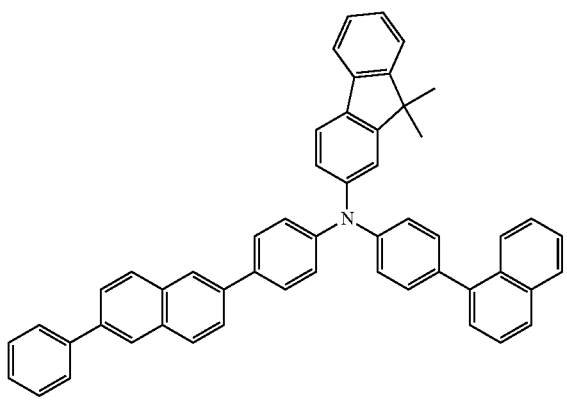
C39

-continued
C40
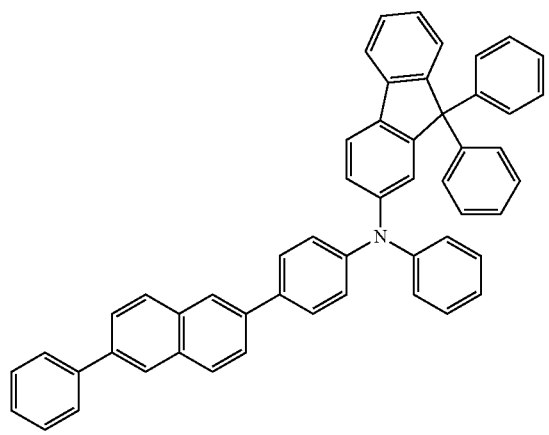
C41
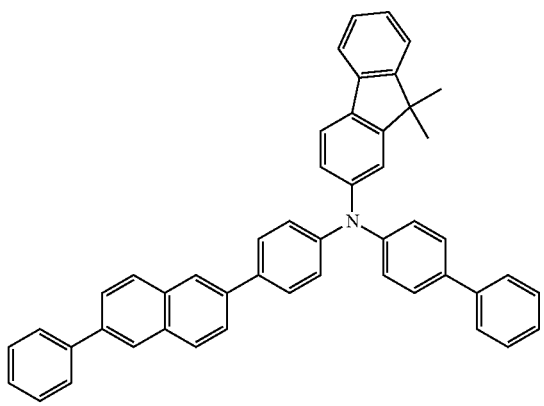
C42
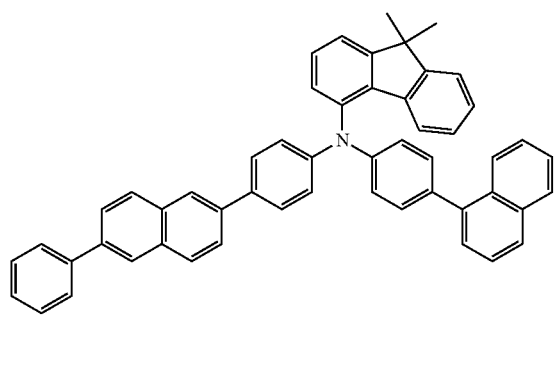
C43
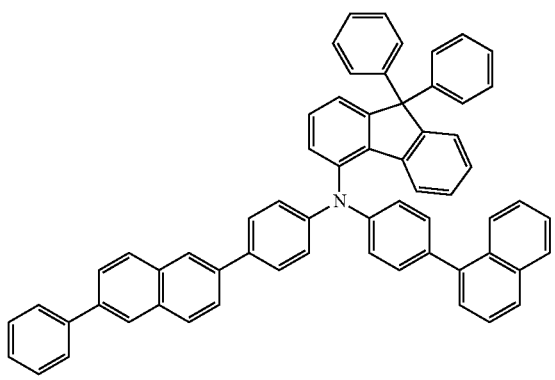
C44
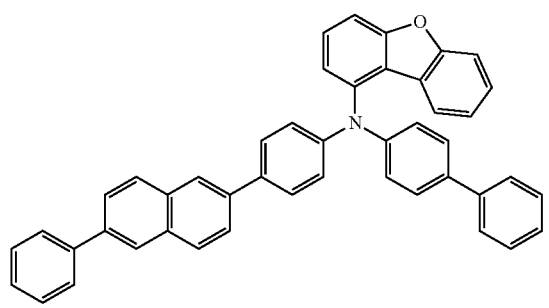
C45
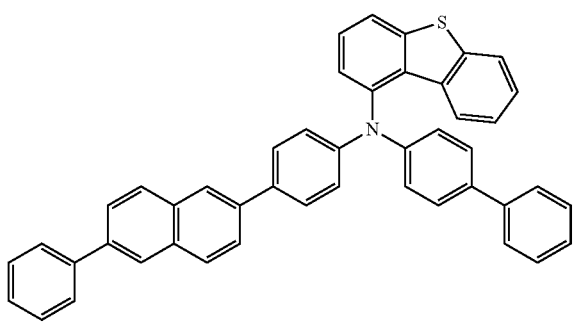
C46
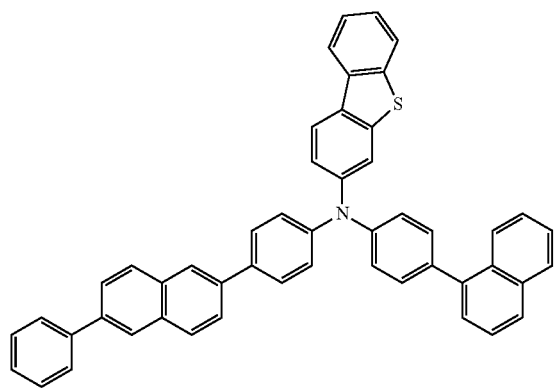
C47
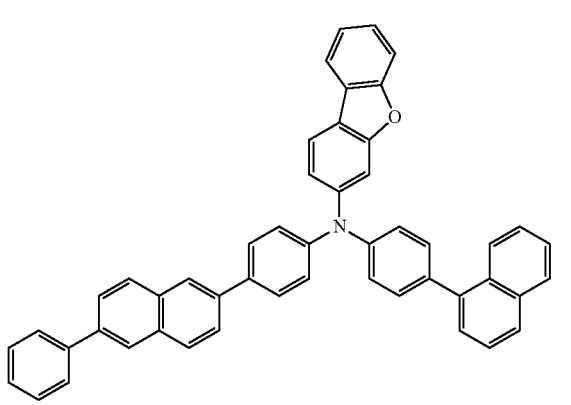

-continued
C48
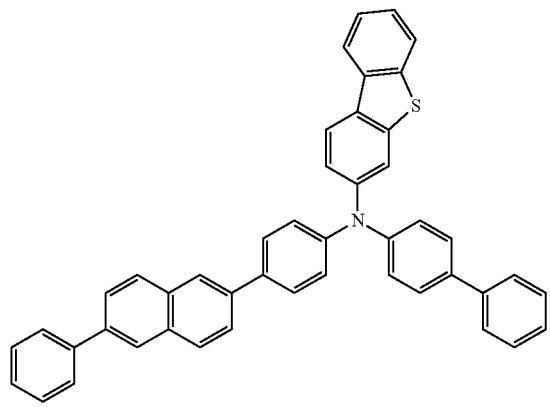
C49
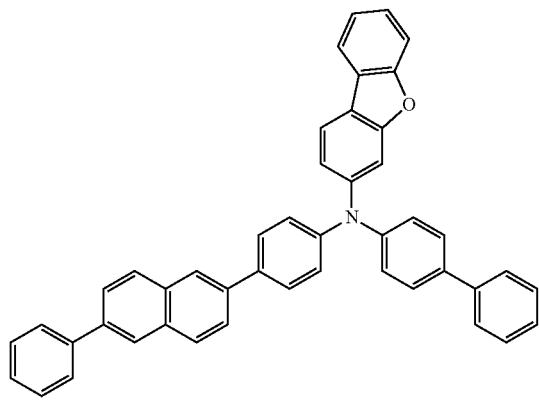
C50
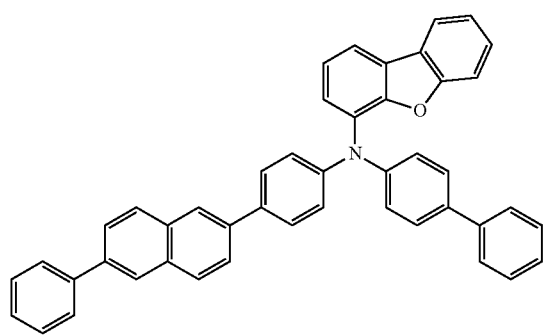
C51
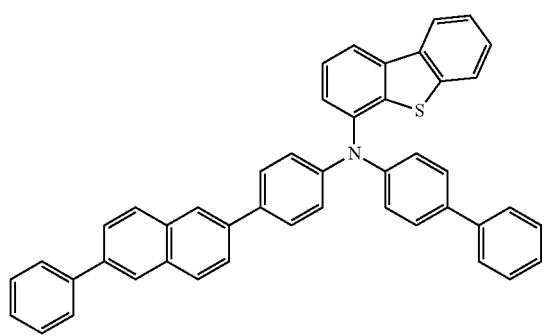
C52
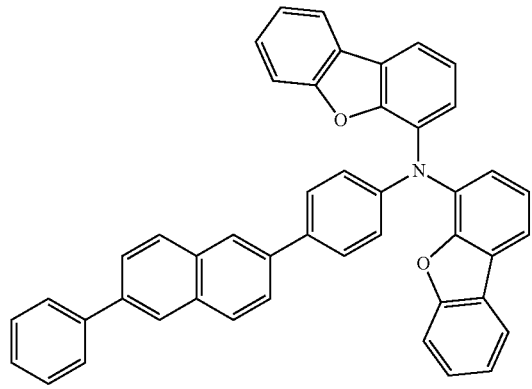
C53
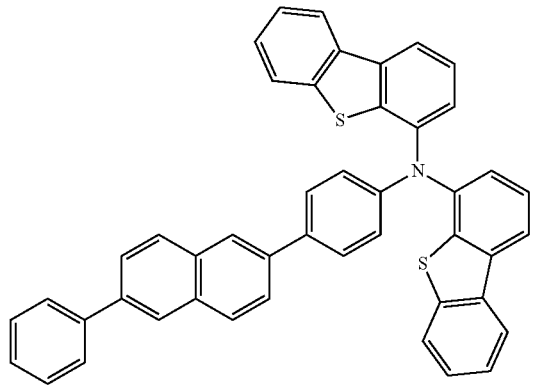
C54
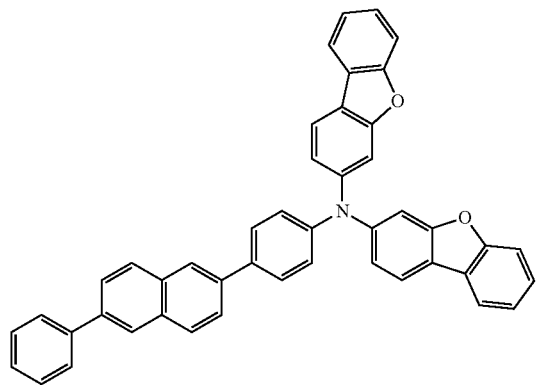
C55
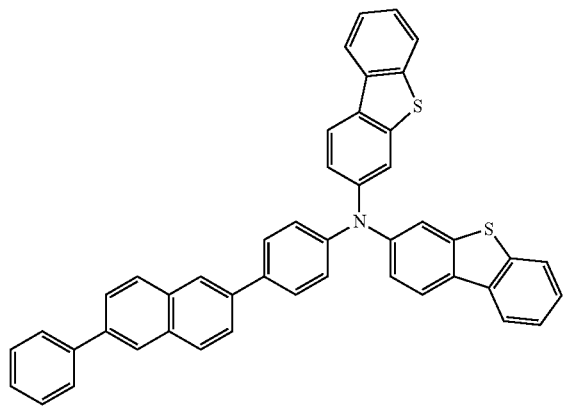

-continued
C56
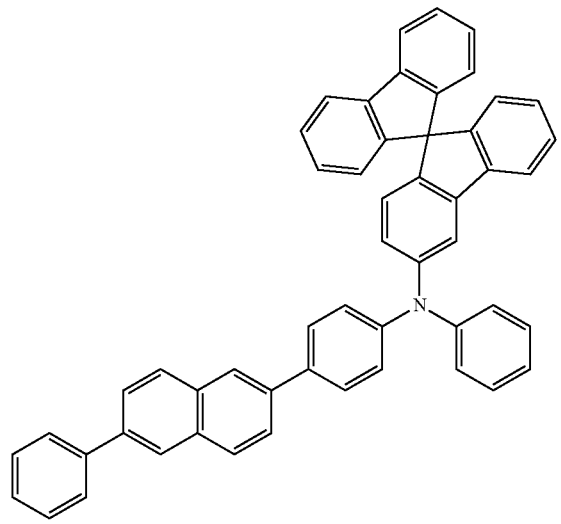
C57
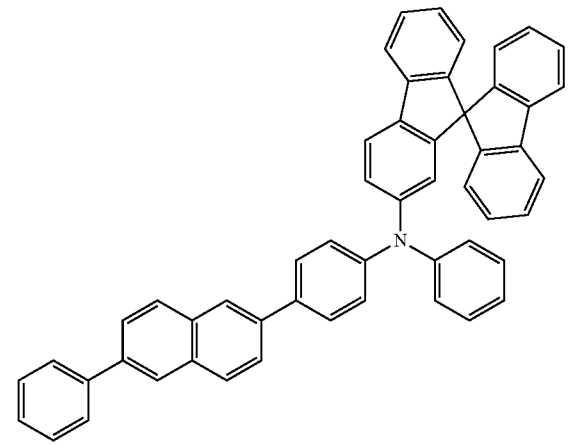
C58
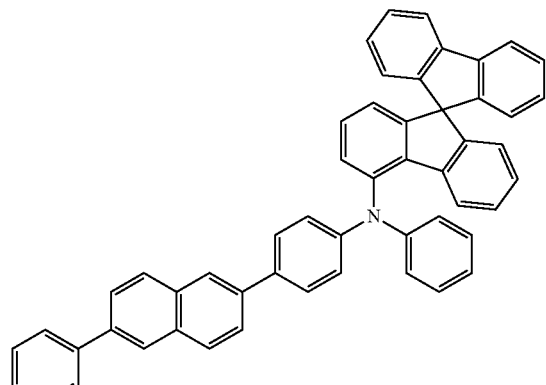
C59
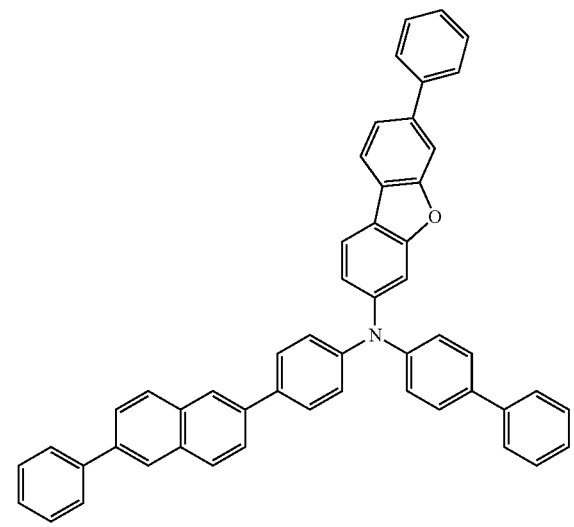
C60
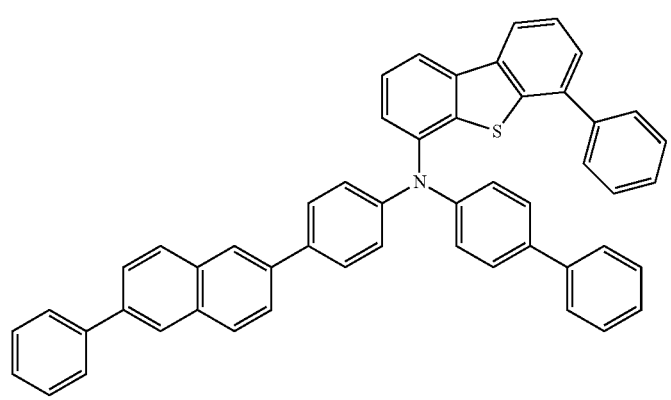

[Compound Group 4]
D1
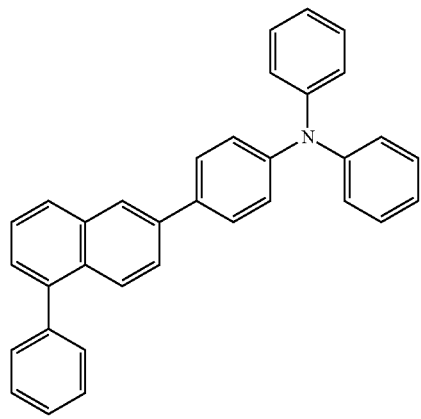
D2
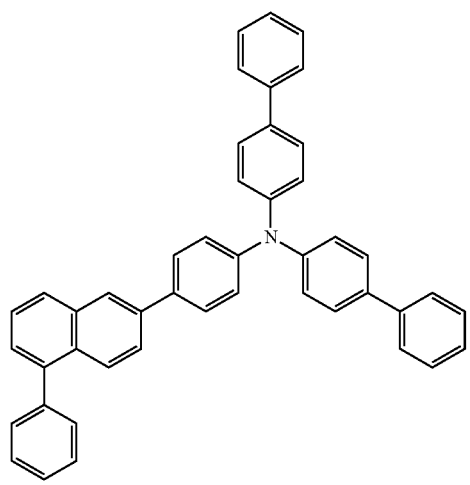
D3
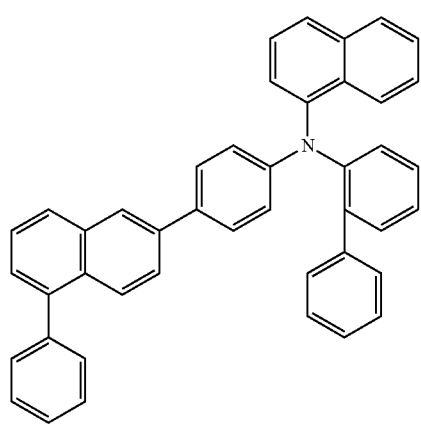
D4
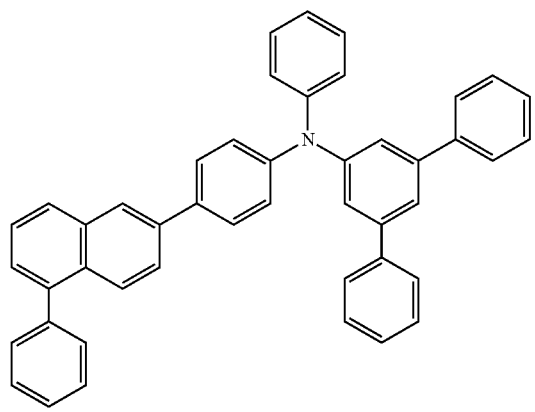
D5
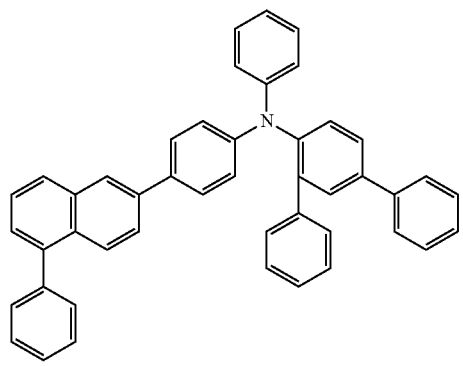
D6
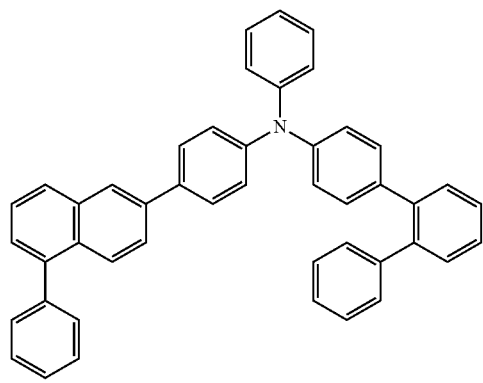

-continued
D7
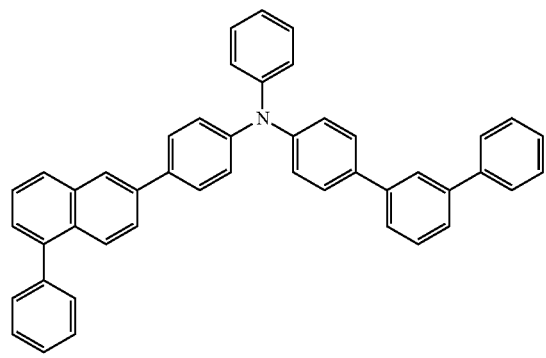
D8
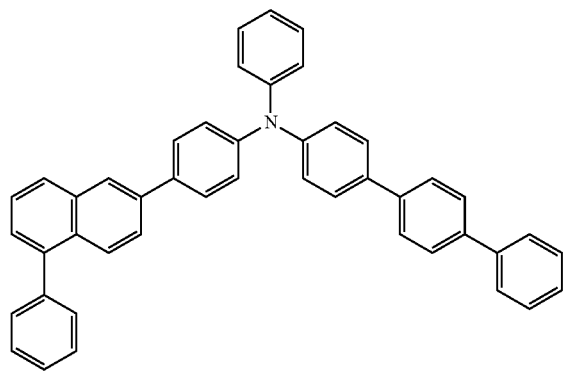
D9
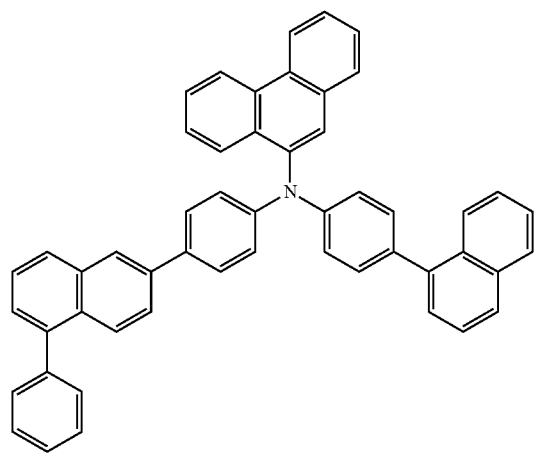
D10
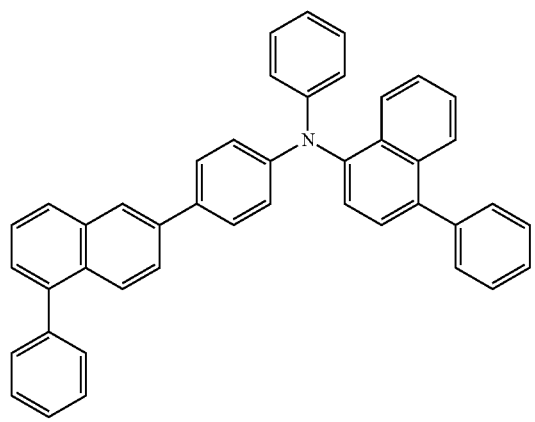
D11
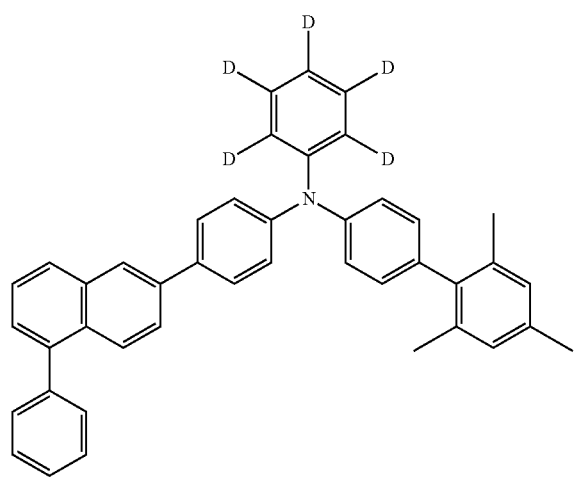
D12
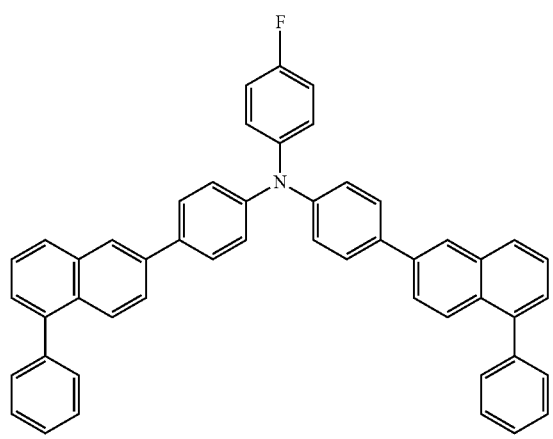

-continued
D13
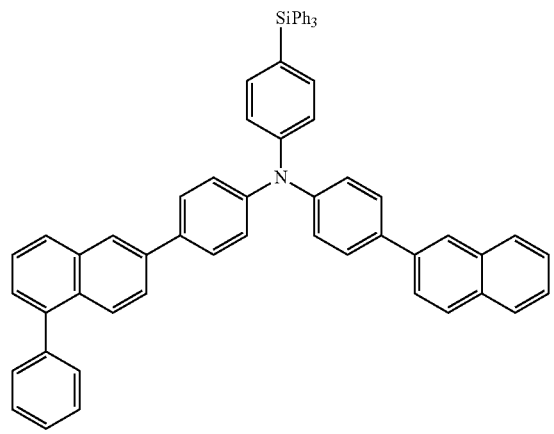
D14
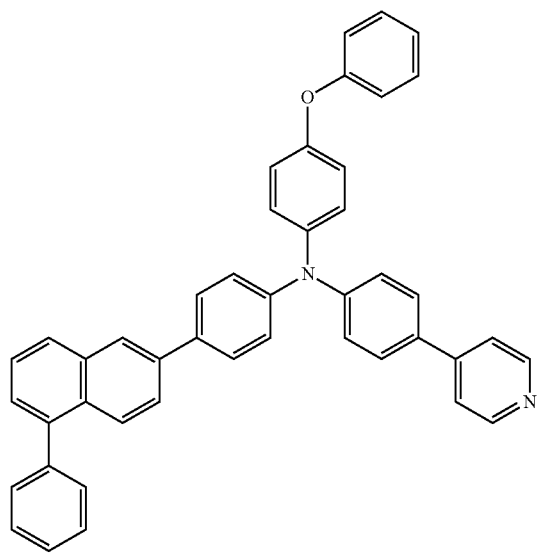
D15
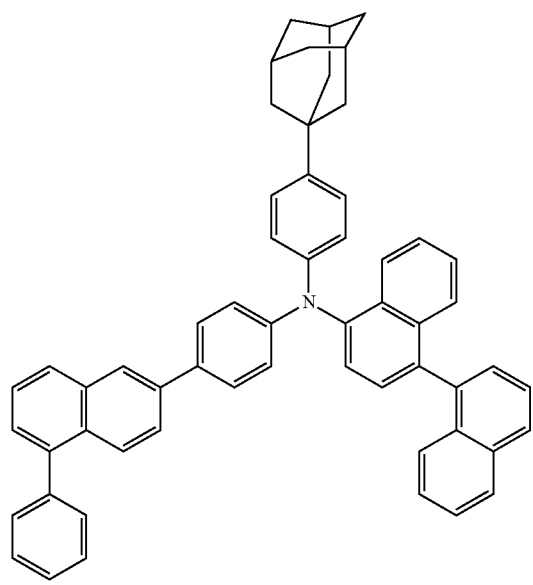
D16
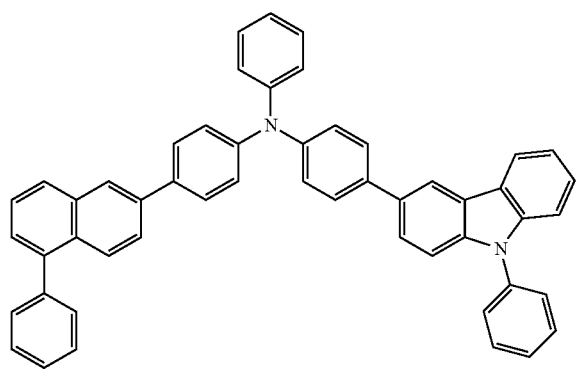

-continued
D17
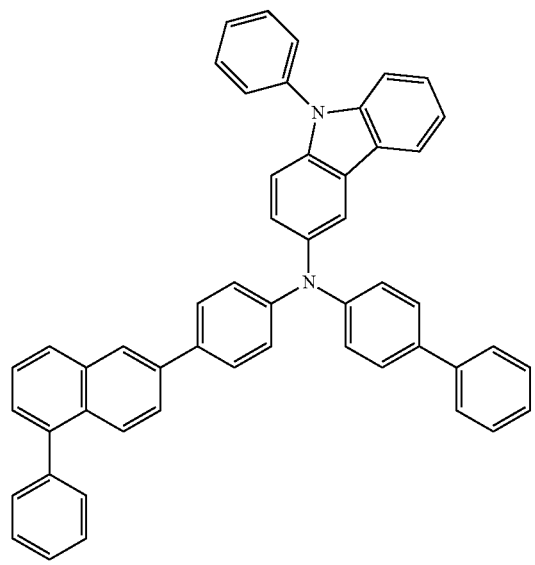
D18
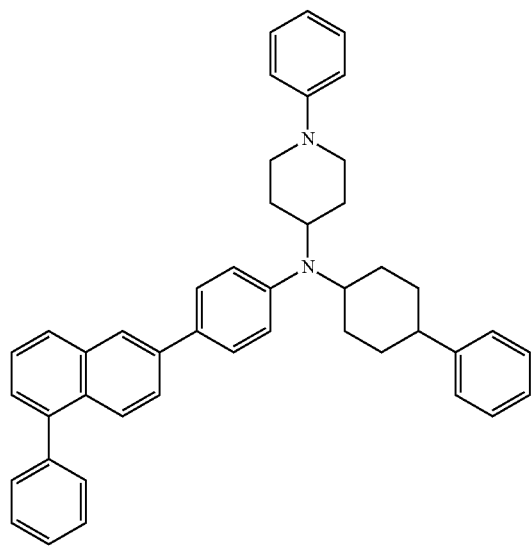
D19
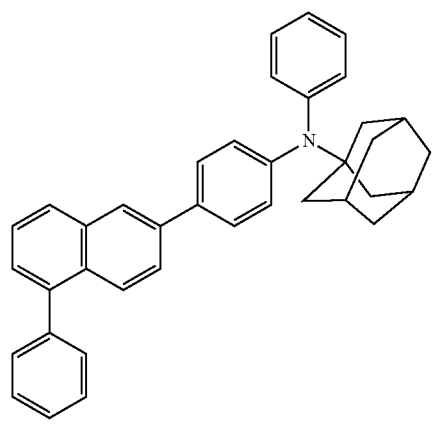
D20
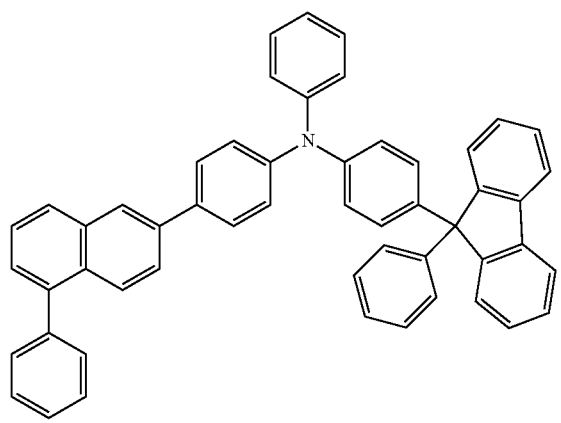
D21
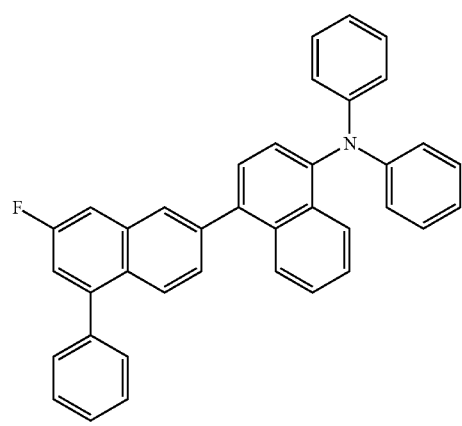
D22
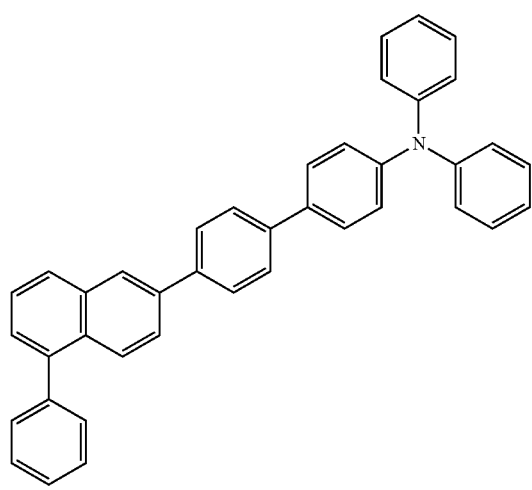

-continued
D23
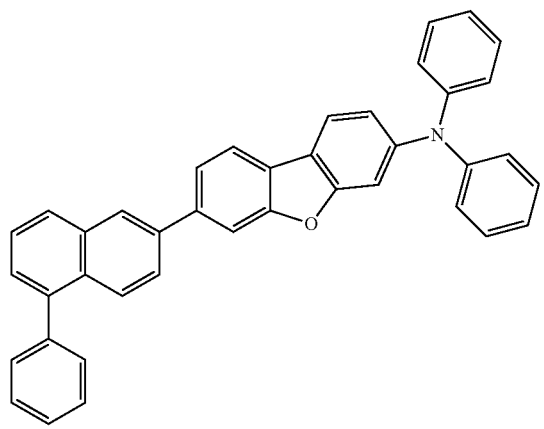
D24
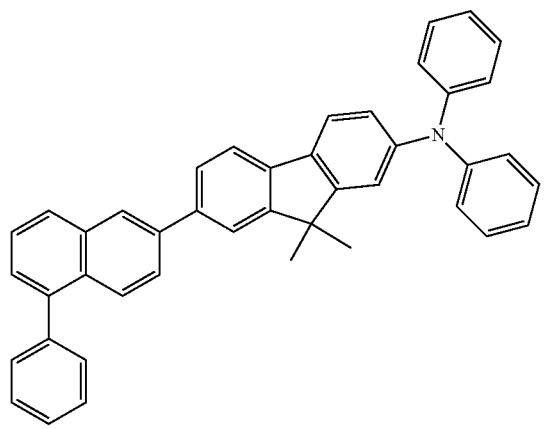
D25
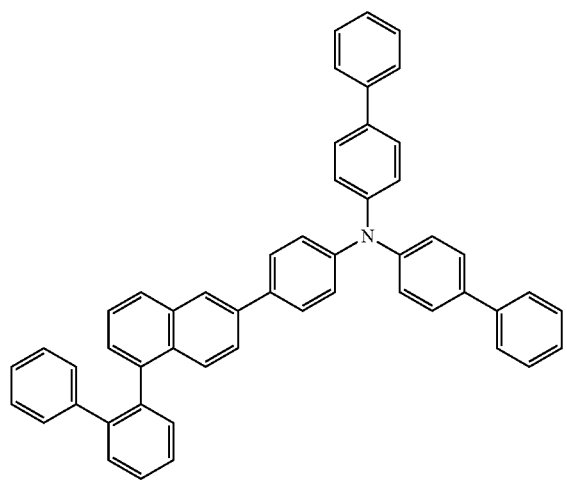
D26
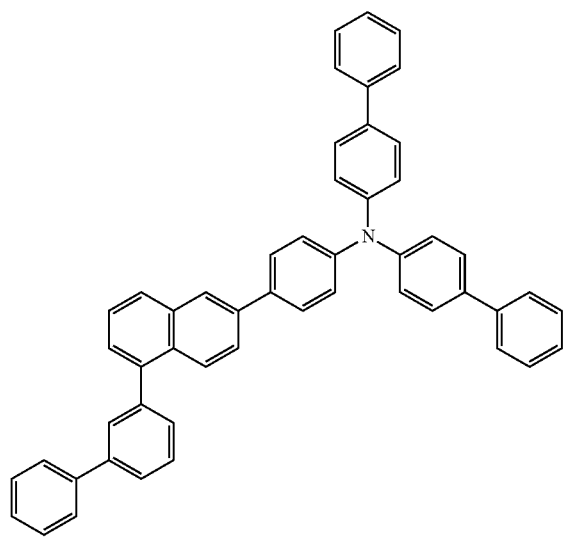
D27
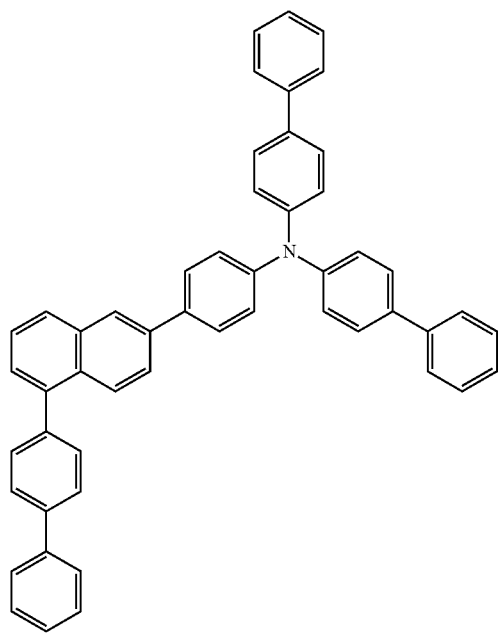
D28
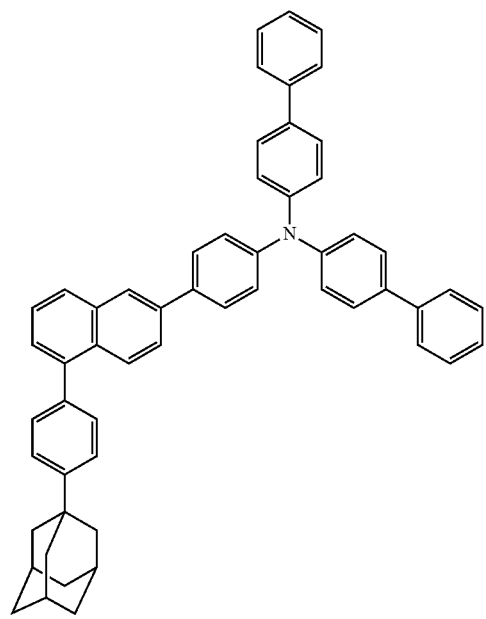

-continued
D29
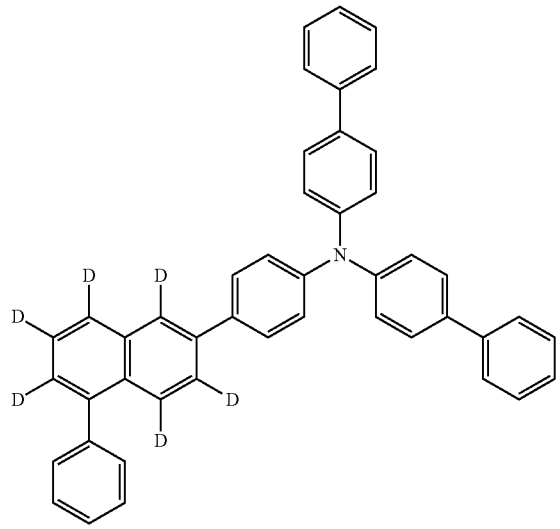
D30
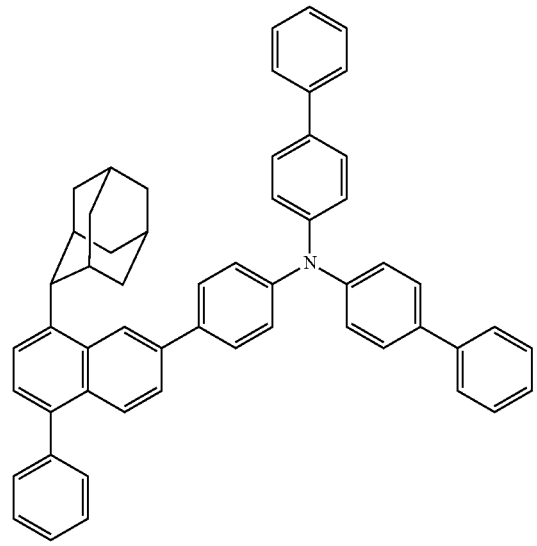
D31
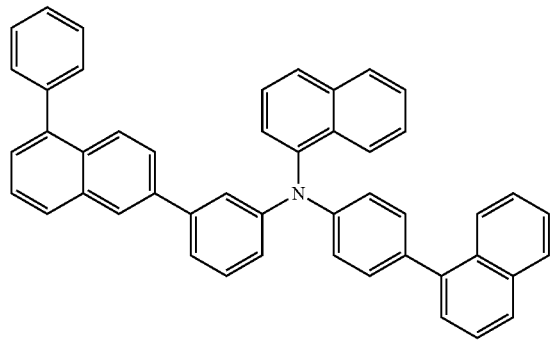
D32
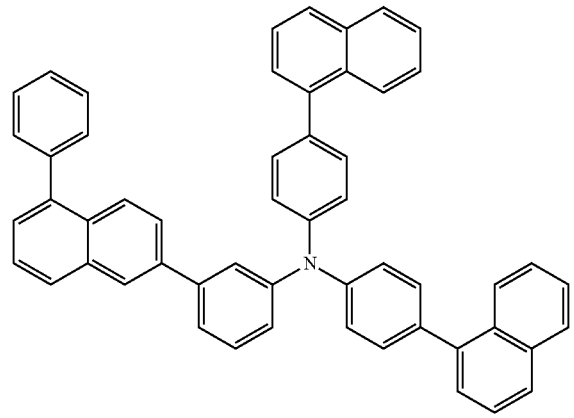
D33
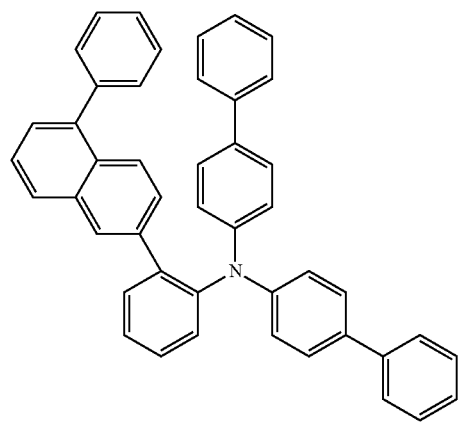
D34
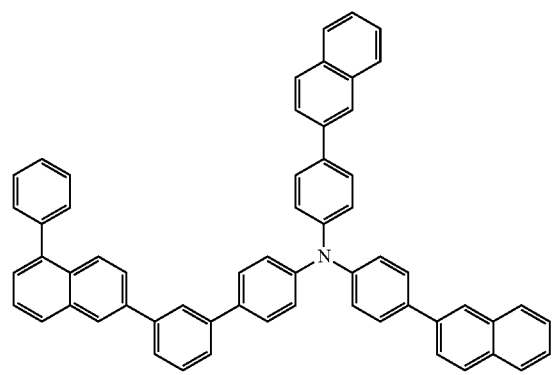

-continued
D35
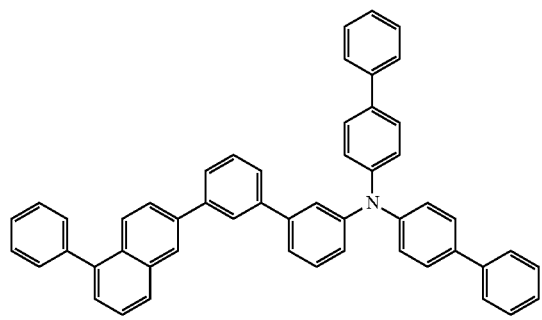
D36
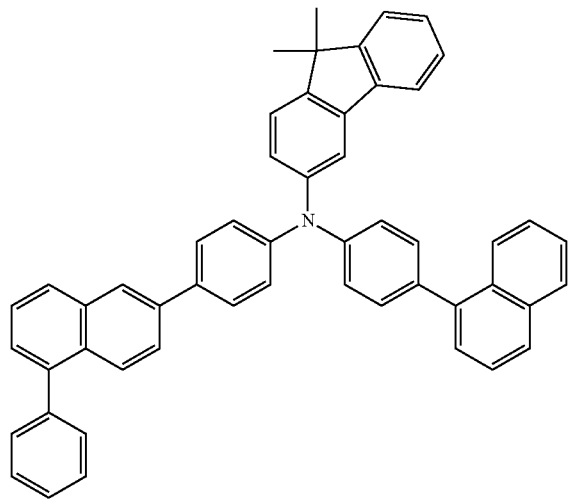
D37
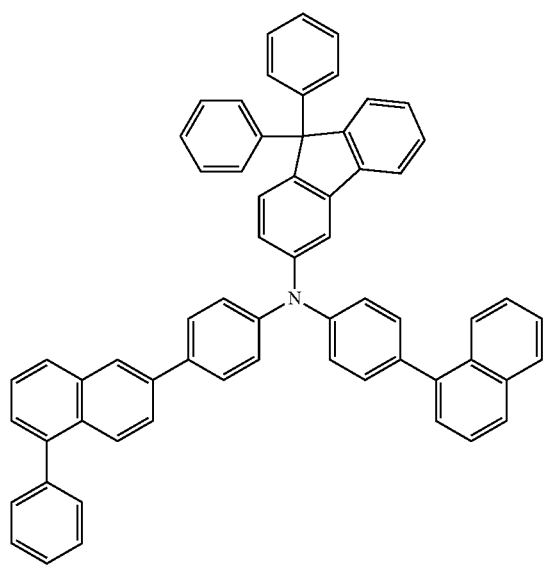
D38
D39
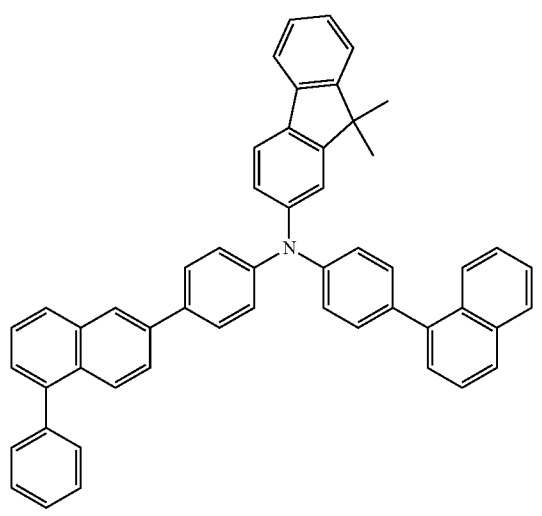
D40
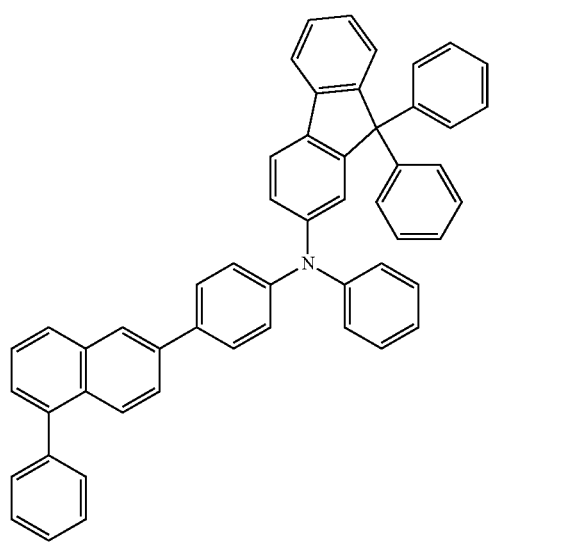

-continued
D41
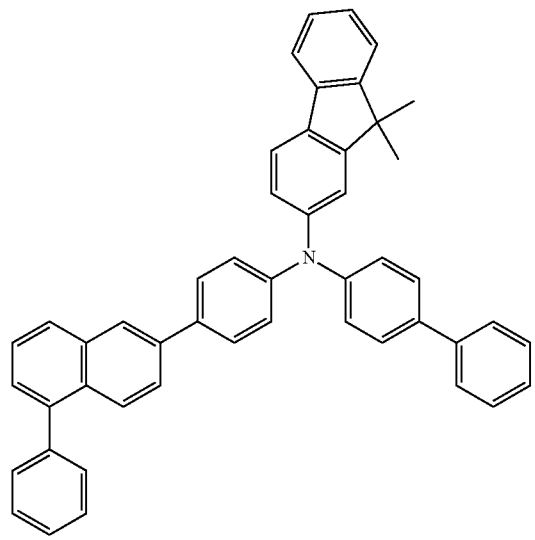
D42
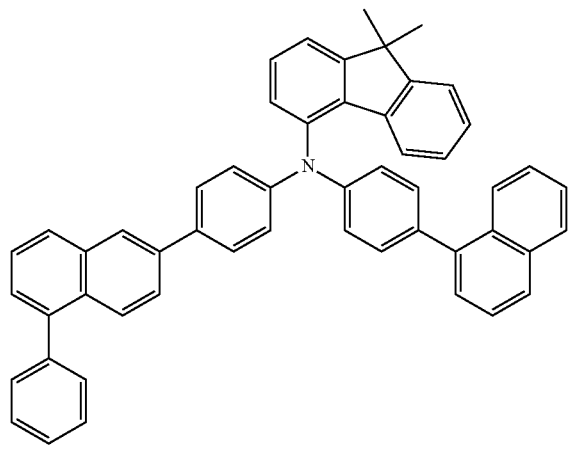
D43
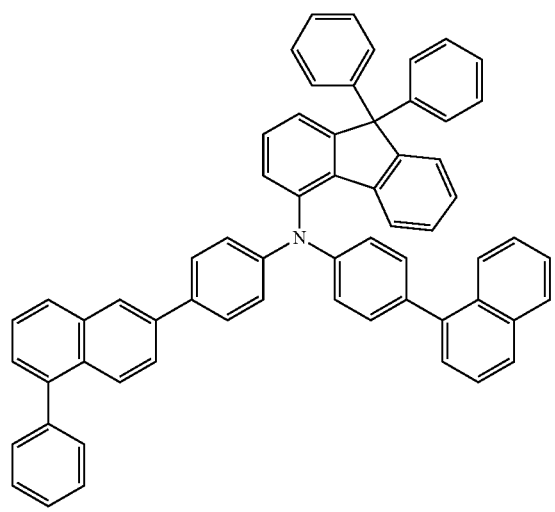
D44
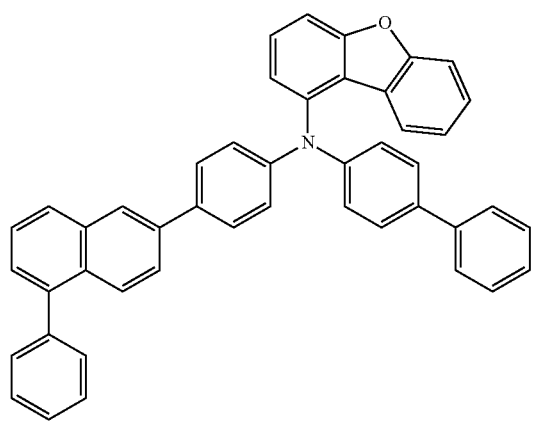
D45
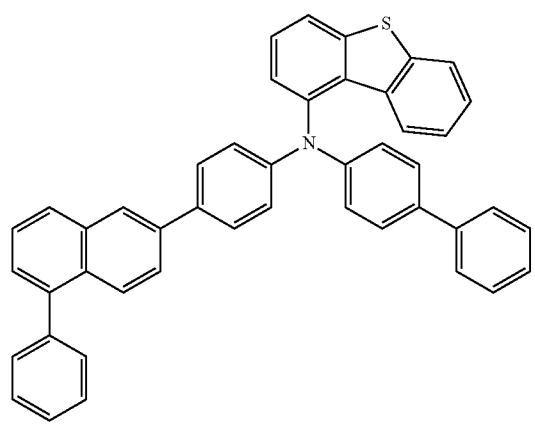
D46
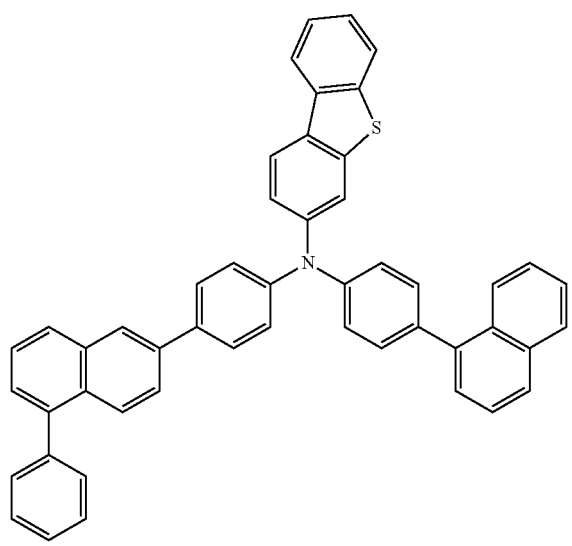

-continued
D47
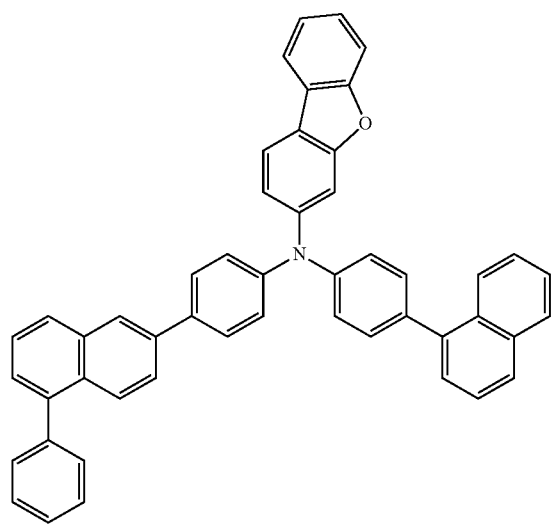
D48
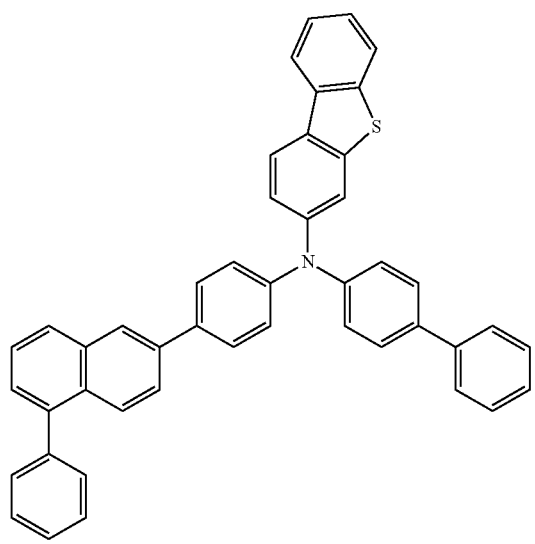
D49
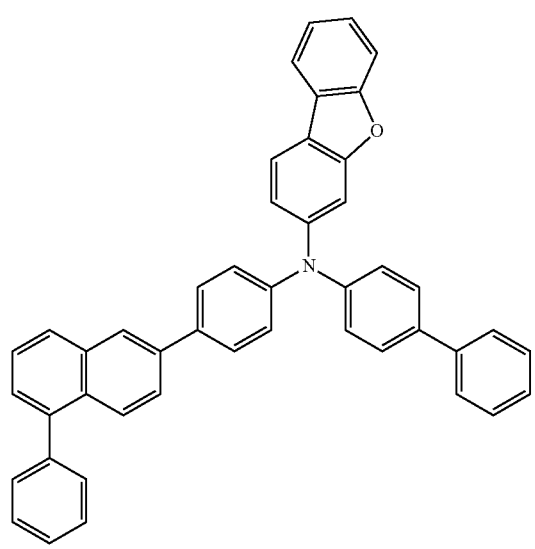
D50
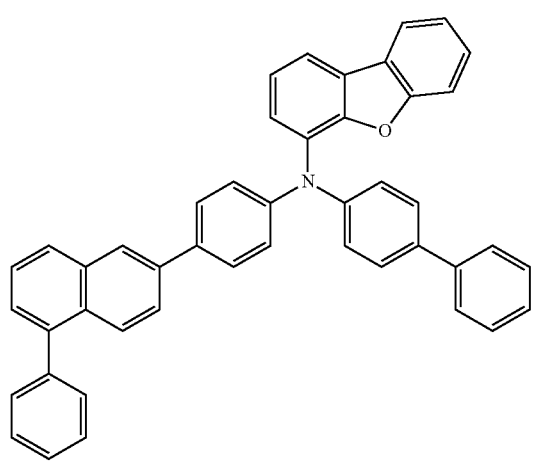
D51
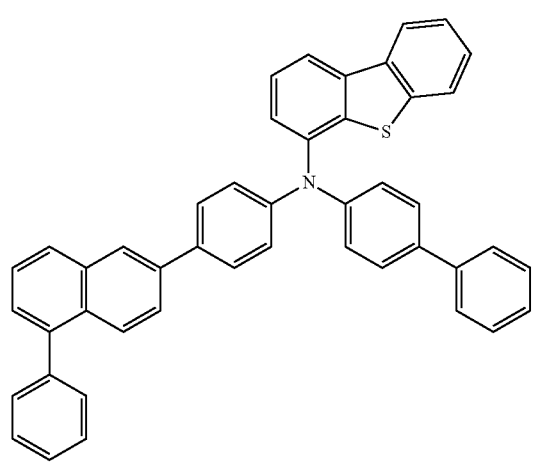
D52
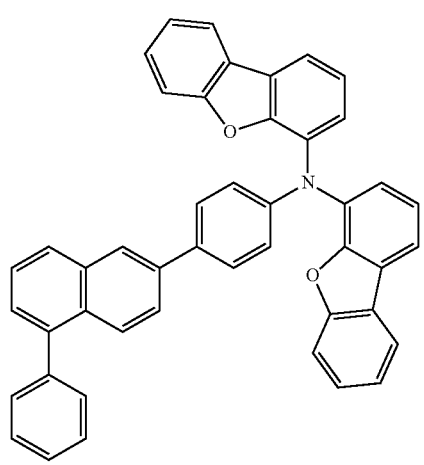

-continued
D53
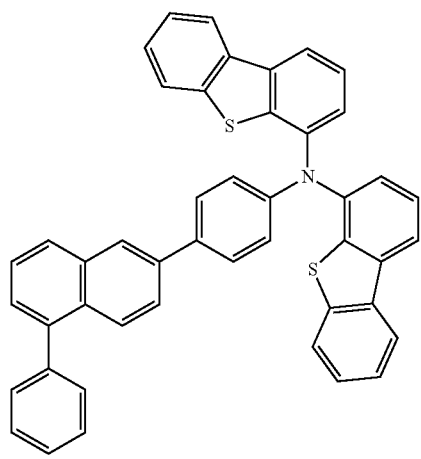
D54
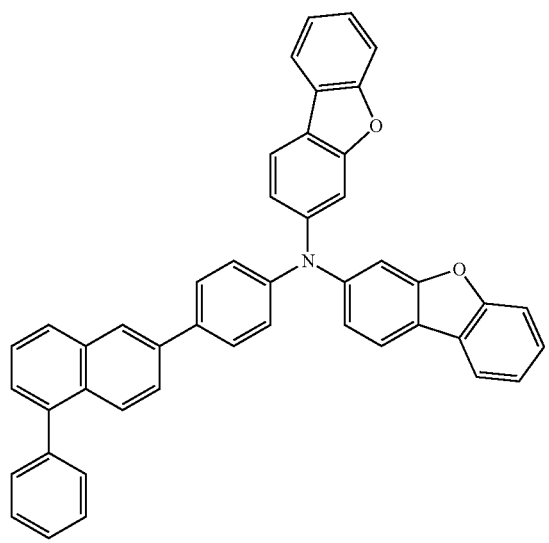
D55
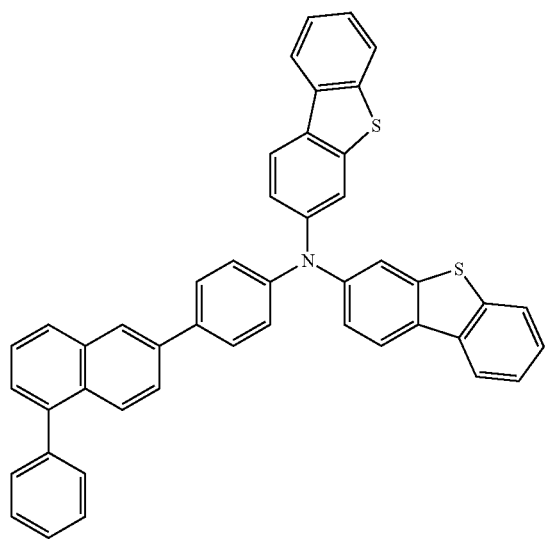
D56
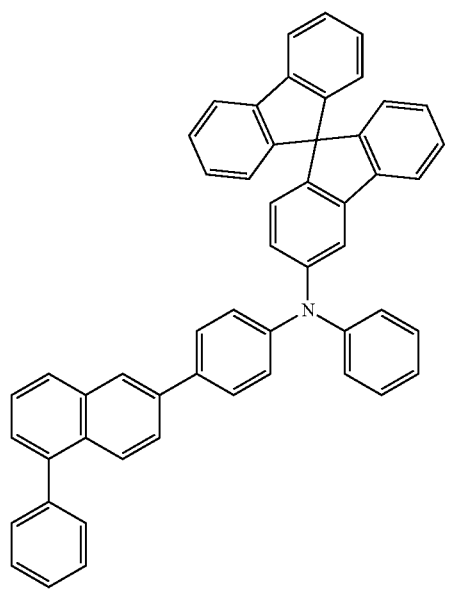
D57
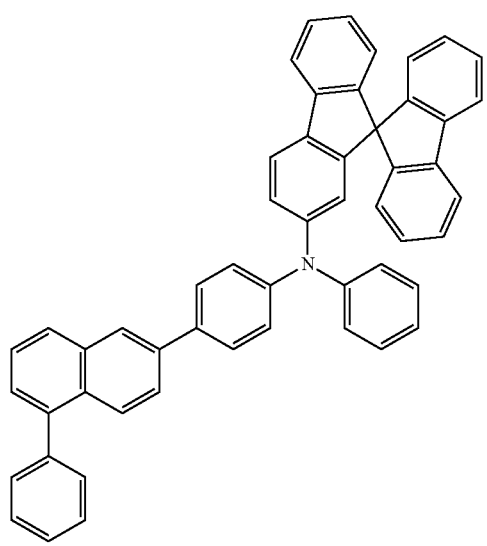
D58
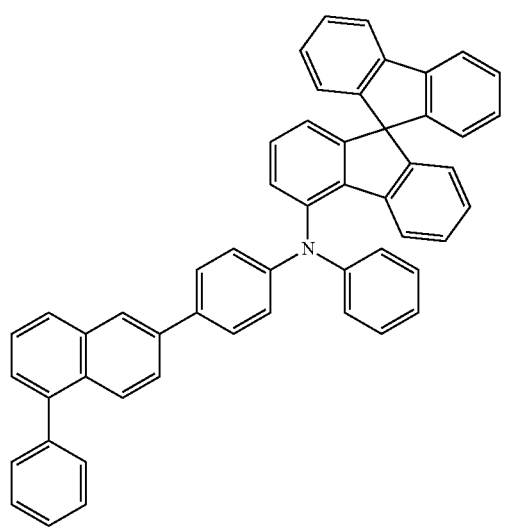

-continued
D59
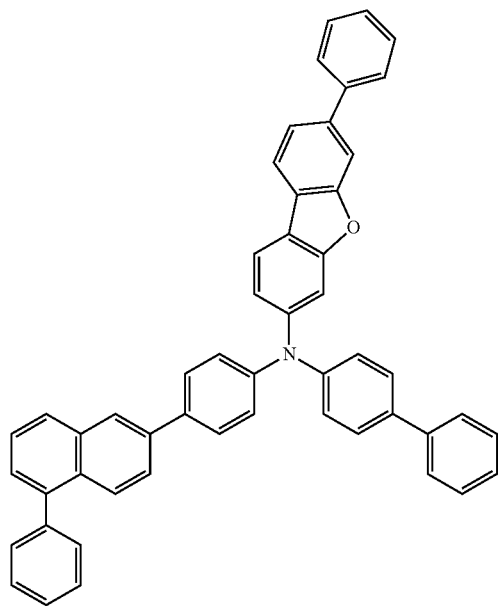
D60
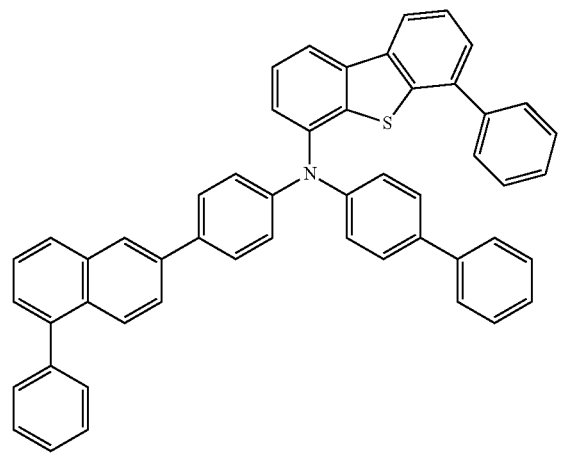
[Compound Group 5]
E1
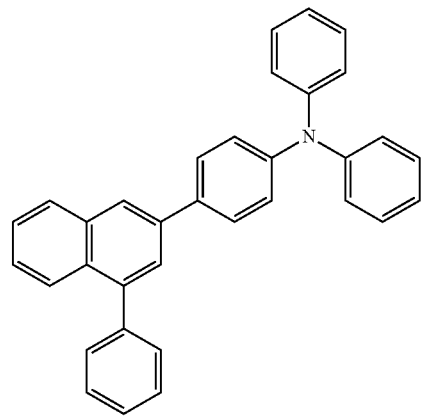
-continued
E2
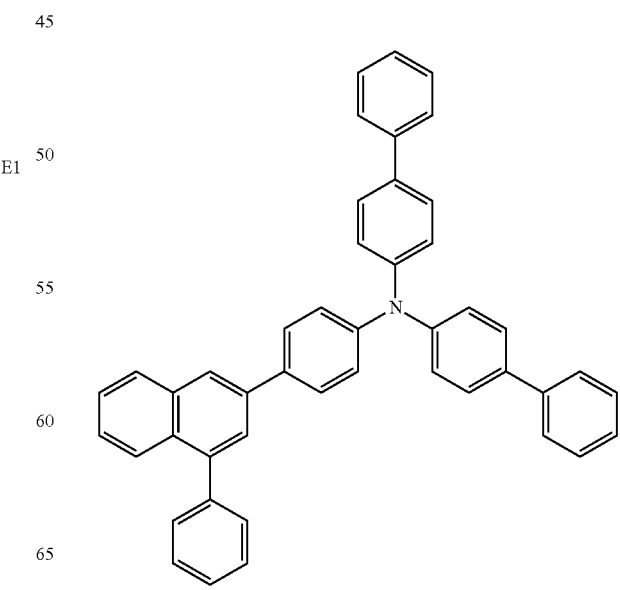

E3
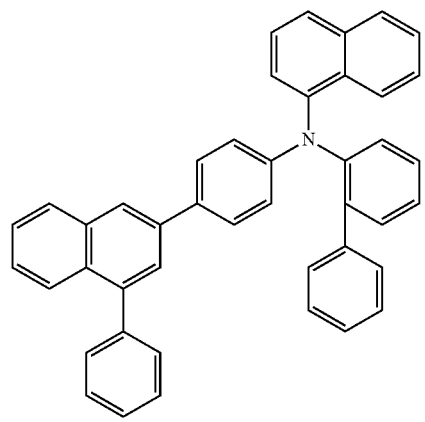
E4
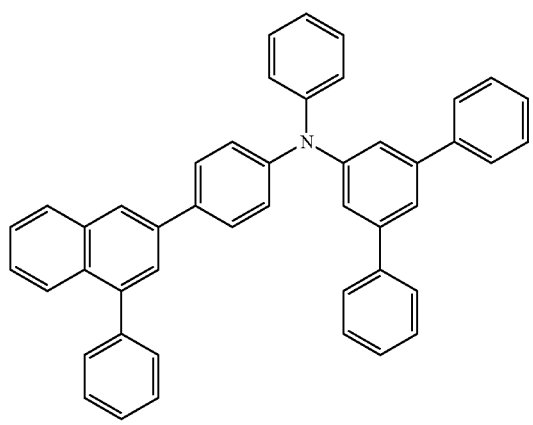
E6
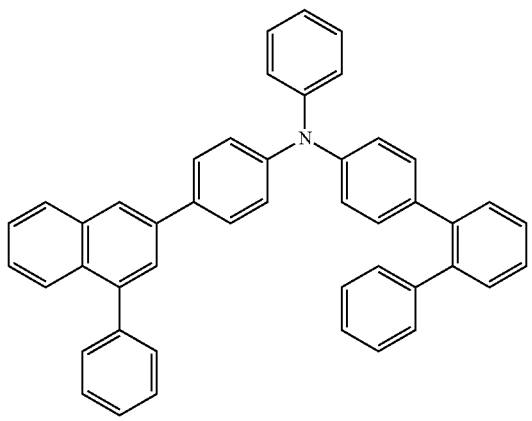
E7
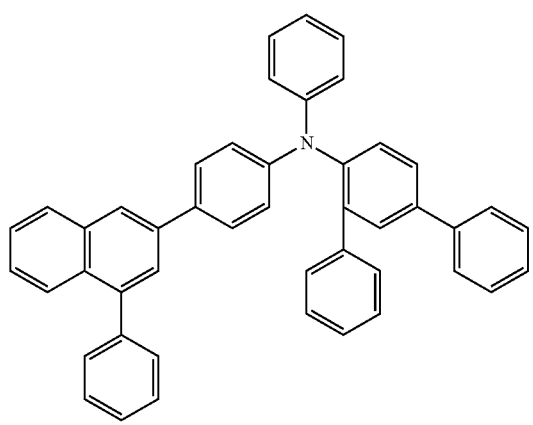
E5
E8

E9
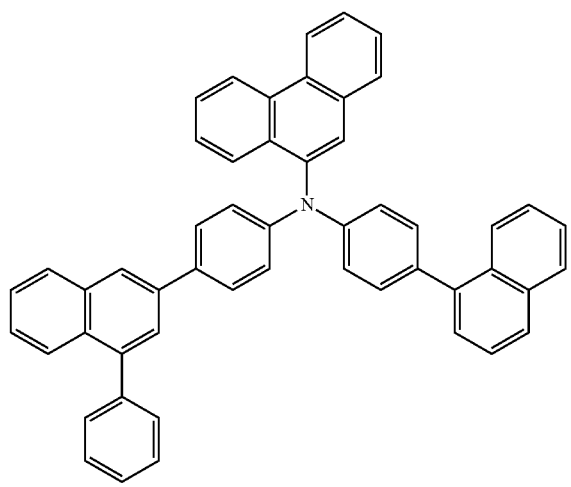
E10
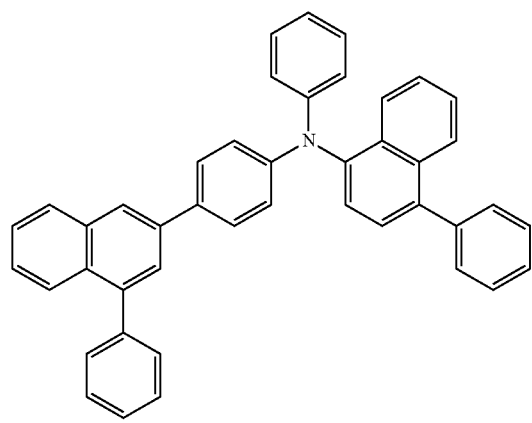
E11
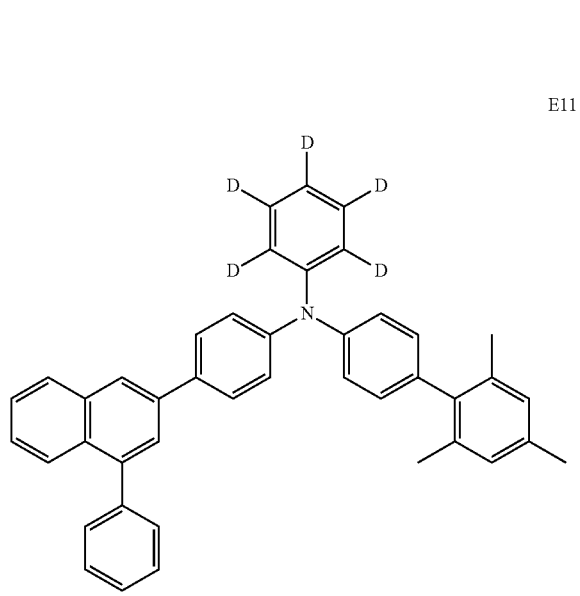
E12
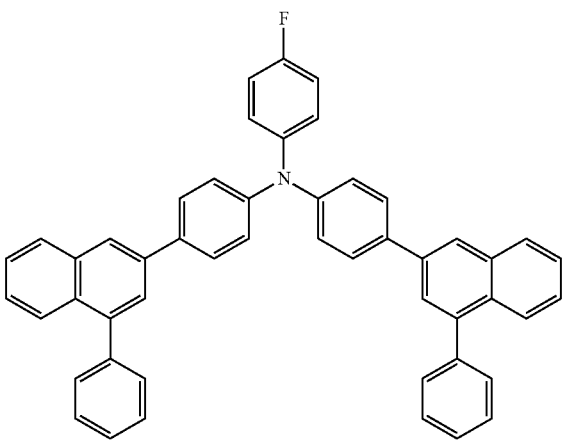
E13
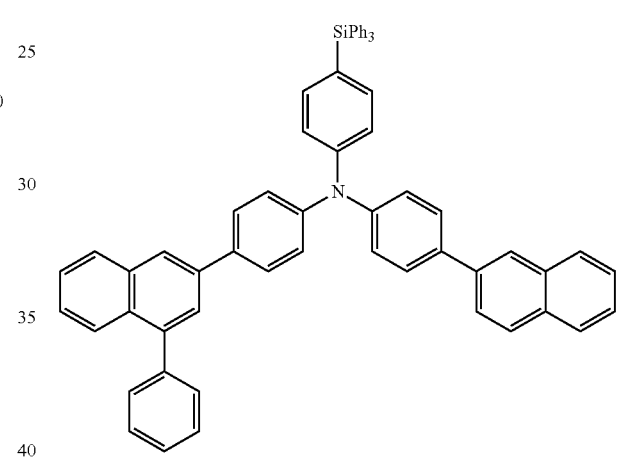
E14
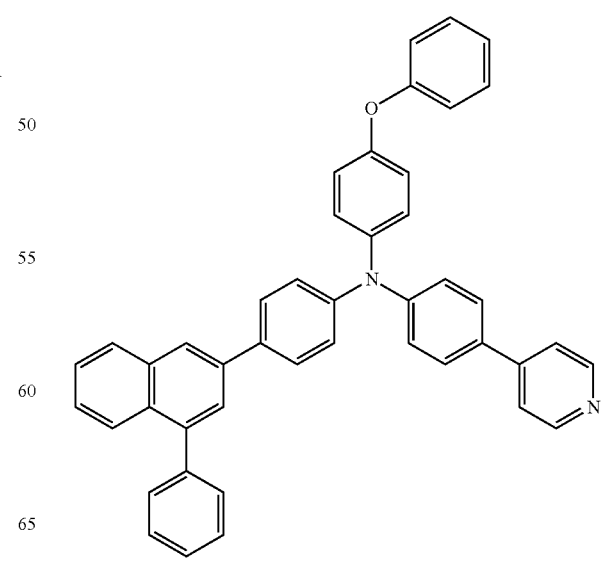

E15
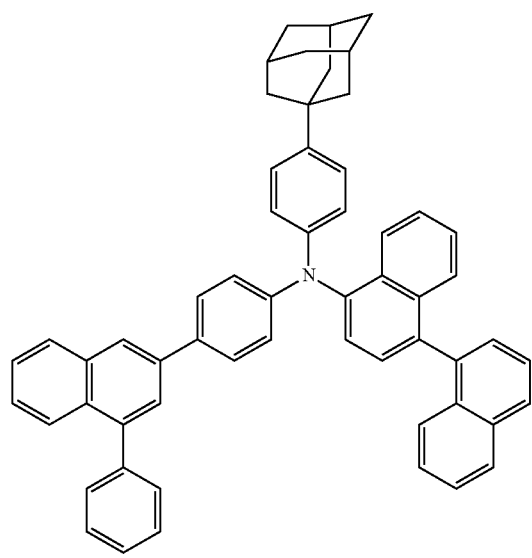
E18
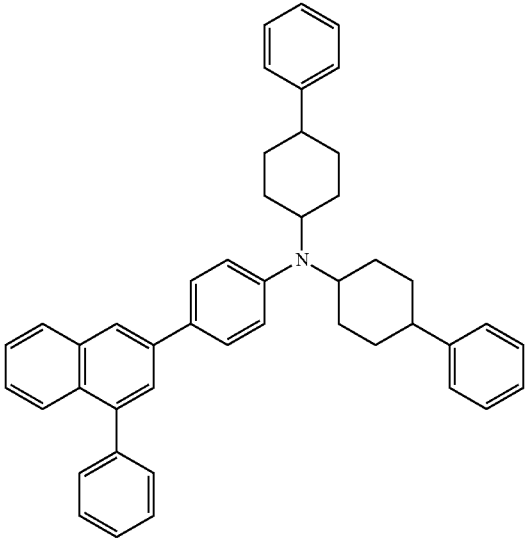
E16
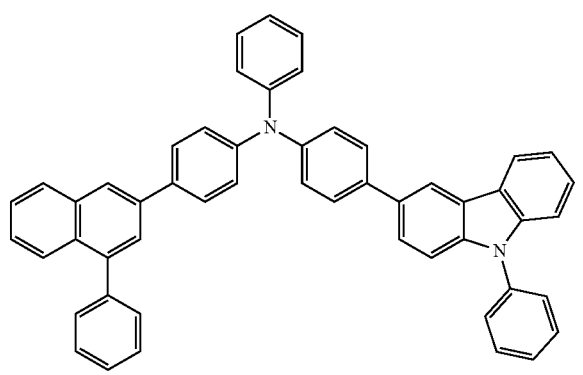
E19
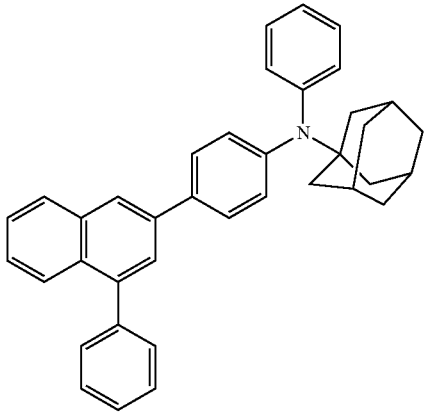
E17
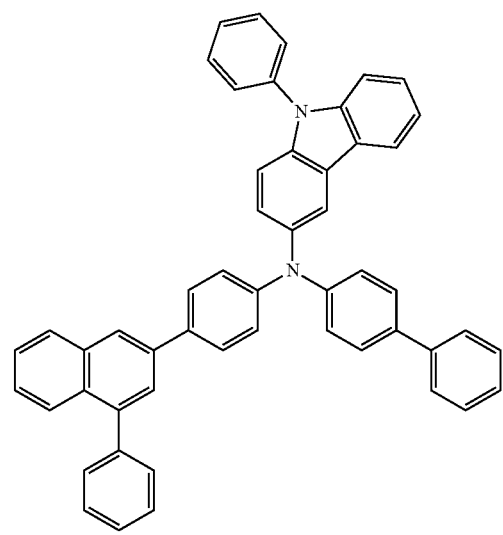
E20

-continued
E21
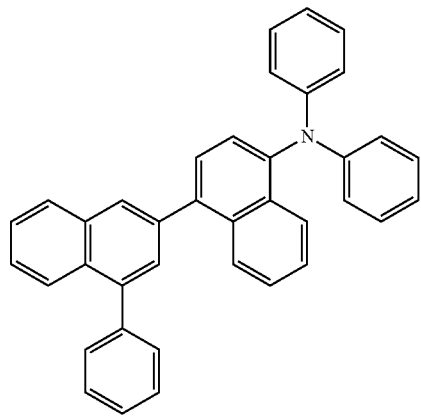
E22
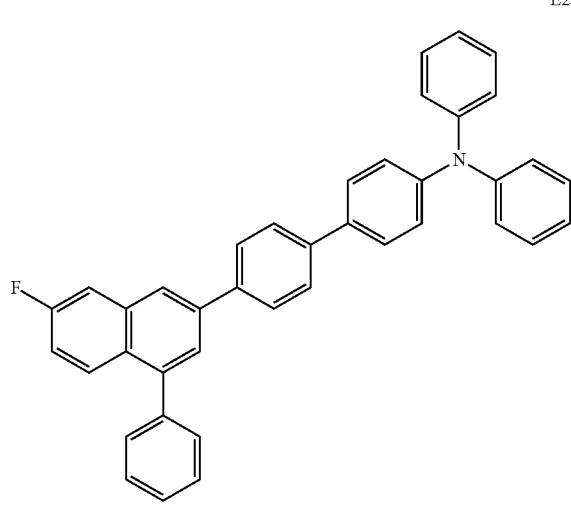
E23
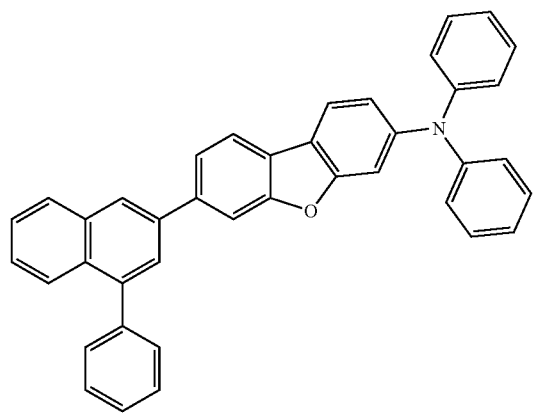
-continued
E24
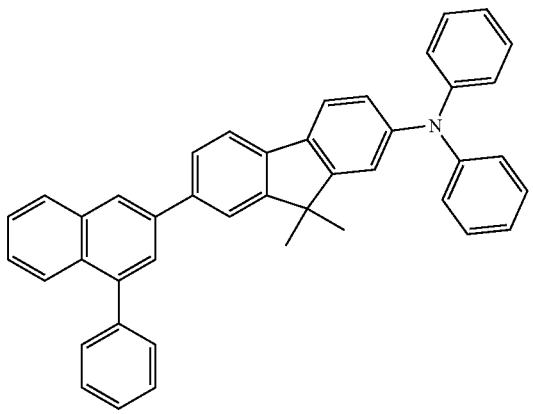
E25
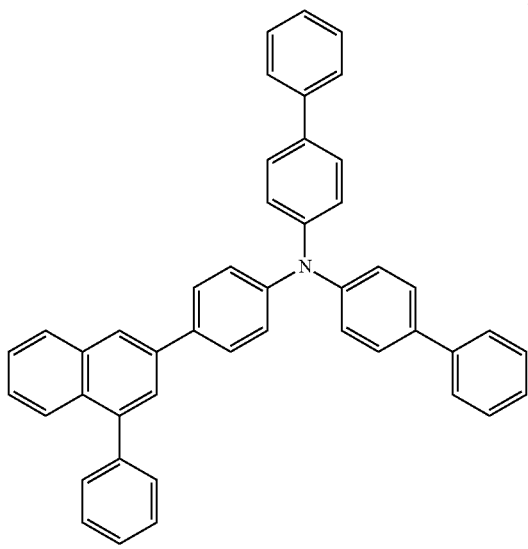
E26
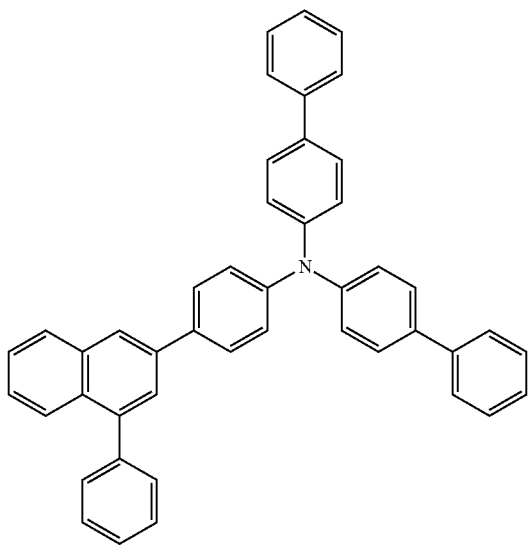

E27
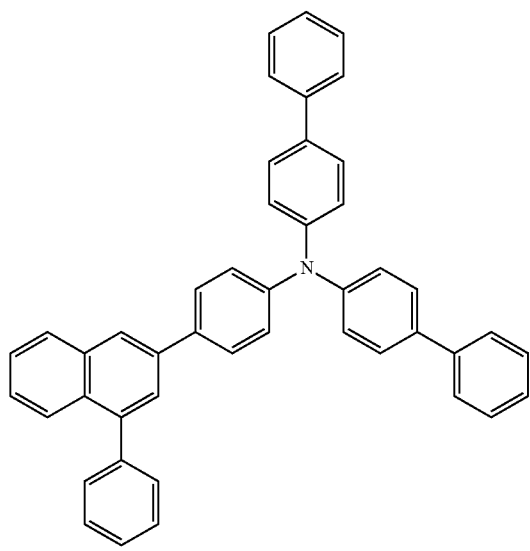
E29
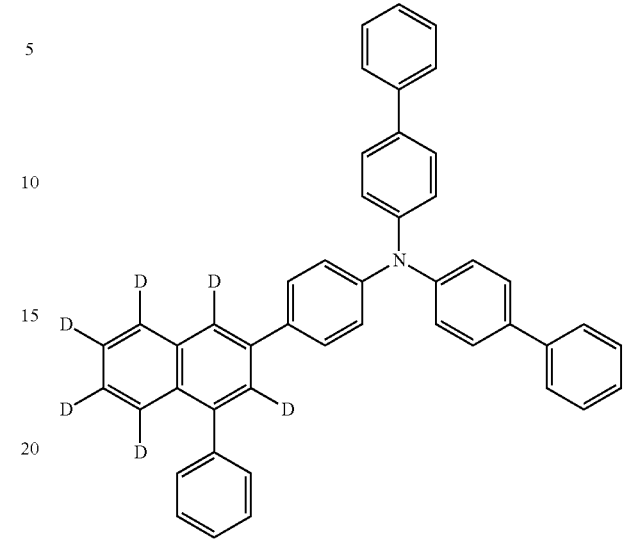
E28
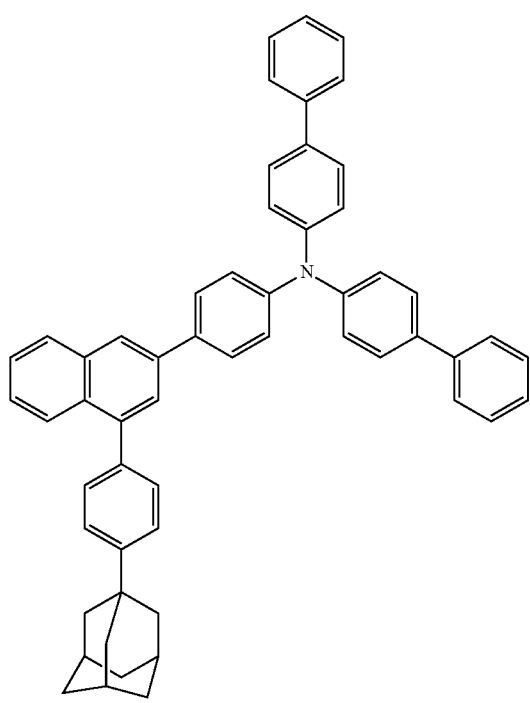
E30
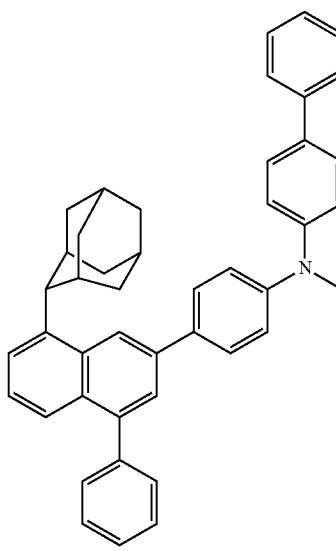
E31
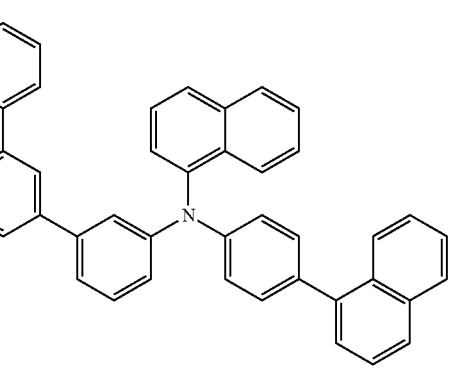

E32
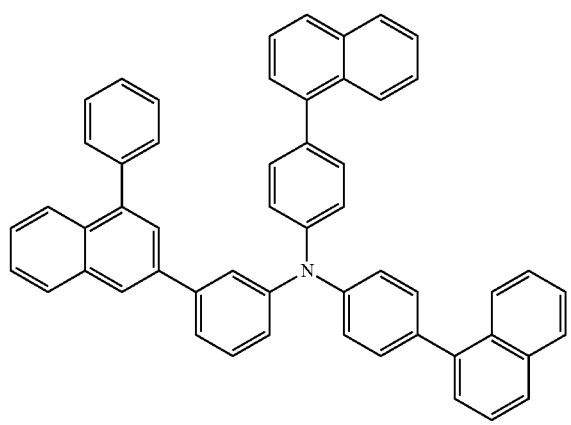
E33
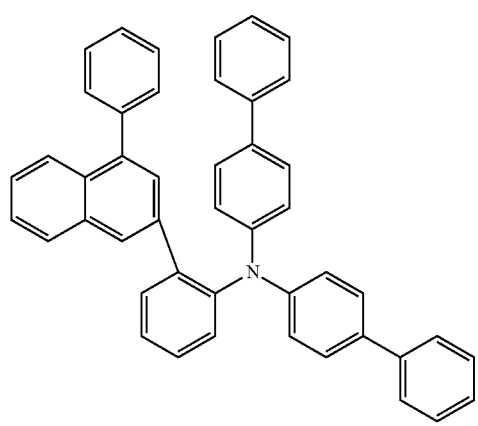
E34
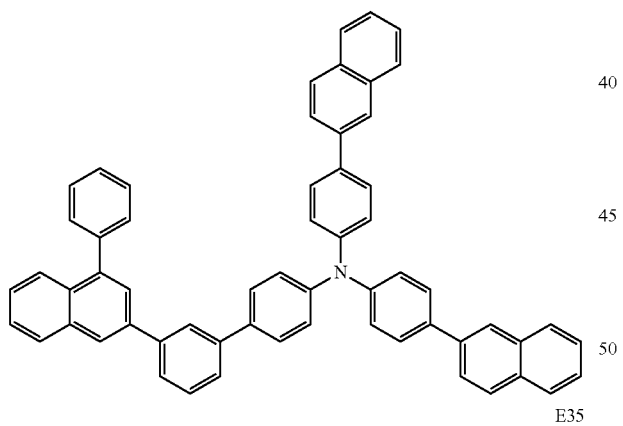
E35
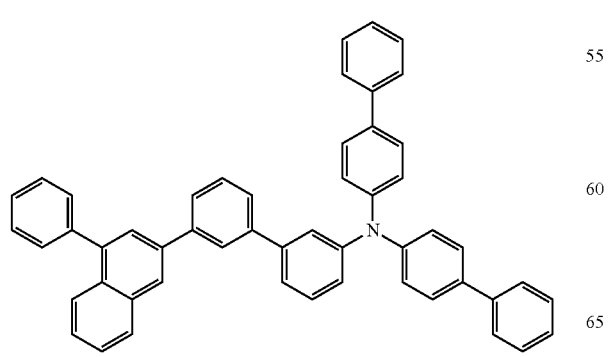
E36
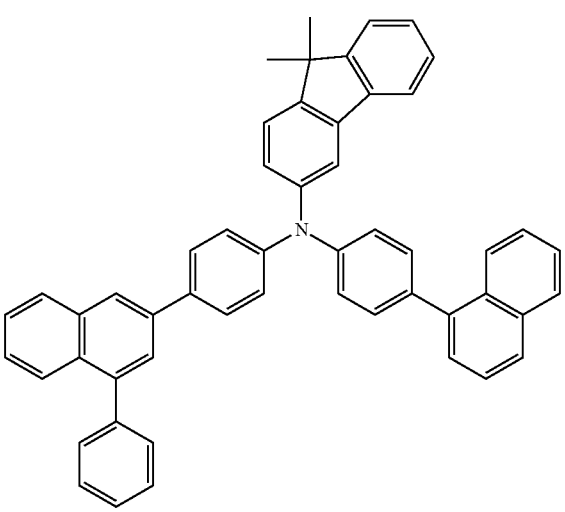
E37
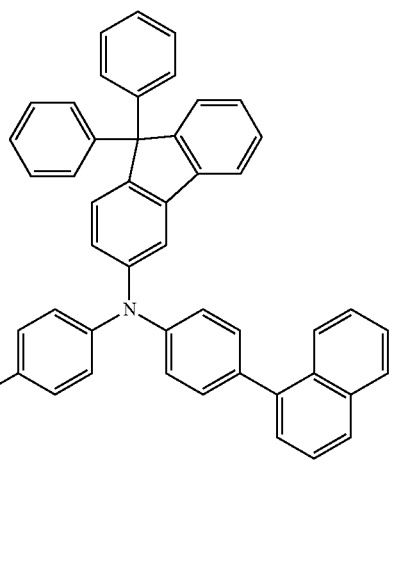

E38
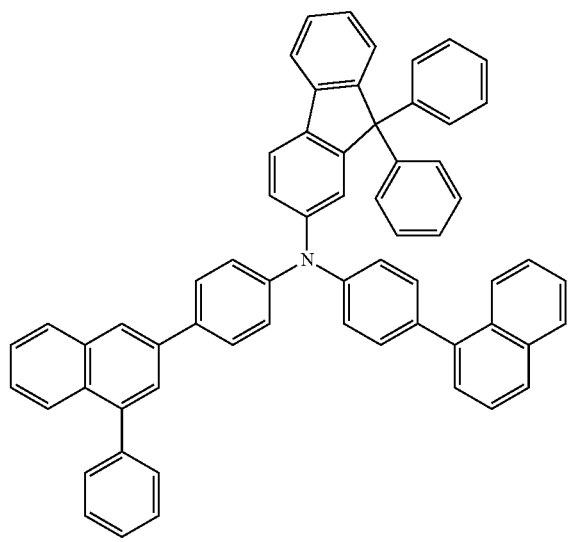
E39
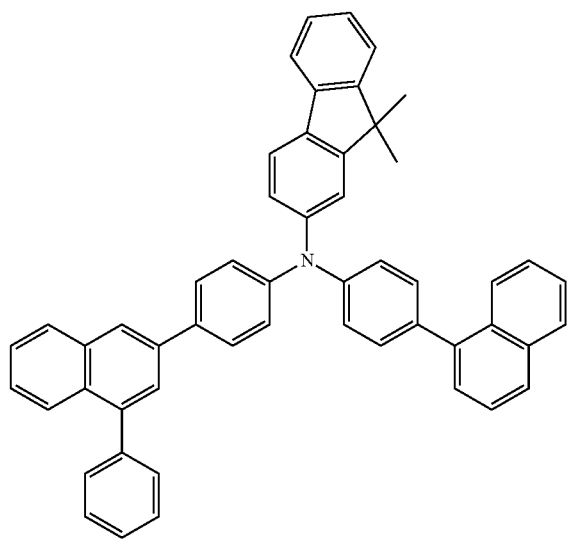
E40
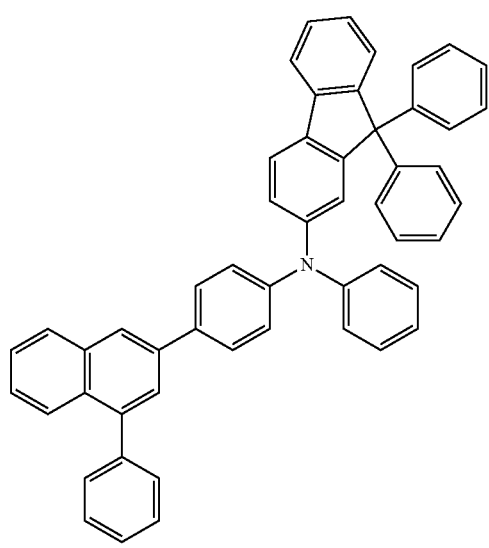
E41
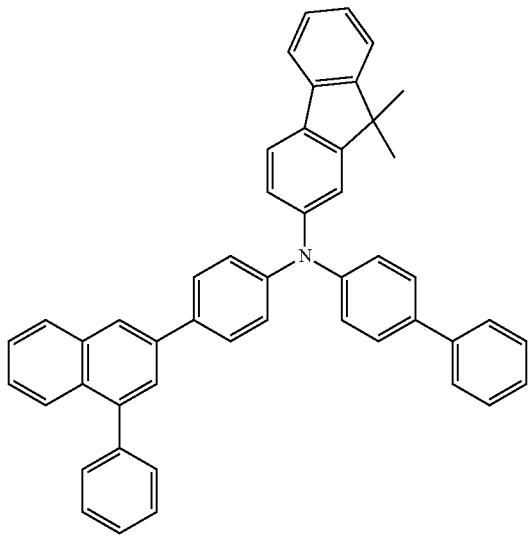
E42
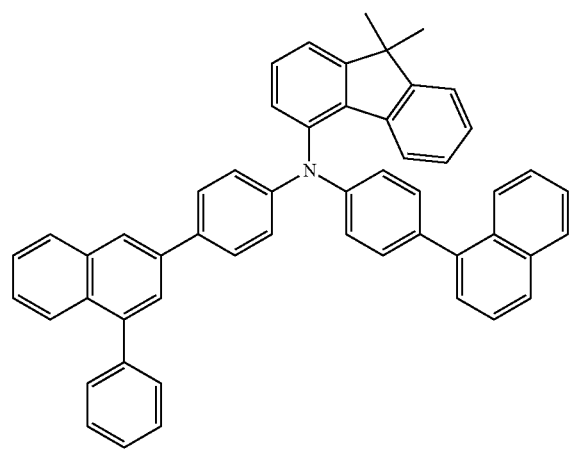
E43
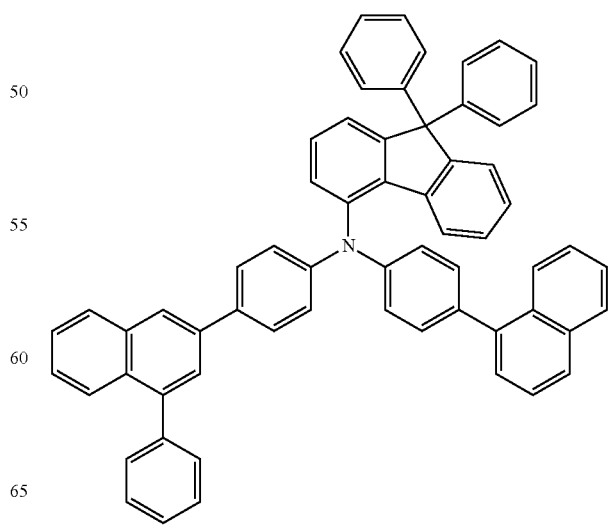

E44
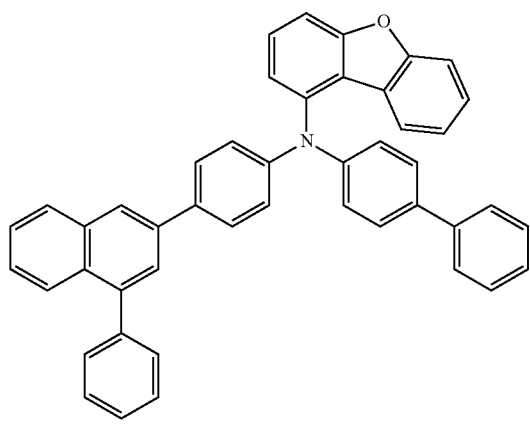
E45
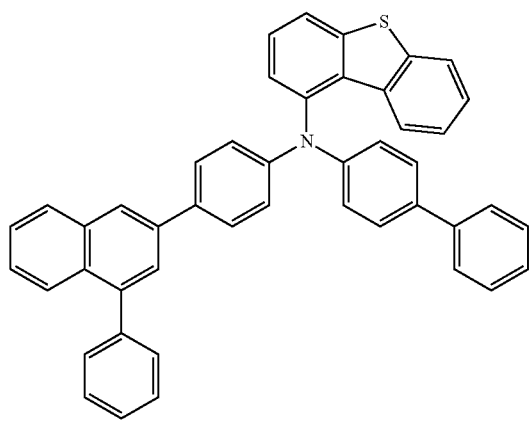
E46
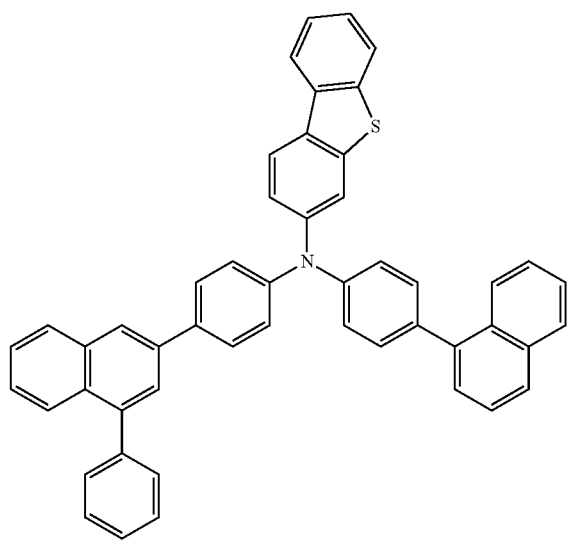
E47
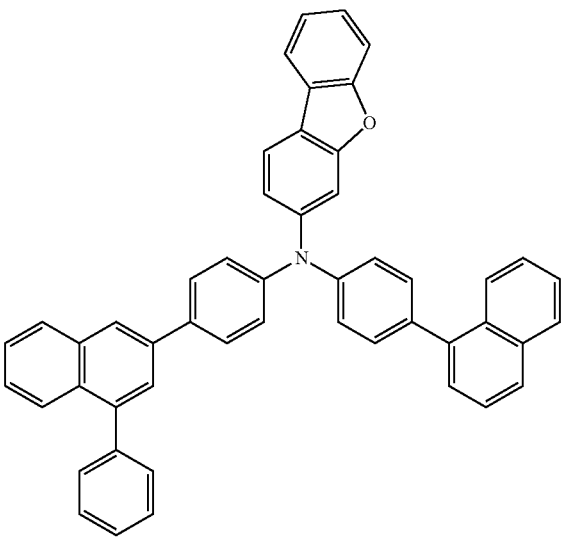
E48
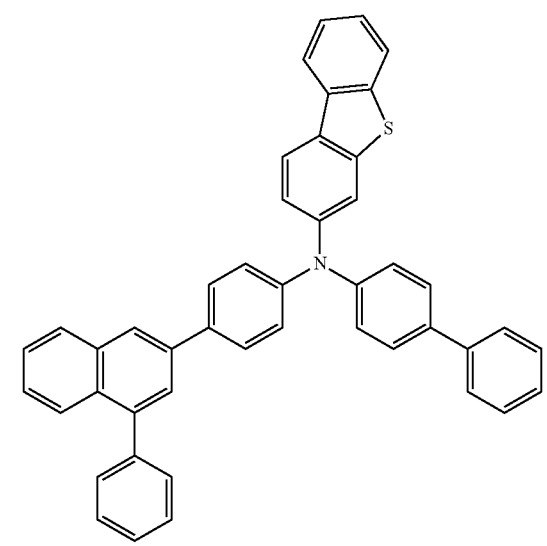
E49
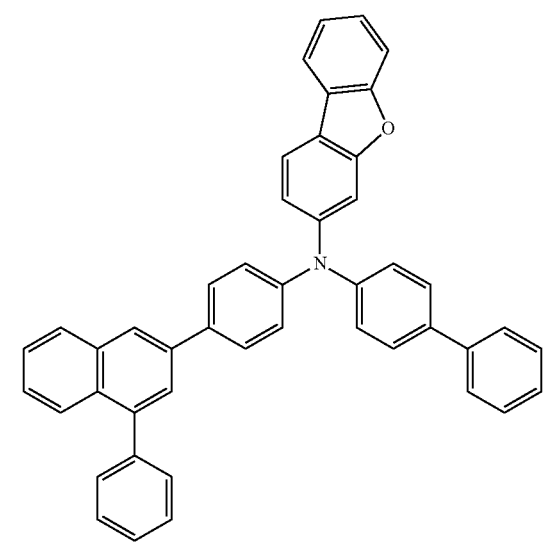

E50
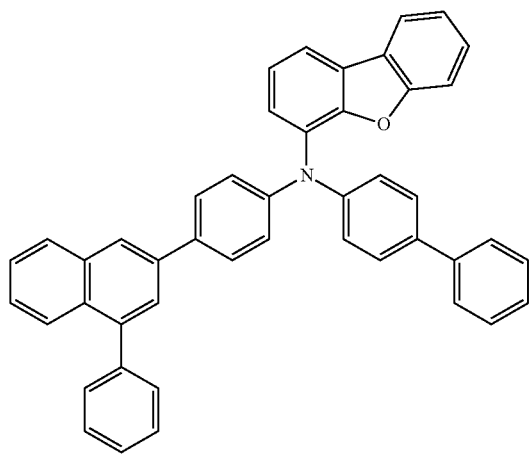
E51
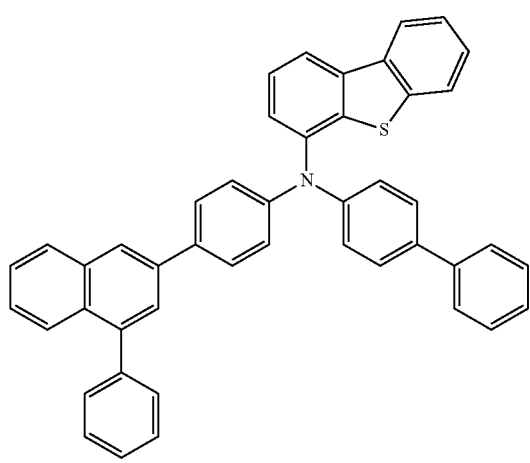
E52
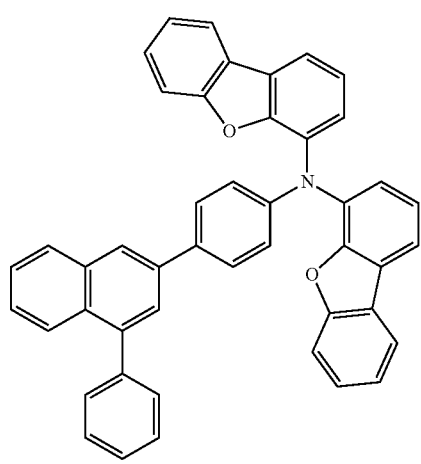
E53
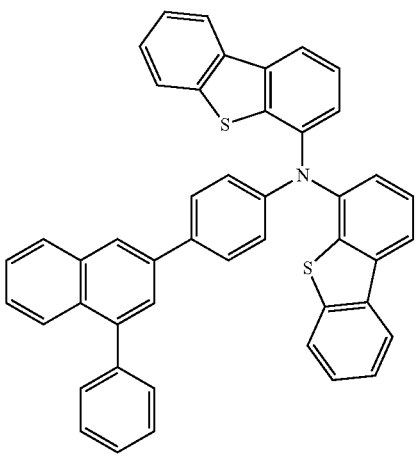
E54
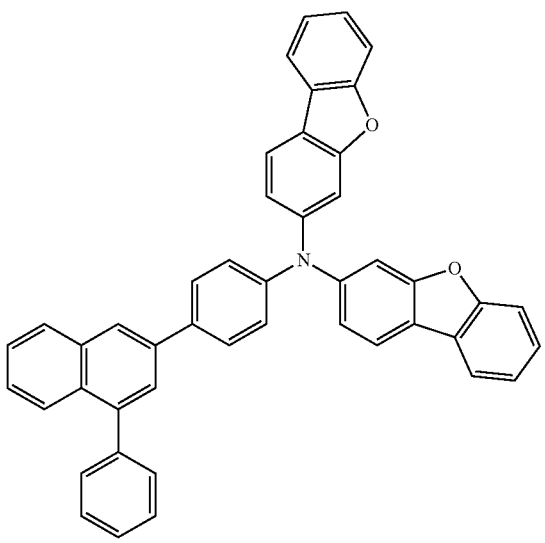
E55
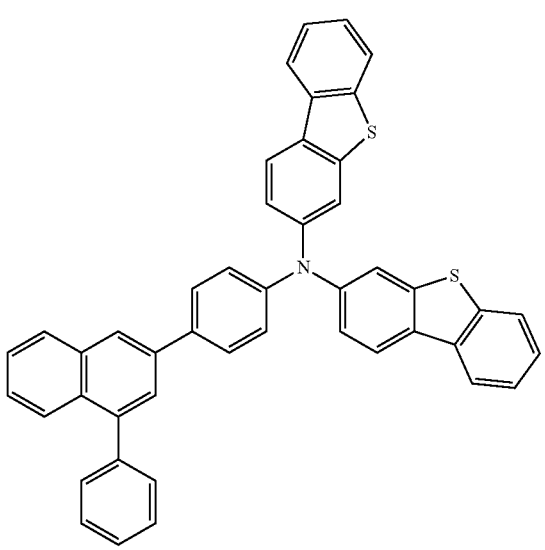

-continued
E56
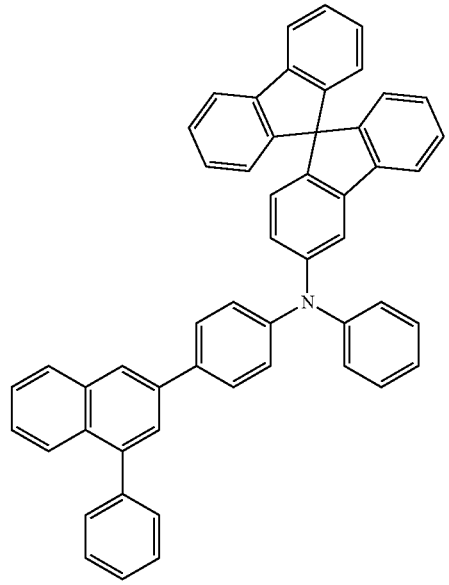
E57
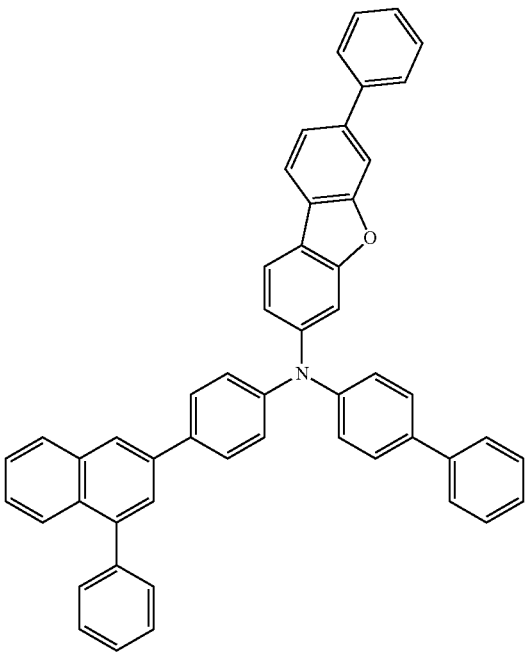
E58
E59
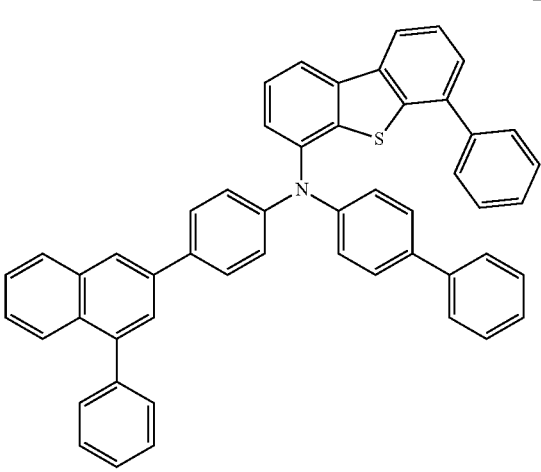
E60
[Compound Group 6]
F1
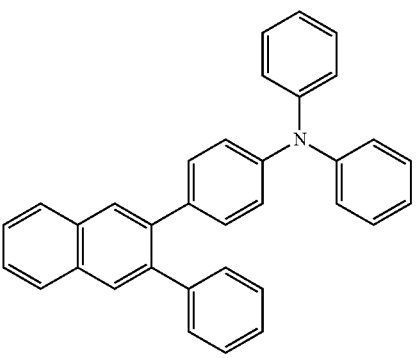

F2
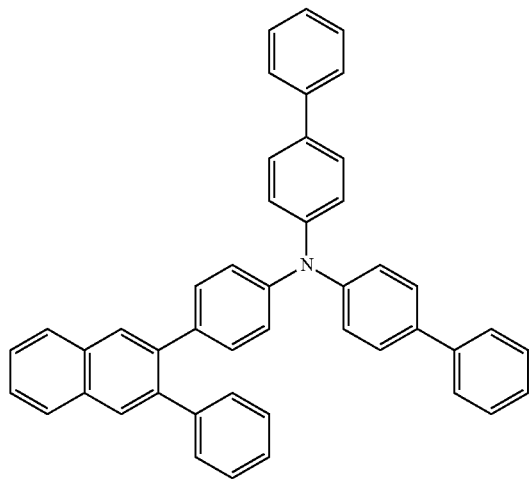
F3
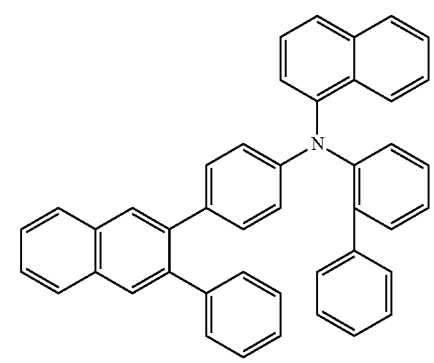
F4
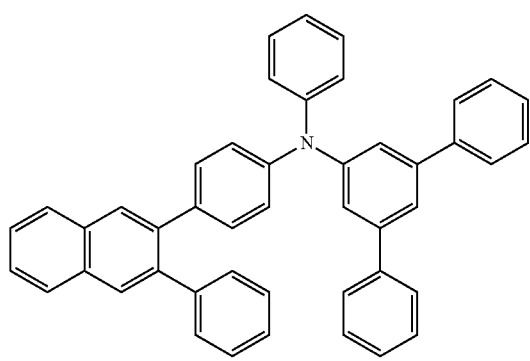
F5
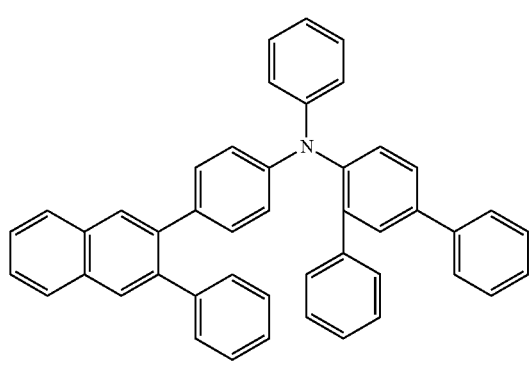
F6
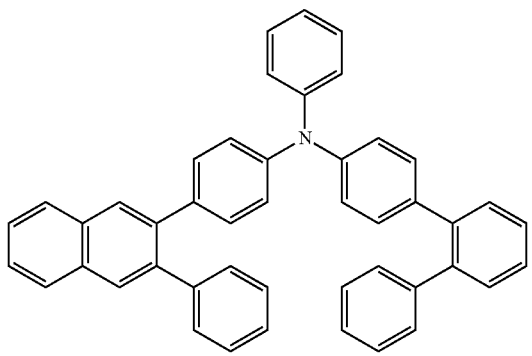
F7
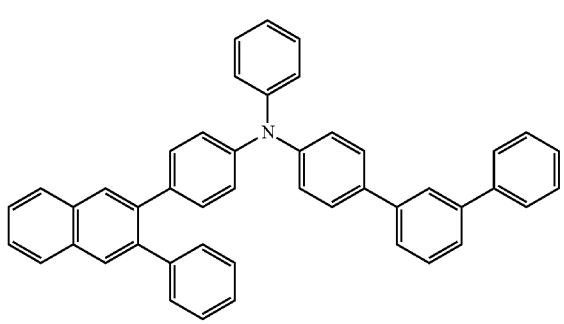
F8
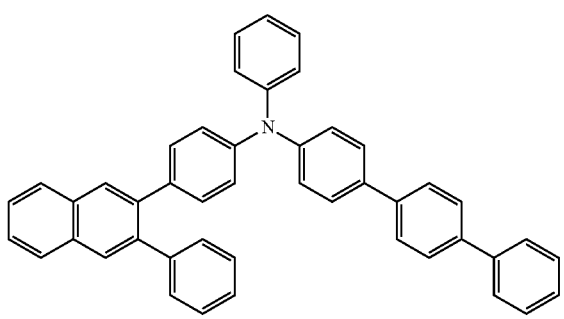
F9
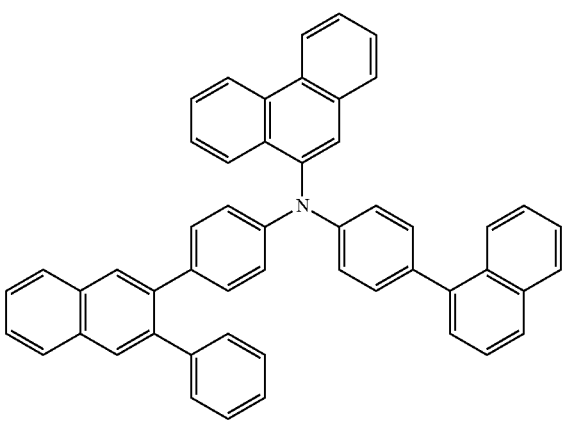

F10
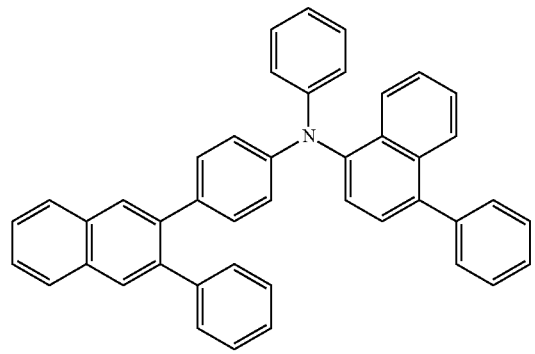
F11
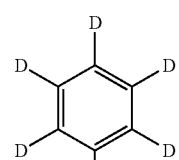
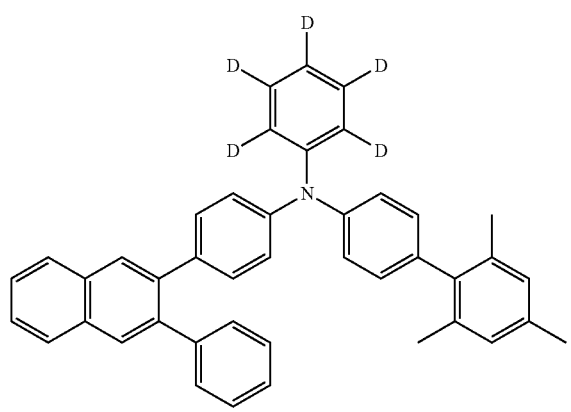
F12
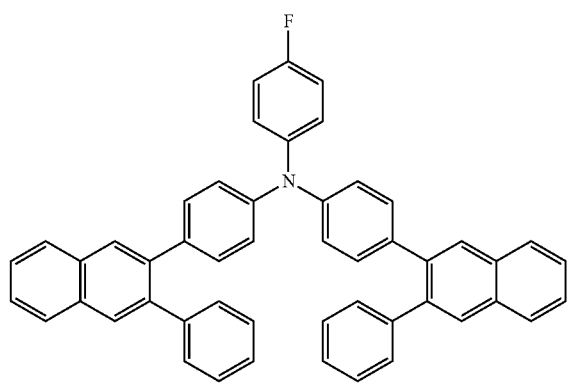
F13
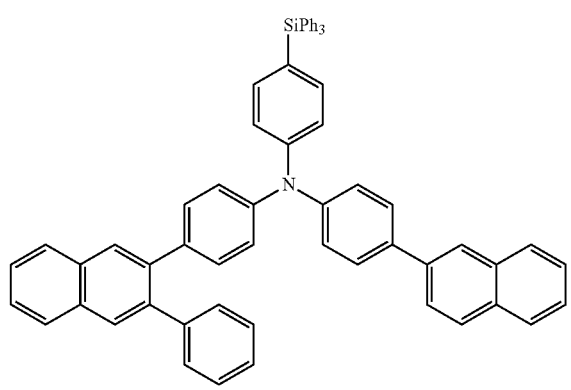
F14
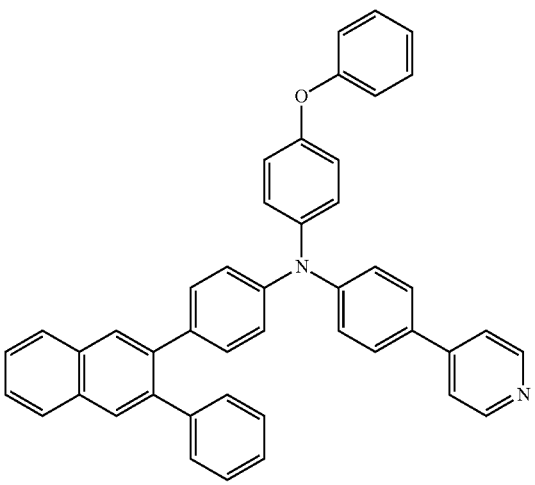
F15
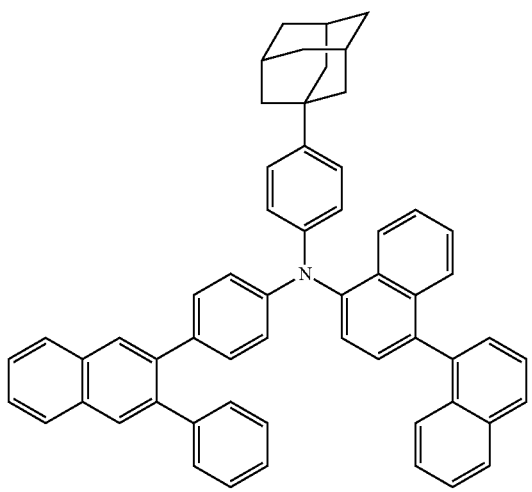
F16
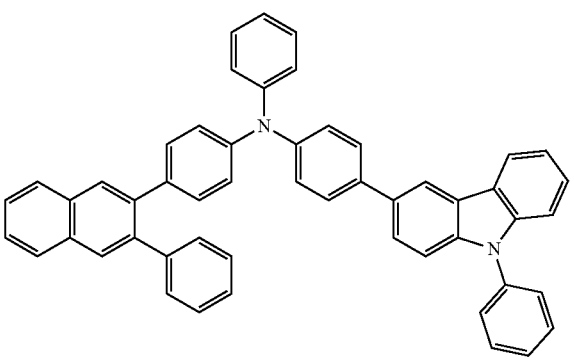

F17
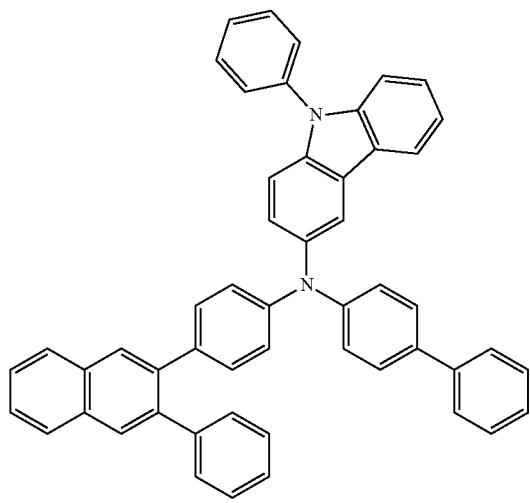
F18
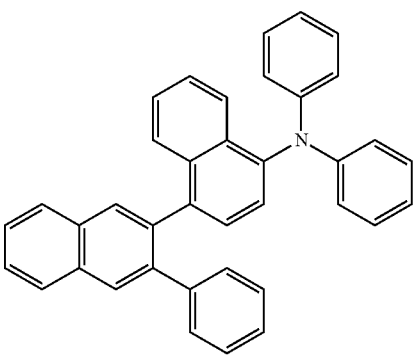
F19
F20
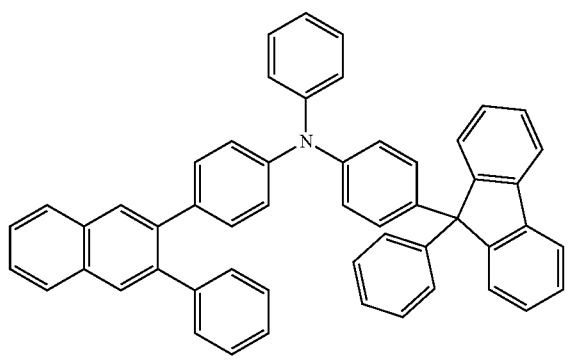
F21
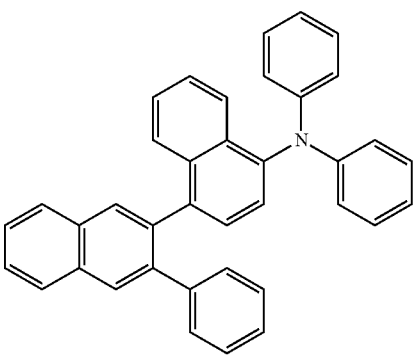
F22
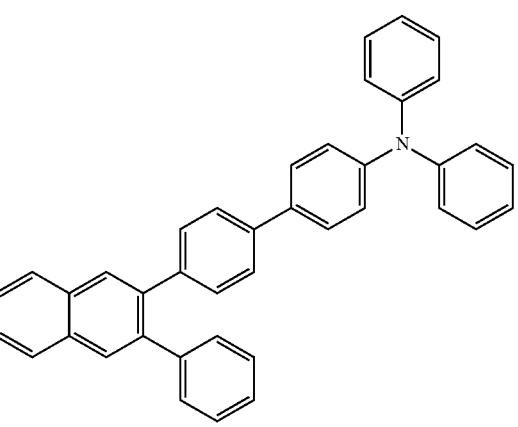
F23
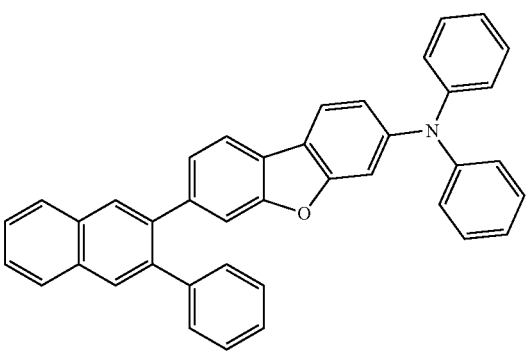

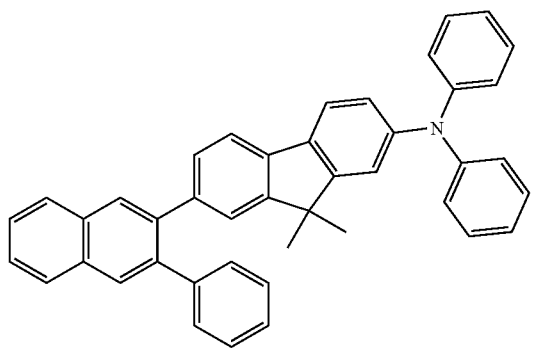
F24
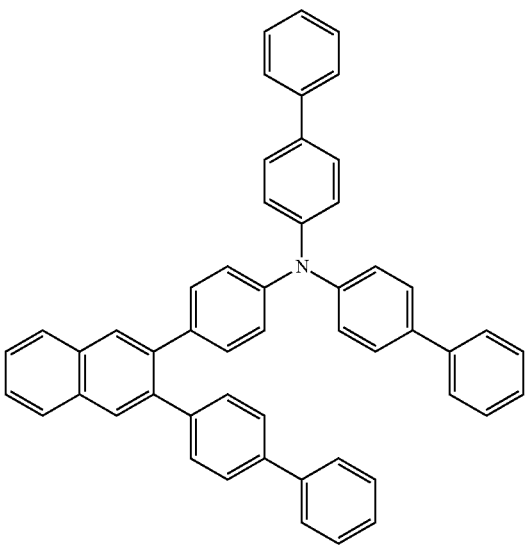
F27
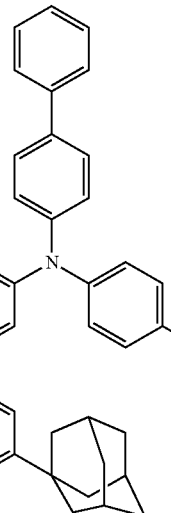
F25
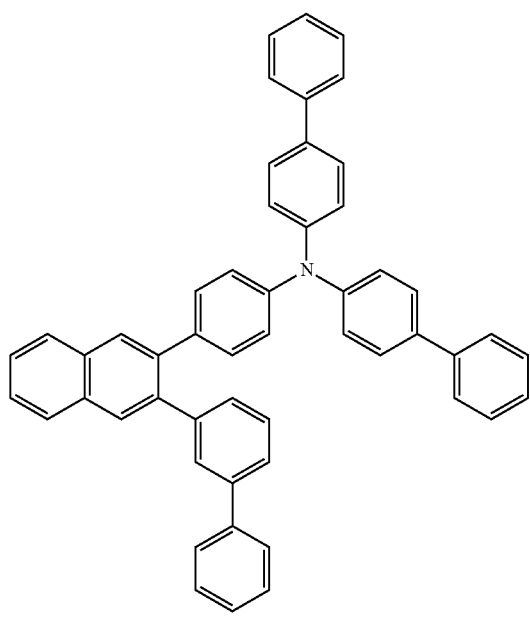
F26
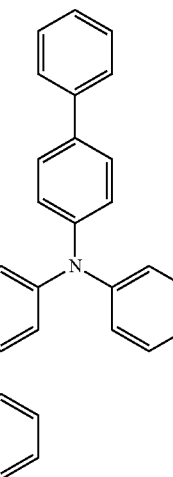
F28
F29

-continued
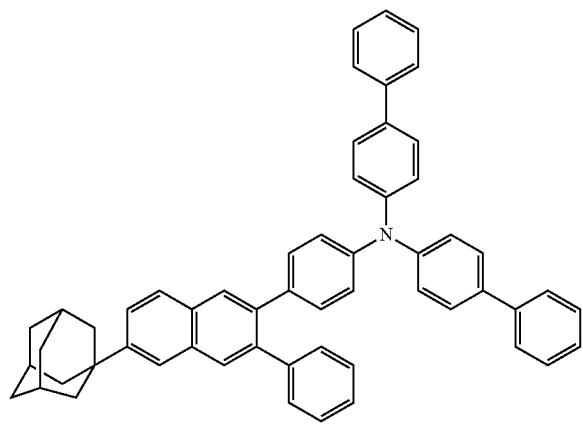
F30
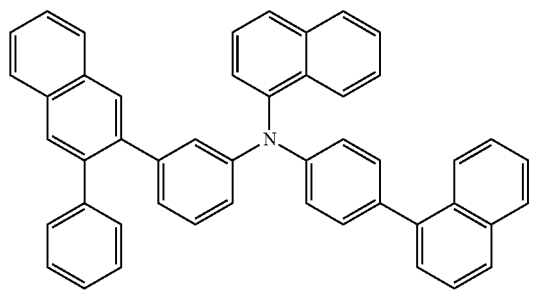
F31
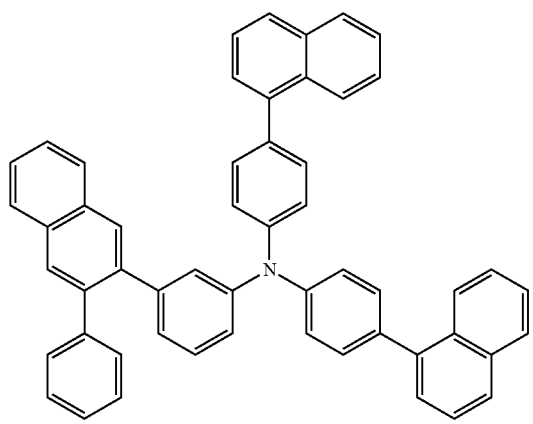
F32
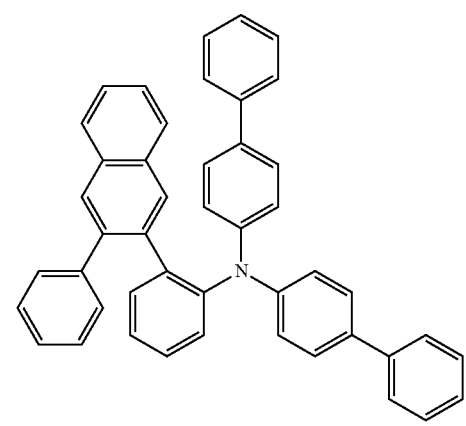
F33
-continued
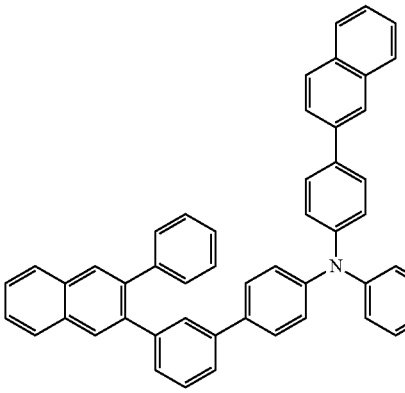
F34
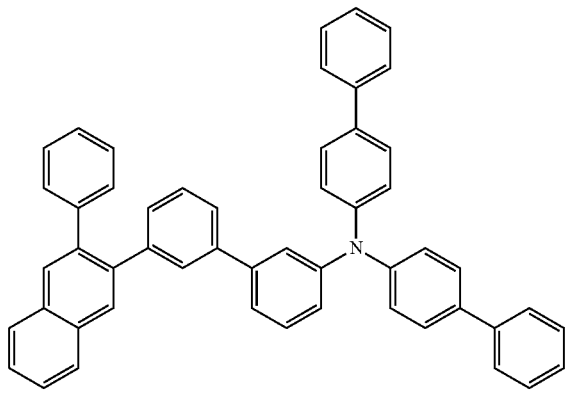
F35
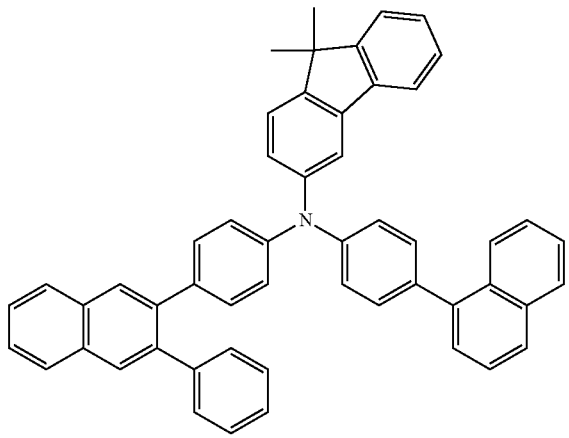
F36

F37
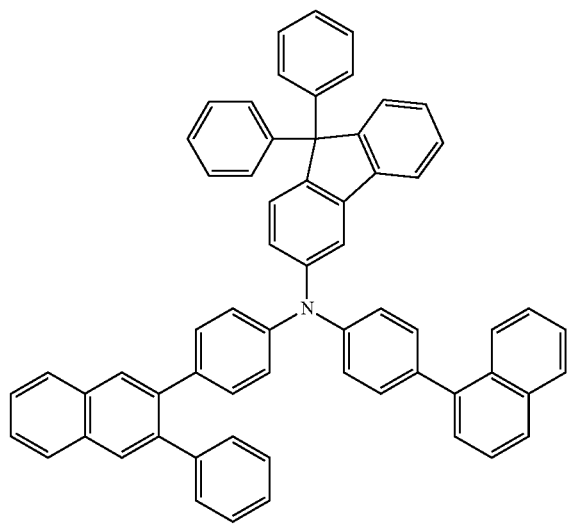
F38
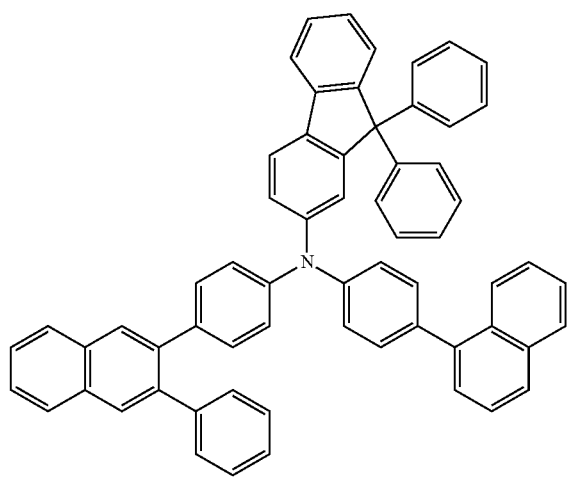
F39
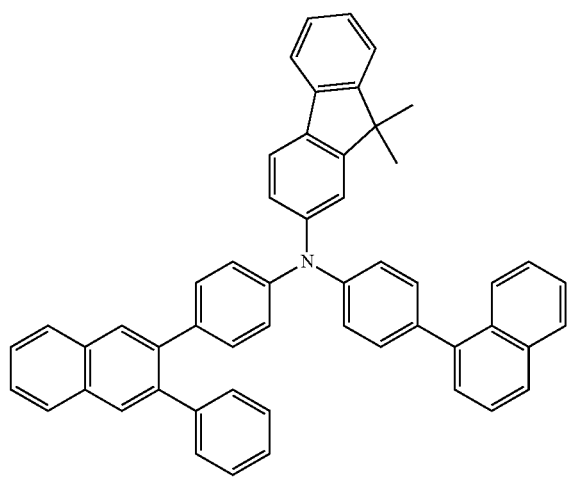
F40
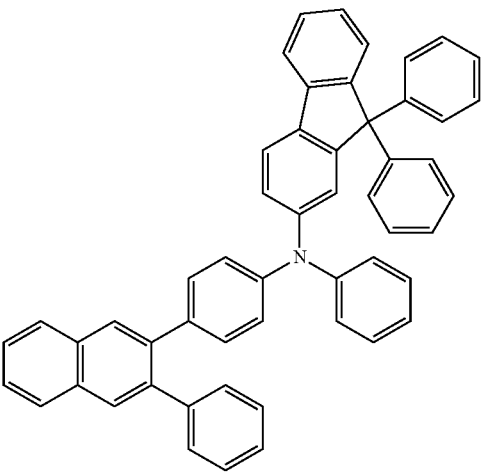
F41
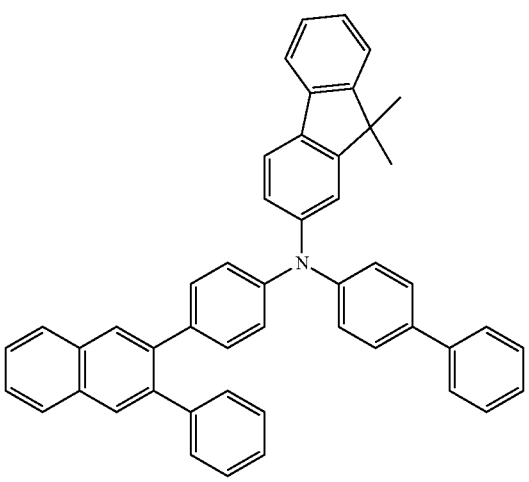
F42
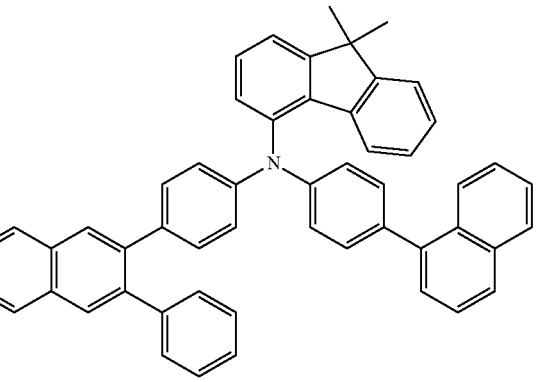

F43
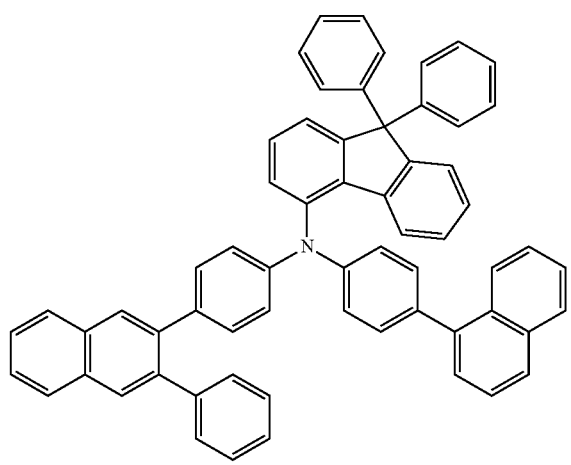
F44
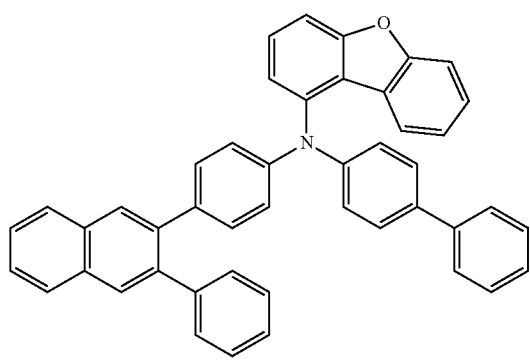
F45
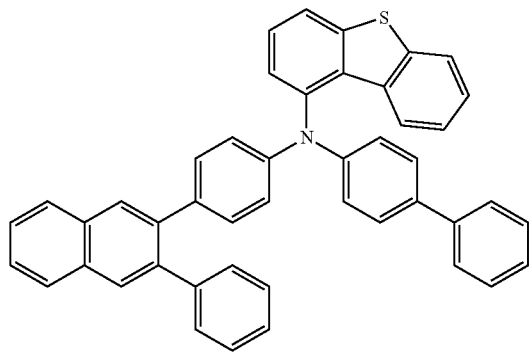
F46
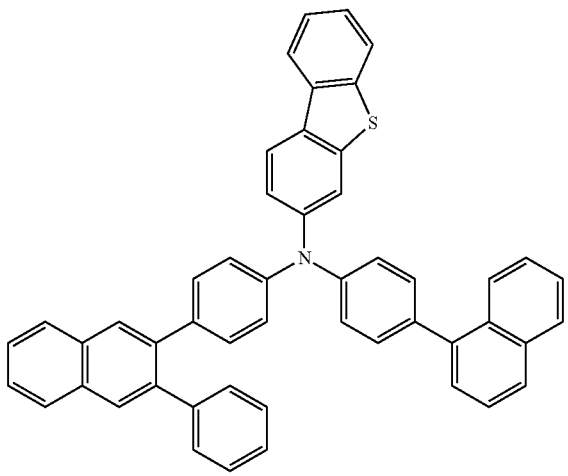
F47
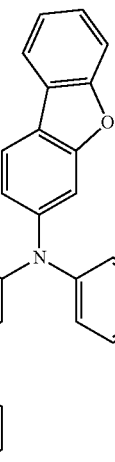
F48
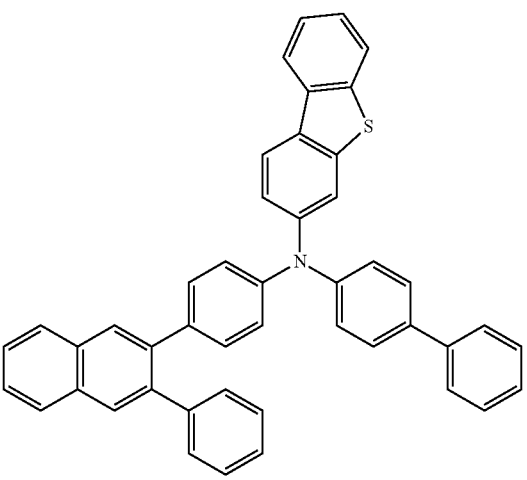

F49
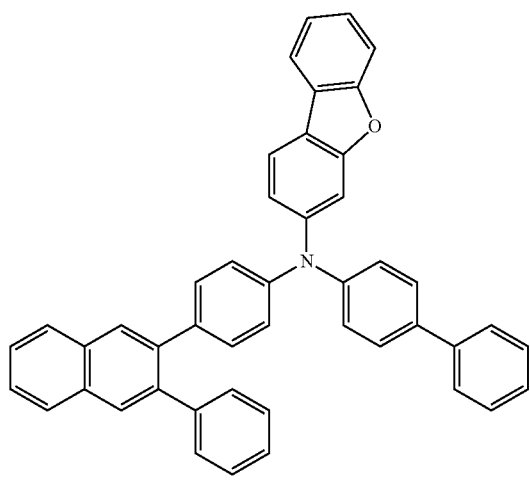
F52
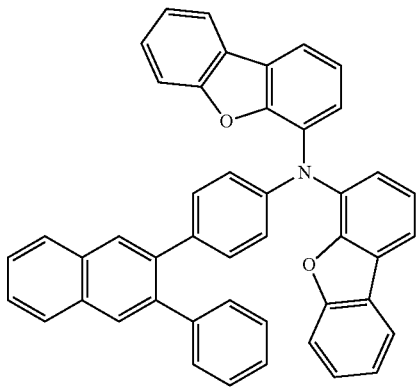
F50
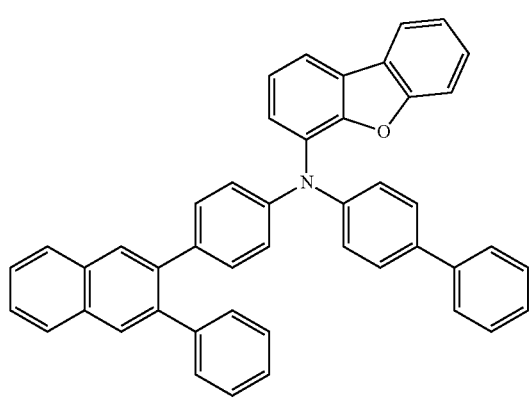
F53
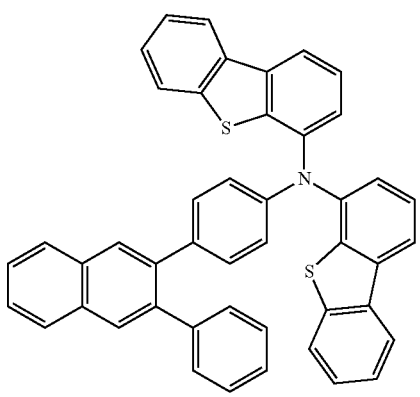
F51
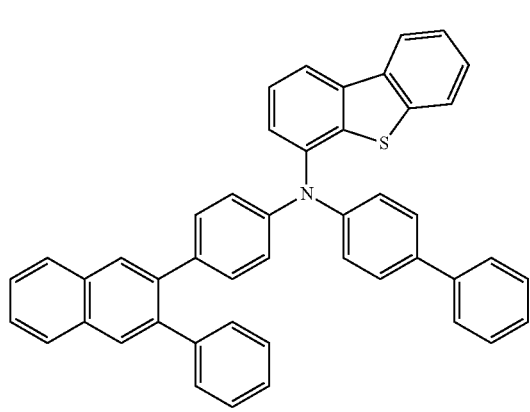
F54
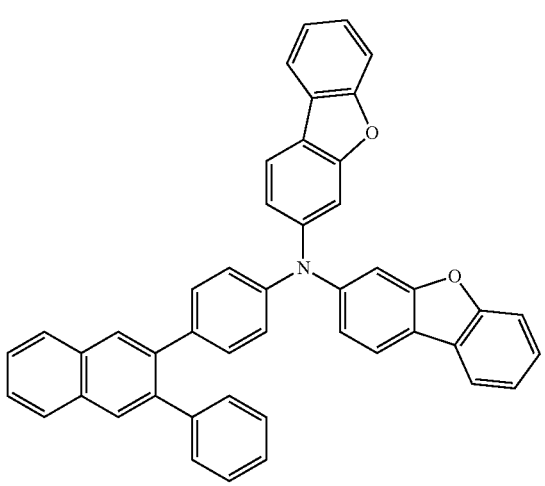

F55
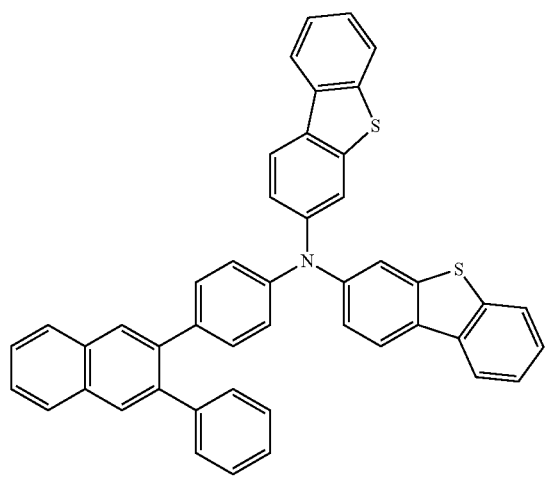
F56
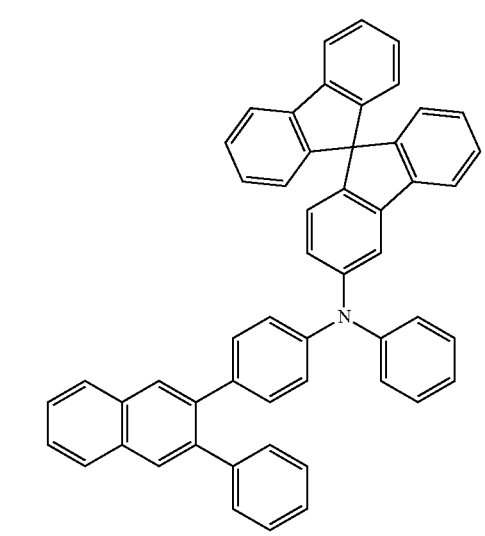
F57
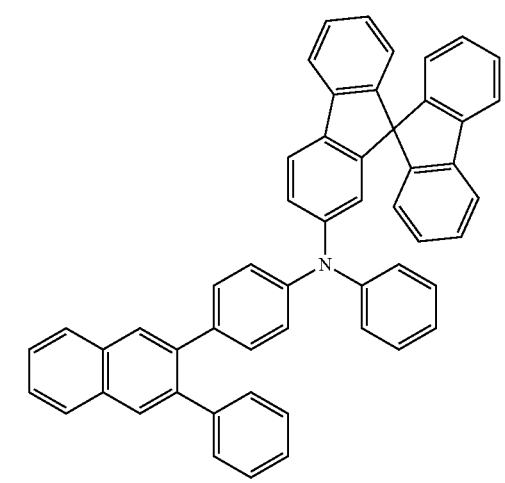
F58
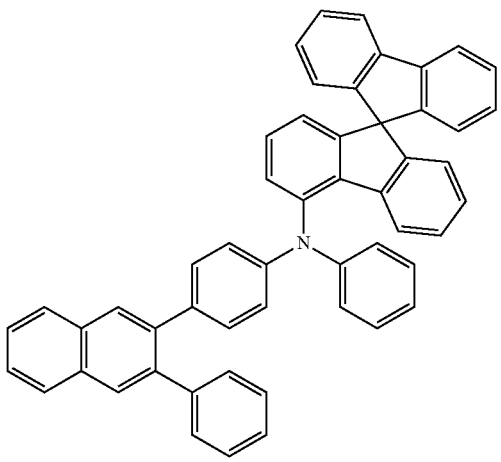
F59
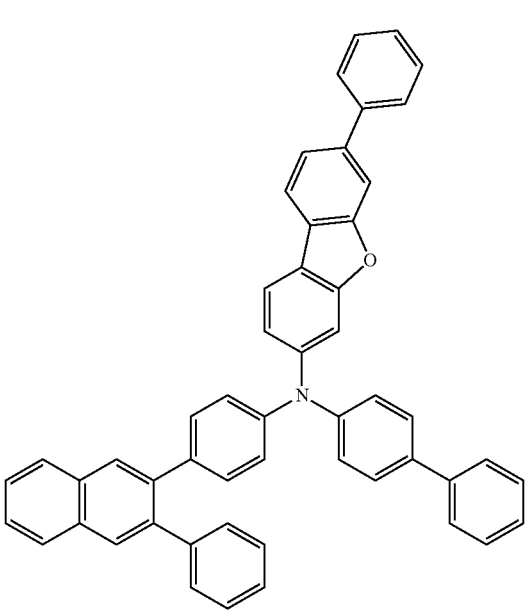
F60
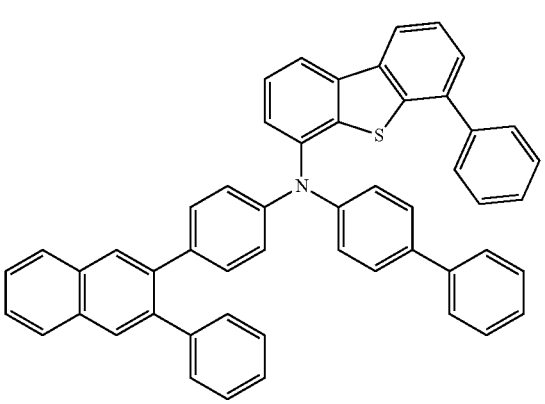

[Compound Group 7]
G1
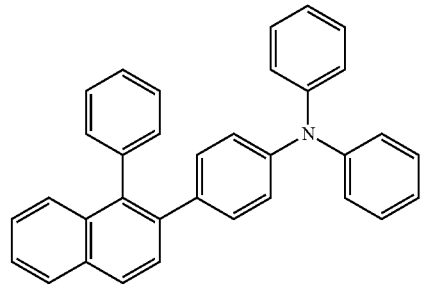
G2
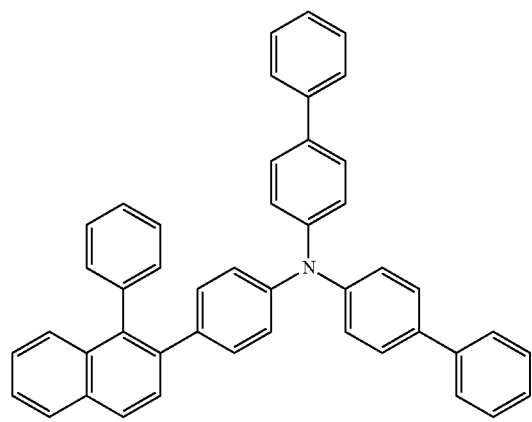
G3
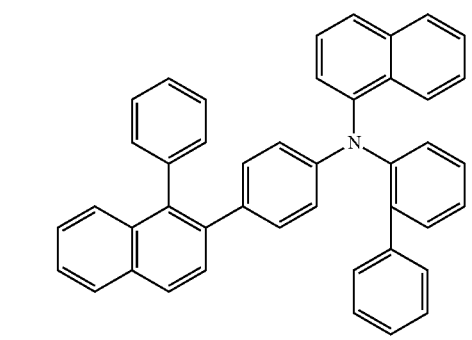
G4
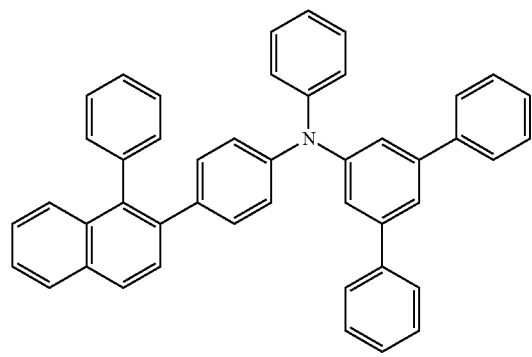
G5
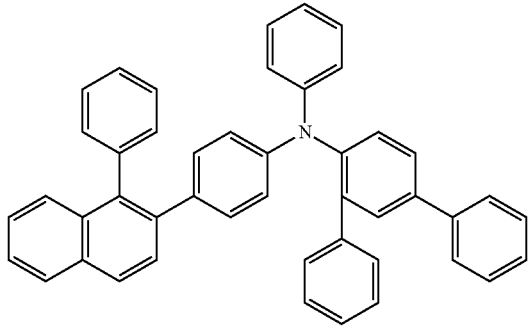
G6
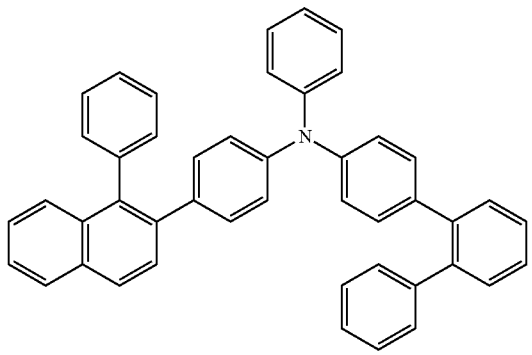
G7
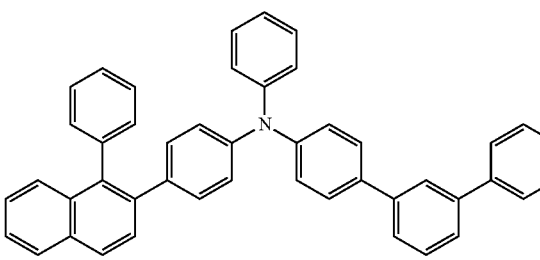
G8
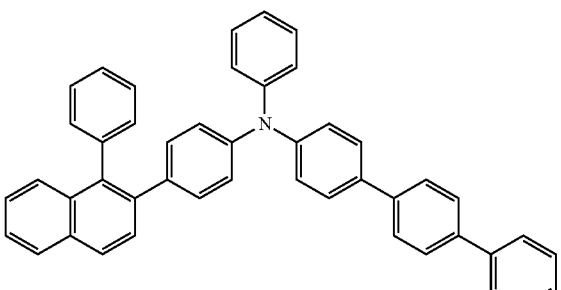
G9
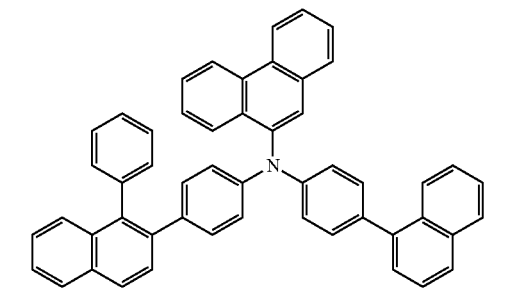

G10
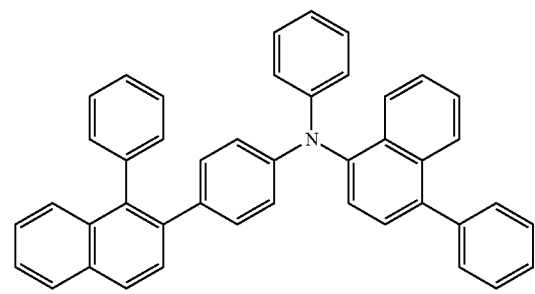
G11
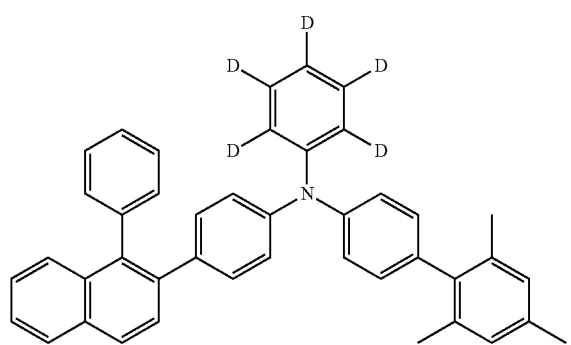
G12
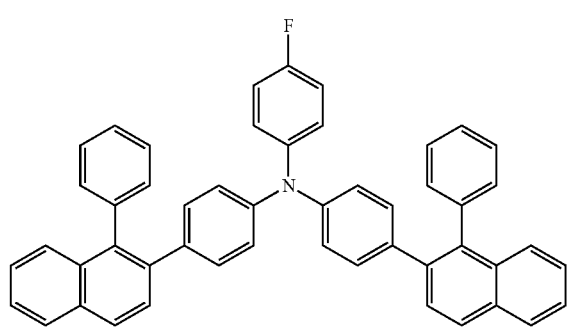
G13
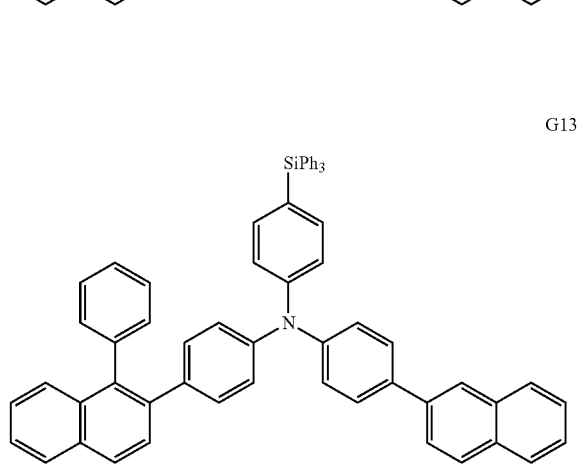
G14
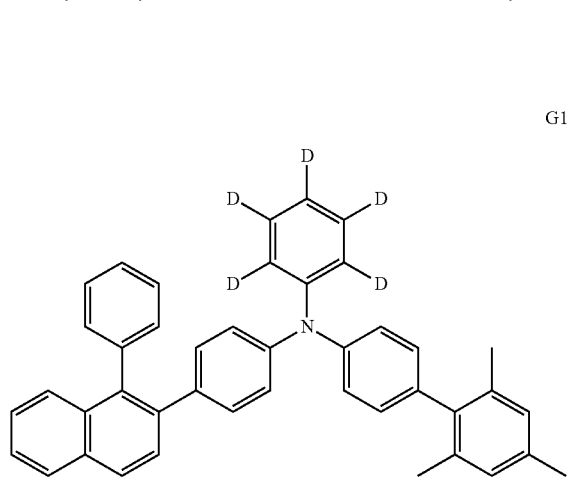
G15
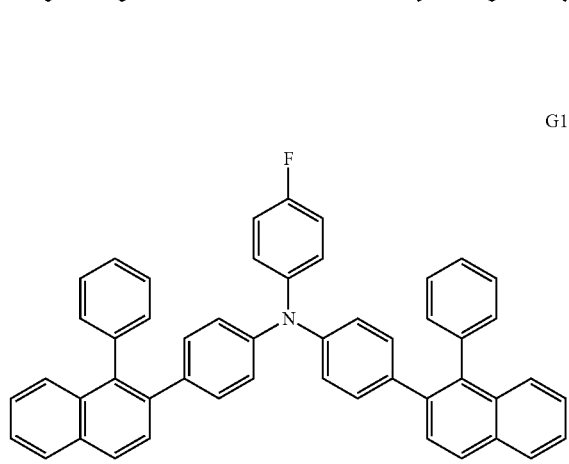
G16
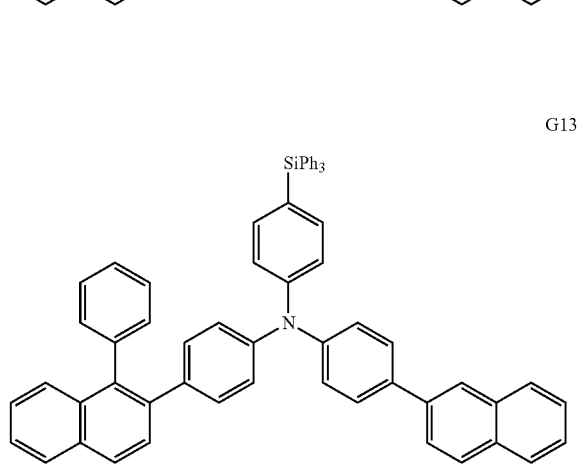

125
-continued
G17
G18
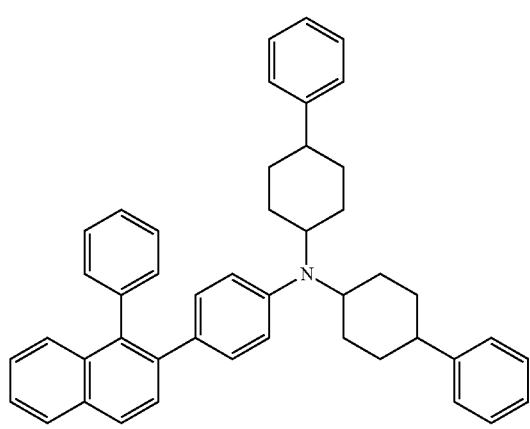
G19
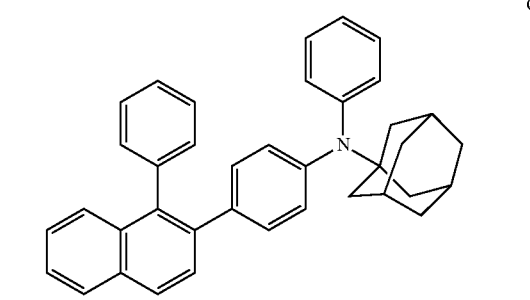
G20
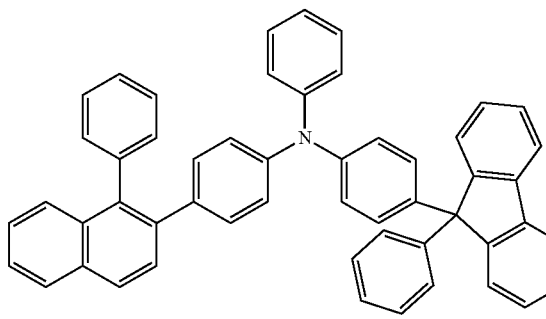
126
-continued
G21
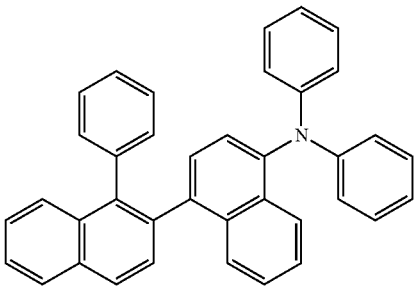
G22
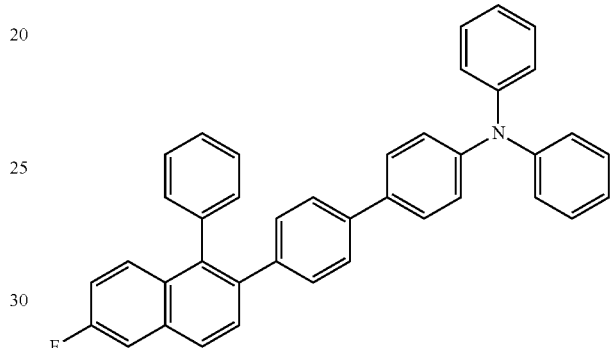
G23
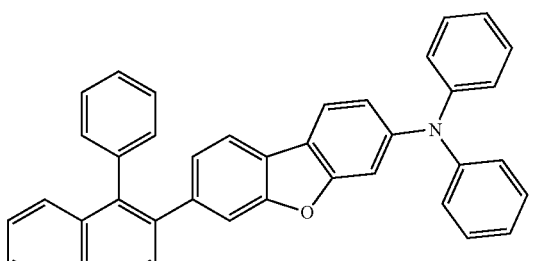
G24
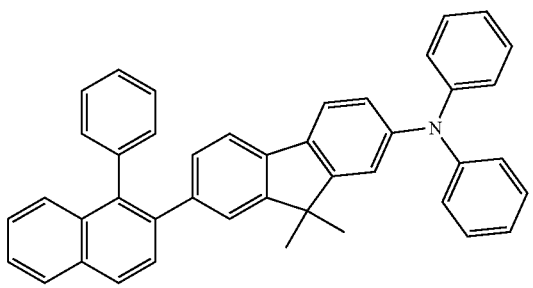

G25
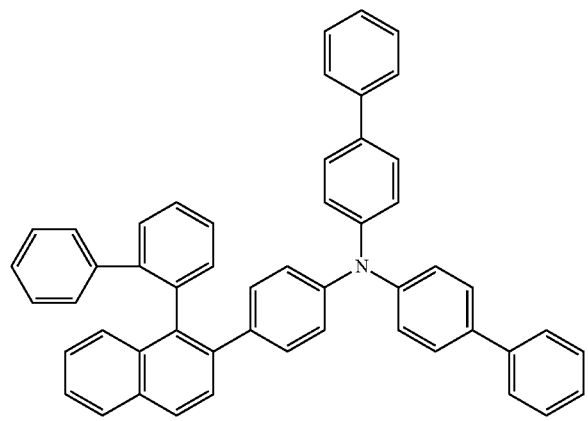
G26
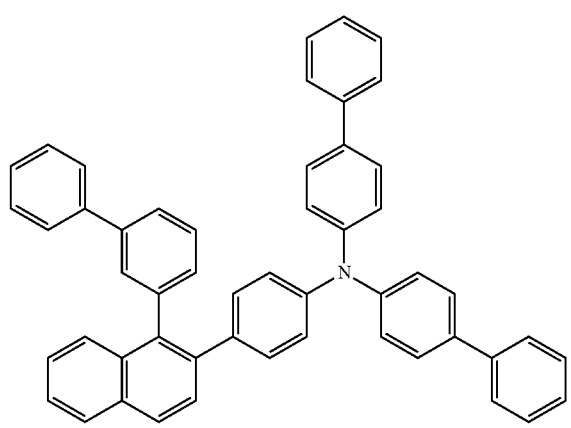
G27
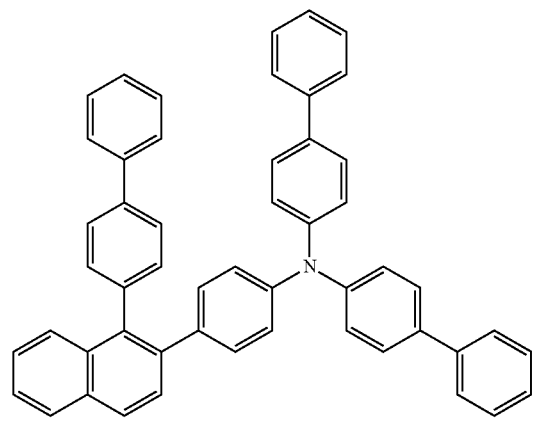
G28
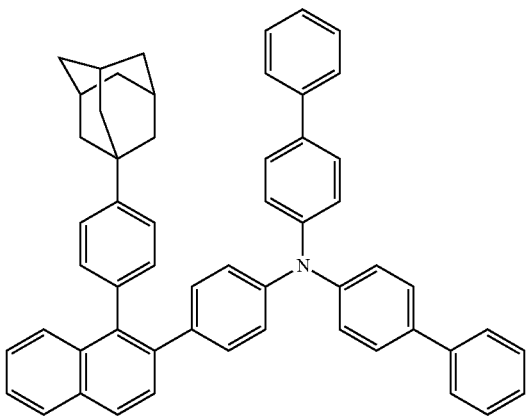
G29
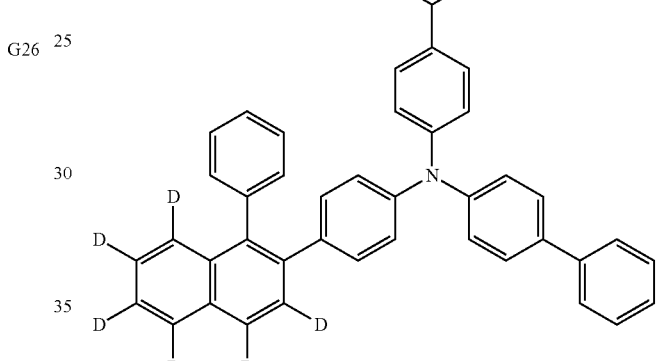
G30
G31
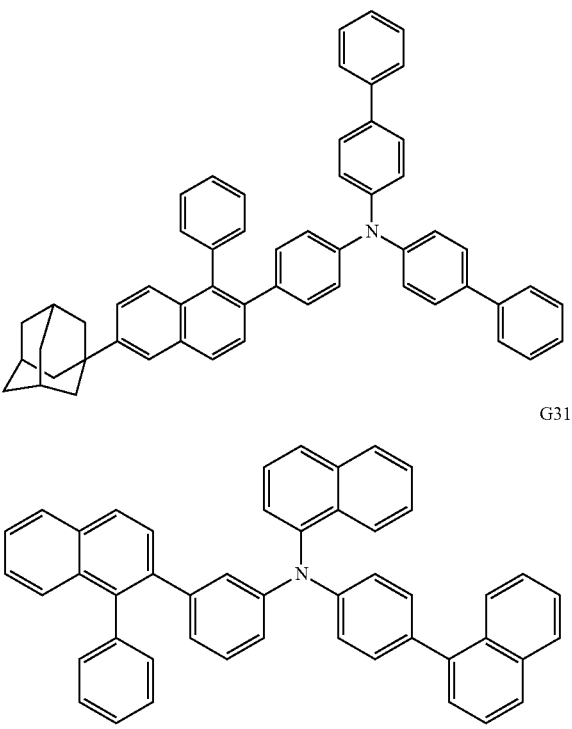

G32
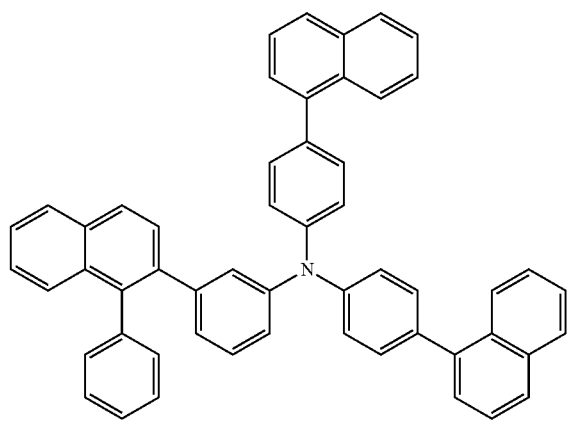
G35
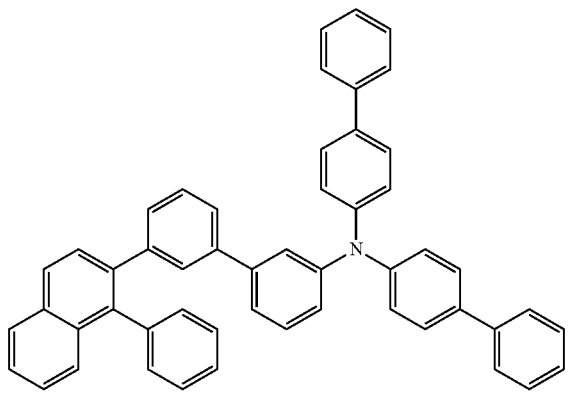
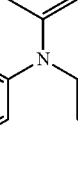
G33
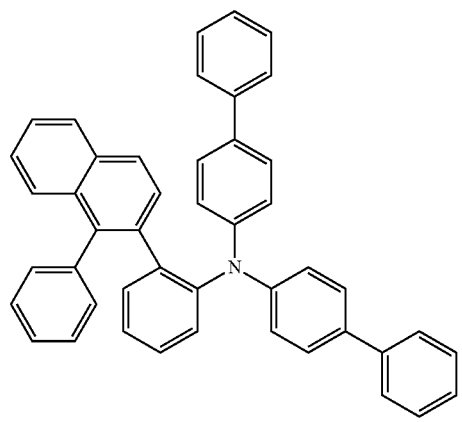
G36
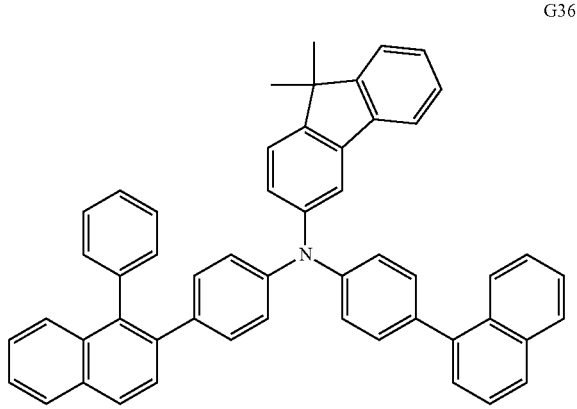
G34
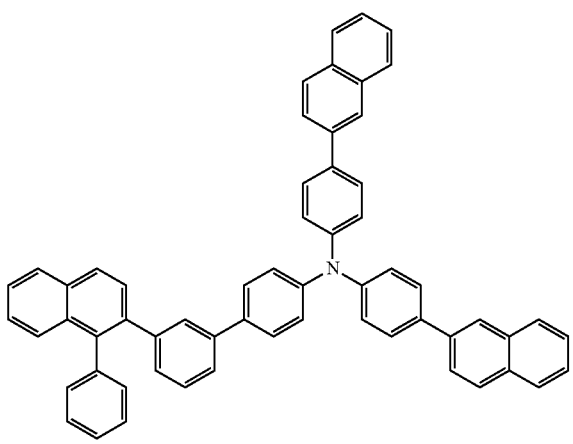
G37
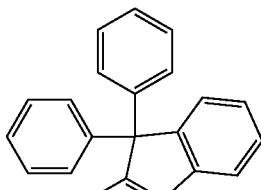
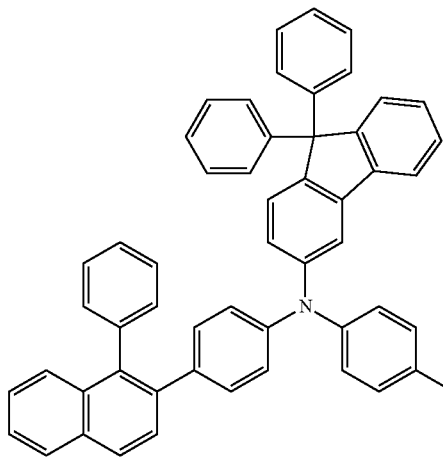

G38
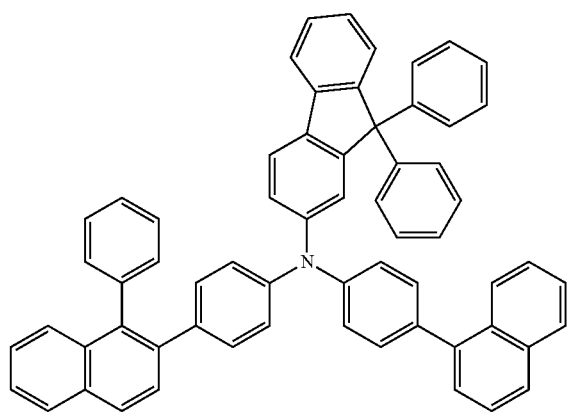
G39
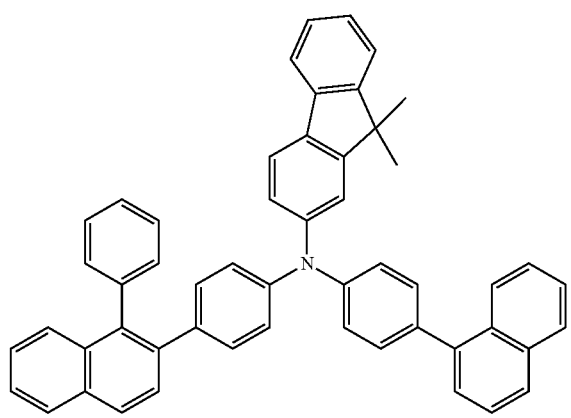
G40
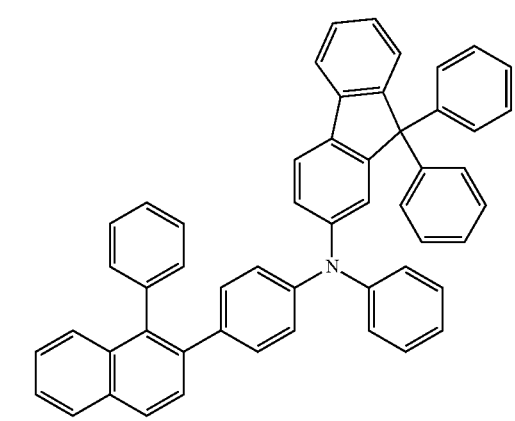
G41
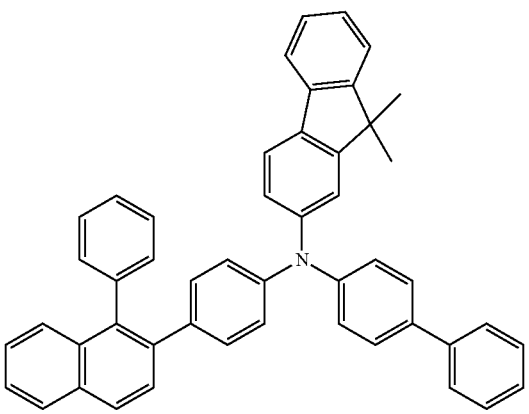
G42
G43
G44
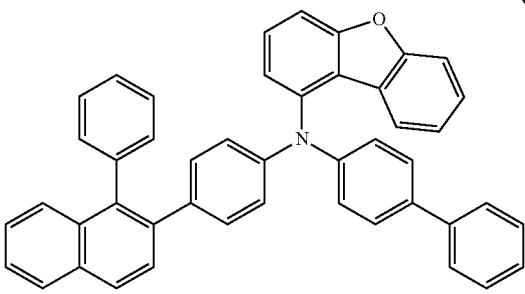

G45
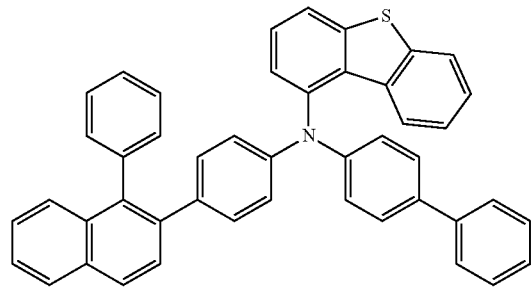
G46
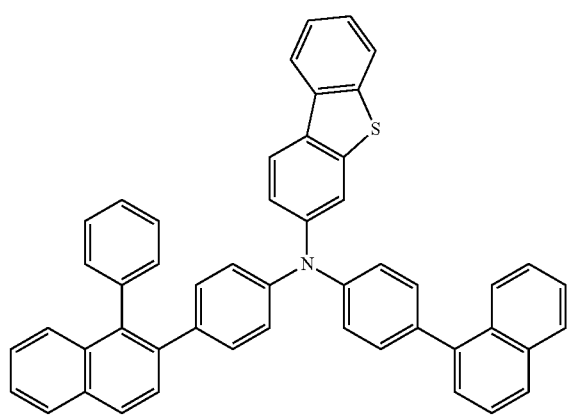
G47
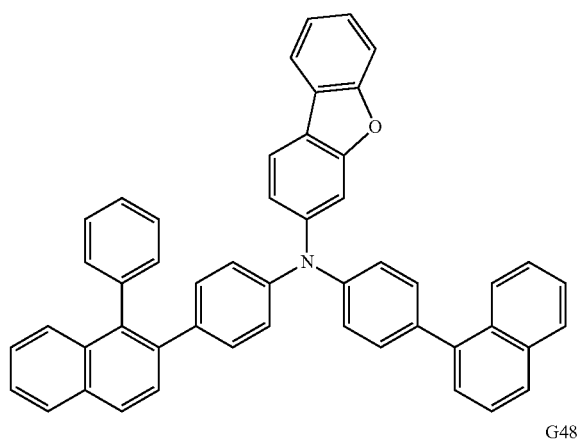
G48
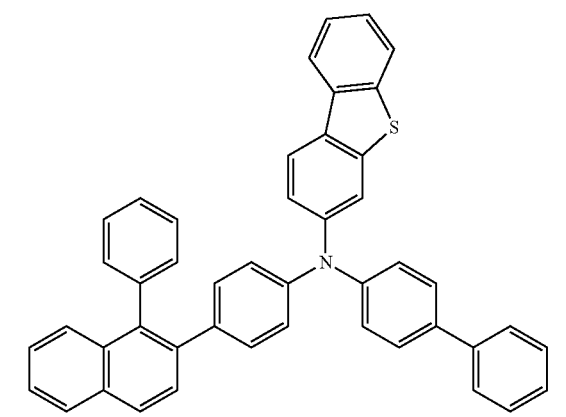
G49
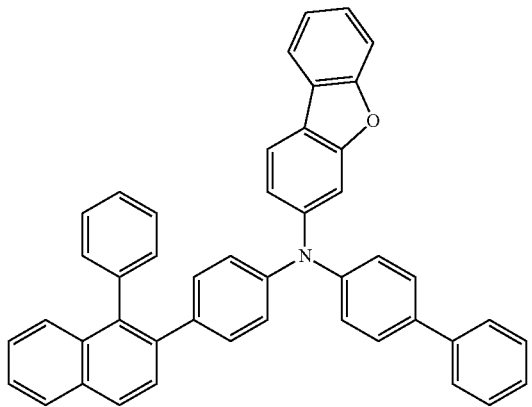
G50
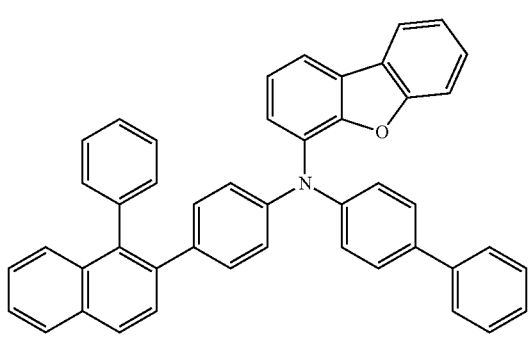
G51
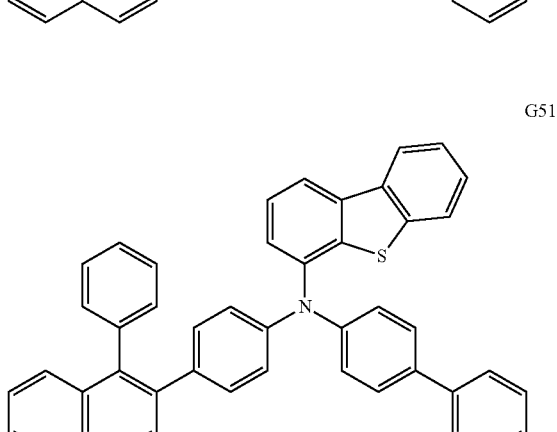
G52

G53
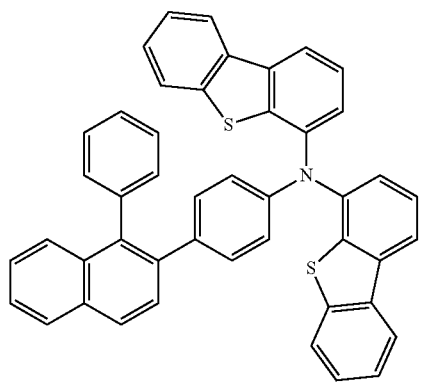
G56
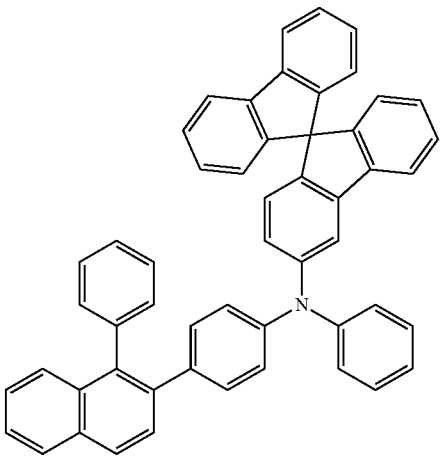
G54
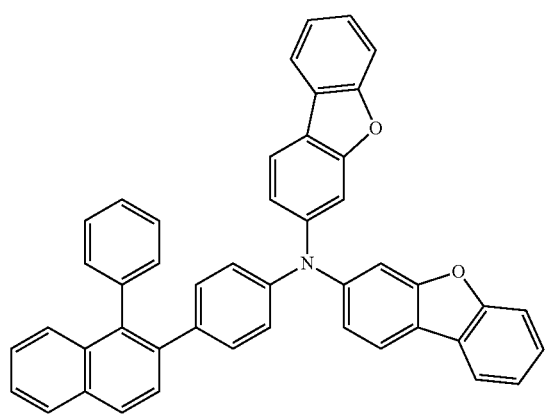
G57
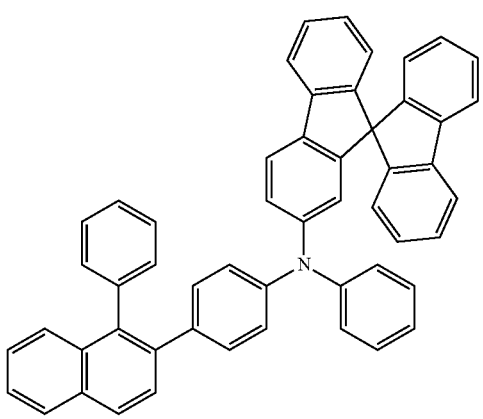
G55
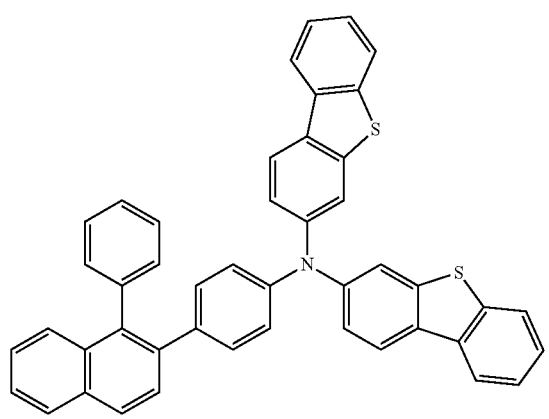
G58
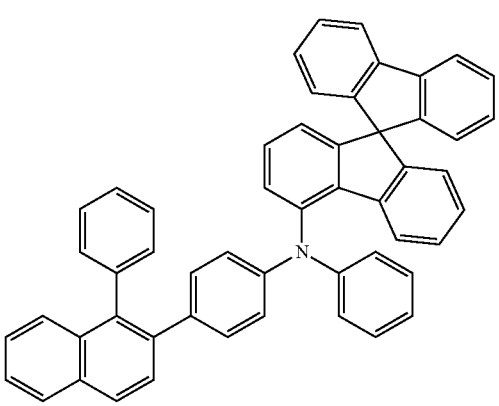

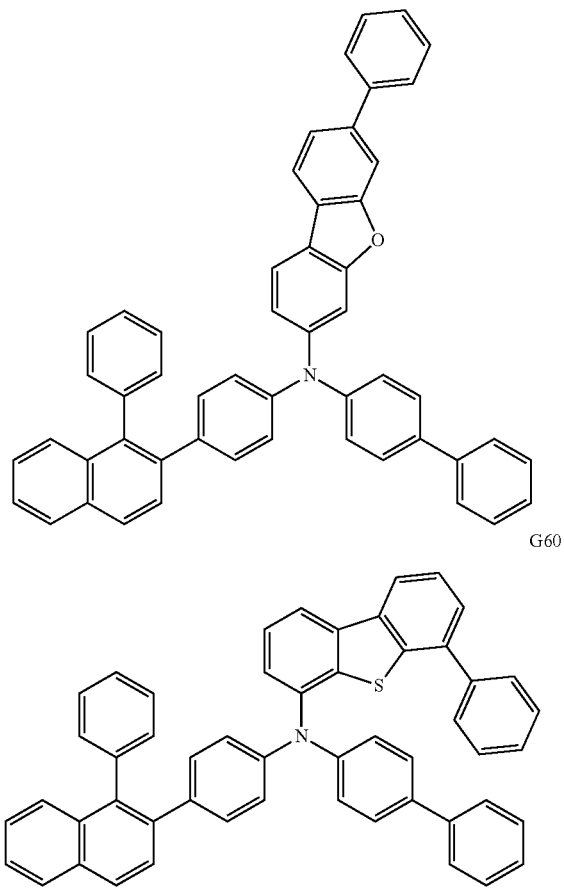

The monoamine compound according to an example embodiment includes may include a fused ring and a phenylnaphthyl group with a high thermal resistance and electric charge resistance, and may help to extend a device life when used as a material for an organic electroluminescence device. When used as a material for an organic electroluminescence device, the monoamine compound may enhance the quality of layers due to the bulky phenylnaphthyl group which decreases symmetry of molecule and inhibits crystallization, thereby contributing to securing high efficiency.

Hereinafter, an organic electroluminescence device according to an example embodiment will be explained, referring to FIGS. 1 to 3. The organic electroluminescence device according to an example embodiment includes the monoamine compound according to an example embodiment. For example, a hole transport region HTR includes the monoamine compound represented by Formula 1.

The following explanation will be mainly given with features different from the monoamine compound according to an example embodiment, and unexplained parts will follow the above description on the monoamine compound according to an example embodiment.

The first electrode EL1 has conductivity. The first electrode EL1 may be a pixel electrode or an anode. The first electrode EL1 may be a transmissive electrode, a transflective electrode, or a reflective electrode. In case the first electrode EL1 is the transmissive electrode, the first electrode EL1 may include a transparent metal oxide such as indium tin oxide (ITO), indium zinc oxide (IZO), zinc oxide (ZnO), or indium tin zinc oxide (ITZO). In case the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, or ITZO. For example, the first electrode EL1 may have a triple-layer structure of ITO/Ag/ITO.

The thickness of the first electrode EL1 may be from about 1,000 Å to about 10,000 Å, for example, from about 1,000 Å to about 3,000 Å.

The hole transport region HTR is on the first electrode EL1. The hole transport region HTR may include at least one of a hole injection layer HIL, a hole transport layer HTL, a hole buffer layer, or an electron blocking layer EBL.

The hole transport region HTR includes the monoamine compound according to an example embodiment, as described above.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1, without limitation.

As described above, the hole transport region HTR may have a multilayer structure having a plurality of layers, and a layer of the plurality of layers contacting the emission layer EML may include the monoamine compound represented by Formula 1. For example, the hole transport region HTR may include a hole injection layer HIL on the first electrode EL1, a hole transport layer HTL on the hole injection layer HIL, and an electron blocking layer EBL on the hole transport layer HTL, and the electron blocking layer EBL may include the monoamine compound represented by Formula 1. In another example, the hole transport region HTR may include a hole injection layer HIL and a hole transport layer HTL, and the hole transport layer HTL may include the monoamine compound represented by Formula 1.

The hole transport region HTR may include one or more of the monoamine compound represented by Formula 1. For example, the hole transport region HTR may include at least one selected from the group of compounds represented in the above-described Compound Groups 1 to 7.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

Furthermore, the hole transport region HTR may include the following materials in each layer.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4', 4"-tris(N,N-diphenylamino)triphenylamine (TDATA), 4,4', 4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPD), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include, for example, carbazole derivatives such as N-phenyl carbazole, polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(naphthalen-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The electron blocking layer EBL may include the monoamine compound represented by Formula 1, as described above. The electron blocking layer EBL may include a suitable material. The electron blocking layer EBL may include, for example, carbazole derivatives such as N-phenyl carbazole, polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(naphthalen-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD) or mCP, etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. In case the thicknesses of the hole transport region HTR, the hole injection layer HIL, the hole transport layer HTL and the electron blocking layer EBL satisfy the above-described ranges, satisfactory hole transport properties may be obtained without substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide and molybdenum oxide, without limitation.

As described above, the hole transport region HTR may further include at least one of a hole buffer layer or an electron blocking layer EBL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer EBL is a layer preventing electron injection from the electron transport region ETR into the hole transport region HTR.

The emission layer EML is on the hole transport region HTR. The thickness of the emission layer EML may be, for example, from about 100 Å to about 1,000 Å, or from about 100 Å to about 600 Å. The emission layer EML may have a single layer formed using a single material, a single layer formed using a plurality of different materials, or a multi-layer structure having a plurality of layers formed using a plurality of different materials.

A suitable emission material may be used as a material for the emission layer EML. The material for the emission layer EML may be selected from, for example, fluoranthene derivatives, pyrene derivatives, arylacetylene derivatives, anthracene derivatives, fluorene derivatives, perylene derivatives, chrysene derivatives, or the like, and preferably, from pyrene derivatives, perylene derivatives, or anthracene derivatives. For example, as the host material of the emission layer EML, anthracene derivatives represented by the following Formula 10 may be used.

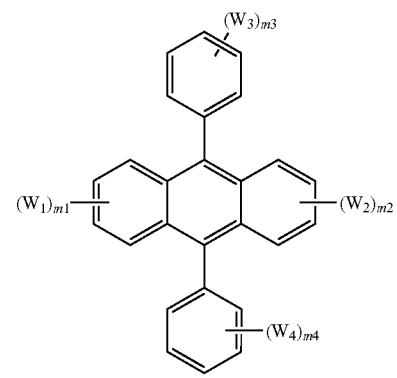

[Formula 10]

In Formula 10, $W_1$ to $W_4$ are each independently a hydrogen atom, a deuterium atom, a halogen atom, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, or may form a ring by combining adjacent groups with each other, $m_1$ and $m_2$ are each independently an integer of 0 to 4, and $m_3$ and $m_4$ are each independently an integer of 0 to 5.

When m1 is 1, $W_1$ may not be a hydrogen atom. When m2 is 1, $W_2$ may not be a hydrogen atom. When m3 is 1, $W_3$ may not be a hydrogen atom. When m4 is 1, $W_4$ may not be a hydrogen atom.

When m1 is an integer of 2 or more, a plurality of $W_1$ may be the same or different from each other. When m2 is an integer of 2 or more, a plurality of $W_2$ may be the same or different from each other. When m3 is an integer of 2 or more, a plurality of $W_3$ may be the same or different from each other. When m4 is an integer of 2 or more, a plurality of $W_4$ may be the same or different from each other.

The compound represented by Formula 10 may include the compounds represented by the following structures, for example.
a-1
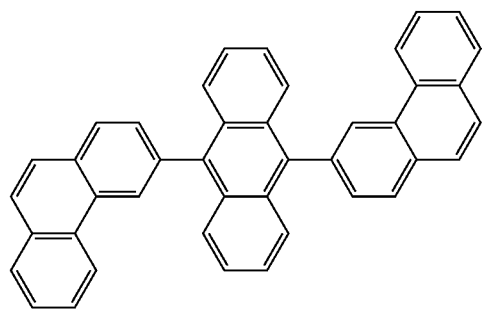
a-2
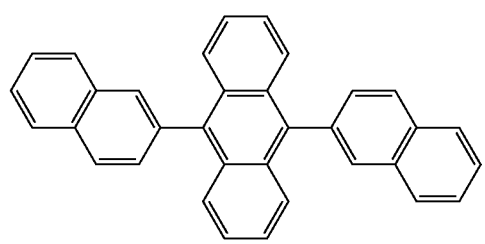
a-3
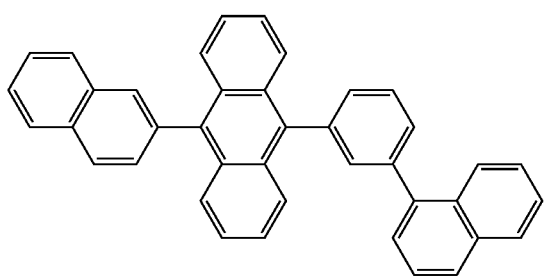
a-4
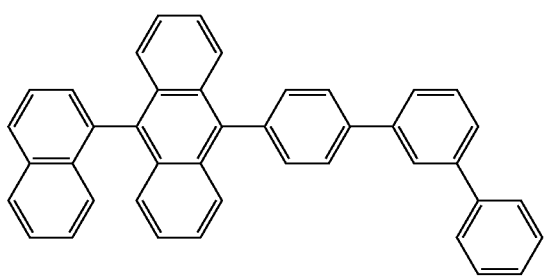
a-5
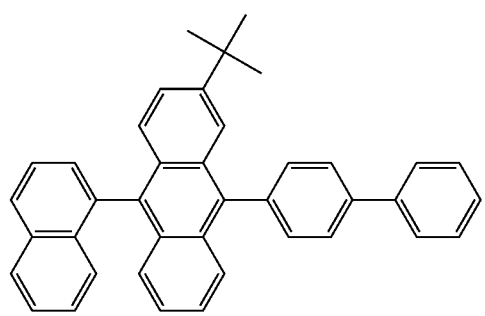
a-6
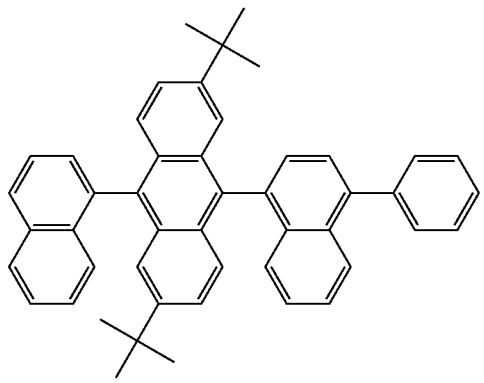
a-7
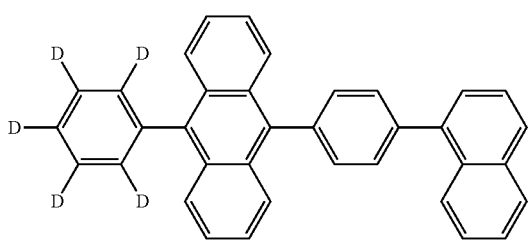
a-8
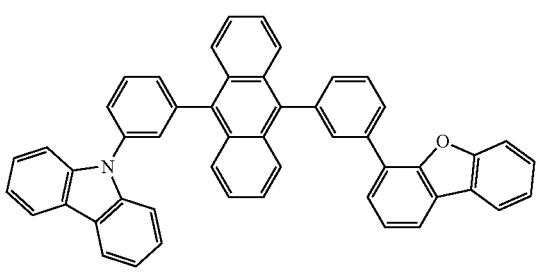
a-9
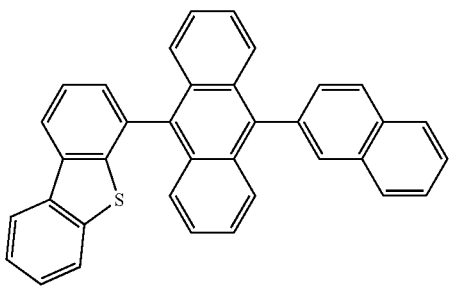
a-10
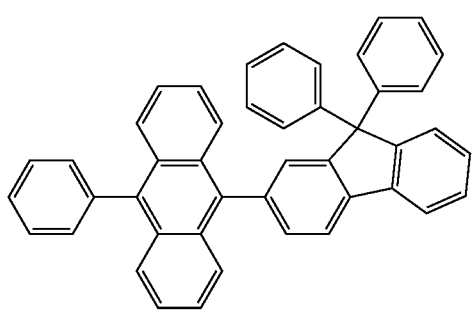

a-11 a-12

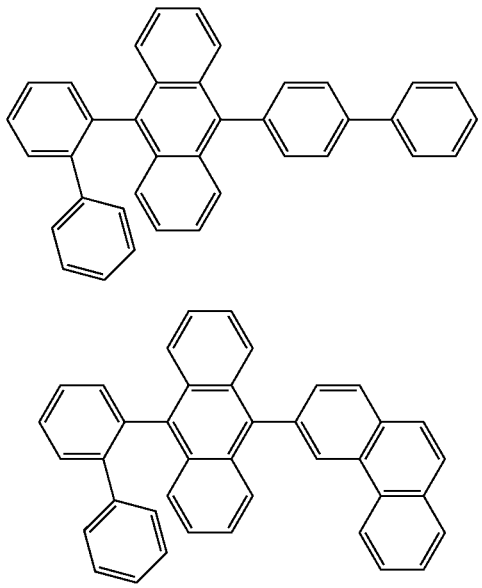

The emission layer EML may include a fluorescent material including any one selected from the group of spiro-DPVBi, 2,2',7,7'-tetrakis(biphenyl-4-yl)-9,9'-spirobifluorene(spiro-sexiphenyl) (spiro-6P), distyryl-benzene (DSB), distyryl-arylene (DSA), polyfluorene (PFO)-based polymer and poly(p-phenylene vinylene) (PPV)-based polymer, for example.

The emission layer EML may further include a dopant, and the dopant may be a suitable material. For example, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene, 1,6-bis(N,N-diphenylamino)pyrene), 2,5,8,11-tetra-t-butylperylene (TBP), 1,3,5-tris(N-phenylbenzimidazole-2-yl)benzene) (TPBi), etc., may be used as a dopant.

The emission layer EML may include, for example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc.

The electron transport region ETR is provided on the emission layer EML. The electron transport region ETR may include at least one of a hole blocking layer HBL, an electron transport layer ETL or an electron injection layer EIL, for example.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In addition, the electron transport region ETR may have a single layer structure having a plurality of different materials, or a laminated structure of electron transport layer ETL/electron injection layer EIL, or hole blocking layer HBL/electron transport layer ETL/electron injection layer EIL, laminated in order from the emission layer EML, without limitation. The thickness of the electron transport region ETR may be, for example, from about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In case the electron transport region ETR includes the electron transport layer ETL, the electron transport region ETR may include tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl] ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-Biphenyl-4-olato)aluminum (BAlq), beryllium bis(benzoquinolin-10-olate) ($Bebq_2$), 9,10-di(naphthalen-2-yl)anthracene (ADN), or a mixture thereof, for example. The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage.

When the electron transport region ETR includes the electron injection layer EIL, the electron transport region ETR may use LiF, lithium quinolate (LIQ), $Li_2O$, BaO, NaCl, CsF, a metal in lanthanides such as Yb, or a metal halide such as RbCl and RbI, without limitation. The electron injection layer EIL also may be formed using a mixture material of an electron transport material and an insulating organo metal salt. The organo metal salt may be a material having an energy band gap of about 4 eV or more. The organo metal salt may include, for example, a metal acetate, a metal benzoate, a metal acetoacetate, a metal acetylacetonate, or a metal stearate. The thickness of the electron injection layer EIL may be from about 1 Å to about 100 Å, for example, from about 3 Å to about 90 Å. In case the thickness of the electron injection layer EIL satisfies the above described range, satisfactory electron injection properties may be obtained without inducing the substantial increase of a driving voltage.

The electron transport region ETR may include a hole blocking layer HBL, as described above. The hole blocking layer HBL may include, for example, 2,9-dimethyl-4,7-diphenyl-1,10-phenanthroline (BCP), 4,7-diphenyl-1,10-phenanthroline (Bphen), or bis[2-(diphenylphosphino)phenyl]ether oxide (DPEPO), etc.

The second electrode EL2 is on the electron transport region ETR. The second electrode EL2 may be a common electrode or a cathode. The second electrode EL2 may be a transmissive electrode, a transflective electrode or a reflective electrode. In case the second electrode EL2 is the transmissive electrode, the second electrode EL2 may be formed using transparent metal oxides, for example, ITO, IZO, ZnO, ITZO, etc.

In case the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed using the above-described materials and a transparent conductive layer formed using ITO, IZO, ZnO, ITZO, etc.

The second electrode EL2 may be connected with an auxiliary electrode. In case the second electrode EL2 is connected with the auxiliary electrode, the resistance of the second electrode EL2 may decrease.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In case the organic electroluminescence device 10 is a top emission type, the first electrode EL1 may be a reflective electrode, and the second electrode EL2 may be a transmissive electrode or a transflective electrode. In case the organic electroluminescence device 10 is a bottom emission type, the first electrode EL1 may be a transmissive electrode or a transflective electrode, and the second electrode EL2 may be a reflective electrode.

The organic electroluminescence device 10 according to an example embodiment includes the monoamine compound represented by Formula 1, thereby securing high efficiency and a long device life, as well as a decreased driving voltage.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Examples

The monoamine compound according to an example embodiment may be synthesized, for example, as follows.

1. Synthesis of Compound A4

Compound A4, a monoamine compound according to an example embodiment may be synthesized, for example, as follows.

(Synthesis of Intermediate IM-1)

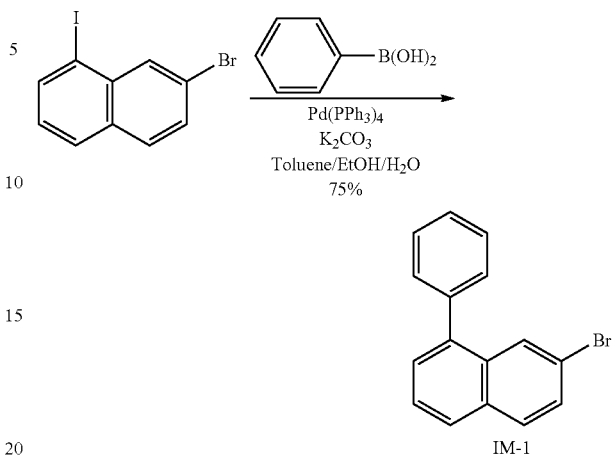

Under an Ar atmosphere, 7-bromo-1-iodonaphthalene (25.00 g, 75.1 mmol), phenylboronic acid (10.07 g, 1.1 equiv., 82.6 mmol), $K_2CO_3$ (31.13 g, 3.0 equiv., 225.2 mmol), Pd(PPh$_3$)$_4$ (4.34 g, 0.05 eq., 3.8 mmol), and a mixture solution of toluene/EtOH/H$_2$O (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-1 (15.95 g, yield 75%). Intermediate IM-1 was identified by measuring FAB-MS in which a molecular ion peak was observed at mass m/z=283.

(Synthesis of Intermediate IM-2)

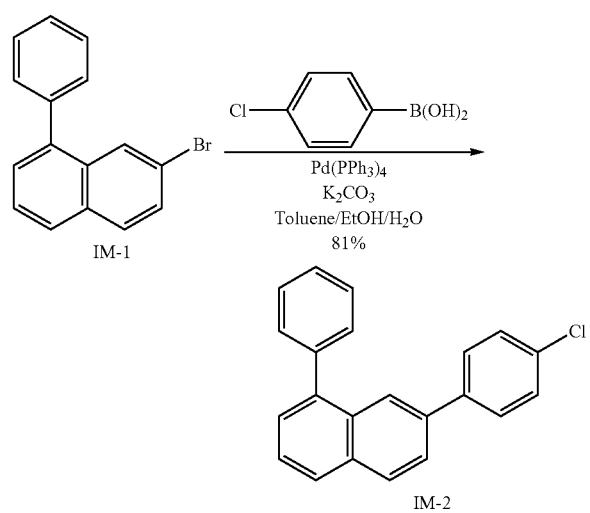

Under an Ar atmosphere, IM-1 (13.00 g, 45.9 mmol), 4-chlorophenylboronic acid (7.90 g, 1.1 equiv., 50.5 mmol), $K_2CO_3$ (19.04 g, 3.0 equiv., 60.7 mmol), Pd(PPh$_3$)$_4$ (2.65 g, 0.05 eq., 2.3 mmol), and a mixture solution of toluene/EtOH/H$_2$O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-2 (11.71 g, yield 81%). Intermediate IM-2 was identified by measuring FAB-MS in which a molecular ion peak was observed at mass m/z=314.

(Synthesis of Intermediate IM-3)

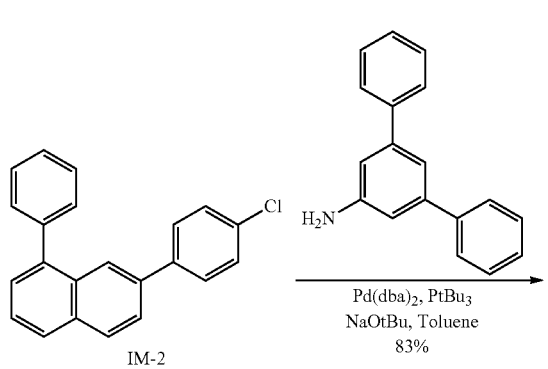

IM-2

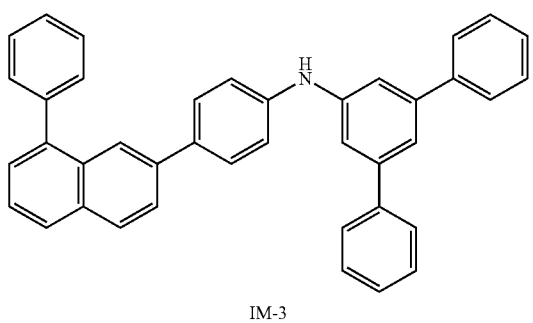

IM-3

Under an Ar atmosphere, IM-2 (10.00 g, 31.8 mmol), Pd(dba)$_2$ (0.55 g, 0.03 equiv., 1.0 mmol), NaOtBu (3.05 g, 1.0 equiv., 31.8 mmol), toluene (159 mL), 3,5-diphenylaniline (8.57 g, 1.1 equiv., 34.9 mmol) and tBu$_3$P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-3 (13.81 g, yield 83%). Intermediate IM-3 was identified by measuring FAB-MS in which a molecular ion peak was observed at mass m/z=523.

(Synthesis of Compound A4)

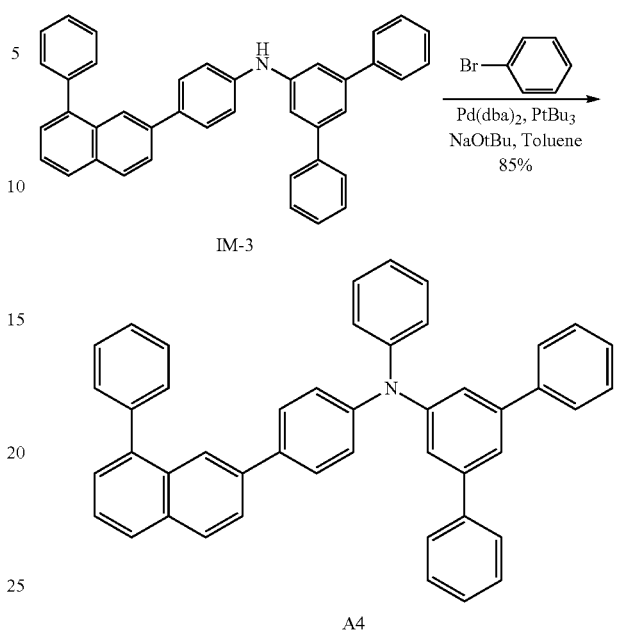

IM-3

A4

Under an Ar atmosphere, IM-3 (8.00 g, 15.3 mmol), Pd(dba)$_2$ (0.26 g, 0.03 equiv., 0.5 mmol), NaOtBu (2.94 g, 2.0 equiv., 30.6 mmol), toluene (76 mL), bromobenzene (2.64 g, 1.1 equiv., 16.8 mmol) and tBu$_3$P (0.31 g, 0.1 equiv., 1.5 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound A4 (7.79 g, yield 85%).

Compound A4 was identified by measuring FAB-MS in which a molecular ion peak was observed at mass m/z=599.

2. Synthesis of Compound A17

Compound A17, a monoamine compound according to an example embodiment may be synthesized, for example, as follows.

(Synthesis of Intermediate IM-4)

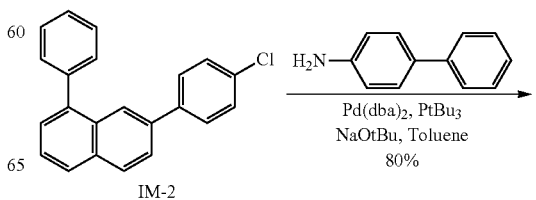

IM-2

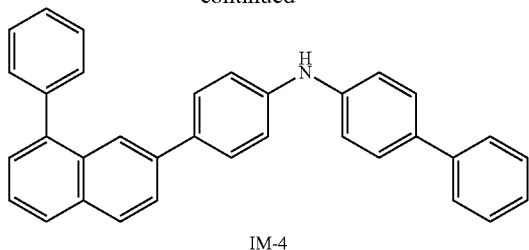

IM-4

Under an Ar atmosphere, IM-2 (10.00 g, 31.8 mmol), Pd(dba)₂ (0.55 g, 0.03 equiv., 1.0 mmol), NaOtBu (3.05 g, 1.0 equiv., 31.8 mmol), toluene (159 mL), p-biphenylamine (5.91 g, 1.1 equiv., 34.9 mmol) and tBu₃P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO₄. MgSO₄ was filtered out and organic layer was concentrated. The crude product thus obtained was purified by silica gel column chromatography (using a mixture of hexane and toluene as developing solvent) to obtain Intermediate IM-4 (11.37 g, yield 80%). Intermediate IM-4 was identified by measuring FAB-MS in which a molecular ion peak was observed at mass m/z=447.

(Synthesis of Compound A17)

Under an Ar atmosphere, IM-4 (8.00 g, 17.9 mmol), Pd(dba)₂ (0.31 g, 0.03 equiv., 0.5 mmol), NaOtBu (3.44 g, 2.0 equiv., 35.7 mmol), toluene (89 mL), 3-bromo-9-phenyl-9H-carbazole (6.33 g, 1.1 equiv., 19.7 mmol) and tBu₃P (0.36 g, 0.1 equiv., 1.8 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO₄. MgSO₄ was filtered out and organic layer was concentrated. The crude product thus obtained was purified by silica gel column chromatography (using a mixture of hexane and toluene as developing solvent) to obtain Compound A17 (9.23 g, yield 75%). Compound A17 was identified by measuring FAB-MS in which a molecular ion peak was observed at mass m/z=688.

3. Synthesis of Compound B13

Compound B13, a monoamine compound according to an example embodiment may be synthesized, for example, as follows.

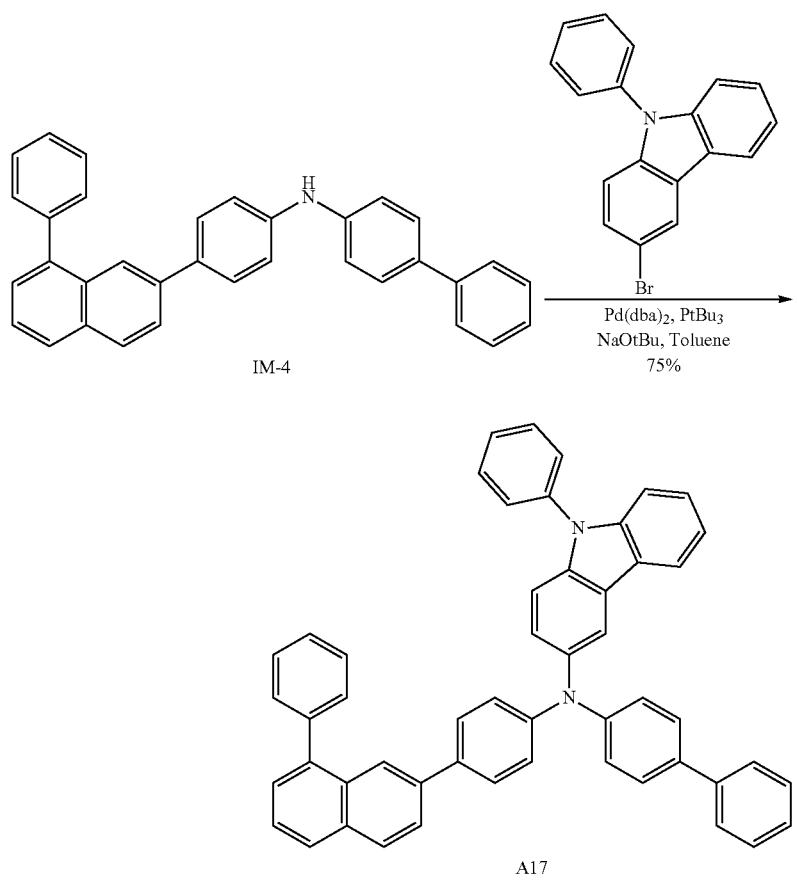

(Synthesis of Intermediate IM-5)

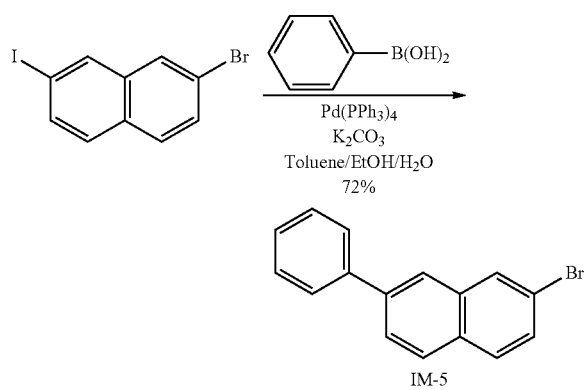

Under an Ar atmosphere, 7-bromo-2-iodonaphthalene (25.00 g, 75.1 mmol), phenylboronic acid (10.07 g, 1.1 equiv., 82.6 mmol), K$_2$CO$_3$ (31.13 g, 3.0 equiv., 225.2 mmol), Pd(PPh$_3$)$_4$ (4.34 g, 0.05 eq., 3.8 mmol), and a mixture solution of toluene/EtOH/H$_2$O (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-5 (15.31 g, yield 72%). Intermediate IM-5 was identified by measuring FAB-MS in which a molecular ion peak was observed at mass m/z=283.

(Synthesis of Intermediate IM-6)

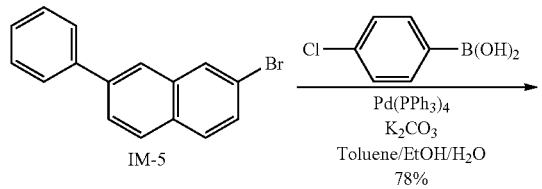

Under an Ar atmosphere, IM-5 (13.00 g, 45.9 mmol), 4-chlorophenylboronic acid (7.90 g, 1.1 equiv., 50.5 mmol), K$_2$CO$_3$ (19.04 g, 3.0 equiv., 60.7 mmol), Pd(PPh$_3$)$_4$ (2.65 g, 0.05 eq., 2.3 mmol), and a mixture solution of toluene/EtOH/H$_2$O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-6 (11.27 g, yield 78%). Intermediate IM-6 was identified by measuring FAB-MS in which a molecular ion peak was observed at mass m/z=314.

(Synthesis of Intermediate IM-7)

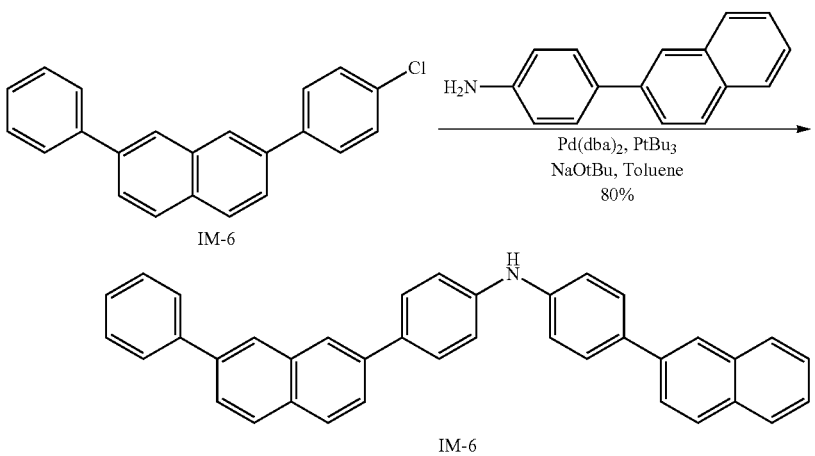

Under an Ar atmosphere, IM-6 (10.00 g, 31.8 mmol), Pd(dba)$_2$ (0.55 g, 0.03 equiv., 1.0 mmol), NaOtBu (3.05 g, 1.0 equiv., 31.8 mmol), toluene (159 mL), 4-(naphthalen-2-yl)aniline (7.66 g, 1.1 equiv., 34.9 mmol) and tBu$_3$P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-7 (12.65 g, yield 80%). Intermediate IM-7 was identified by measuring FAB-MS in which a molecular ion peak was observed at mass m/z=497.

(Synthesis of Compound B13)

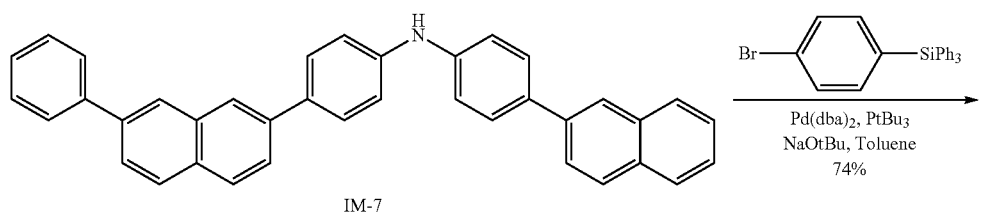

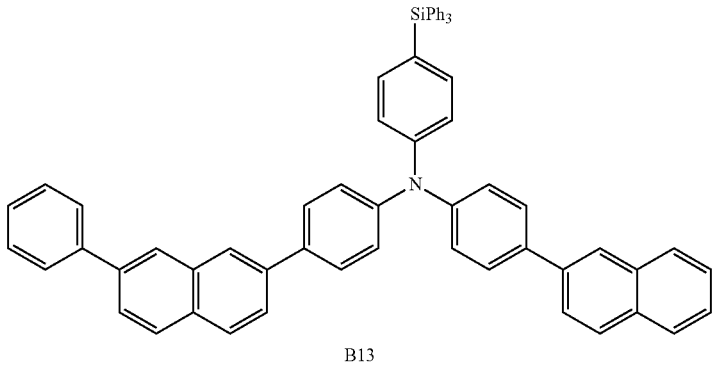

Under an Ar atmosphere, IM-7 (8.00 g, 16.1 mmol), Pd(dba)$_2$ (0.27 g, 0.03 equiv., 0.5 mmol), NaOtBu (3.09 g, 2.0 equiv., 32.2 mmol), toluene (80 mL), 1-bromo-4-triphenylsilylbenzene (7.35 g, 1.1 equiv., 17.7 mmol) and tBu$_3$P (0.33 g, 0.1 equiv., 1.6 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound B13 (9.90 g, yield 74%). Compound B13 was identified by measuring FAB-MS in which a molecular ion peak was observed at mass m/z=832.

4. Synthesis of Compound B20

Compound B20, a monoamine compound according to an example embodiment may be synthesized, for example, as follows.

(Synthesis of Intermediate IM-8)

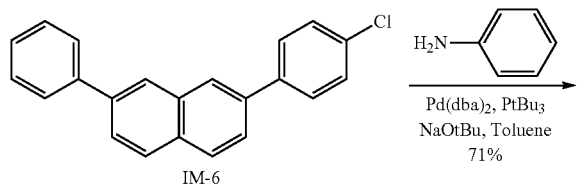

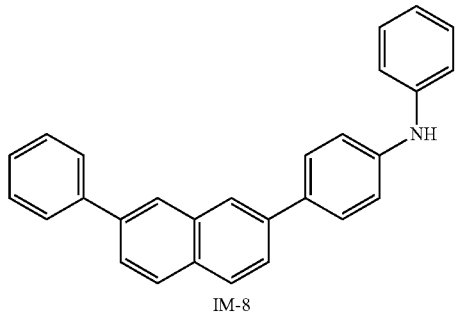

Under an Ar atmosphere, IM-6 (10.00 g, 31.8 mmol), Pd(dba)$_2$ (0.55 g, 0.03 equiv., 1.0 mmol), NaOtBu (3.05 g, 1.0 equiv., 31.8 mmol), toluene (159 mL), aniline (3.25 g, 1.1 equiv., 34.9 mmol) and tBu$_3$P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-8 (8.38 g, yield 71%). Intermediate IM-8 was identified by measuring FAB-MS in which a molecular ion peak was observed at mass m/z=371.

155

(Synthesis of Compound B20)

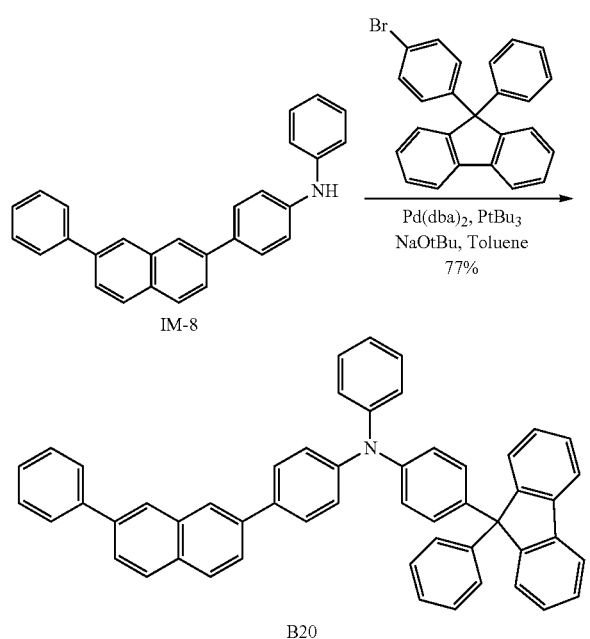

Under an Ar atmosphere, IM-8 (8.00 g, 21.5 mmol), Pd(dba)₂ (0.37 g, 0.03 equiv., 0.6 mmol), NaOtBu (4.14 g, 2.0 equiv., 43.1 mmol), toluene (108 mL), 9-(4-bromophenyl)-9-phenyl-9H-fluorene (9.41 g, 1.1 equiv., 23.7 mmol) and tBu₃P (0.44 g, 0.1 equiv., 2.1 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO₄. MgSO₄ was filtered out and organic layer was concentrated. The crude product thus obtained was purified by silica gel column chromatography (using a mixture of hexane and toluene as developing solvent) to obtain Compound B20 (11.41 g, yield 77%). Compound B20 was identified by measuring FAB-MS in which a molecular ion peak was observed at mass m/z=687.

5. Synthesis of Compound B40

Compound B40, a monoamine compound according to an example embodiment may be synthesized, for example, as follows.

(Synthesis of Compound B40)

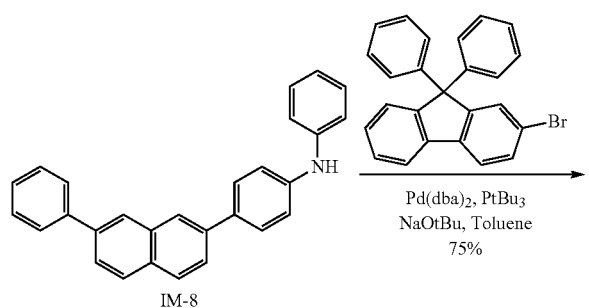

156

-continued

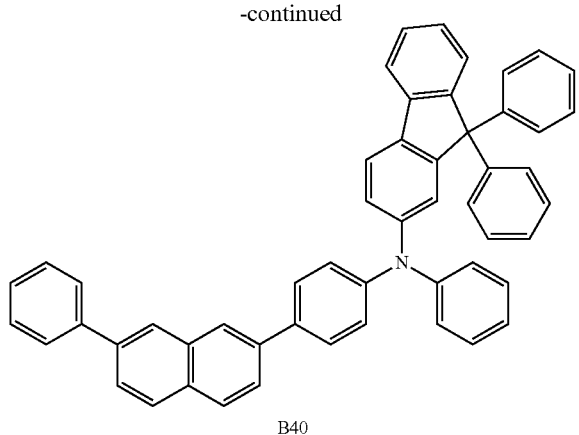

Under an Ar atmosphere, IM-8 (8.00 g, 21.5 mmol), Pd(dba)₂ (0.37 g, 0.03 equiv., 0.6 mmol), NaOtBu (4.14 g, 2.0 equiv., 43.1 mmol), toluene (108 mL), 2-bromo-9,9-diphenyl-9H-fluorene (9.41 g, 1.1 equiv., 23.7 mmol) and tBu₃P (0.44 g, 0.1 equiv., 2.1 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO₄. MgSO₄ was filtered out and organic layer was concentrated. The crude product thus obtained was purified by silica gel column chromatography (using a mixture of hexane and toluene as developing solvent) to obtain Compound B40 (11.42 g, yield 75%). Compound B40 was identified by measuring FAB-MS in which a molecular ion peak was observed at mass m/z=687.

6. Synthesis of Compound C25

Compound C25, a monoamine compound according to an example embodiment may be synthesized, for example, as follows.

(Synthesis of Intermediate IM-9)

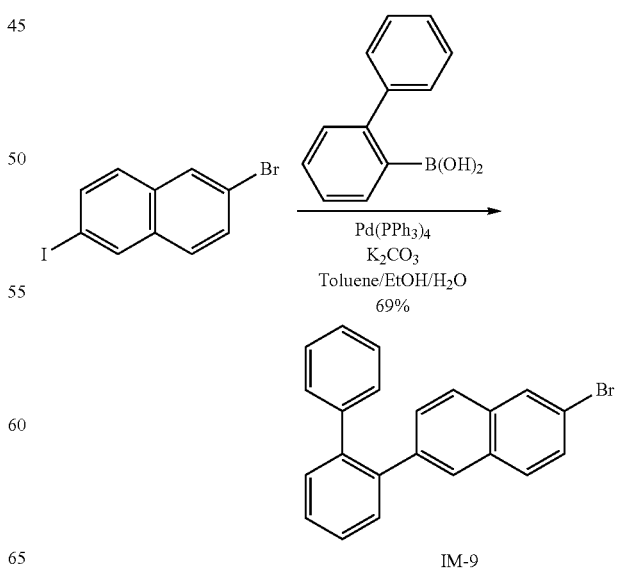

Under an Ar atmosphere, 2-bromo-6-iodonaphthalene (25.00 g, 75.1 mmol), 2-biphenylboronic acid (16.35 g, 1.1 equiv., 82.6 mmol), $K_2CO_3$ (31.13 g, 3.0 equiv., 225.2 mmol), $Pd(PPh_3)_4$ (4.34 g, 0.05 eq., 3.8 mmol), and a mixture solution of toluene/EtOH/$H_2O$ (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over $MgSO_4$. $MgSO_4$ was filtered out and organic layer was concentrated. The crude product thus obtained was purified by silica gel column chromatography (using a mixture of hexane and toluene as developing solvent) to obtain Intermediate IM-9 (18.61 g, yield 69%). Intermediate IM-9 was identified by measuring FAB-MS in which a molecular ion peak was observed at mass m/z=359.

(Synthesis of Intermediate IM-10)

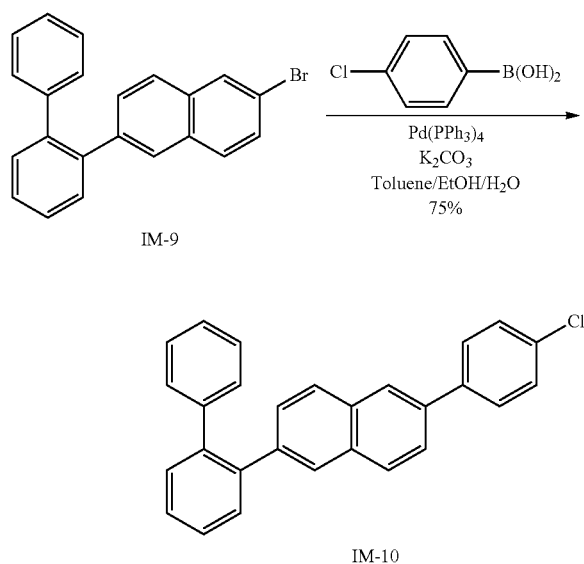

IM-9

IM-10

Under an Ar atmosphere, IM-9 (15.00 g, 41.8 mmol), 4-chlorophenylboronic acid (7.18 g, 1.1 equiv., 45.9 mmol), $K_2CO_3$ (17.31 g, 3.0 equiv., 125.3 mmol), $Pd(PPh_3)_4$ (2.41 g, 0.05 eq., 3.8 mmol), and a mixture solution of toluene/EtOH/$H_2O$ (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over $MgSO_4$. $MgSO_4$ was filtered out and organic layer was concentrated. The crude product thus obtained was purified by silica gel column chromatography (using a mixture of hexane and toluene as developing solvent) to obtain Intermediate IM-10 (12.24 g, yield 75%). Intermediate IM-10 was identified by measuring FAB-MS in which a molecular ion peak was observed at mass m/z=390.

(Synthesis of Compound C25)

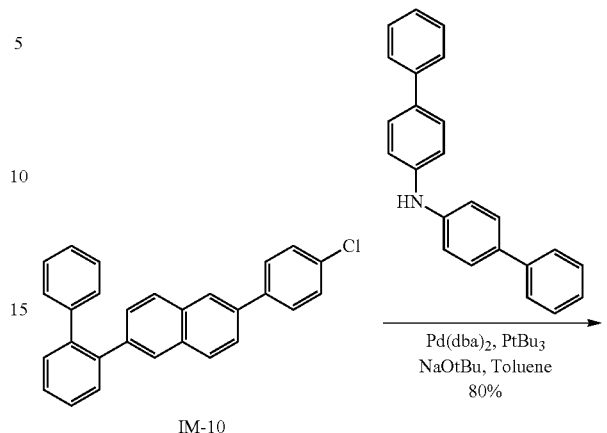

IM-10

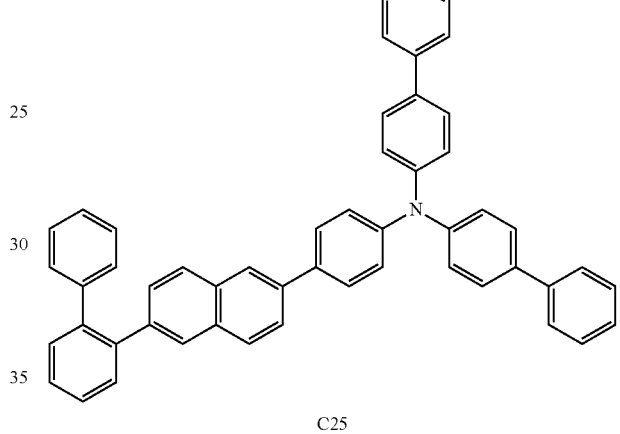

C25

Under an Ar atmosphere, IM-10 (10.00 g, 25.6 mmol), $Pd(dba)_2$ (0.44 g, 0.03 equiv., 0.6 mmol), NaOtBu (4.92 g, 2.0 equiv., 51.2 mmol), toluene (128 mL), bis(4-biphenyl)amine (9.04 g, 1.1 equiv., 28.1 mmol) and $tBu_3P$ (0.52 g, 0.1 equiv., 2.6 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over $MgSO_4$. $MgSO_4$ was filtered out and organic layer was concentrated. The crude product thus obtained was purified by silica gel column chromatography (using a mixture of hexane and toluene as developing solvent) to obtain Compound C25 (13.83 g, yield 80%). Compound C25 was identified by measuring FAB-MS in which a molecular ion peak was observed at mass m/z=675.

7. Synthesis of Compound C51

Compound C51, a monoamine compound according to an example embodiment may be synthesized, for example, as follows.

(Synthesis of Intermediate IM-11)

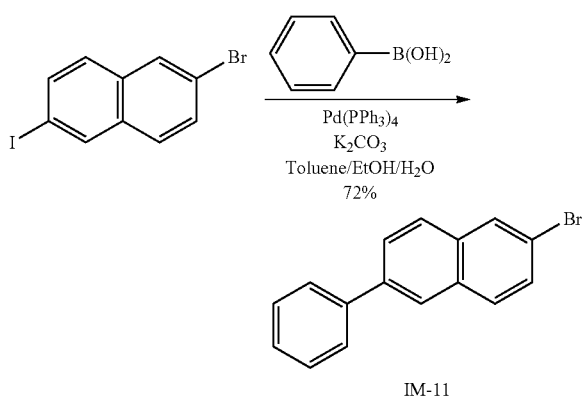

IM-11

Under an Ar atmosphere, 2-bromo-6-iodonaphthalene (25.00 g, 75.1 mmol), phenylboronic acid (10.07 g, 1.1 equiv., 82.6 mmol), K$_2$CO$_3$ (31.13 g, 3.0 equiv., 225.2 mmol), Pd(PPh$_3$)$_4$ (4.34 g, 0.05 eq., 3.8 mmol), and a mixture solution of toluene/EtOH/H$_2$O (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-11 (15.31 g, yield 72%). Intermediate IM-11 was identified by measuring FAB-MS in which a molecular ion peak was observed at mass m/z=283.

(Synthesis of Intermediate IM-12)

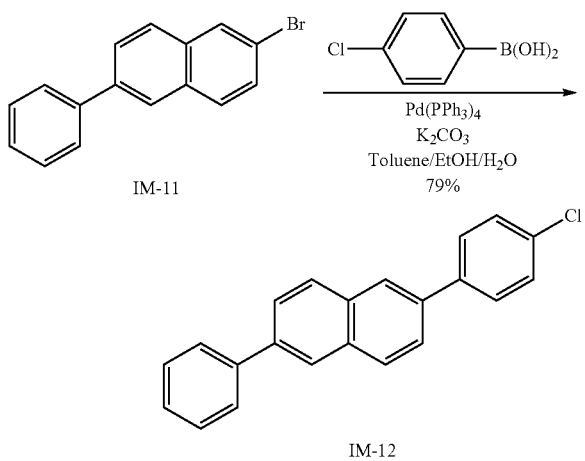

IM-12

Under an Ar atmosphere, IM-11 (13.00 g, 45.9 mmol), 4-chlorophenylboronic acid (7.90 g, 1.1 equiv., 50.5 mmol), K$_2$CO$_3$ (19.04 g, 3.0 equiv., 60.7 mmol), Pd(PPh$_3$)$_4$ (2.65 g, 0.05 eq., 2.3 mmol), and a mixture solution of toluene/ EtOH/H$_2$O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-12 (11.42 g, yield 79%).

Intermediate IM-12 was identified by measuring FAB-MS in which a molecular ion peak was observed at mass m/z=314.

(Synthesis of Compound C51)

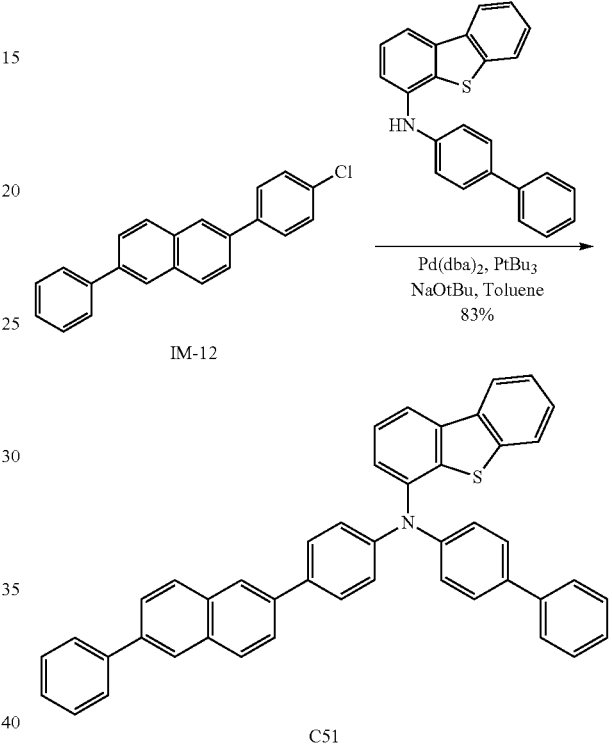

C51

Under an Ar atmosphere, IM-12 (8.00 g, 25.4 mmol), Pd(dba)$_2$ (0.44 g, 0.03 equiv., 0.8 mmol), NaOtBu (4.88 g, 2.0 equiv., 50.8 mmol), toluene (128 mL), N-([1,1'-biphenyl]-4-yl)dibenzothiophen-4-amine (9.82 g, 1.1 equiv., 28.0 mmol) and tBu$_3$P (0.51 g, 0.1 equiv., 2.5 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound C51 (13.28 g, yield 83%). Compound C51 was identified by measuring FAB-MS in which a molecular ion peak was observed at mass m/z=629.

8. Synthesis of Compound D12

Compound D12, a monoamine compound according to an example embodiment may be synthesized, for example, as follows.

(Synthesis of Intermediate IM-13)

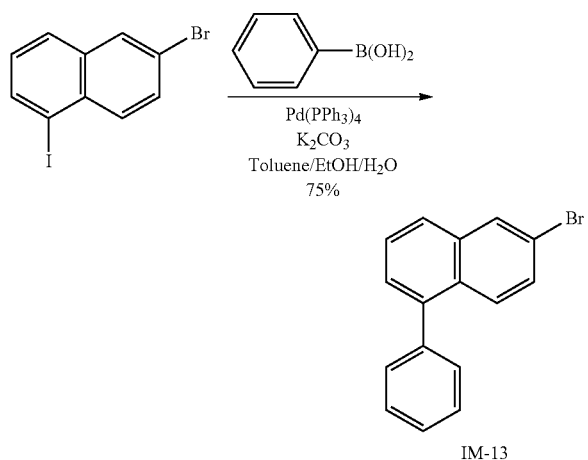

IM-13

Under an Ar atmosphere, 2-bromo-5-iodonaphthalene (25.00 g, 75.1 mmol), phenylboronic acid (10.07 g, 1.1 equiv., 82.6 mmol), K₂CO₃ (31.13 g, 3.0 equiv., 225.2 mmol), Pd(PPh₃)₄ (4.34 g, 0.05 eq., 3.8 mmol), and a mixture solution of toluene/EtOH/H₂O (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO₄. MgSO₄ was filtered out and organic layer was concentrated. The crude product thus obtained was purified by silica gel column chromatography (using a mixture of hexane and toluene as developing solvent) to obtain Intermediate IM-13 (15.95 g, yield 75%).

Intermediate IM-13 was identified by measuring FAB-MS in which a molecular ion peak was observed at mass m/z=283.

(Synthesis of Intermediate IM-14)

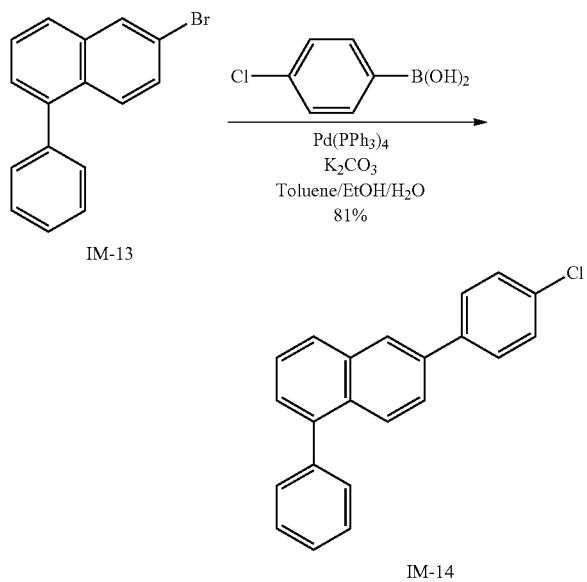

IM-14

Under an Ar atmosphere, IM-13 (13.00 g, 45.9 mmol), 4-chlorophenylboronic acid (7.90 g, 1.1 equiv., 50.5 mmol), K₂CO₃ (19.04 g, 3.0 equiv., 60.7 mmol), Pd(PPh₃)₄ (2.65 g, 0.05 eq., 2.3 mmol), and a mixture solution of toluene/EtOH/H₂O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO₄. MgSO₄ was filtered out and organic layer was concentrated. The crude product thus obtained was purified by silica gel column chromatography (using a mixture of hexane and toluene as developing solvent) to obtain Intermediate IM-14 (11.71 g, yield 81%). Intermediate IM-14 was identified by measuring FAB-MS in which a molecular ion peak was observed at mass m/z=314.

(Synthesis of Compound D12)

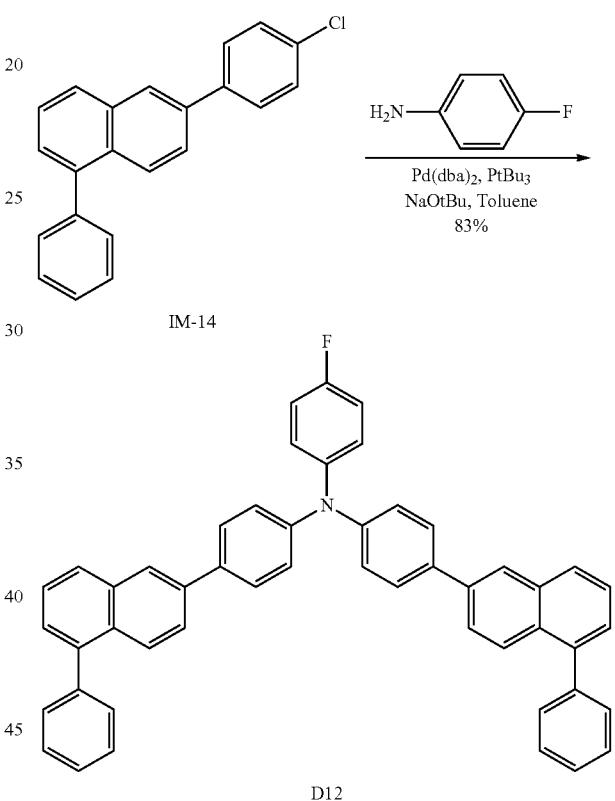

D12

Under an Ar atmosphere, IM-14 (9.35 g, 2.2 equiv., 29.7 mmol), Pd(dba)₂ (0.23 g, 0.03 equiv., 0.4 mmol), NaOtBu (2.59 g, 2.0 equiv., 27.0 mmol), toluene (67 mL), 4-fluoroaniline (1.5 g, 13.5 mmol) and tBu₃P (0.27 g, 0.1 equiv., 1.3 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO₄. MgSO₄ was filtered out and organic layer was concentrated. The crude product thus obtained was purified by silica gel column chromatography (using a mixture of hexane and toluene as developing solvent) to obtain Compound D12 (7.48 g, yield 83%).

Compound D12 was identified by measuring FAB-MS in which a molecular ion peak was observed at mass m/z=667.

9. Synthesis of Compound D22

Compound D22, a monoamine compound according to an example embodiment may be synthesized, for example, as follows.

(Synthesis of Compound D22)

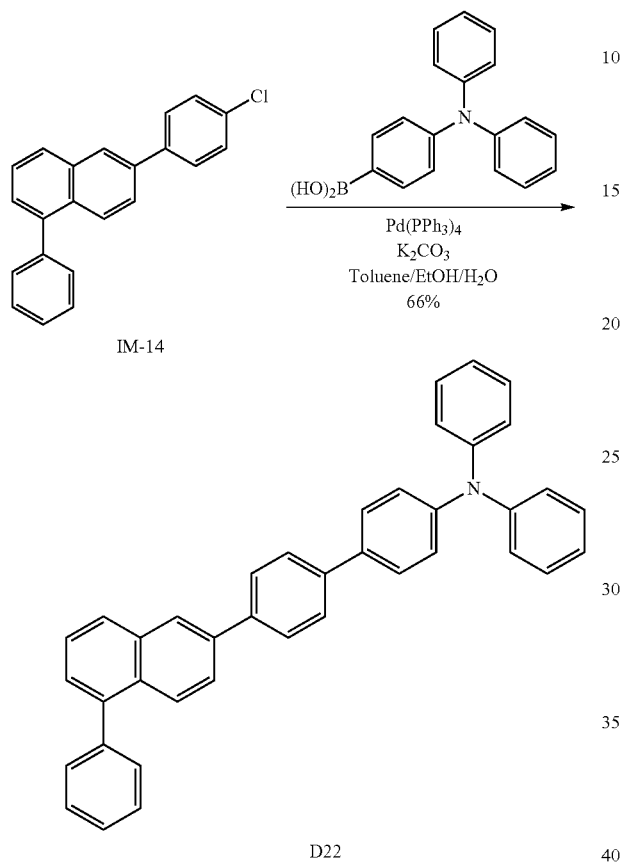

Under an Ar atmosphere, IM-14 (10.00 g, 31.8 mmol), (4-(diphenylamino)phenyl)boronic acid (10.10 g, 1.1 equiv., 34.9 mmol), K$_2$CO$_3$ (13.17 g, 3.0 equiv., 95.3 mmol), Pd(PPh$_3$)$_4$ (1.84 g, 0.05 eq., 1.6 mmol), and a mixture solution of toluene/EtOH/H$_2$O (4/2/1) (222 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound D22 (10.98 g, yield 66%).

Compound D22 was identified by measuring FAB-MS in which a molecular ion peak was observed at mass m/z=523.

10. Synthesis of Compound E3

Compound E3, a monoamine compound according to an example embodiment may be synthesized, for example, as follows.

(Synthesis of Intermediate IM-15)

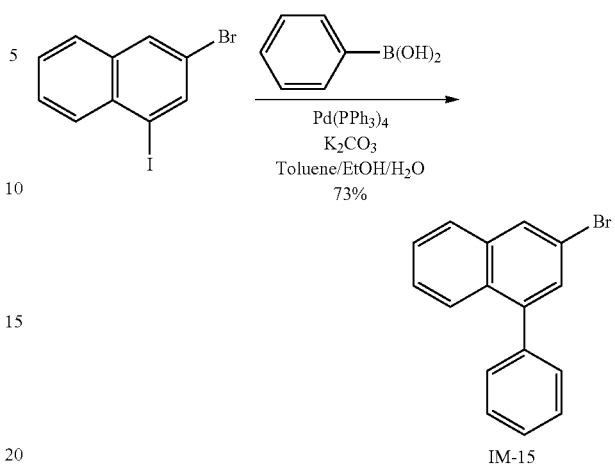

Under an Ar atmosphere, 3-bromo-1-iodonaphthalene (25.00 g, 75.1 mmol), phenylboronic acid (10.07 g, 1.1 equiv., 82.6 mmol), K$_2$CO$_3$ (31.13 g, 3.0 equiv., 225.2 mmol), Pd(PPh$_3$)$_4$ (4.34 g, 0.05 eq., 3.8 mmol), and a mixture solution of toluene/EtOH/H$_2$O (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-15 (15.52 g, yield 73%).

Intermediate IM-15 was identified by measuring FAB-MS in which a molecular ion peak was observed at mass m/z=283.

(Synthesis of Intermediate IM-16)

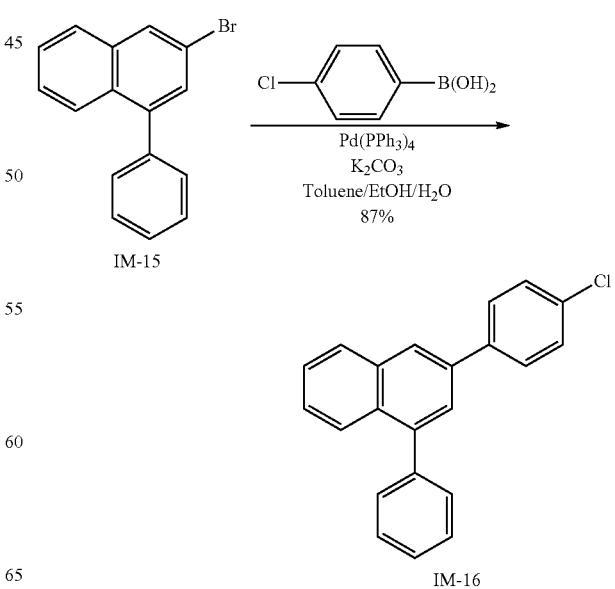

Under an Ar atmosphere, IM-15 (13.00 g, 45.9 mmol), 4-chlorophenylboronic acid (7.90 g, 1.1 equiv., 50.5 mmol), K$_2$CO$_3$ (19.04 g, 3.0 equiv., 60.7 mmol), Pd(PPh$_3$)$_4$ (2.65 g, 0.05 eq., 2.3 mmol), and a mixture solution of toluene/EtOH/H$_2$O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-16 (12.57 g, yield 87%).

Intermediate IM-16 was identified by measuring FAB-MS in which a molecular ion peak was observed at mass m/z=314.

(Synthesis of Intermediate IM-17)

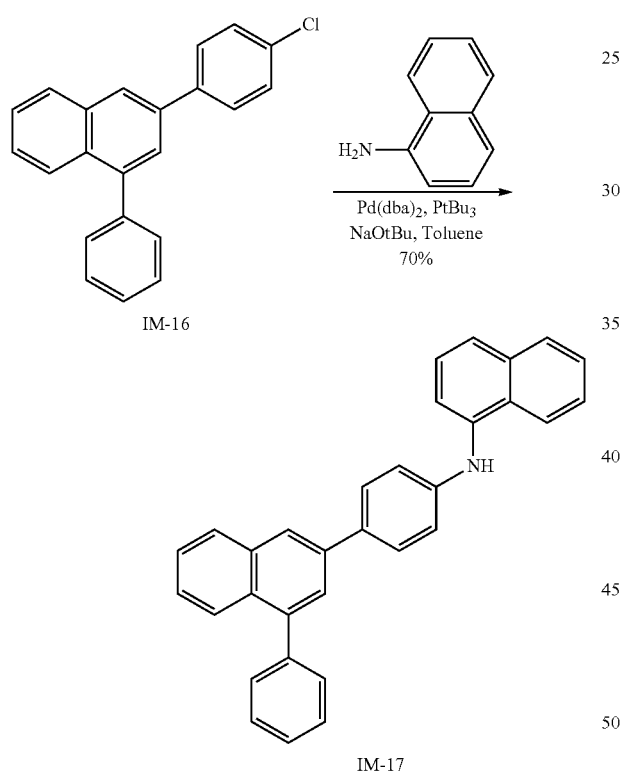

Under an Ar atmosphere, IM-16 (10.00 g, 31.8 mmol), Pd(dba)$_2$ (0.55 g, 0.03 equiv., 1.0 mmol), NaOtBu (3.05 g, 1.0 equiv., 31.8 mmol), toluene (159 mL), 1-naphthylamine (5.00 g, 1.1 equiv., 34.9 mmol) and tBu$_3$P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-17 (9.37 g, yield 70%).

Intermediate IM-17 was identified by measuring FAB-MS in which a molecular ion peak was observed at mass m/z=421.

(Synthesis of Compound E3)

Under an Ar atmosphere, IM-17 (8.00 g, 19.0 mmol), Pd(dba)$_2$ (0.33 g, 0.03 equiv., 0.6 mmol), NaOtBu (3.65 g, 2.0 equiv., 38.0 mmol), toluene (95 mL), 2-bromobiphenyl (4.87 g, 1.1 equiv., 20.9 mmol) and tBu$_3$P (0.39 g, 0.1 equiv., 1.9 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound E3 (7.40 g, yield 68%).

Compound E3 was identified by measuring FAB-MS in which a molecular ion peak was observed at mass m/z=573.

11. Synthesis of Compound E32

Compound E32, a monoamine compound according to an example embodiment may be synthesized, for example, as follows.

(Synthesis of Intermediate IM-18)

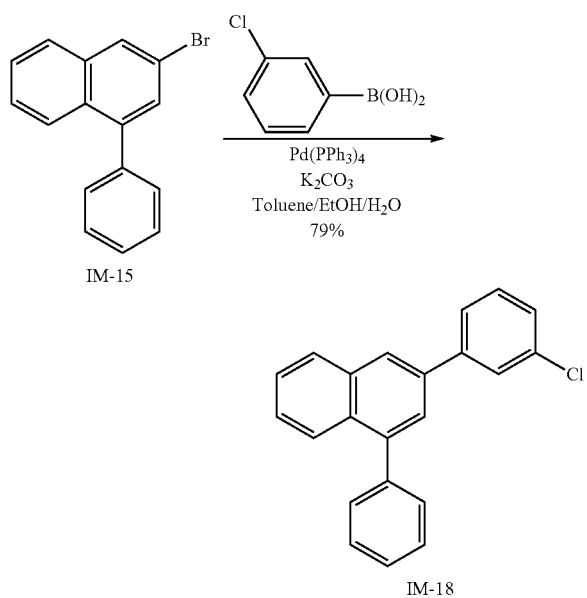

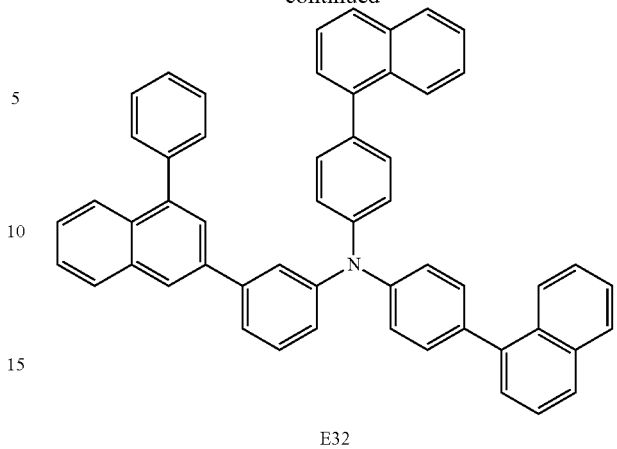

Under an Ar atmosphere, IM-15 (13.00 g, 45.9 mmol), 3-chlorophenylboronic acid (7.90 g, 1.1 equiv., 50.5 mmol), $K_2CO_3$ (19.04 g, 3.0 equiv., 60.7 mmol), $Pd(PPh_3)_4$ (2.65 g, 0.05 eq., 2.3 mmol), and a mixture solution of toluene/ $EtOH/H_2O$ (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over $MgSO_4$. $MgSO_4$ was filtered out and organic layer was concentrated. The crude product thus obtained was purified by silica gel column chromatography (using a mixture of hexane and toluene as developing solvent) to obtain Intermediate IM-18 (11.42 g, yield 79%).

Intermediate IM-18 was identified by measuring FAB-MS in which a molecular ion peak was observed at mass m/z=314.

(Synthesis of Compound E32)

Under an Ar atmosphere, IM-18 (10.00 g, 31.8 mmol), $Pd(dba)_2$ (0.55 g, 0.03 equiv., 1.0 mmol), NaOtBu (6.11 g, 2.0 equiv., 63.5 mmol), toluene (158 mL), bis(4-(naphthalen-1-yl)phenyl)amine (14.73 g, 1.1 equiv., 34.9 mmol) and $tBu_3P$ (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over $MgSO_4$. $MgSO_4$ was filtered out and organic layer was concentrated. The crude product thus obtained was purified by silica gel column chromatography (using a mixture of hexane and toluene as developing solvent) to obtain Compound E32 (18.23 g, yield 82%).

Compound E32 was identified by measuring FAB-MS in which a molecular ion peak was observed at mass m/z=699.

12. Synthesis of Compound F46

Compound F46, a monoamine compound according to an example embodiment may be synthesized, for example, as follows.

(Synthesis of Intermediate IM-19)

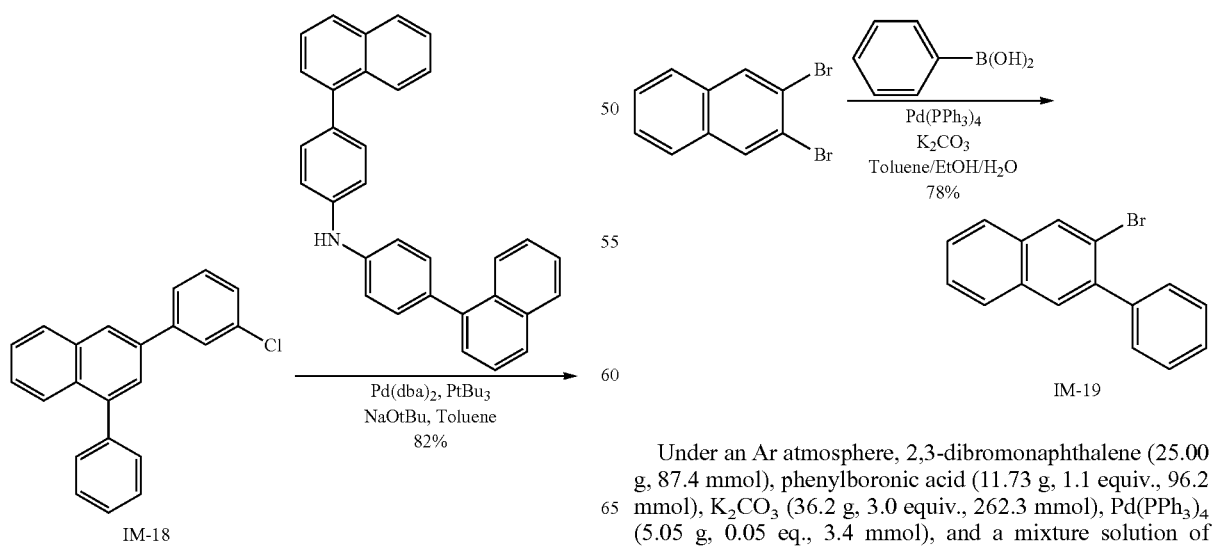

Under an Ar atmosphere, 2,3-dibromonaphthalene (25.00 g, 87.4 mmol), phenylboronic acid (11.73 g, 1.1 equiv., 96.2 mmol), $K_2CO_3$ (36.2 g, 3.0 equiv., 262.3 mmol), $Pd(PPh_3)_4$ (5.05 g, 0.05 eq., 3.4 mmol), and a mixture solution of toluene/$EtOH/H_2O$ (4/2/1) (612 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO₄. MgSO₄ was filtered out and organic layer was concentrated. The crude product thus obtained was purified by silica gel column chromatography (using a mixture of hexane and toluene as developing solvent) to obtain Intermediate IM-19 (19.31 g, yield 78%).

Intermediate IM-19 was identified by measuring FAB-MS in which a molecular ion peak was observed at mass m/z=283.

(Synthesis of Intermediate IM-20)

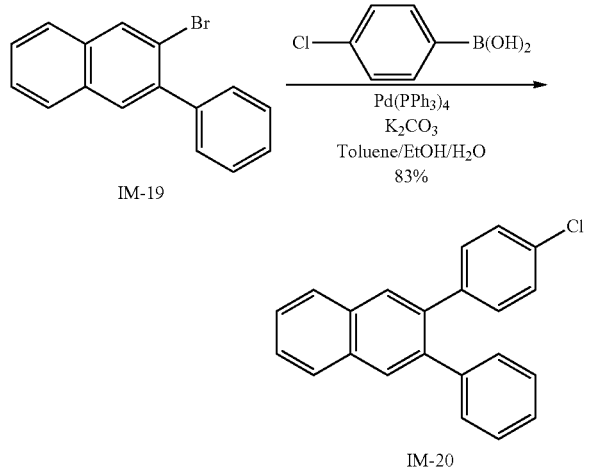

Under an Ar atmosphere, IM-19 (13.00 g, 45.9 mmol), 4-chlorophenylboronic acid (7.90 g, 1.1 equiv., 50.5 mmol), K₂CO₃ (19.04 g, 3.0 equiv., 60.7 mmol), Pd(PPh₃)₄ (2.65 g, 0.05 eq., 2.3 mmol), and a mixture solution of toluene/EtOH/H₂O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO₄. MgSO₄ was filtered out and organic layer was concentrated. The crude product thus obtained was purified by silica gel column chromatography (using a mixture of hexane and toluene as developing solvent) to obtain Intermediate IM-20 (12.00 g, yield 83%).

Intermediate IM-20 was identified by measuring FAB-MS in which a molecular ion peak was observed at mass m/z=314.

(Synthesis of Intermediate IM-21)

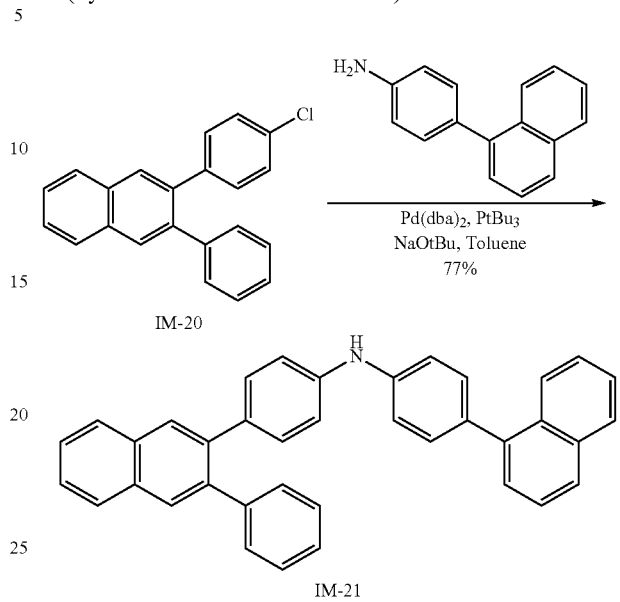

Under an Ar atmosphere, IM-20 (10.00 g, 31.8 mmol), Pd(dba)₂ (0.55 g, 0.03 equiv., 1.0 mmol), NaOtBu (3.05 g, 1.0 equiv., 31.8 mmol), toluene (159 mL), 4-(naphthalen-1-yl)aniline (7.66 g, 1.1 equiv., 34.9 mmol) and tBu₃P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO₄. MgSO₄ was filtered out and organic layer was concentrated. The crude product thus obtained was purified by silica gel column chromatography (using a mixture of hexane and toluene as developing solvent) to obtain Intermediate IM-21 (10.31 g, yield 77%).

Intermediate IM-21 was identified by measuring FAB-MS in which a molecular ion peak was observed at mass m/z=421.

(Synthesis of Compound F46)

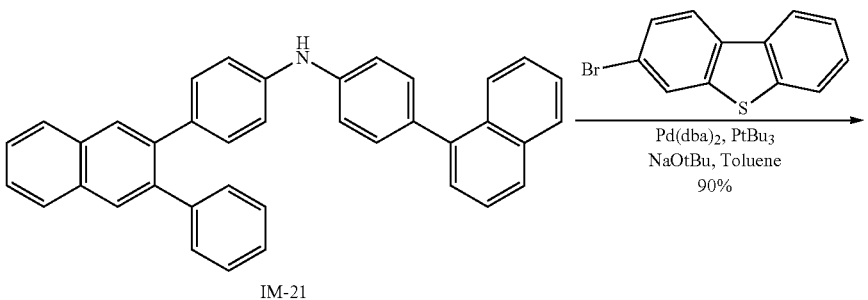

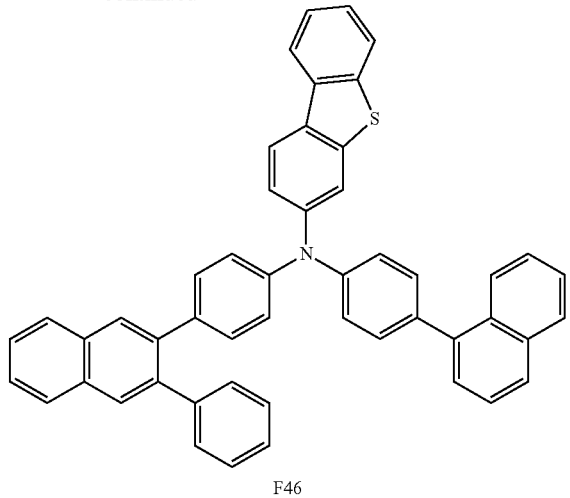

F46

Under an Ar atmosphere, IM-21 (8.00 g, 19.0 mmol), Pd(dba)$_2$ (0.33 g, 0.03 equiv., 0.6 mmol), NaOtBu (3.65 g, 2.0 equiv., 38.0 mmol), toluene (95 mL), 3-bromo-dibenzothiophen (5.49 g, 1.1 equiv., 20.9 mmol) and tBu$_3$P (0.39 g, 0.1 equiv., 1.9 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound F46 (11.61 g, yield 90%).

Compound F46 was identified by measuring FAB-MS in which a molecular ion peak was observed at mass m/z=679.

13. Synthesis of Compound F53

Compound F53, a monoamine compound according to an example embodiment may be synthesized, for example, as follows.

(Synthesis of Compound F53)

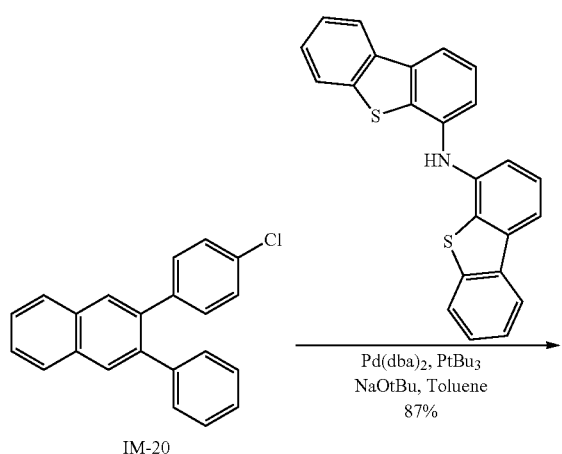

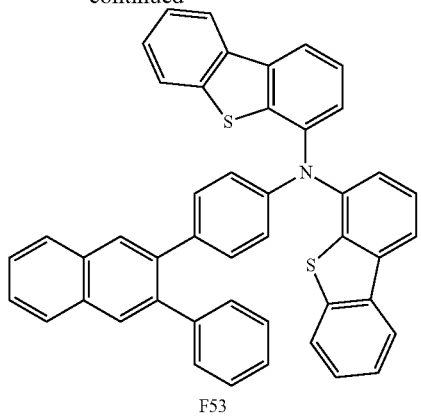

F53

Under an Ar atmosphere, IM-20 (8.00 g, 23.4 mmol), Pd(dba)$_2$ (0.40 g, 0.03 equiv., 0.7 mmol), NaOtBu (4.50 g, 2.0 equiv., 46.8 mmol), toluene (117 mL), bis(dibenzothiophen-4-yl)amine (9.82 g, 1.1 equiv., 25.7 mmol) and tBu$_3$P (0.47 g, 0.1 equiv., 2.3 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound F53 (13.44 g, yield 87%).

Compound F53 was identified by measuring FAB-MS in which a molecular ion peak was observed at mass m/z=659.

14. Synthesis of Compound G54

Compound G54, a monoamine compound according to an example embodiment may be synthesized, for example, as follows.

(Synthesis of Intermediate IM-22)

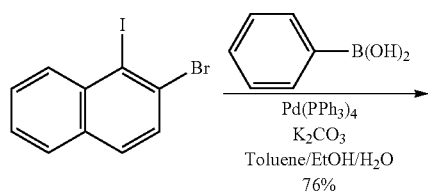

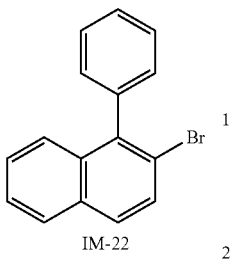

IM-22

Under an Ar atmosphere, 2-bromo-1-iodo-naphthalene (25.00 g, 75.1 mmol), phenylboronic acid (10.07 g, 1.1 equiv., 82.6 mmol), K$_2$CO$_3$ (31.1 g, 3.0 equiv., 225.2 mmol), Pd(PPh$_3$)$_4$ (4.34 g, 0.05 eq., 3.8 mmol), and a mixture solution of toluene/EtOH/H$_2$O (4/2/1) (525 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-22 (16.16 g, yield 76%).

Intermediate IM-22 was identified by measuring FAB-MS in which a molecular ion peak was observed at mass m/z=283.

(Synthesis of Intermediate IM-23)

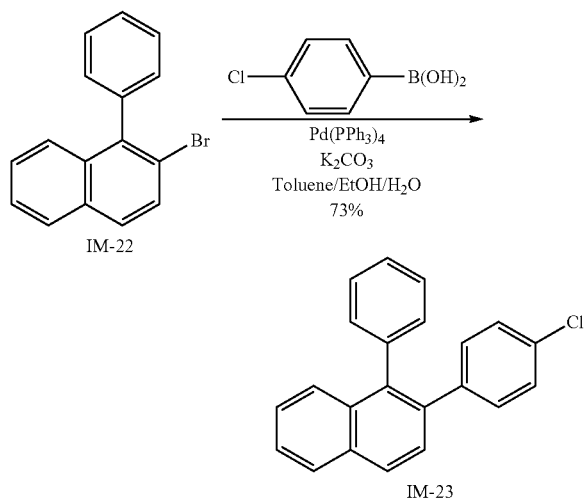

IM-23

Under an Ar atmosphere, IM-22 (13.00 g, 45.9 mmol), 4-chlorophenylboronic acid (7.90 g, 1.1 equiv., 50.5 mmol), K$_2$CO$_3$ (19.04 g, 3.0 equiv., 60.7 mmol), Pd(PPh$_3$)$_4$ (2.65 g, 0.05 eq., 2.3 mmol), and a mixture solution of toluene/EtOH/H$_2$O (4/2/1) (321 mL) were added in order to an 1 L three-neck flask, and the mixture was stirred and heated at about 80° C. After cooling in air to room temperature, the reaction solution was extracted with toluene. After removing aqueous layer, organic layer was washed with saturated brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-23 (10.55 g, yield 73%).

Intermediate IM-23 was identified by measuring FAB-MS in which a molecular ion peak was observed at mass m/z=314.

(Synthesis of Compound G54)

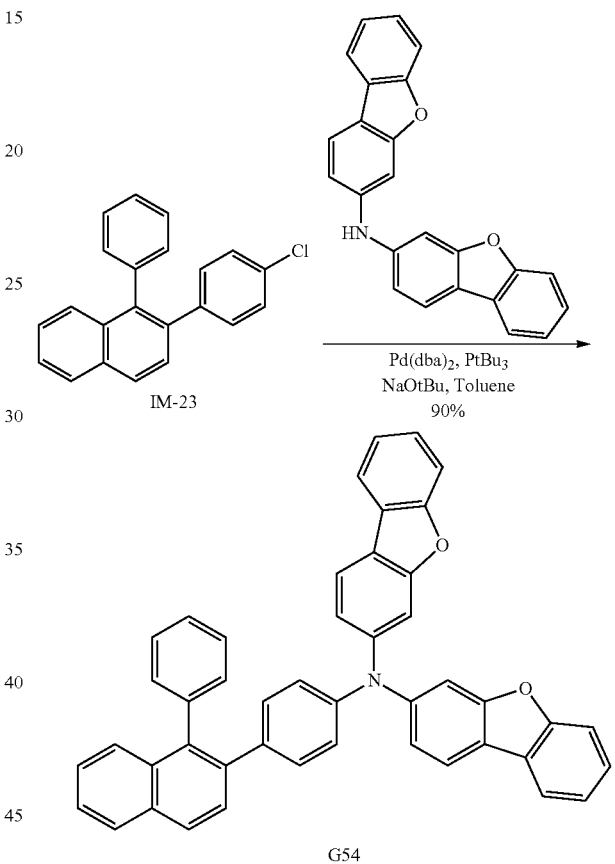

G54

Under an Ar atmosphere, IM-23 (8.00 g, 25.4 mmol), Pd(dba)$_2$ (0.44 g, 0.03 equiv., 0.8 mmol), NaOtBu (4.88 g, 2.0 equiv., 50.8 mmol), toluene (127 mL), bis(dibenzofuran-3-yl)amine (9.77 g, 1.1 equiv., 28.0 mmol) and tBu$_3$P (0.51 g, 0.1 equiv., 2.5 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound G54 (14.4 g, yield 90%).

Compound G54 was identified by measuring FAB-MS in which a molecular ion peak was observed at mass m/z=627.

15. Synthesis of Compound G58

Compound G58, a monoamine compound according to an example embodiment may be synthesized, for example, as follows.

(Synthesis of Intermediate IM-24)

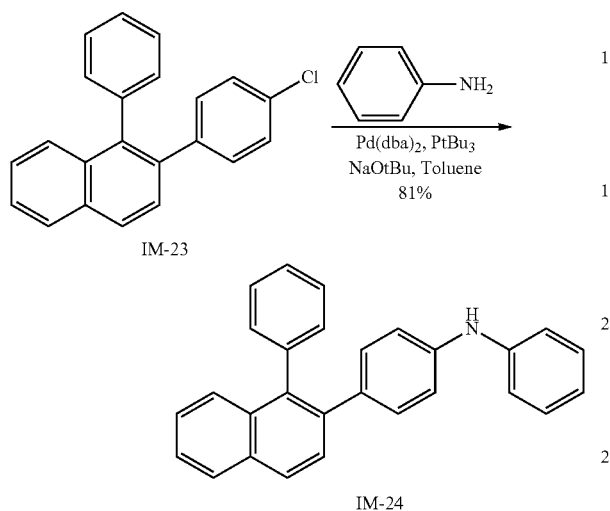

Under an Ar atmosphere, IM-23 (10.00 g, 31.8 mmol), Pd(dba)$_2$ (0.55 g, 0.03 equiv., 1.0 mmol), NaOtBu (3.05 g, 1.0 equiv., 31.8 mmol), toluene (159 mL), aniline (3.25 g, 1.1 equiv., 34.9 mmol) and tBu$_3$P (0.64 g, 0.1 equiv., 3.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Intermediate IM-24 (9.56 g, yield 81%).

Intermediate IM-24 was identified by measuring FAB-MS in which a molecular ion peak was observed at mass m/z=371.

(Synthesis of Compound G58)

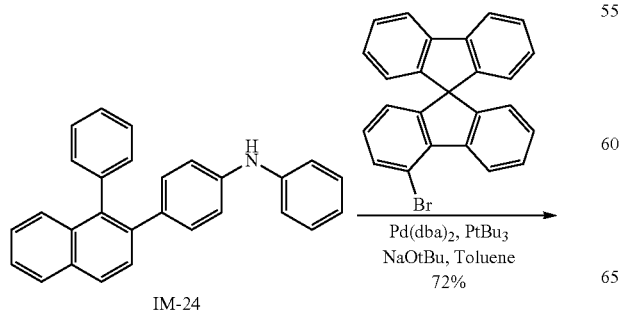

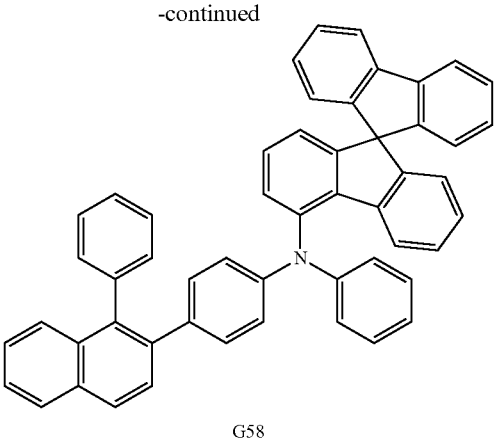

Under an Ar atmosphere, IM-24 (8.00 g, 21.5 mmol), Pd(dba)$_2$ (0.37 g, 0.03 equiv., 0.6 mmol), NaOtBu (4.14 g, 2.0 equiv., 43.1 mmol), toluene (108 mL), 4-bromo-9,9'-spirobifluorene (9.36 g, 1.1 equiv., 23.7 mmol) and tBu$_3$P (0.44 g, 0.1 equiv., 2.2 mmol) were added in order to a 300 mL three-neck flask, and the mixture was stirred and heated to reflux. After cooling in air to room temperature, water was added to the reaction solvent and an organic layer was separated and taken. Toluene was added to the remaining aqueous layer, followed by extraction of the aqueous layer to obtain another organic layer. Organic layers were combined and washed with brine, and then dried over MgSO$_4$. MgSO$_4$ was filtered out and organic layer was concentrated. The crude product thus obtained was purified by silica gel column chromatography (using a mixture of hexane and toluene as developing solvent) to obtain Compound G58 (10.63 g, yield 72%).

Compound G58 was identified by measuring FAB-MS in which a molecular ion peak was observed at mass m/z=685.

(Device Manufacturing Example)

Organic electroluminescence devices of Examples 1 to 15 were manufactured by using the above Compounds A4, A17, B13, B20, B40, C25, C51, D12, D22, E3, E32, F46, F53, G54, and G58 as an electron blocking material.

[Example Compounds]

A4

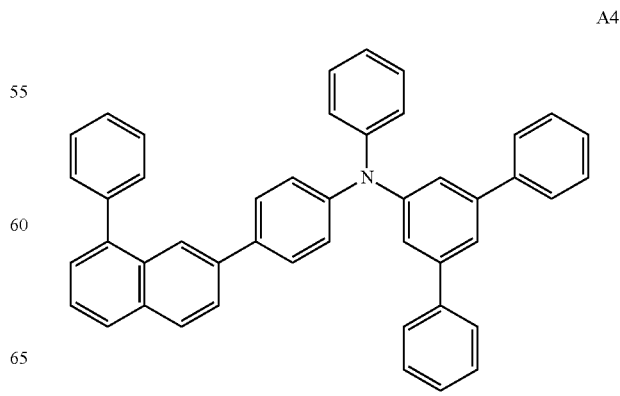

A17
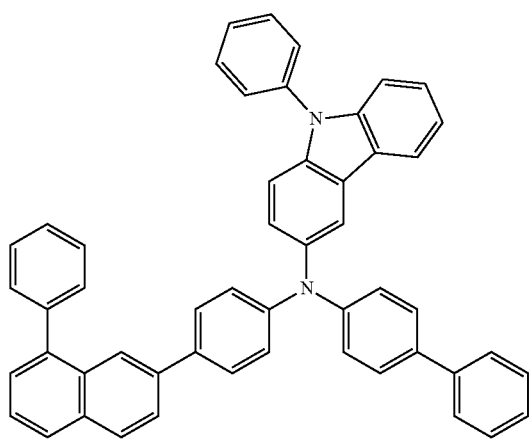
B13
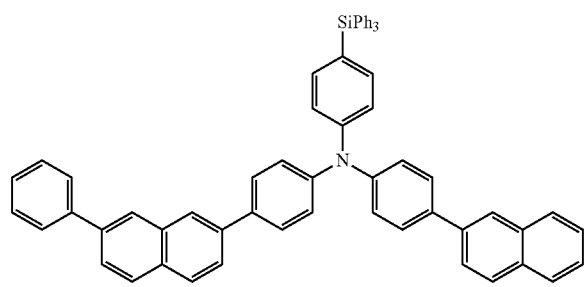
B20
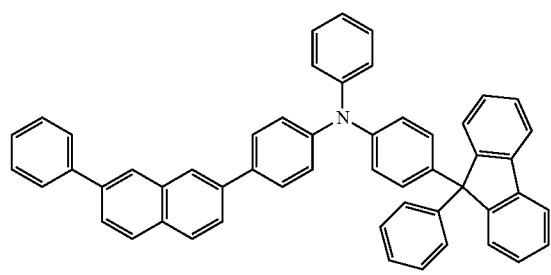
B40
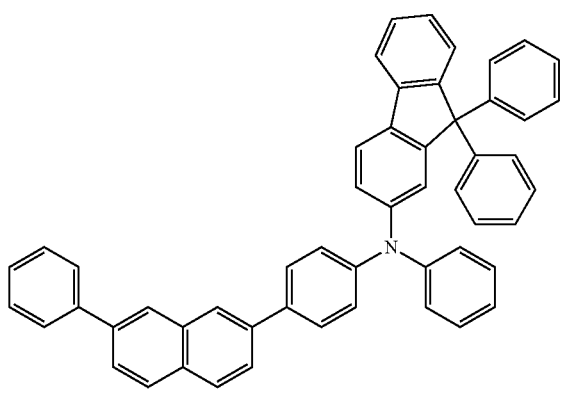
C25
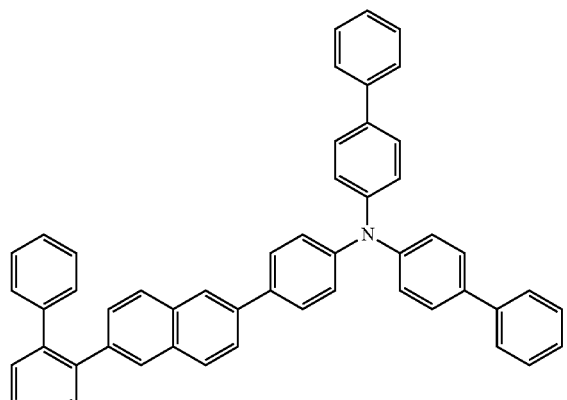
C51
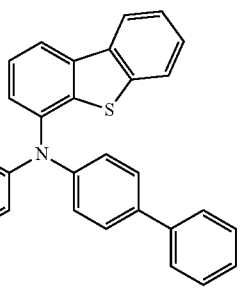
D12

D22
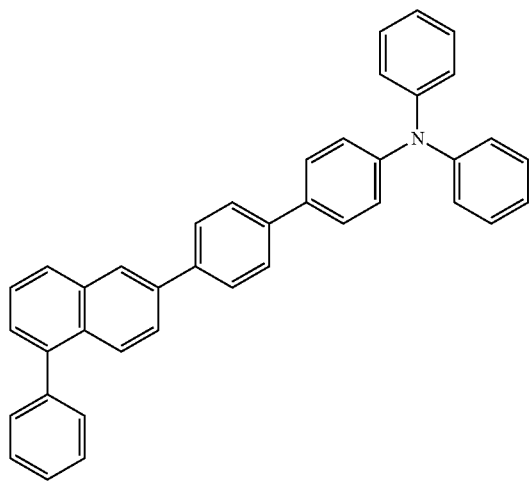
E3
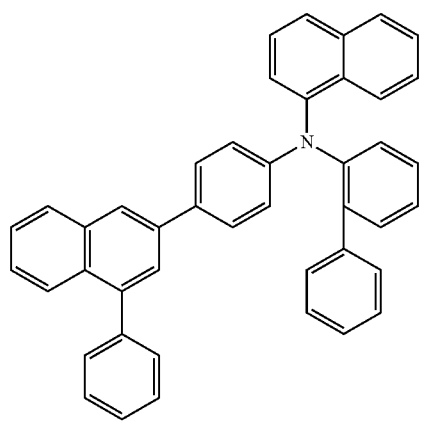
E32
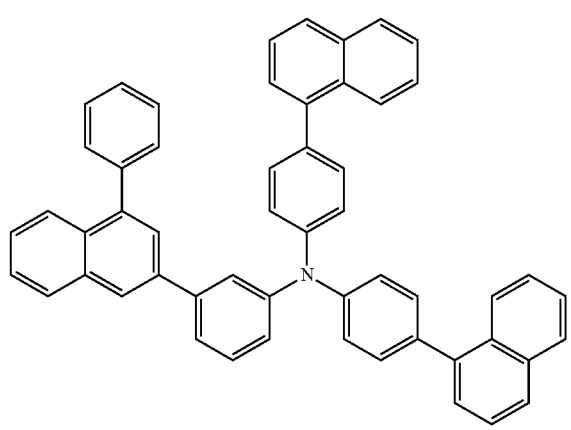
F46
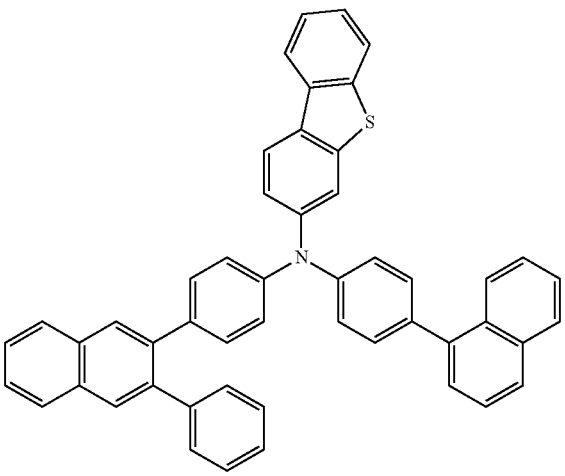
F53
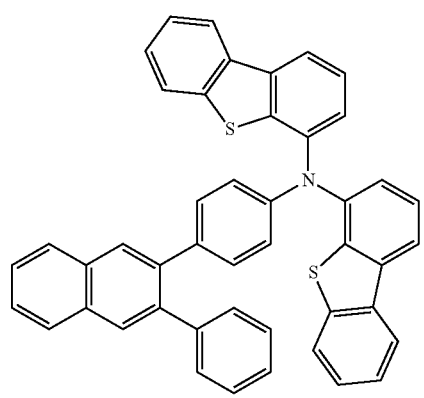
G54
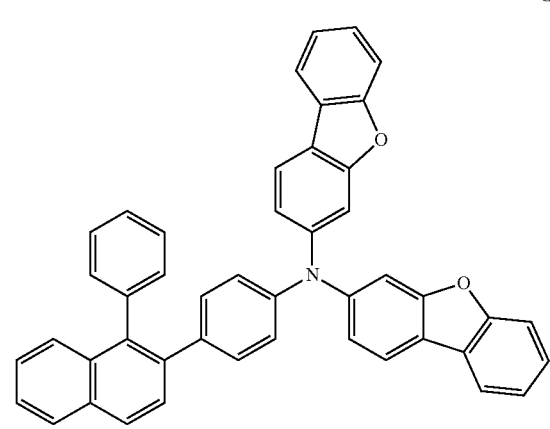

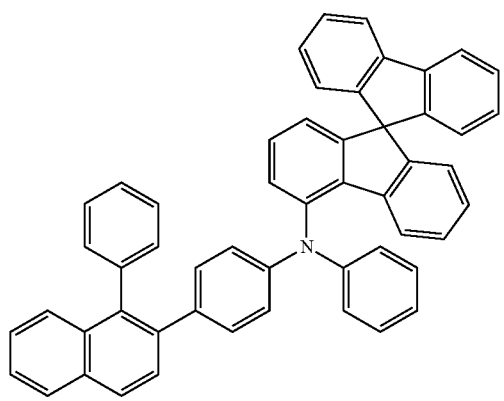
G58
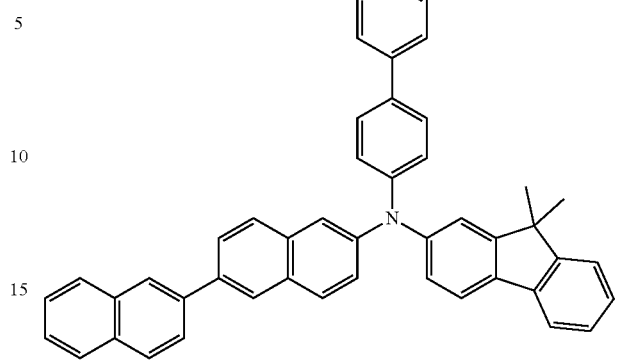
R3
Organic electroluminescent devices of Comparative Examples 1 to 8 were manufactured by using the following Comparative Compounds R-1 to R-8.
[Comparative Compounds]
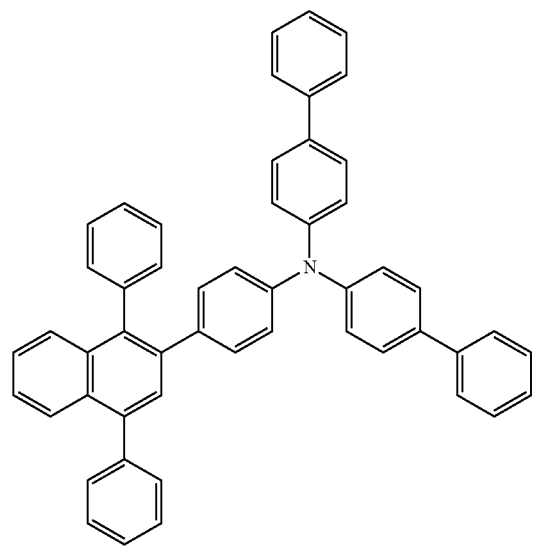
R1
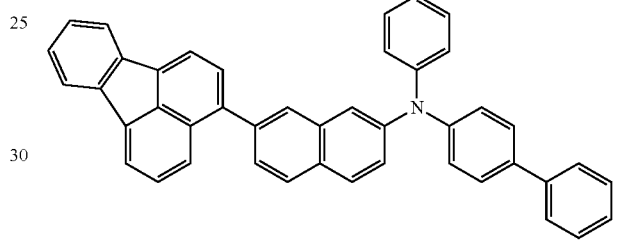
R4
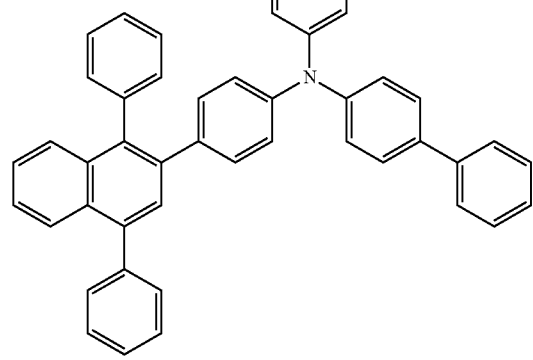
R2
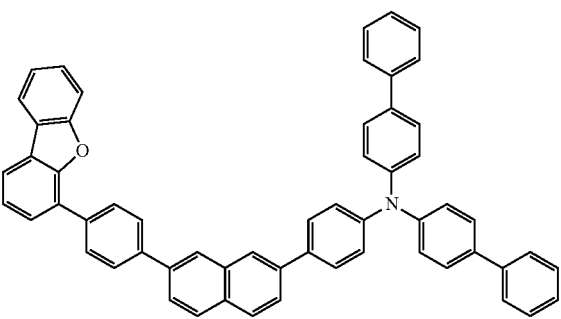
R5
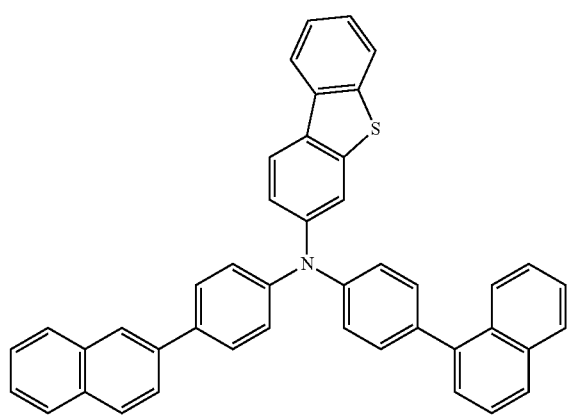
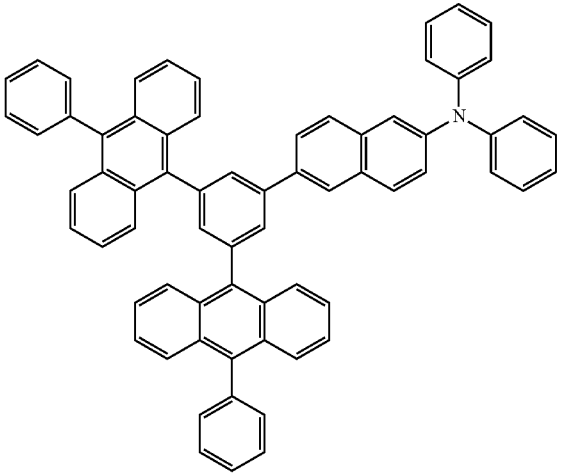
R6

R7

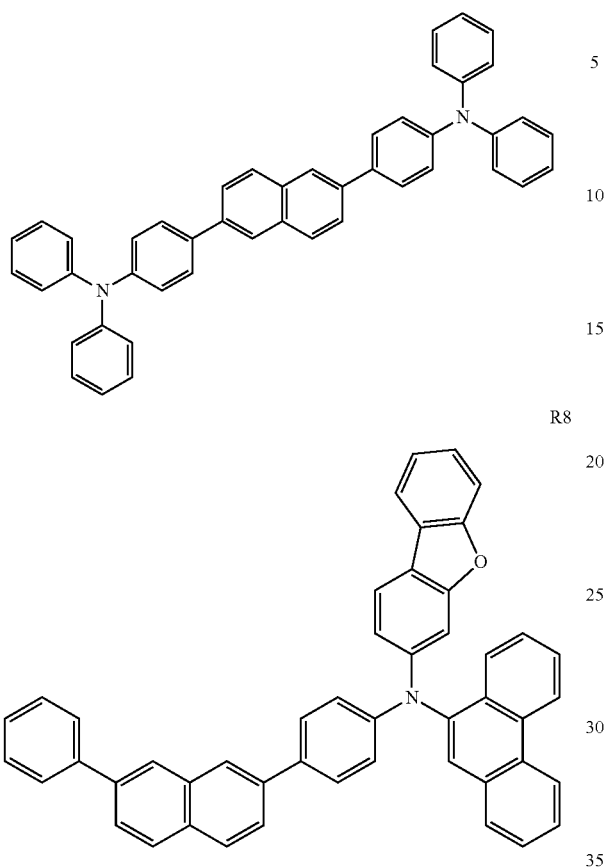

R8

HT1

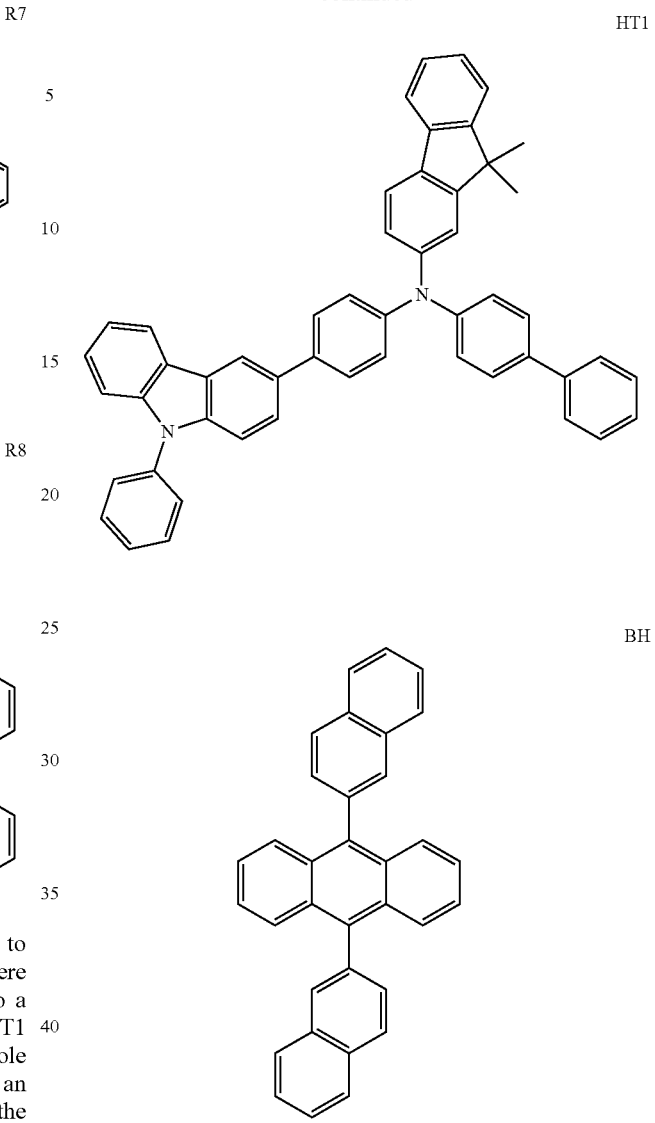

BH

BD

The organic electroluminescence devices according to Examples 1 to 15 and Comparative Examples 1 to 8 were manufactured by forming a first electrode using ITO to a thickness of about 150 nm, a hole injection layer using HT1 doped with 2% HIL-M to a thickness of about 10 nm, a hole transport layer using HT1 to a thickness of about 120 nm, an electron blocking layer using the example compounds or the comparative compounds to a thickness of about 10 nm, an emission layer using BH doped with 2% BD to a thickness of about 30 nm, a hole blocking layer using ET1 to a thickness of about 10 nm, an electron transport layer using ET2 to a thickness of about 20 nm, an electron injection layer using LiF to a thickness of about 1 nm, and a second electrode using a Mg/Ag alloy co-deposited at a volumetric ratio of 9:1 to a thickness of about 120 nm. Each layer was formed by a vacuum deposition method.

HIL-M

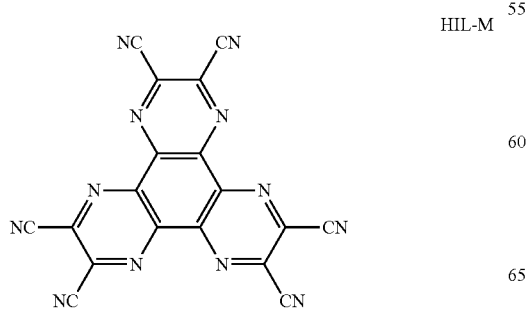

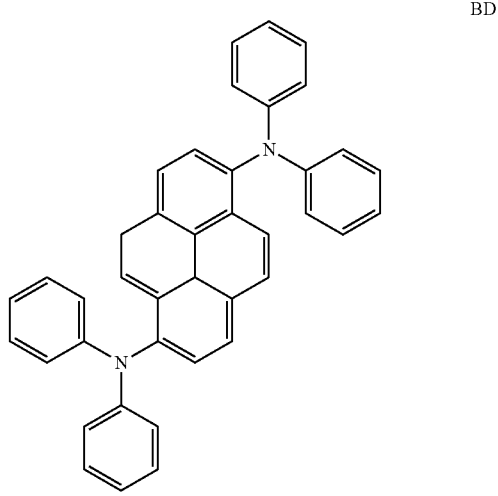

ET1

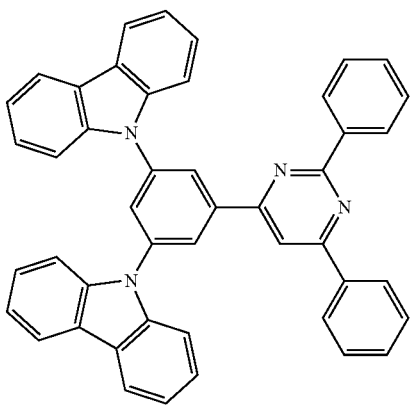

ET2

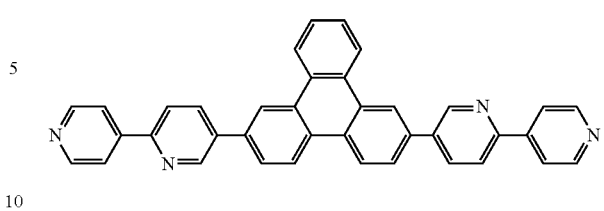

The voltage, half-life, emission efficiency, and color coordinate of the organic electroluminescence devices manufactured in Examples 1 to 15 and Comparative Examples 1 to 8 are shown in Table 1 below.

TABLE 1

|  | Electron blocking layer | Voltage (V) | Life LT50 (h) | Emission efficiency (cd/A) | Color coordinate CIE (x, y) |
| --- | --- | --- | --- | --- | --- |
| Example 1 | Example Compound A4 | 4.8 | 5.5 | 189 | 0.141, 0.051 |
| Example 2 | Example Compound A17 | 4.6 | 5.5 | 190 | 0.142, 0.051 |
| Example 3 | Example Compound B13 | 4.7 | 5.6 | 196 | 0.141, 0.051 |
| Example 4 | Example Compound B20 | 4.6 | 5.5 | 195 | 0.141, 0.052 |
| Example 5 | Example Compound B40 | 4.6 | 5.4 | 197 | 0.142, 0.052 |
| Example 6 | Example Compound C22 | 4.6 | 5.4 | 199 | 0.142, 0.051 |
| Example 7 | Example Compound C51 | 4.8 | 5.4 | 196 | 0.141, 0.051 |
| Example 8 | Example Compound D12 | 4.8 | 5.5 | 188 | 0.142, 0.052 |
| Example 9 | Example Compound D22 | 4.7 | 5.4 | 190 | 0.142, 0.051 |
| Example 10 | Example Compound E3 | 4.8 | 5.6 | 184 | 0.141, 0.052 |
| Example 11 | Example Compound E32 | 4.8 | 5.6 | 189 | 0.141, 0.052 |
| Example 12 | Example Compound F46 | 4.7 | 5.3 | 193 | 0.141, 0.051 |
| Example 13 | Example Compound F53 | 4.8 | 5.5 | 192 | 0.141, 0.051 |
| Example 14 | Example Compound G54 | 4.8 | 5.6 | 197 | 0.141, 0.052 |
| Example 15 | Example Compound G58 | 4.8 | 5.6 | 185 | 0.142, 0.052 |
| Comparative Example 1 | Comparative Compound R1 | 5.0 | 4.9 | 167 | 0.140, 0.052 |
| Comparative Example 2 | Comparative Compound R2 | 5.2 | 3.8 | 165 | 0.141, 0.053 |
| Comparative Example 3 | Comparative Compound R3 | 5.1 | 4.0 | 167 | 0.142, 0.051 |
| Comparative Example 4 | Comparative Compound R4 | 5.3 | 4.2 | 163 | 0.139, 0.049 |
| Comparative Example 5 | Comparative Compound R5 | 5.1 | 5.0 | 168 | 0.140, 0.050 |
| Comparative Example 6 | Comparative Compound R6 | 5.5 | 3.5 | 155 | 0.137, 0.047 |
| Comparative Example 7 | Comparative Compound R7 | 4.9 | 5.0 | 157 | 0.143, 0.053 |
| Comparative Example 8 | Comparative Compound R8 | 4.9 | 4.9 | 169 | 0.142, 0.052 |

In the above table, the emission efficiency was a measured value at a current density of about 10 mA/cm², and the half-life was a value at about 1.0 mA/cm².

Referring to the results in Table 1, it may be found that the organic electroluminescence devices of Examples 1 to 15 had decreased driving voltage, extended life and enhanced efficiency when compared with those of Comparative Examples 1 to 8.

A monoamine compound according to an example embodiment may includes a substituted β-phenylnaphthyl group, which may help provide decreased driving voltage, extended life, and enhanced efficiency of the device. Furthermore, the monoamine compound may achieve an extended device life by the introduction of a naphthyl group having a high thermal resistance and electric charge resistance, with the maintenance of the property of amine group. Furthermore, the monoamine compound may have a bulky naphthyl group substituted with a phenyl group, which may decrease symmetry of molecule and inhibit crystallization, to thereby enhance quality of layers and attain high efficiency of the device.

The organic electroluminescence devices of Examples 1, 2, 8 to 11, 14 and 15 had significantly enhanced efficiency. Without being bound by theory, it is believed that Example Compounds A4, A17, D12, D22, E3, E32, G54 and G58, including a substituent at a position of the naphthyl group, may have a steric electron repulsion between the substituent of a position and the hydrogen atom of other α' position, and distortion of the naphthyl structure and phenyl group substituted therein may lead to decreased planarity of the whole molecule and inhibit crystallization, thereby improving hole transport property and enhancing the chance of recombining holes and electrons in an emission layer.

Furthermore, the organic electroluminescence devices of Examples 3 to 7, 12 and 13 had significantly extended device life. Without being bound by theory, it is believed that Example Compounds B13, B20, B40, C25, C51, F46 and F53, including a substituent at β position of the naphthyl group, may have a steric conformation close to plane for the naphthyl group and the substituent at β position, which may result in a stabilized radical state due to the delocalized conjugation around amine, thereby enhancing device life.

The organic electroluminescence device of Comparative Example 1 showed decreased device life when compared with those of Examples. Comparative Compound R1 has an amine group substituted at β position of naphthyl group via a linker similar to Example Compounds, but has two phenyl groups substituted in naphthyl group, which may result in largely distributed HOMO in naphthyl group and decreased electron density in amine group, thereby making it difficult to maintain the property of amine to extend device life.

The organic electroluminescence device of Comparative Example 2 uses an amine compound including a naphthyl group but not a phenylnaphthyl group, which results in low electric charge resistance, thereby decreasing device life and emission efficiency due to the insufficient quality of layers.

The organic electroluminescence devices of Comparative Examples 3 and 4 use Comparative Compounds R3 and R4 having an amine group substituted at β position of naphthyl group via a linker similar to Example Compounds, but having polycyclic aromatic groups connected to naphthyl group, contrary to Example Compounds having a phenyl group connected to naphthyl group, which may cause a strong molecular stacking and increased deposition temperature due to the polycyclic aromatic group, thereby resulting in easy thermal decomposition and decreased efficiency and device life, when compared with those of Examples.

The organic electroluminescence device of Comparative Example 6 uses Comparative Compound R6 having an amine group substituted at β position of naphthyl group via a linker similar to Example Compounds, but having a phenyl group with two substituents, which may cause a strong molecular stacking and increased deposition temperature, thereby resulting in easy thermal decomposition and decreased efficiency and device life, when compared with those of Examples.

The organic electroluminescence devices of Comparative Examples 5 and 7 showed especially decreased emission efficiency when compared with those of Examples. Comparative Compound R5 has a naphthyl group substituted with phenyl group that is substituted with dibenzofuran heterocycle, and Comparative Compound R7 is a diamine compound, both of which may disturb carrier balance.

The organic electroluminescence device of Comparative Example 8 showed decreased emission efficiency and device life when compared with those of Examples. Comparative Compound R8 has a nitrogen atom substituted with both of 3-dibenzofuranyl and 9-phenanthryl, which may result in easy thermal decomposition. Comparative Compound R8 has a nitrogen atom substituted with 9-phenanthryl, which may increase molecular stacking, and is further substituted with 3-dibenzofuranyl, which may increase planarity of the whole molecule, thereby causing a strong molecular stacking and increased deposition temperature, which seems to result in easy thermal decomposition and decreased efficiency and device life.

By way of summation and review, in an application of an organic electroluminescence device to a display, decrease of a driving voltage, increase of emission efficiency and extension of life for the organic electroluminescence device are desired, and development of a material which may stably implement these requirements in the organic electroluminescence device is also desired.

Embodiments may provide an organic electroluminescence device and a monoamine compound for an organic electroluminescence device. Embodiments may provide an organic electroluminescence device with high efficiency and a monoamine compound included in a hole transport region of an organic electroluminescence device.

A monoamine compound according to an example embodiment may be used as a material for a hole transport region of an organic electroluminescence device, which may contribute to a decrease of a driving voltage, increase of emission efficiency, and extension of life for the organic electroluminescence device.

The organic electroluminescence device according to an example embodiment may have high efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

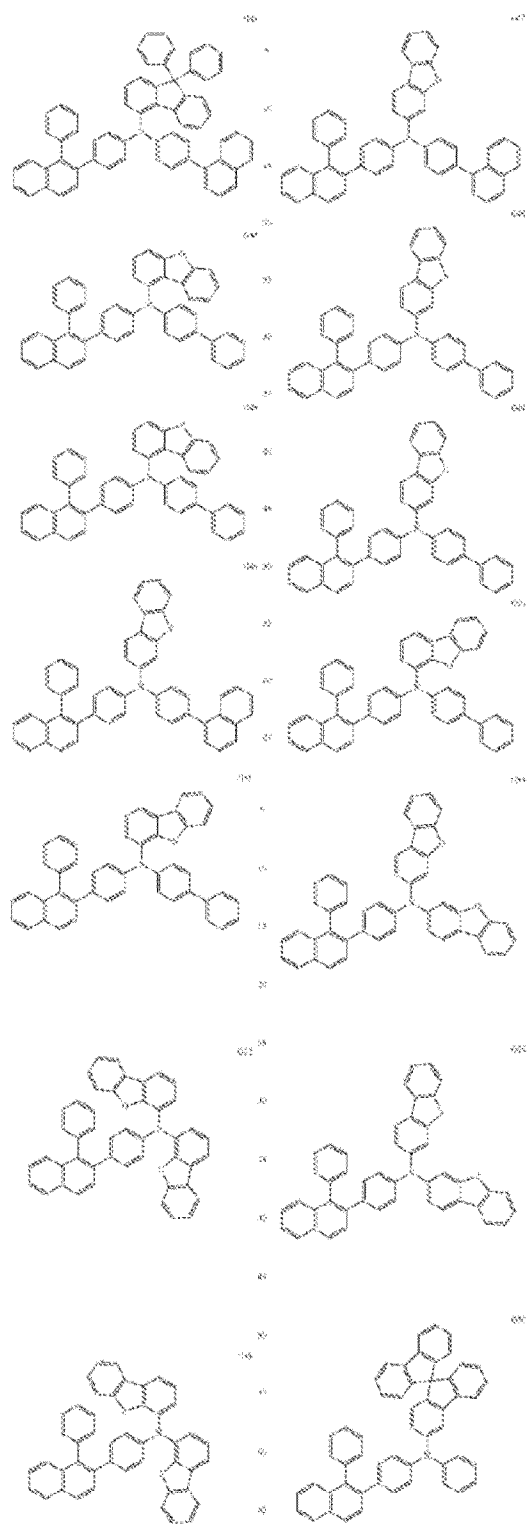

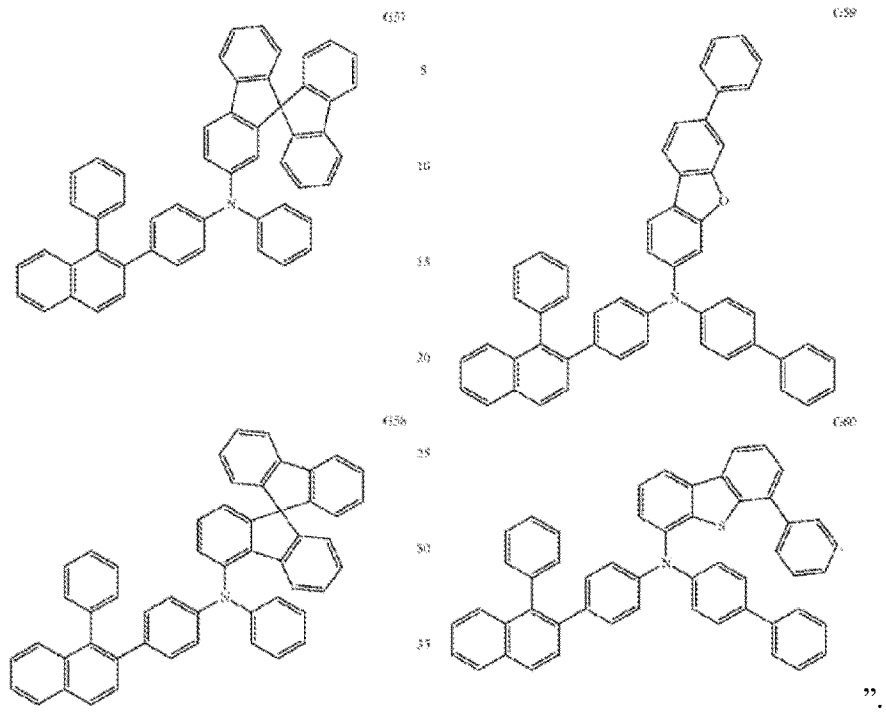

What is claimed is:

1. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region includes a monoamine compound represented by at least one of the following Formulae 2 to 8:

[Formula 2]
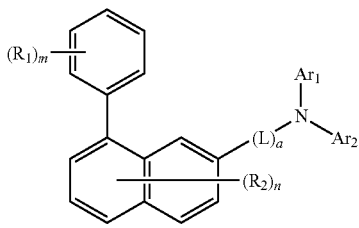

[Formula 3]
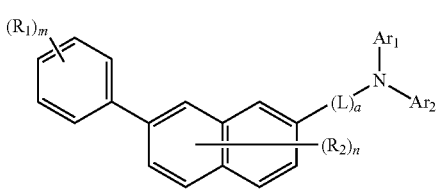

[Formula 4]
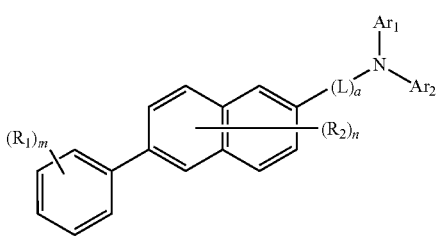

[Formula 5]
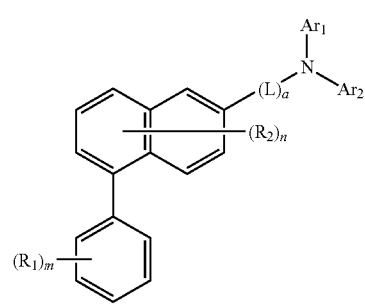

[Formula 6]
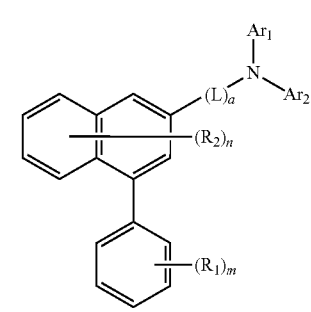

[Formula 7]
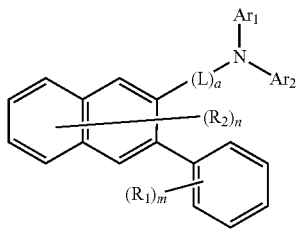

[Formula 8]
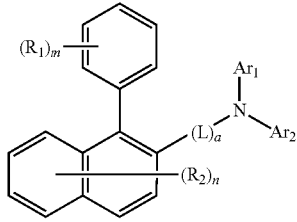

wherein in Formula 2 to 8,
$Ar_1$ and $Ar_2$ are each independently a substituted or unsubstituted alkyl group having 1 to 10 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 2 to 30 ring carbon atoms, provided that when any one of $Ar_1$ and $Ar_2$ is 3-dibenzofuranyl, the other one of $Ar_1$ and $Ar_2$ is not 9-phenanthryl,
L is a substituted or unsubstituted arylene group having 6 to 30 ring carbon atoms, or a substituted or unsubstituted heteroarylene group having 2 to 30 ring carbon atoms,
$R_1$ is a hydrogen atom, a deuterium atom, a halogen atom, a substituted or unsubstituted alkyl group having 1 to 20 carbon atoms, a substituted or unsubstituted cycloalkyl group having 3 to 20 ring carbon atoms, or a substituted or unsubstituted aryl group having 6 to 30 ring carbon atoms,
$R_2$ is a hydrogen atom, a deuterium atom, a halogen atom, a substituted or unsubstituted alkyl group having 1 to 20 carbon atoms, or a substituted or unsubstituted cycloalkyl group having 3 to 20 ring carbon atoms,
a is an integer of 0 to 3,
m is an integer of 0 to 1, and
n is an integer of 0 to 6,
wherein in Formula 3,
i) when one of $Ar_1$ and $Ar_2$ is a naphthalene group or a phenyl group substituted with a naphthalene group and the other one of $Ar_1$ and $Ar_2$ is a substituted or unsubstituted aryl group,
the naphthalene group in the one of $Ar_1$ and $Ar_2$ is unsubstituted, or
the substituted or unsubstituted aryl group of the other one of $Ar_1$ and $Ar_2$ is a substituted or unsubstituted aryl group having 7 to 30 ring carbon atoms, and
ii) L is a substituted or unsubstituted arylene group having 6 to 30 ring carbon atoms,
wherein in Formula 4, a is an integer of 1 to 3,
wherein in Formula 6,
i) $Ar_1$ and $Ar_2$ are not dimethylfluorenyl groups,
ii) when any one of $Ar_1$ and $Ar_2$ is a p-biphenyl group and the other one of $Ar_1$ and $Ar_2$ includes an aryl substituent, the number of ring carbon atoms in the aryl substituent is 13 to 30, iii) L is a phenylene group, a is an integer of 1 or more and 3 or less, and when L includes an m-phenylene group, Ar₁ and Ar₂ are not an unsubstituted or alkyl-substituted phenyl group, or an unsubstituted p-biphenyl group, and
vi) when Ar₁ and Ar₂ are each a heteroaryl group comprising S, or one of Ar₁ or Ar₂ is a heteroaryl group comprising S, and an other one of Ar₁ or Ar₂ is a heteroaryl group comprising O, the heteroaryl group comprising S is a substituted or unsubstituted dibenzothiophene group, and the heteroaryl group comprising O is a substituted or unsubstituted dibenzofuran group, and wherein in Formula 7 and Formula 8,
i) Ar₁ and Ar₂ are not an unsubstituted p-biphenyl group or an unsubstituted p-terphenyl group,
ii) when Ar₁ and Ar₂ are a fluorene group or a fluorene derivative, Ar₁ and Ar₂ are substituents represented by Formula 7a;

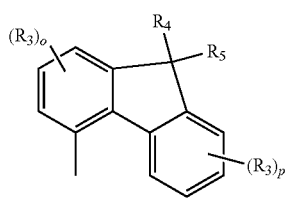

[Formula 7a]

wherein in Formula 7a,
R₃ is a hydrogen atom, a deuterium atom, a halogen atom, a substituted or unsubstituted alkyl group having 1 to 20 carbon atoms, a substituted or unsubstituted cycloalkyl group having 3 to 20 ring carbon atoms, or a substituted or unsubstituted aryl group having 6 to 30 ring carbon atoms,
R₄ and R₅ are each independently a hydrogen atom, a deuterium atom, a halogen atom, a substituted or unsubstituted cycloalkyl group having 3 to 20 ring carbon atoms, or a substituted or unsubstituted aryl group having 6 to 30 ring carbon atoms, and/or combine with each other to form a ring,
is an integer of 0 or more and 3 or less,
p is an integer of 0 or more and 4 or less,
iii) L is a substituted or unsubstituted phenylene group, and
vi) when one of Ar₁ and Ar₂ is an unsubstituted 2-dibenzofuran group, an unsubstituted 2-dibenzothiophene group, an unsubstituted 3-dibenzofuran group, or an unsubstituted 3-dibenzothiophene group, the other one of Ar₁ and Ar₂ is a substituted or unsubstituted phenylnaphthyl group, a substituted or unsubstituted dibenzofuran group, or a substituted or unsubstituted dibenzothiophene group.

2. The organic electroluminescence device as claimed in claim 1, wherein L is a substituted or unsubstituted arylene group having 6 to 12 ring carbon atoms.

3. The organic electroluminescence device as claimed in claim 2, wherein L is a substituted or unsubstituted phenylene group.

4. The organic electroluminescence device as claimed in claim 1, wherein Ar₁ and Ar₂ are each independently a substituted or unsubstituted aryl group having 6 to 12 ring carbon atoms.

5. The organic electroluminescence device as claimed in claim 4, wherein Ar₁ and Ar₂ are each independently a substituted or unsubstituted phenyl group, a substituted or unsubstituted biphenyl group, a substituted or unsubstituted naphthyl group, or a substituted or unsubstituted fluorenyl group.

6. The organic electroluminescence device as claimed in claim 1, wherein Ar₁ and Ar₂ are each independently a substituted or unsubstituted heteroaryl group having 5 to 12 ring carbon atoms.

7. The organic electroluminescence device as claimed in claim 6, wherein Ar₁ and Ar₂ are each independently a substituted or unsubstituted dibenzofuran group, a substituted or unsubstituted dibenzothiophene group, or a substituted or unsubstituted carbazole group.

8. The organic electroluminescence device as claimed in claim 1, wherein R₂ is a hydrogen atom or a deuterium atom.

9. The organic electroluminescence device as claimed in claim 1, wherein the hole transport region has a plurality of layers, and a layer of the plurality of layers contacting the emission layer includes the monoamine compound.

10. The organic electroluminescence device as claimed in claim 1, wherein the hole transport region includes:
a hole injection layer on the first electrode;
a hole transport layer on the hole injection layer; and
an electron blocking layer on the hole transport layer, the electron blocking layer including the monoamine compound.

11. The organic electroluminescence device as claimed in claim 1, wherein the electron transport region includes:
a hole blocking layer on the emission layer;
an electron transport layer on the hole blocking layer; and
an electron injection layer on the electron transport layer.

12. The organic electroluminescence device as claimed in claim 1, wherein the monoamine compound is at least one selected from the group of compounds represented in the following Compound Groups 1 to 7:

[Compound Group 1]

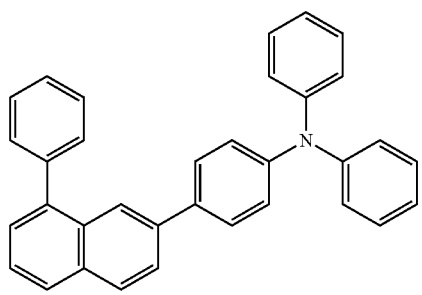

A1

-continued
A2
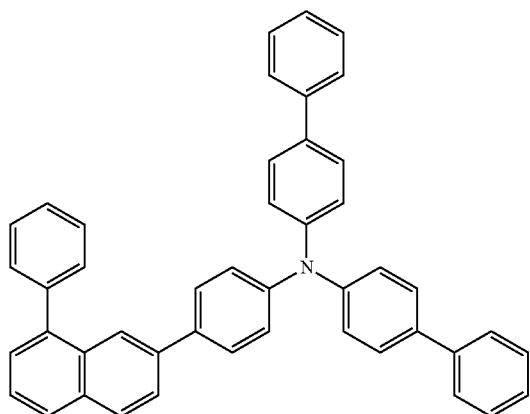
A3
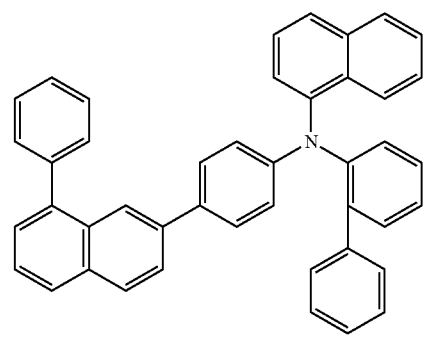
A4
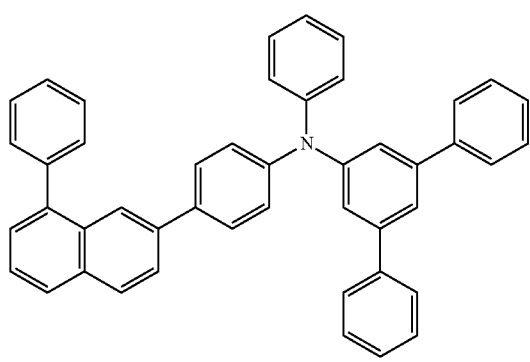
A5
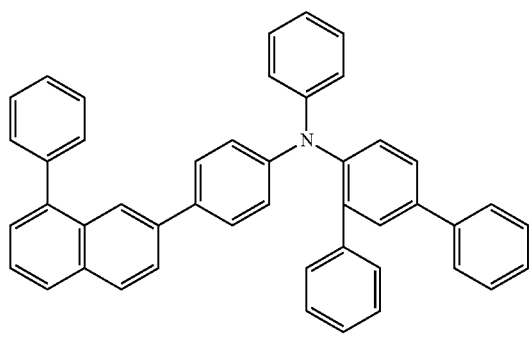
-continued
A6
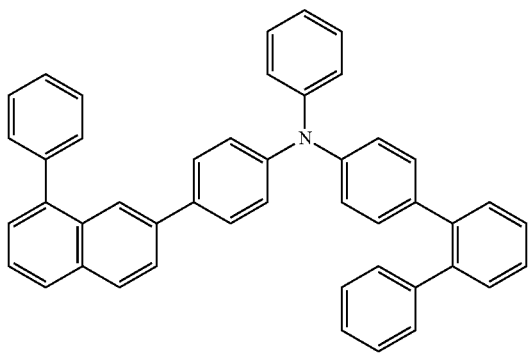
A7
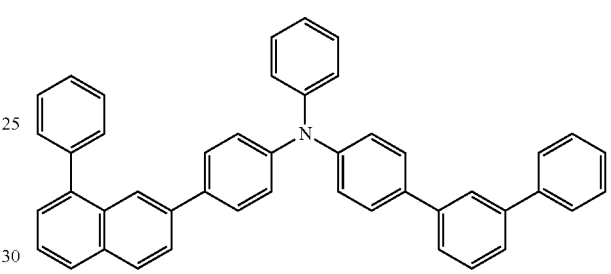
A8
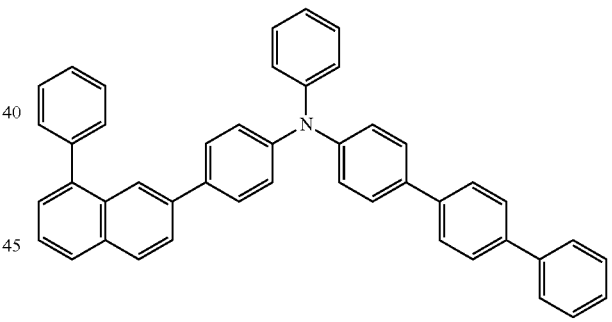
A9
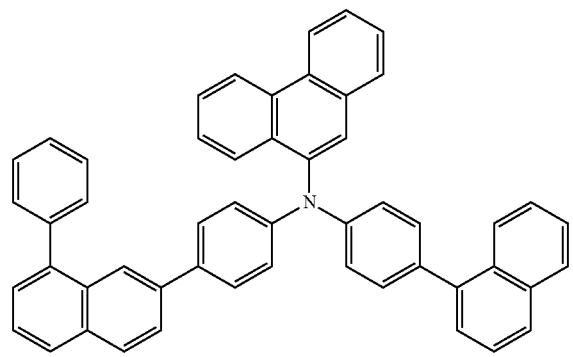

-continued
A10
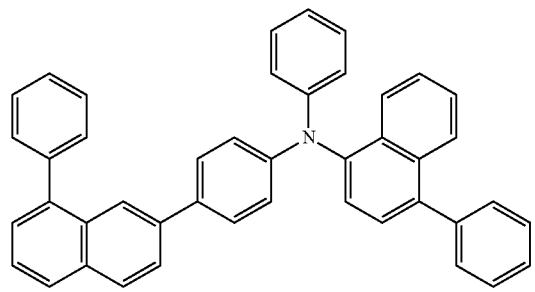
A11
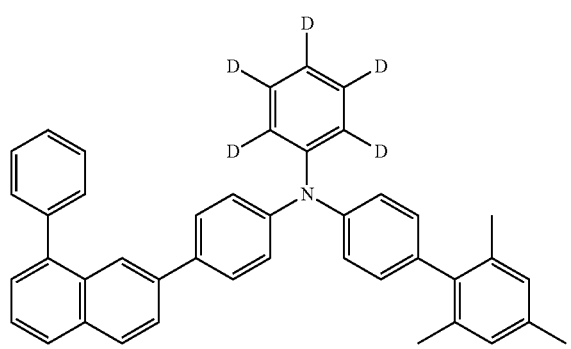
A12
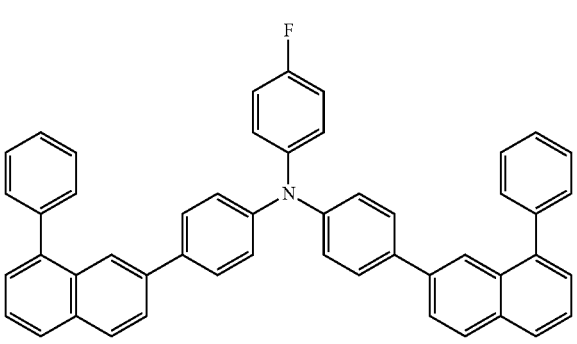
A13
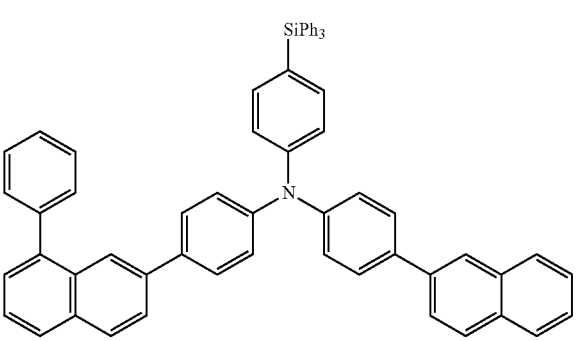
-continued
A14
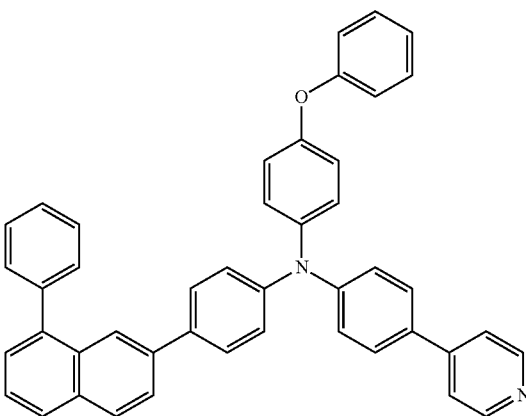
A15
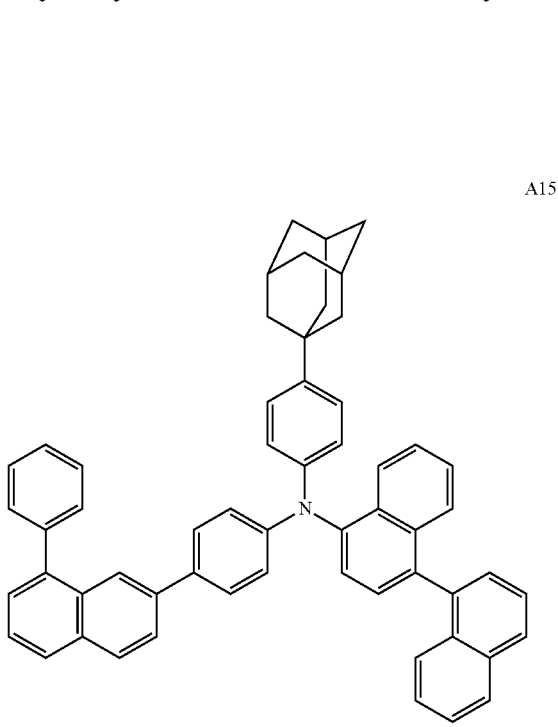
A16
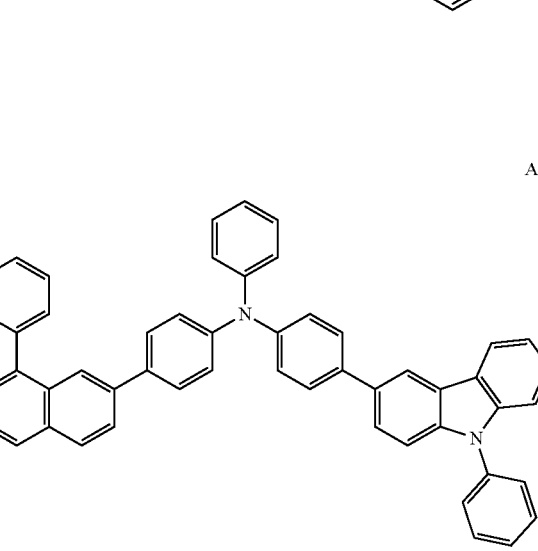

-continued
A17
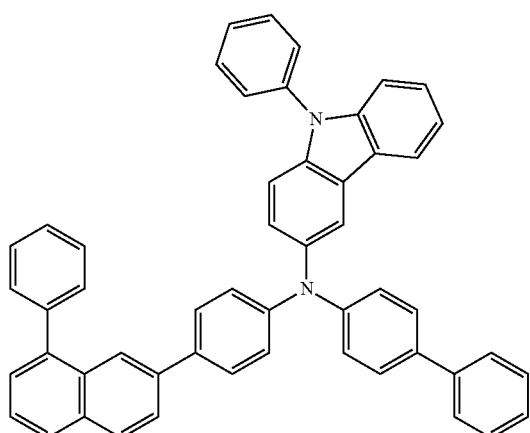
A18
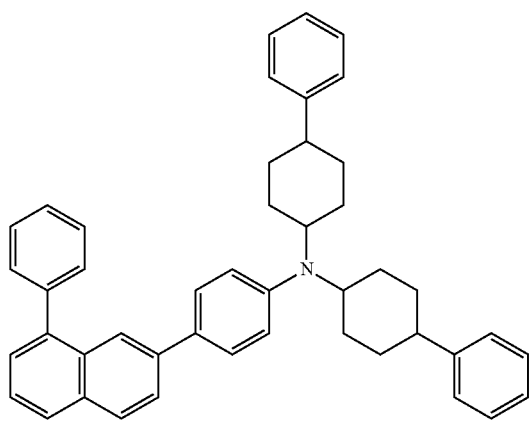
A19
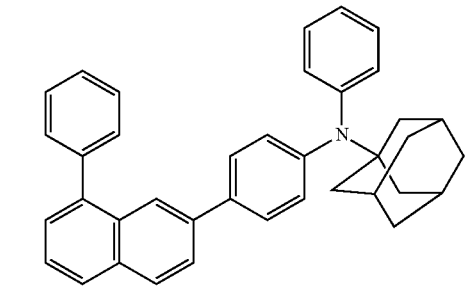
A20
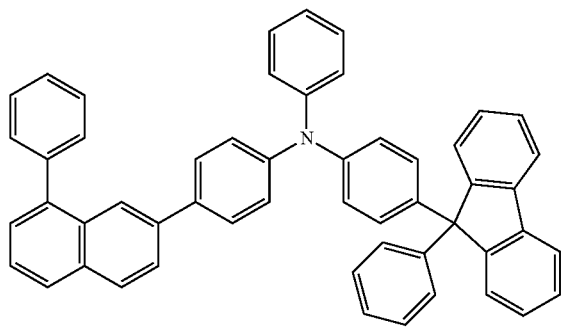
-continued
A21
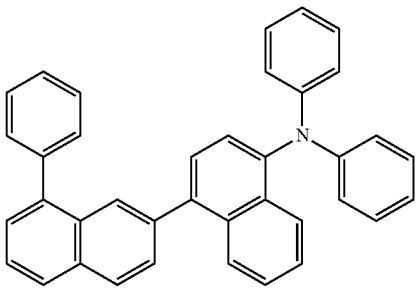
A22
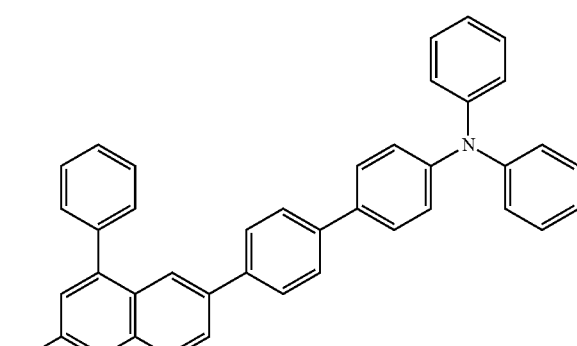
A23
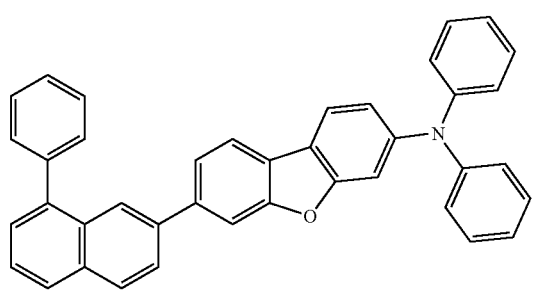
A24
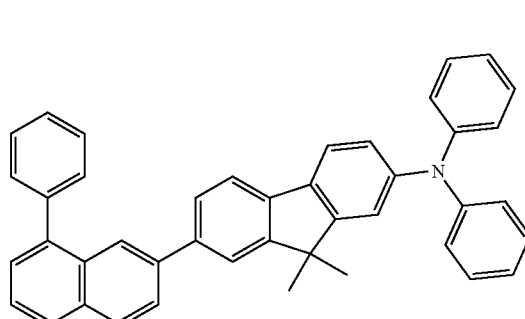

A25
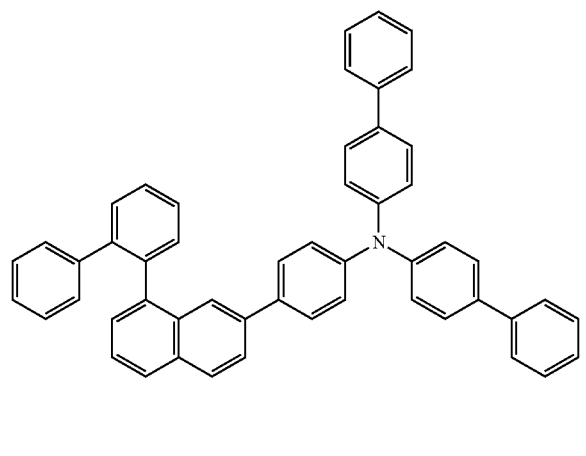
A28
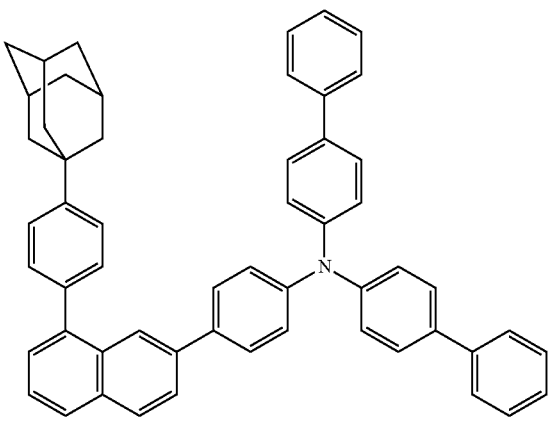
A26
A29
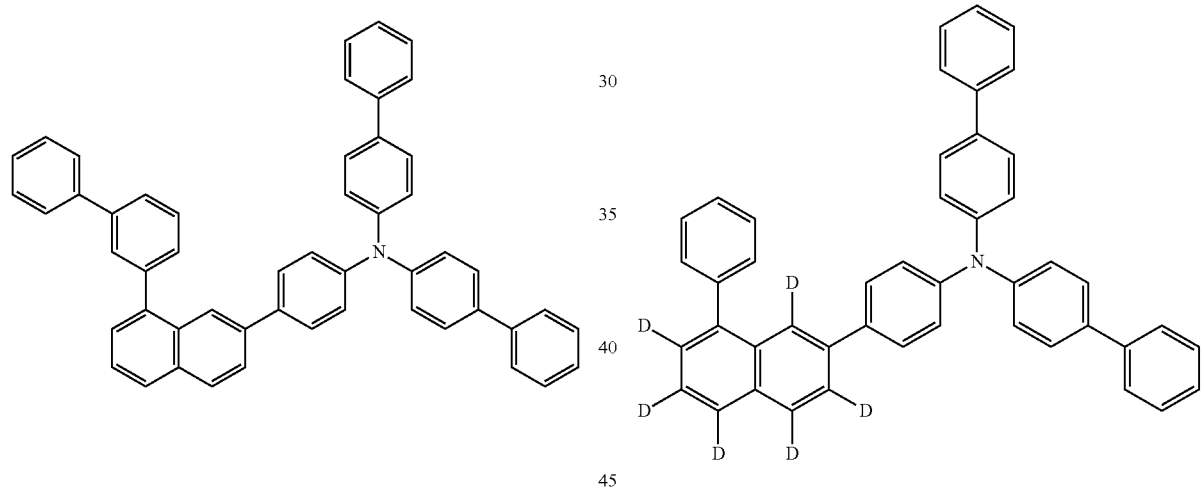
A27
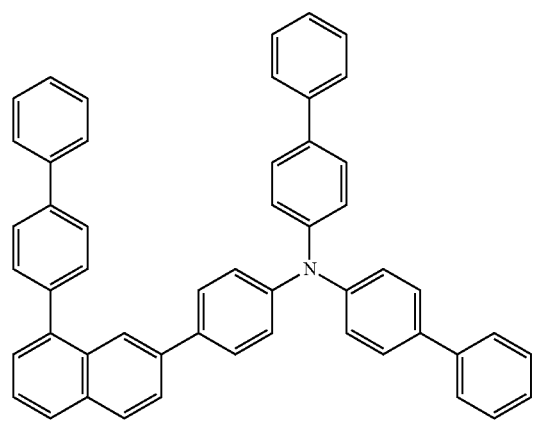
A30
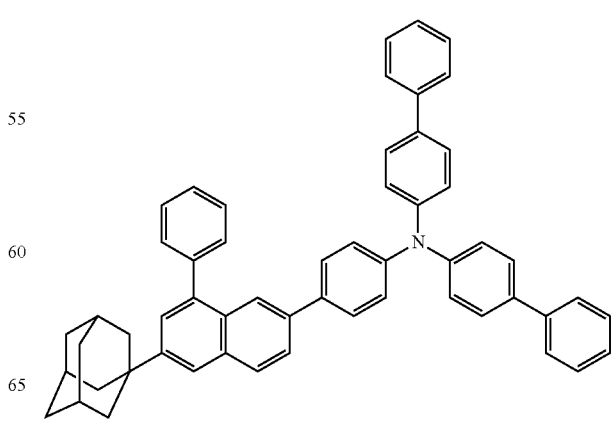

A31
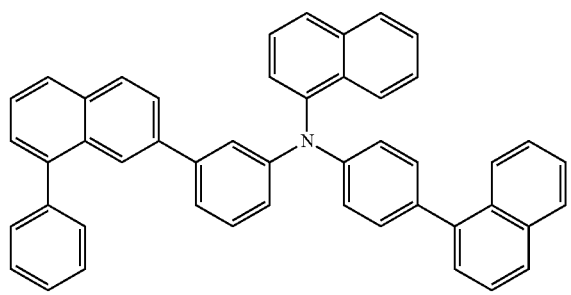
A32
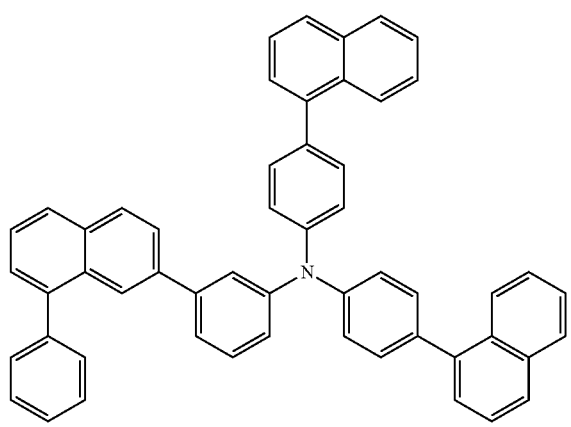
A33
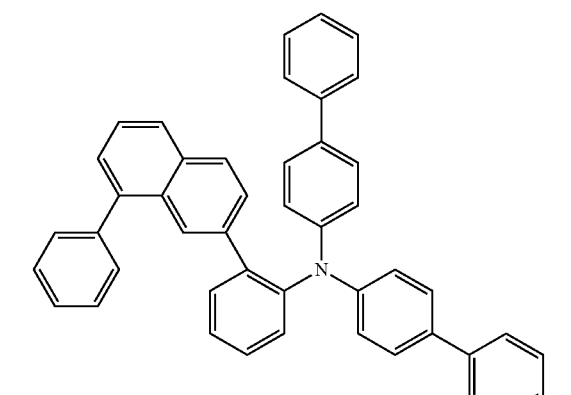
A34
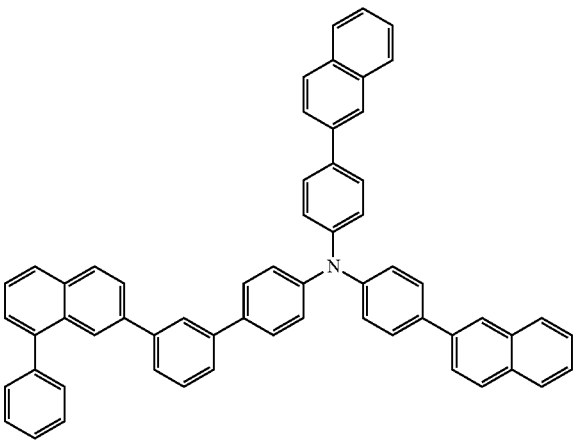
A35
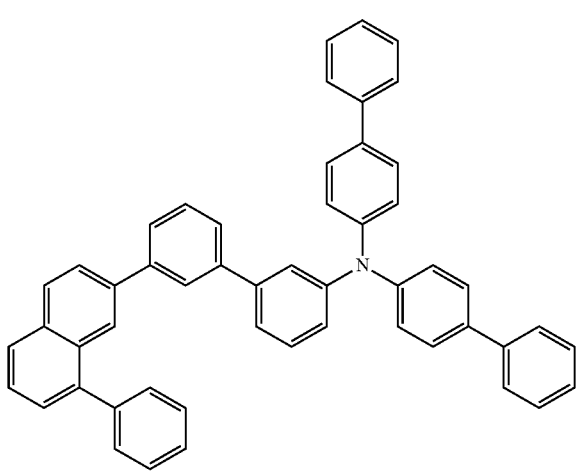
A36
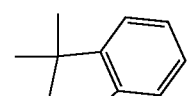
A37
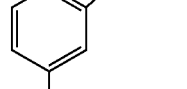

203
-continued
A38
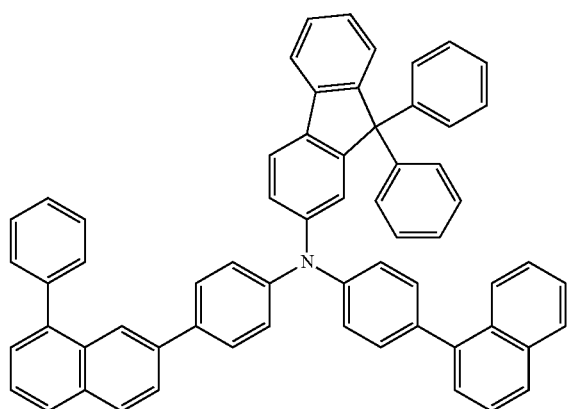
A39
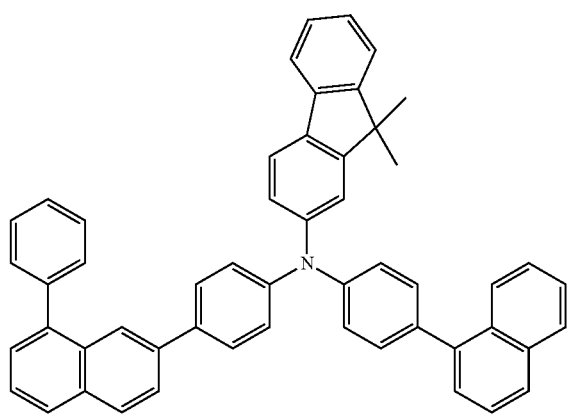
A40
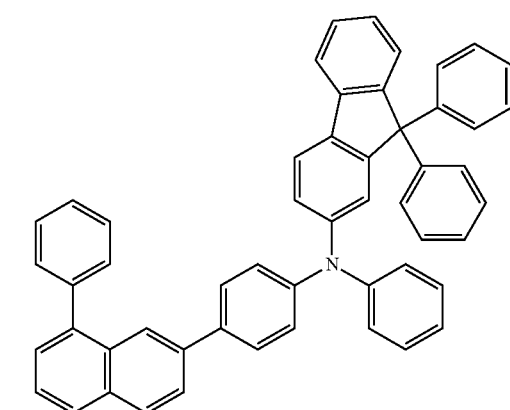
204
-continued
A41
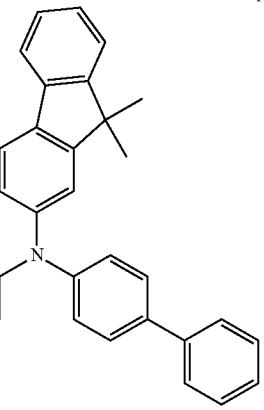
A42
A43
A44

A45
A46
A47
A48
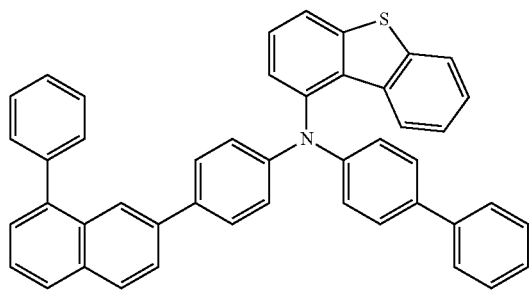
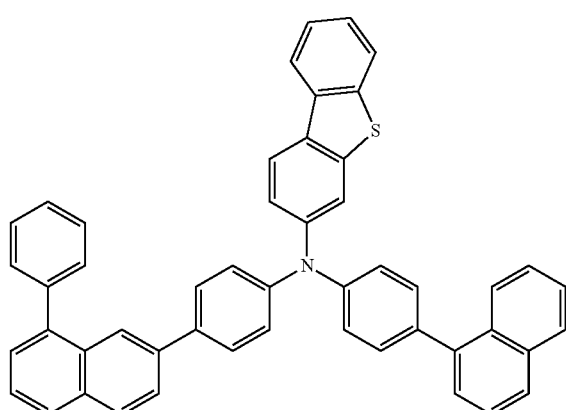
A49
A50
A51
A52
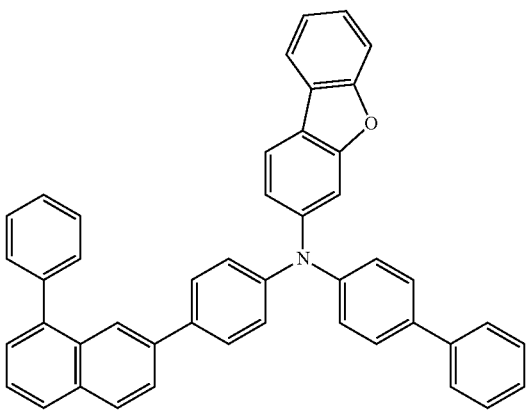
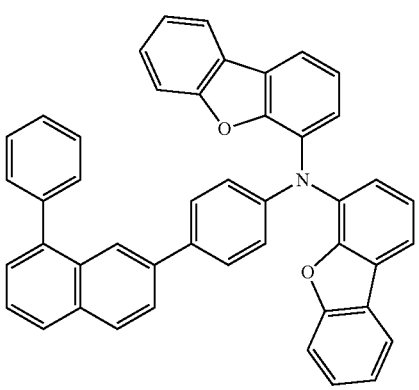

A53
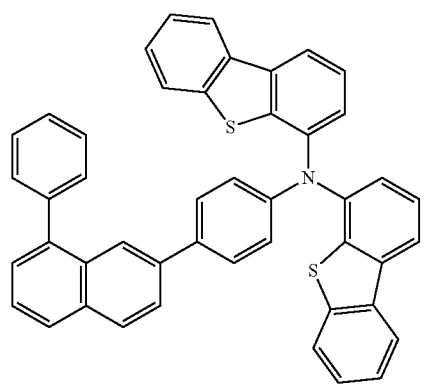
A56
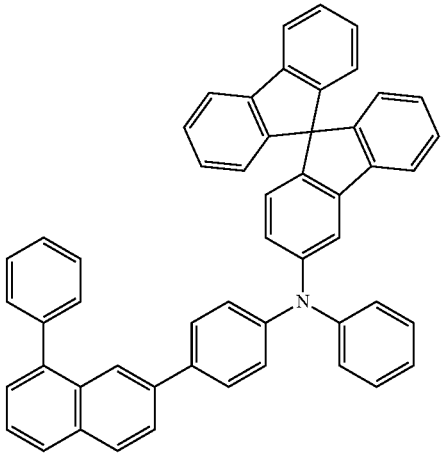
A54
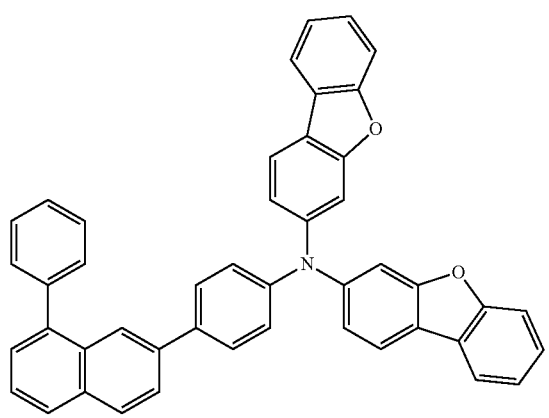
A57
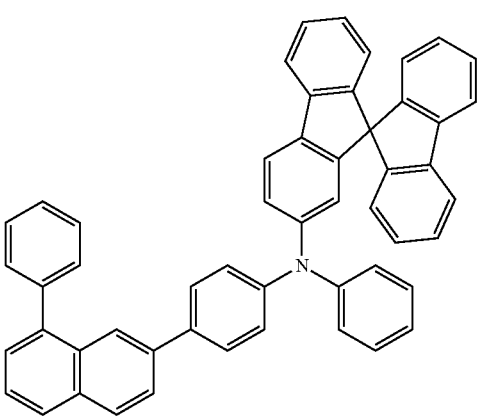
A55
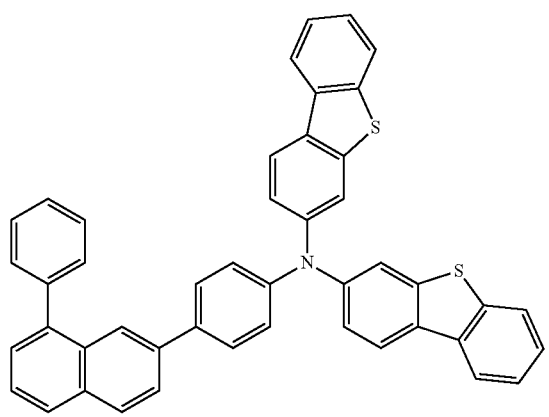
A58
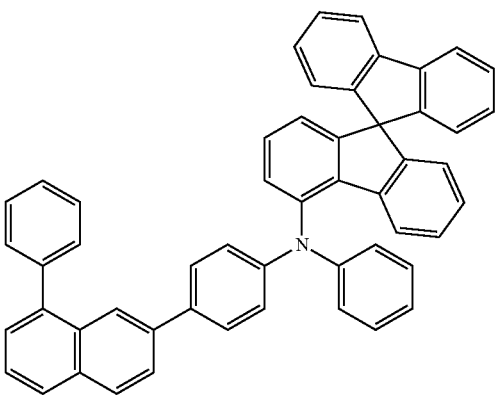

A59
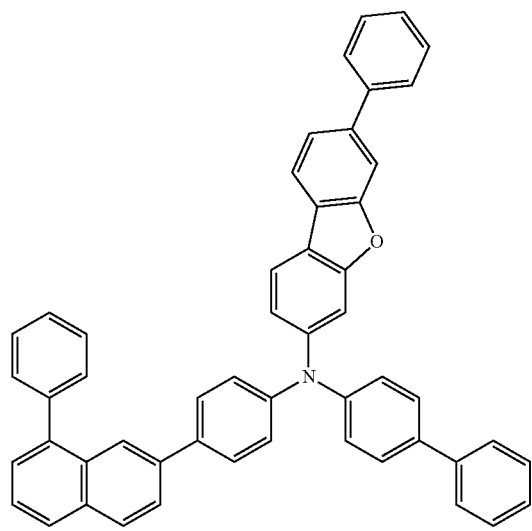
A60
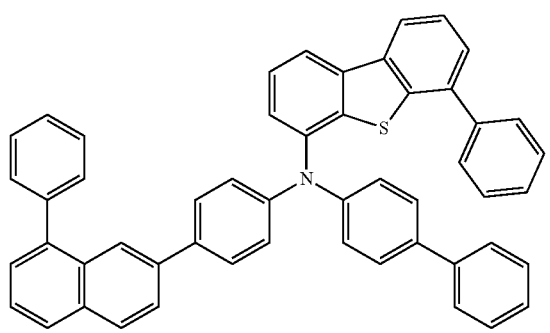
[Compound Group 2]
B1
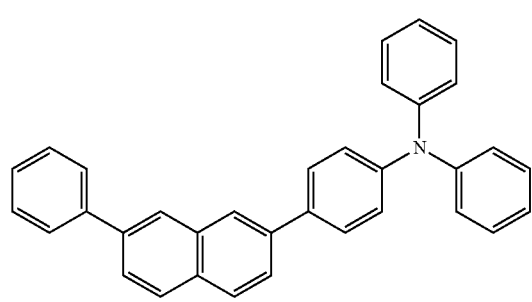
B2
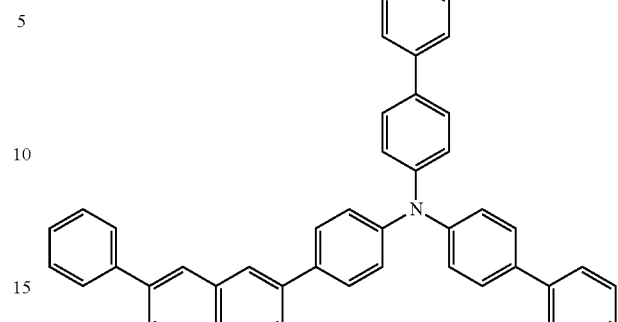
B3
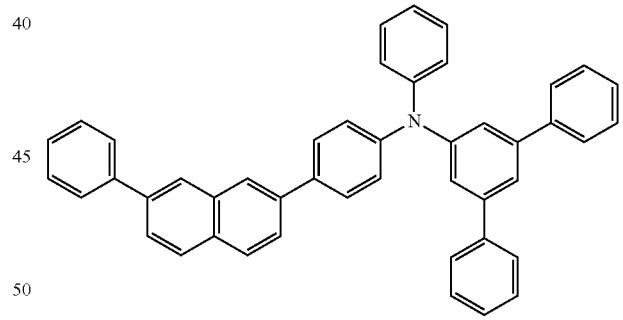
B4
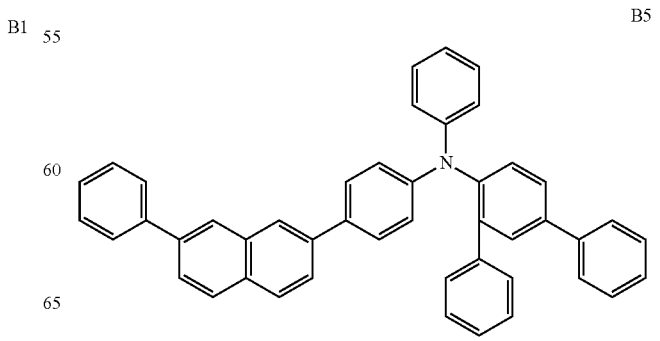
B5

B6
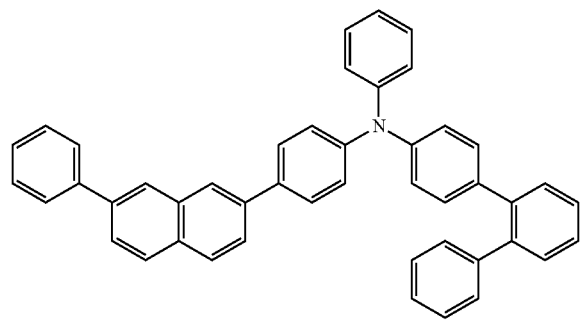
B7
B8
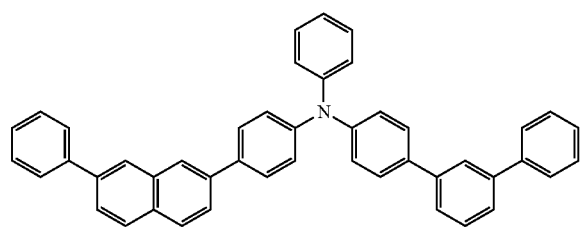
B9
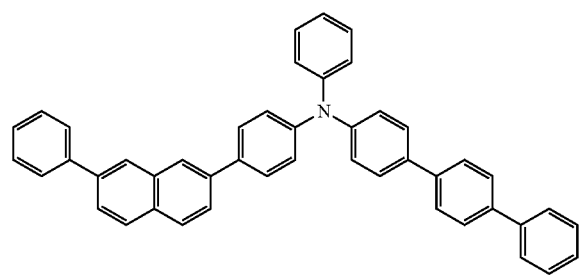
B10
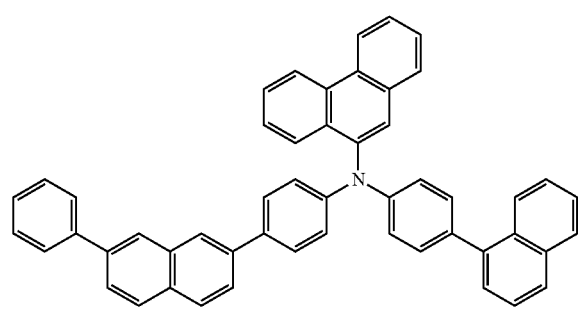
B11
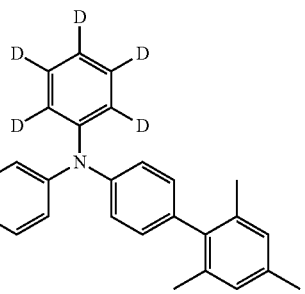
B13
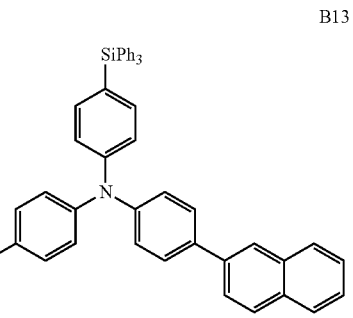
B14
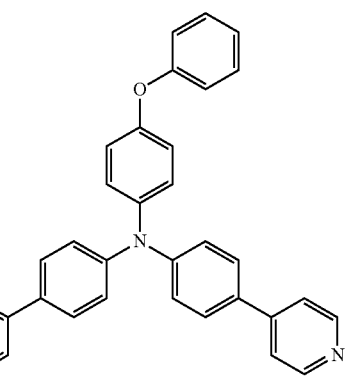
B16
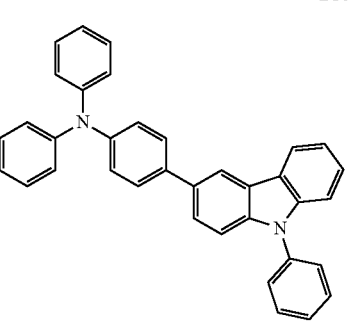

B17
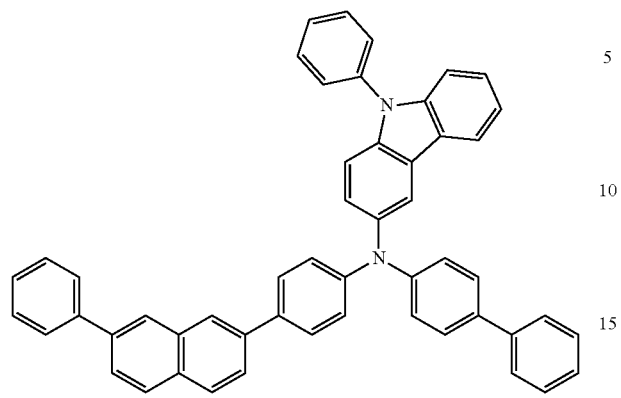
B18
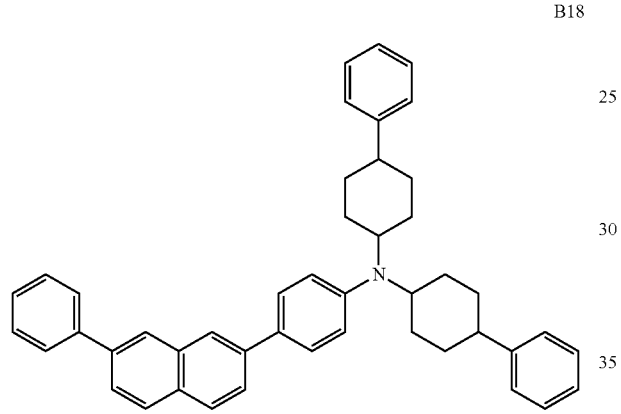
B19
B20
B21
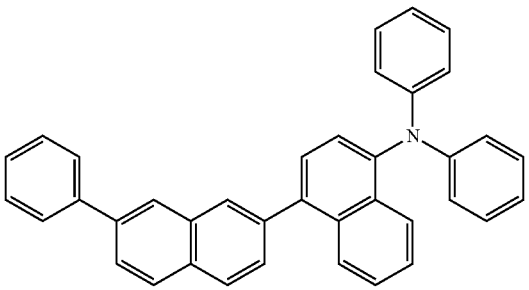
B22
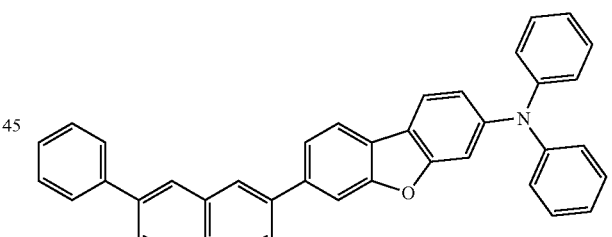
B23
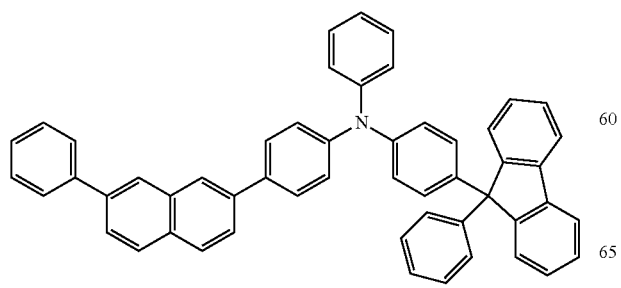
B24
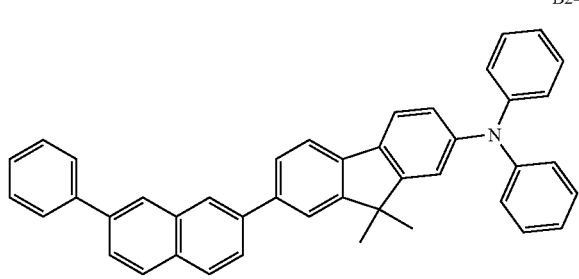

-continued
B25
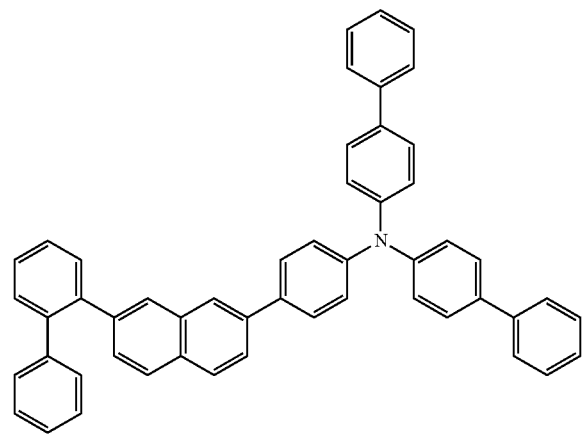
B26
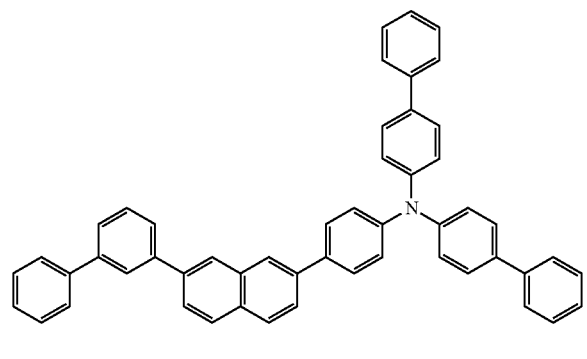
B27
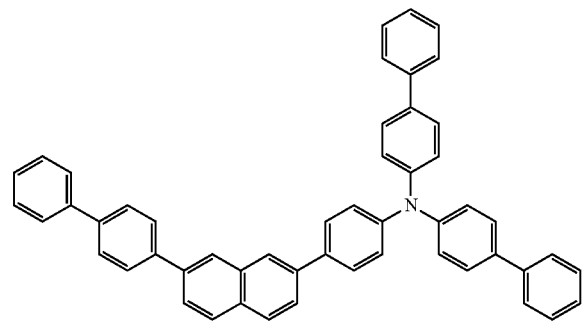
B28
-continued
B29
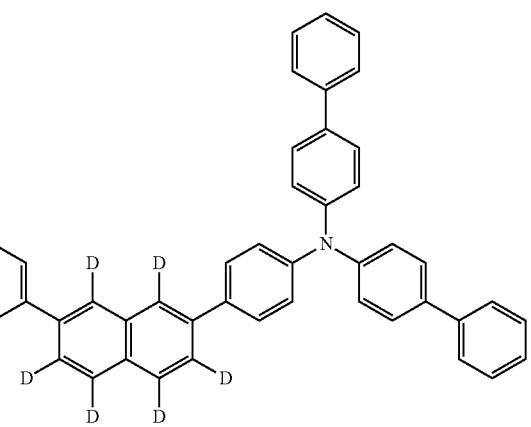
B30
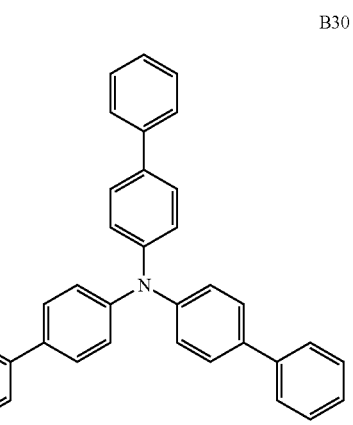
B31
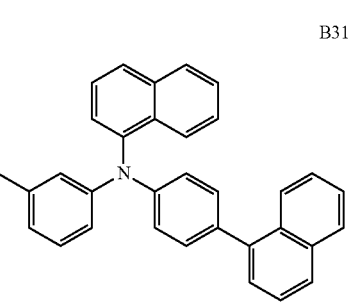
B32
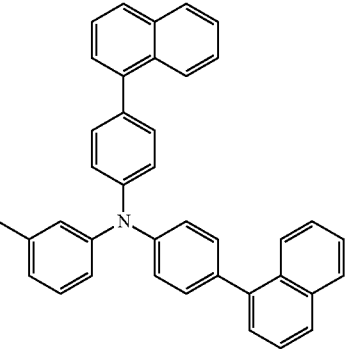

-continued
B33
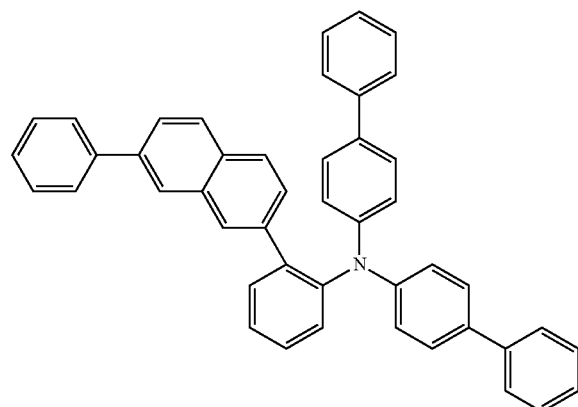
B34
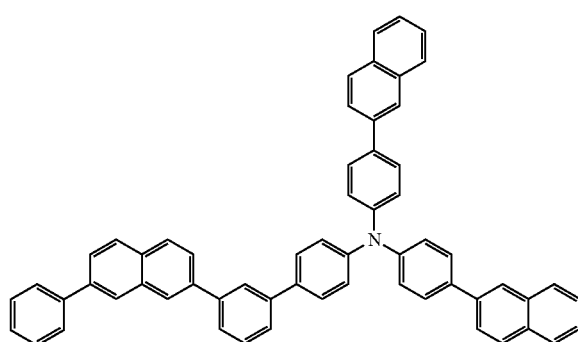
B35
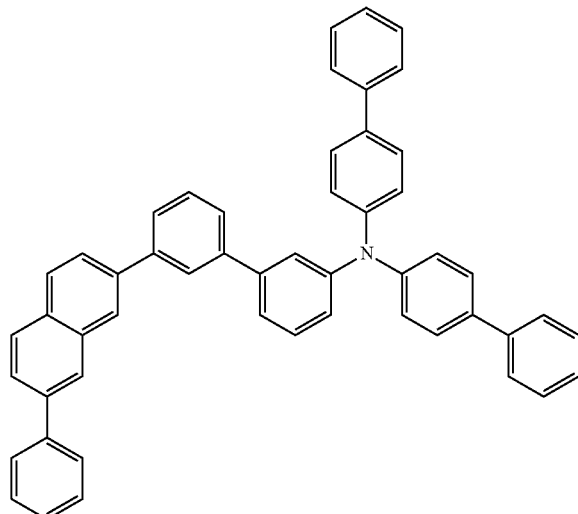
-continued
B36
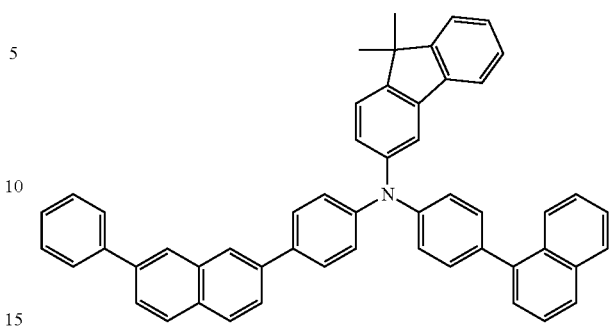
B37
B38
B39

-continued
B40
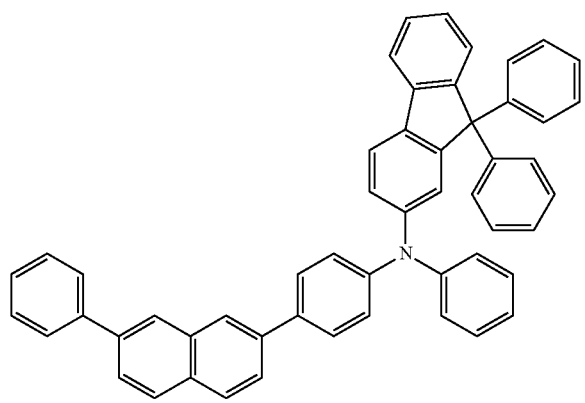
B41
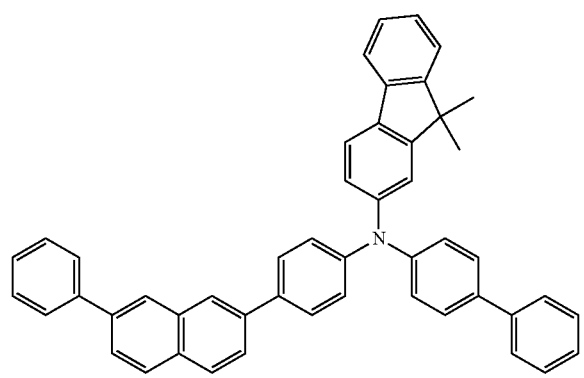
B42
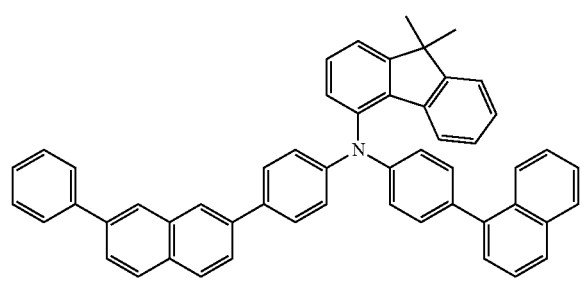
B43
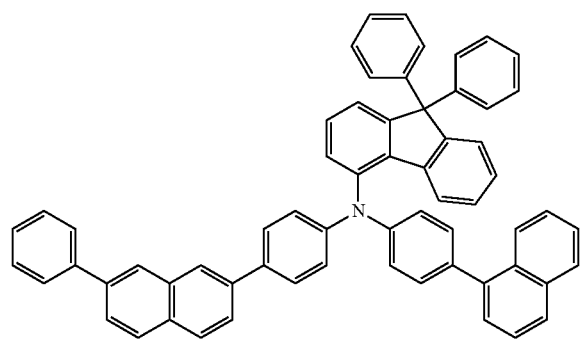
-continued
B44
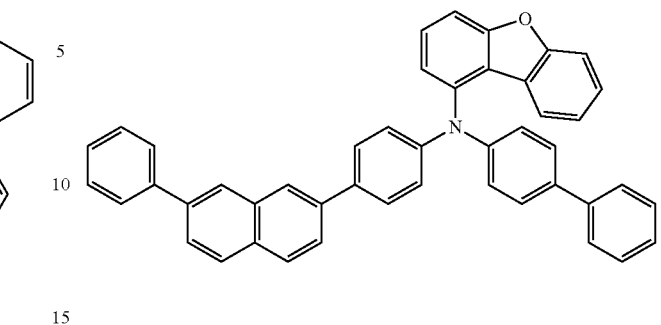
B45
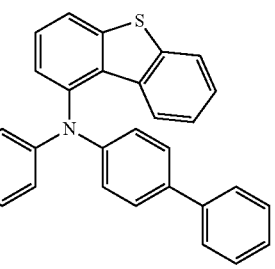
B46
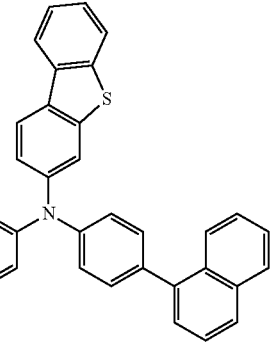
B47
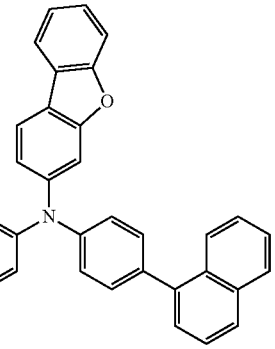

B48
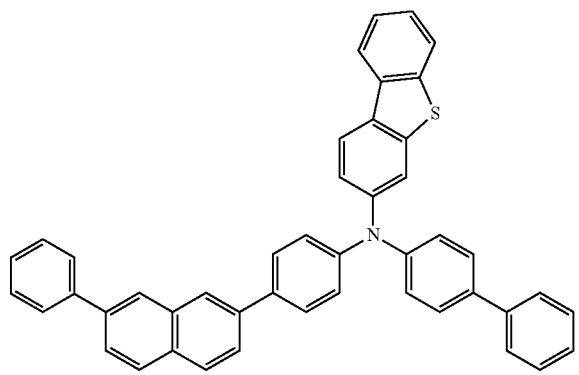
B49
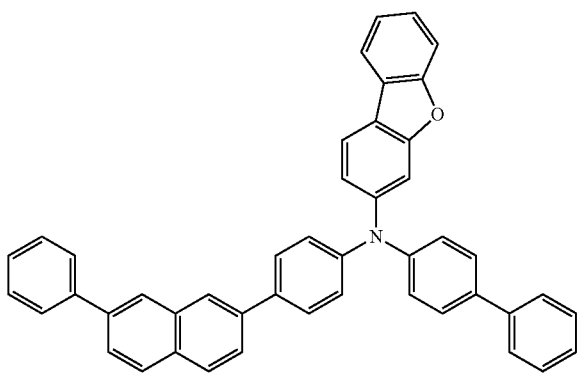
B50
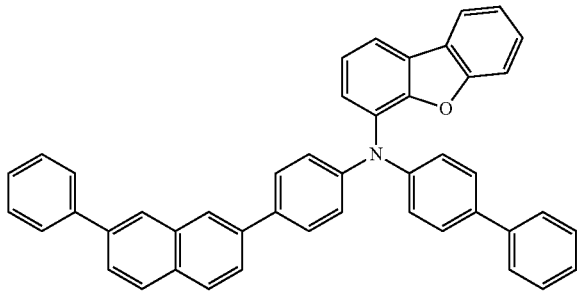
B51
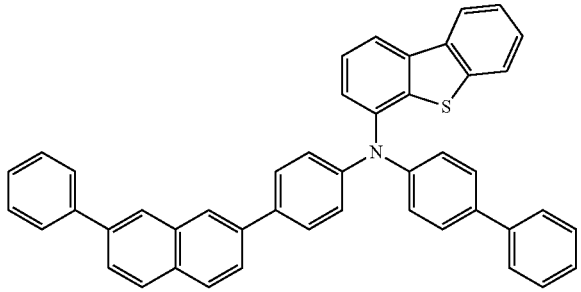
B52
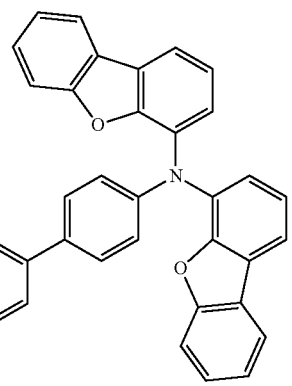
B53
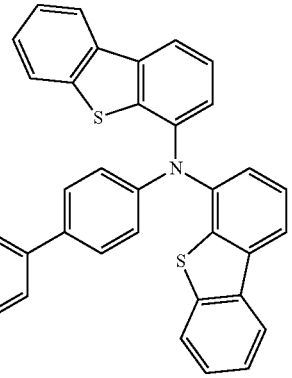
B54
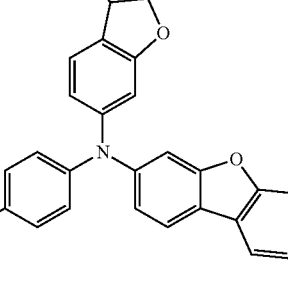
B55
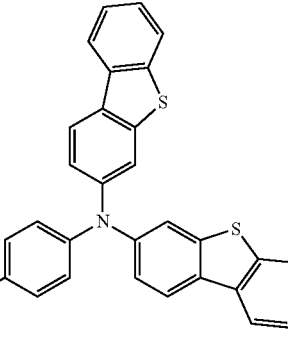

B56
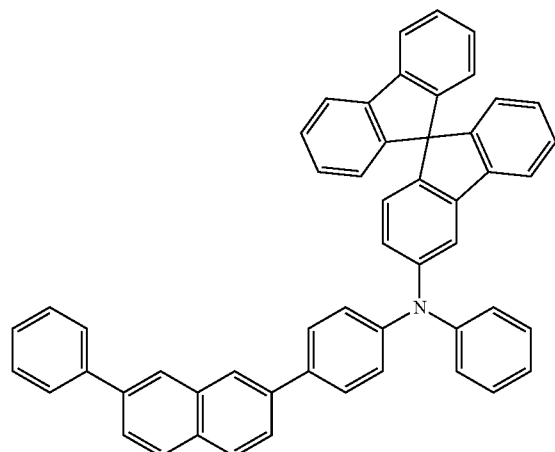
B57
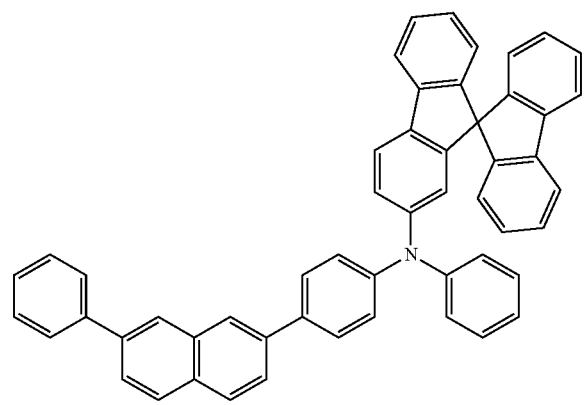
B58
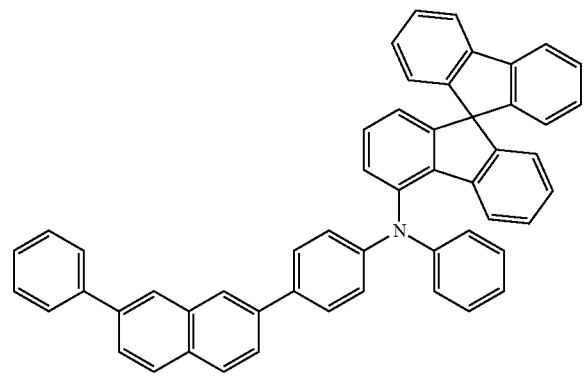
B59
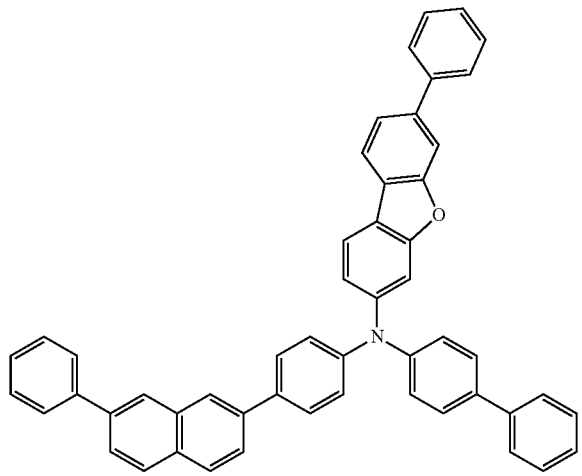
B60
[Compound Group 3]
C1
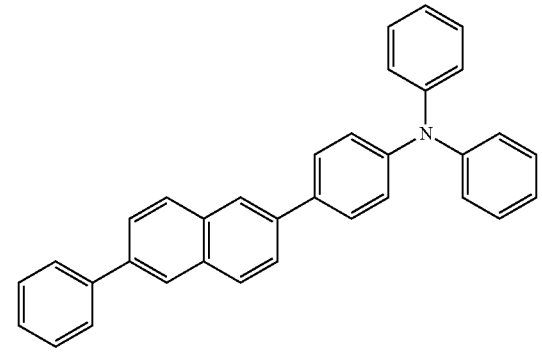

C2
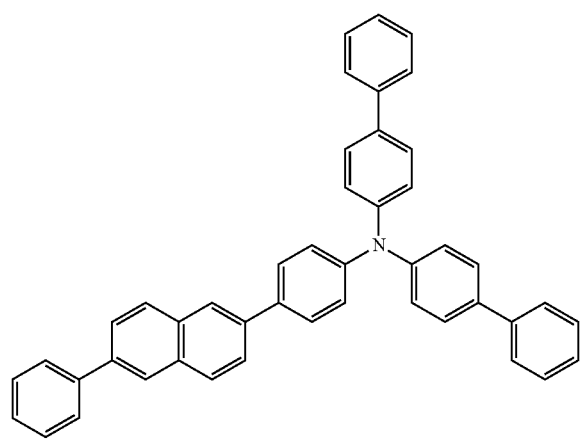
C3
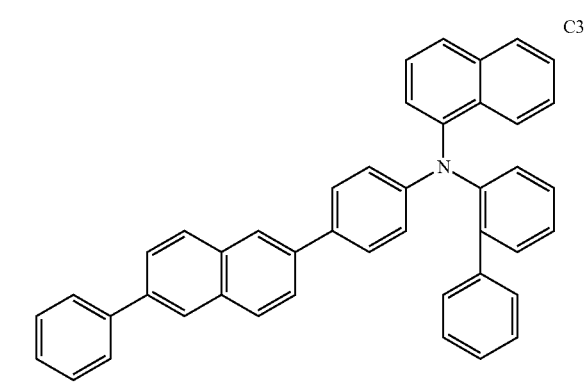
C4
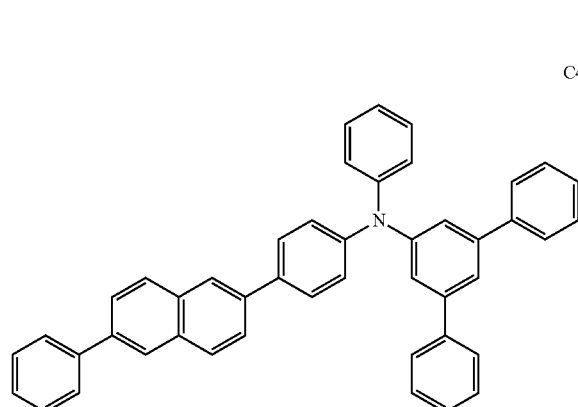
C5
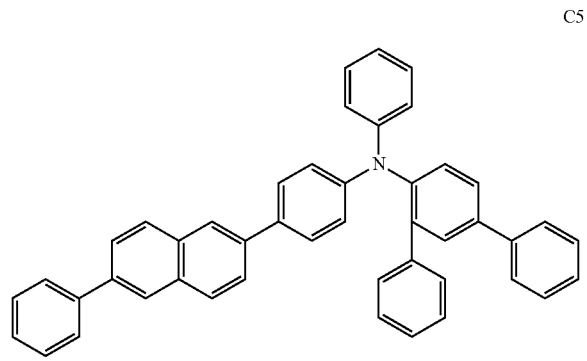
C6
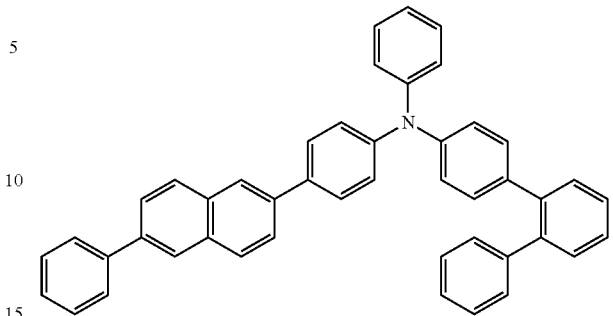
C7
C8
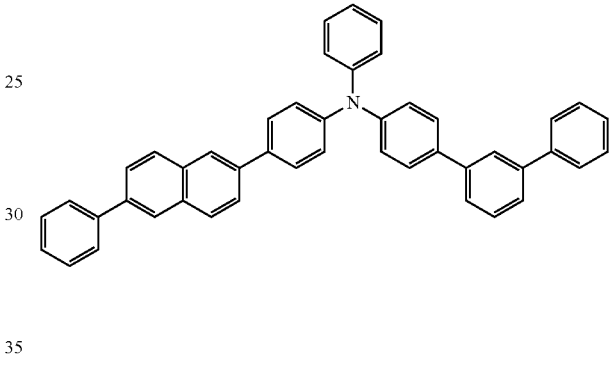
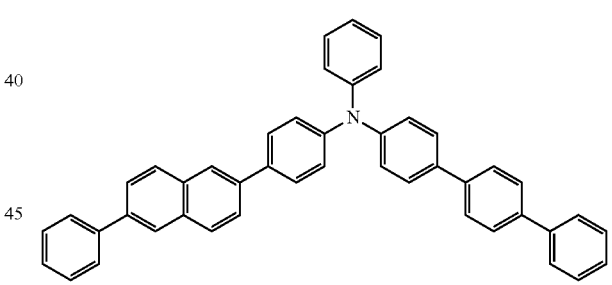
C9
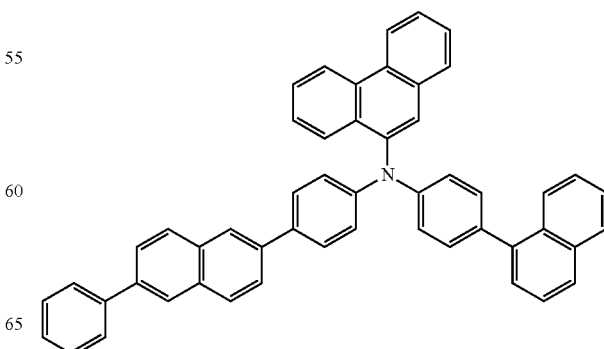

C10
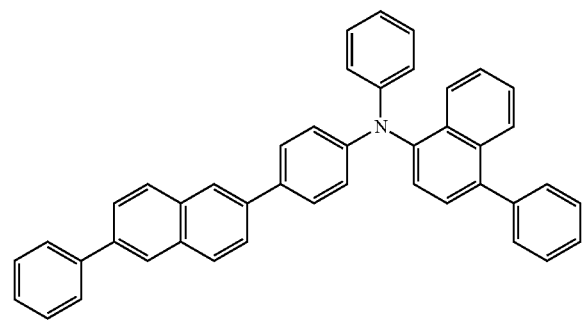
C11
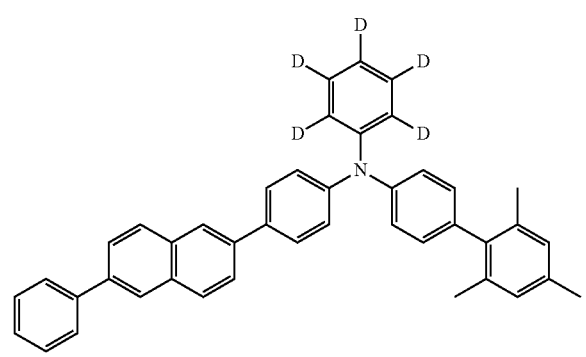
C12
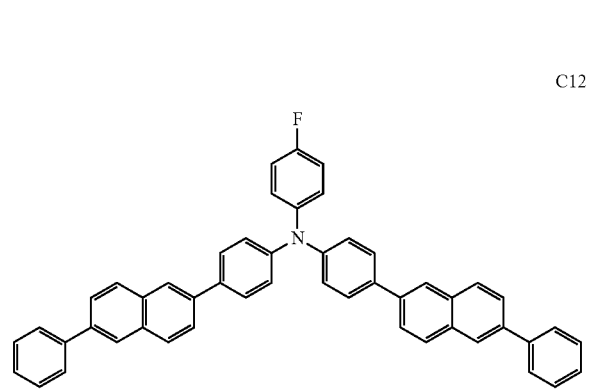
C13
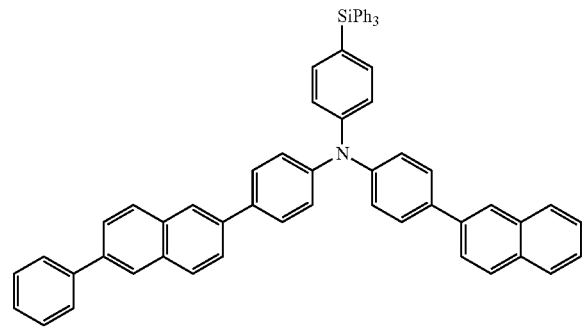
C14
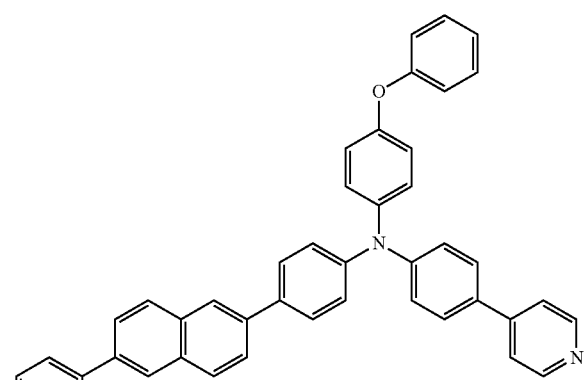
C15
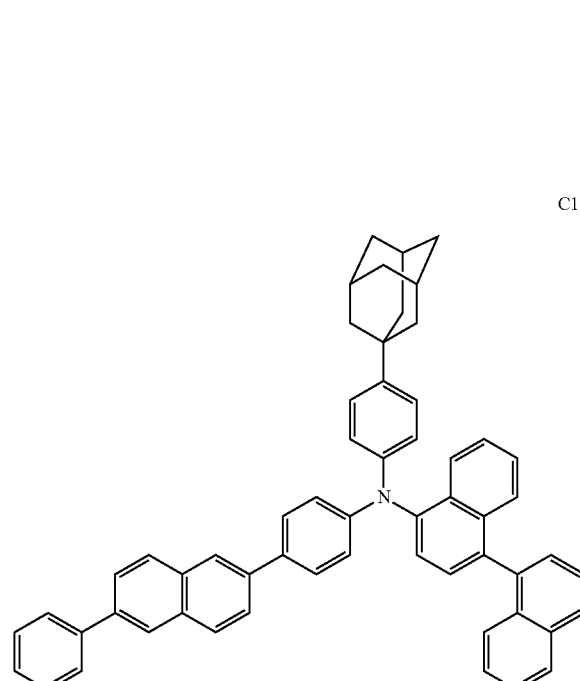
C16
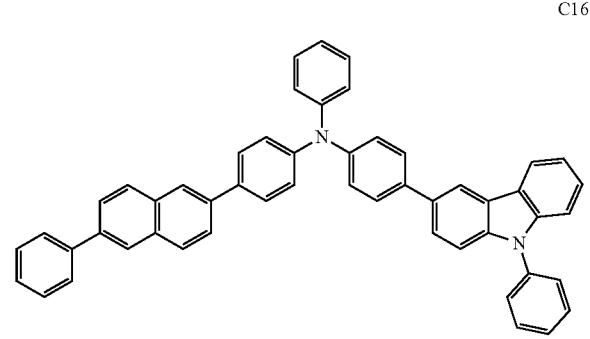

C17
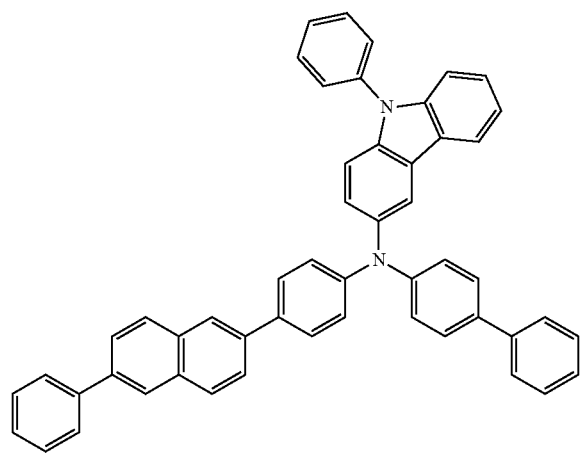
C18
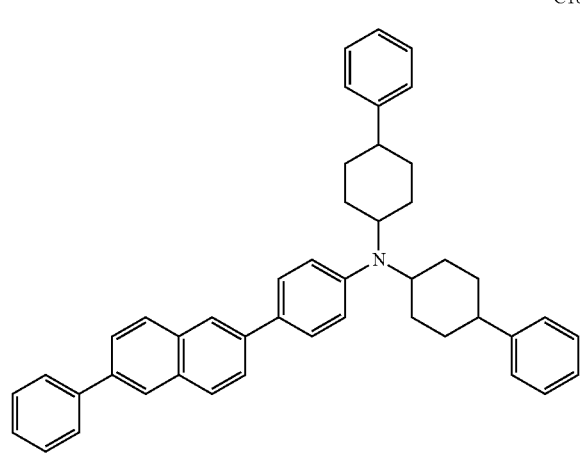
C19
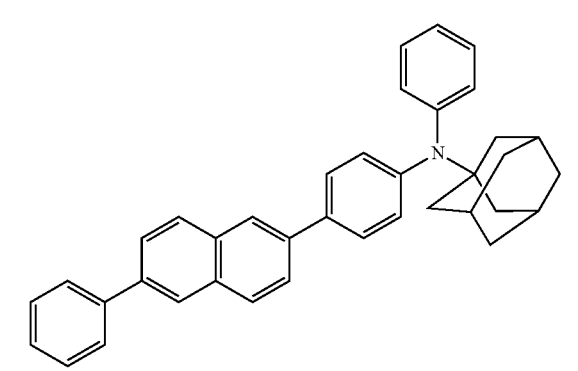
C20
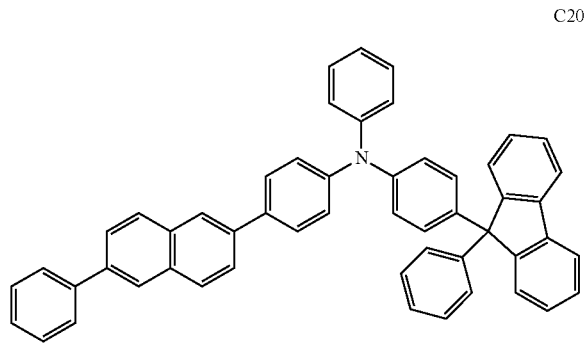
C21
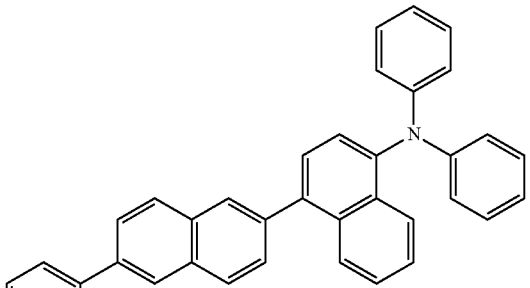
C22
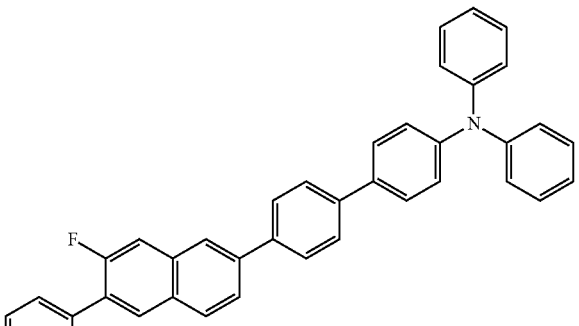
C23
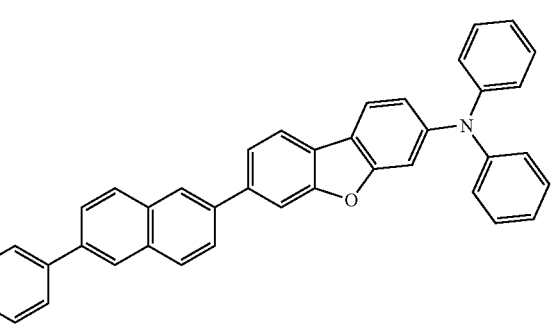
C24
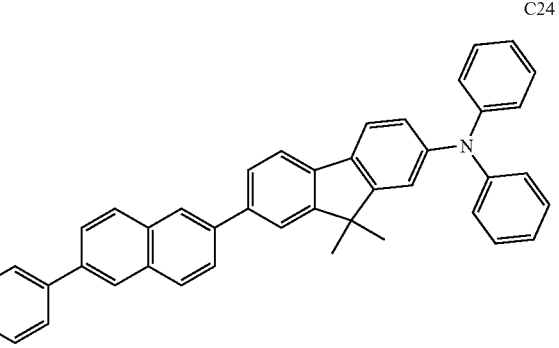

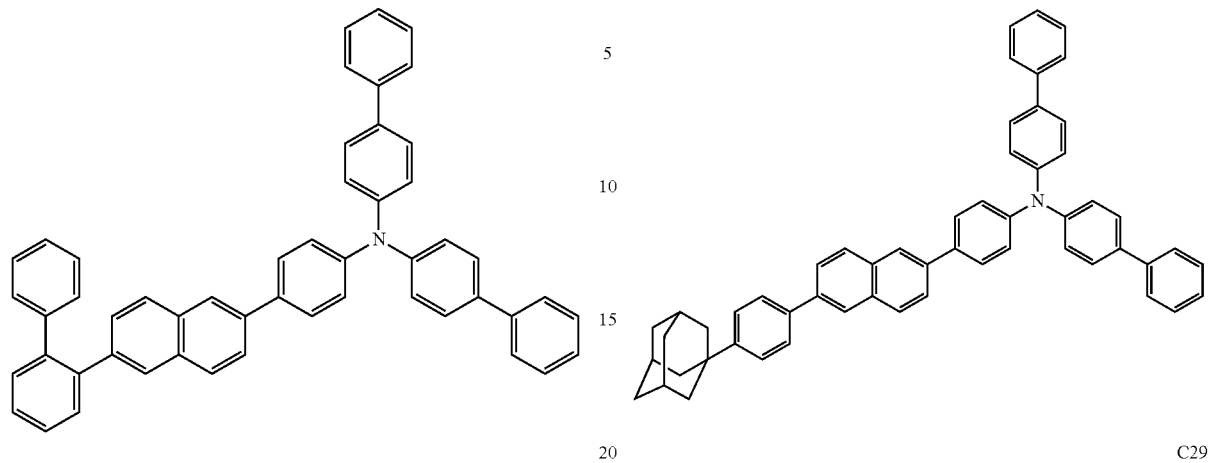

233
-continued
C32
C33
C34
C35
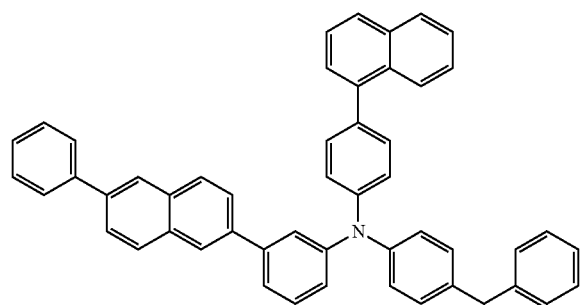
234
-continued
C36
C37
C38
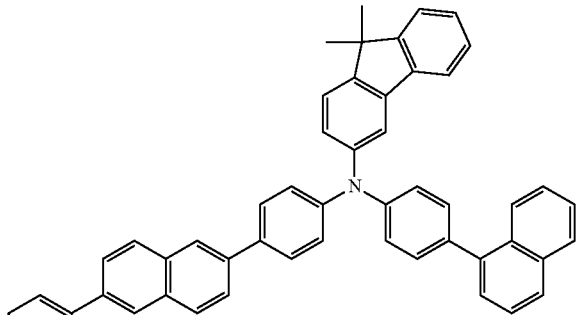

-continued
C39
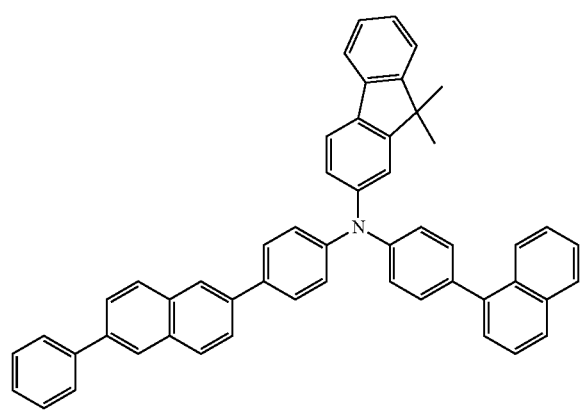
C40
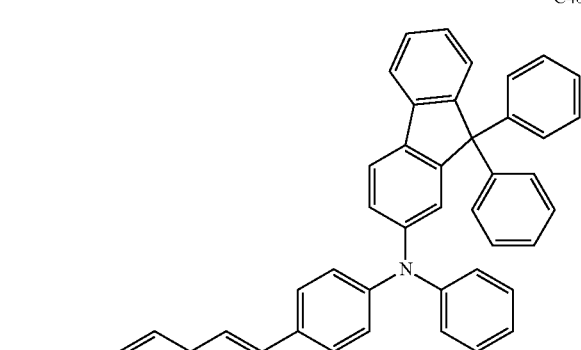
C41
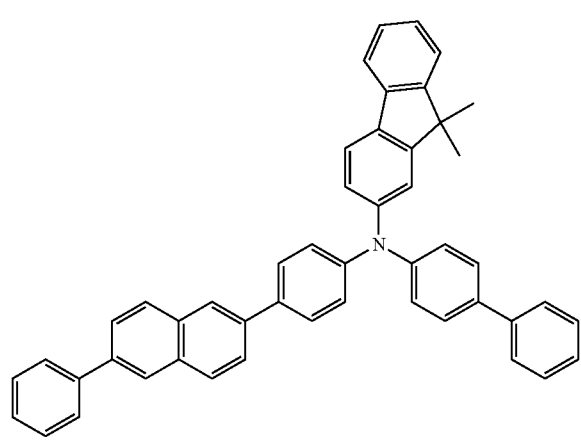
-continued
C42
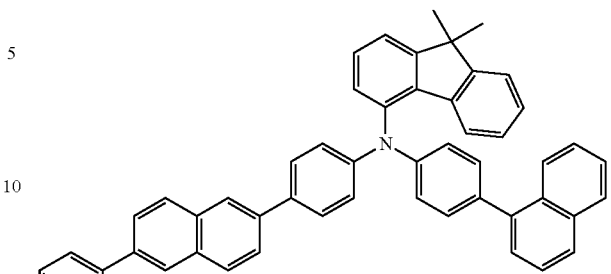
C43
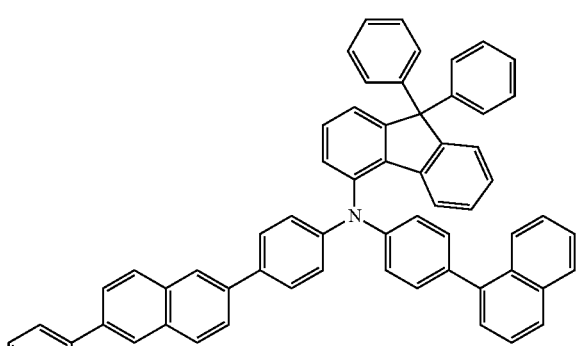
C44
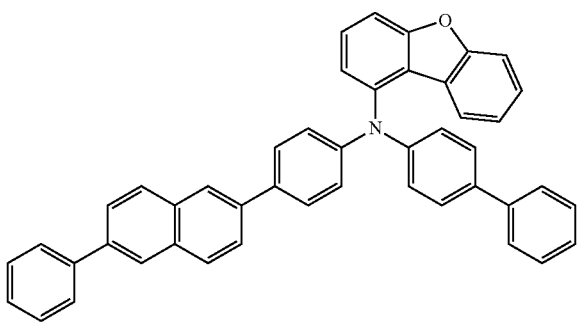
C45
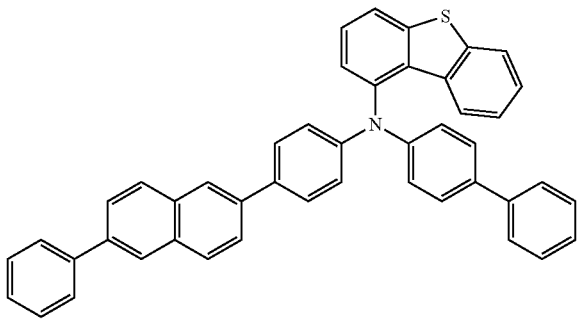

C46
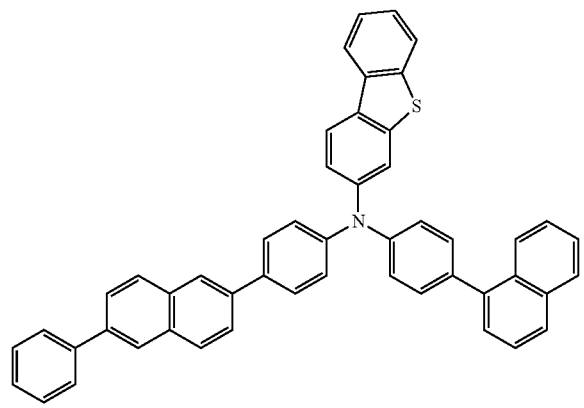
C47
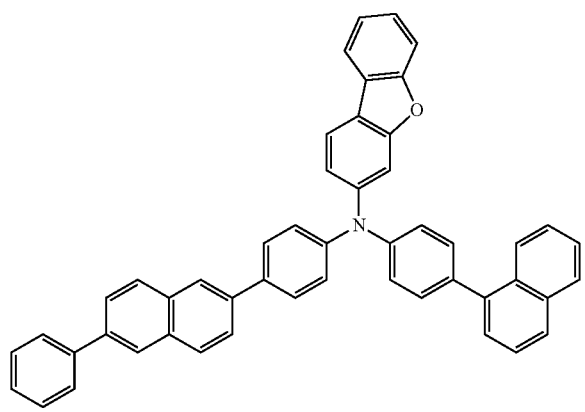
C48
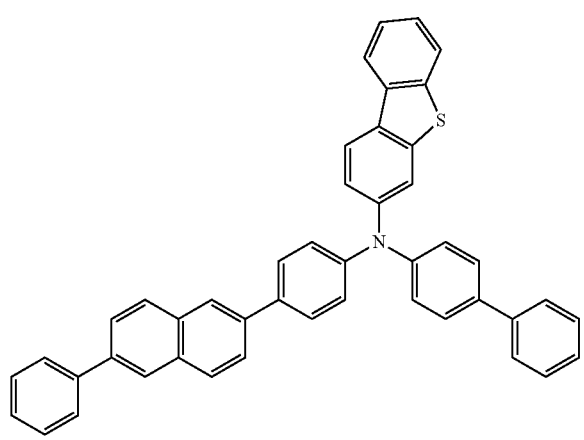
C49
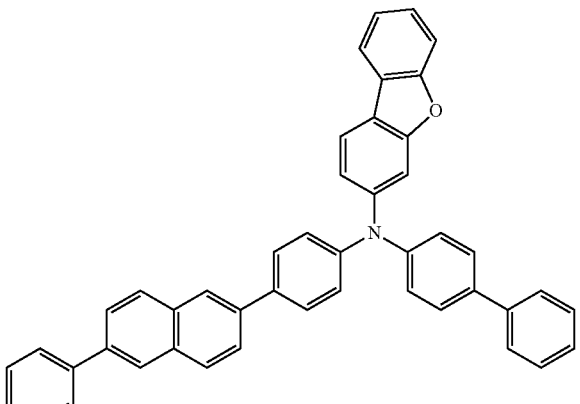
C50
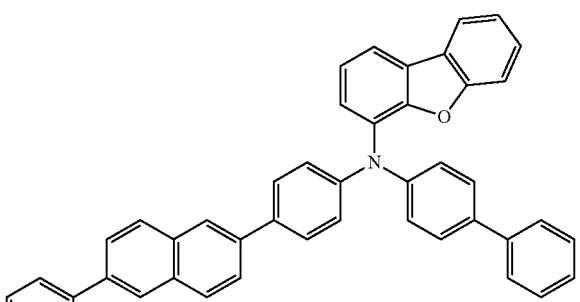
C51
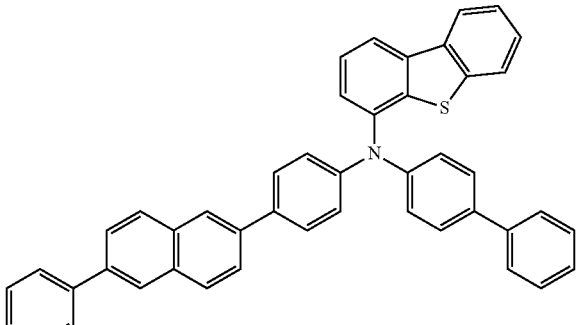
C52
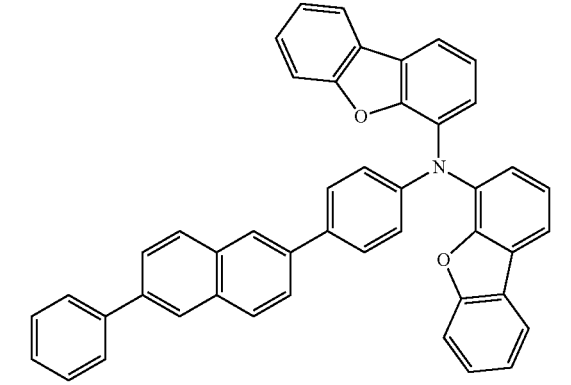

-continued
C53
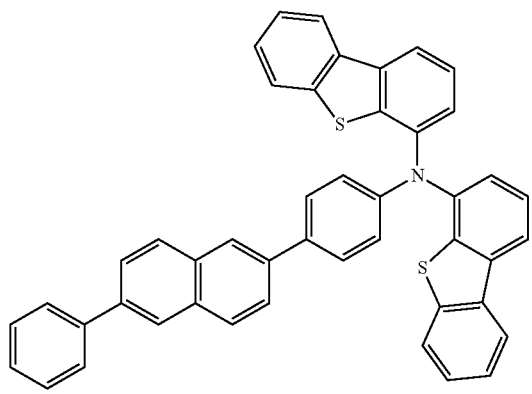
C54
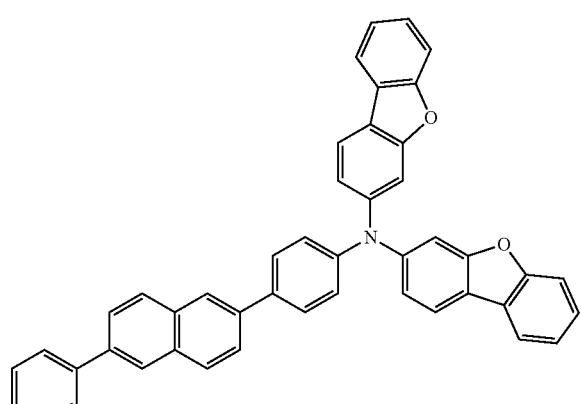
C55
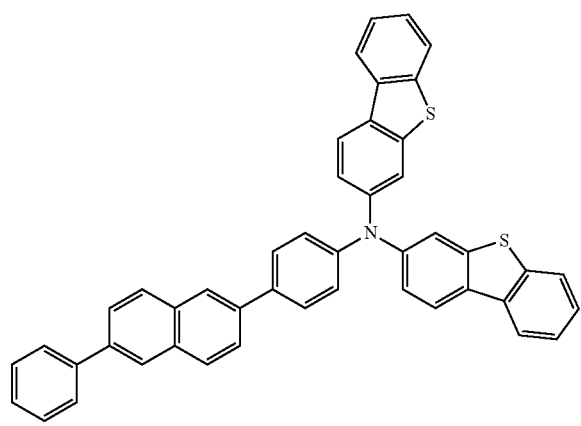
-continued
C56
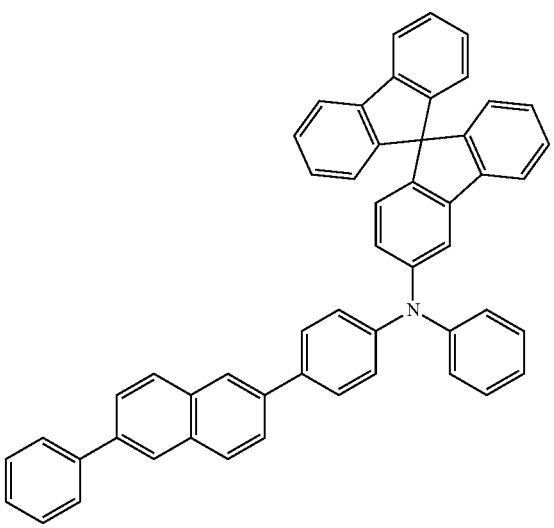
C57
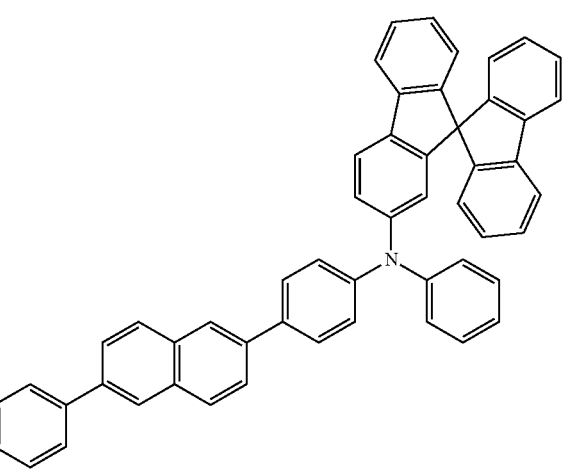
C58
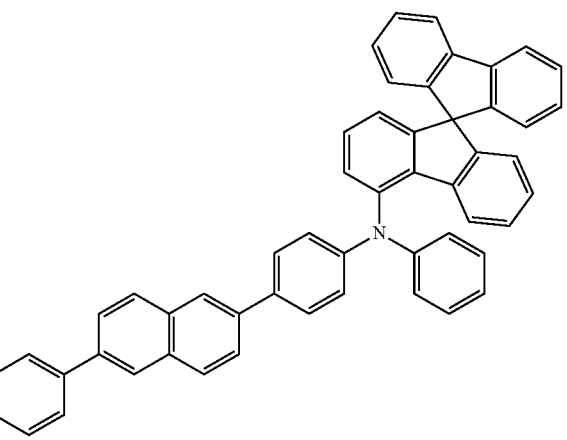

C59
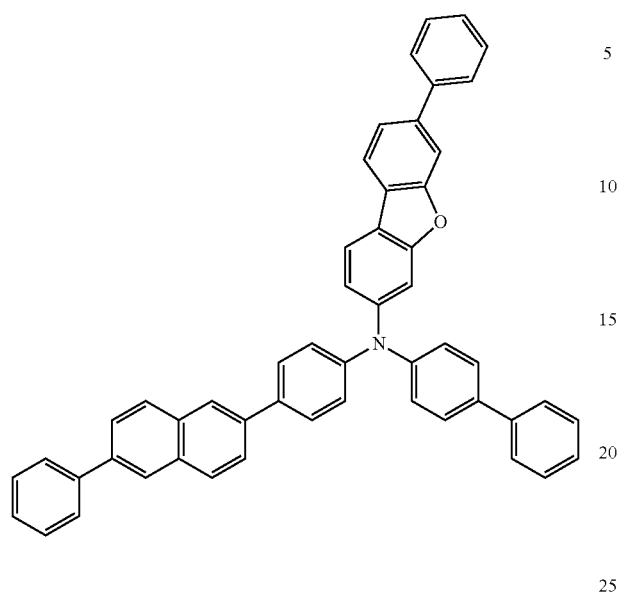
D2
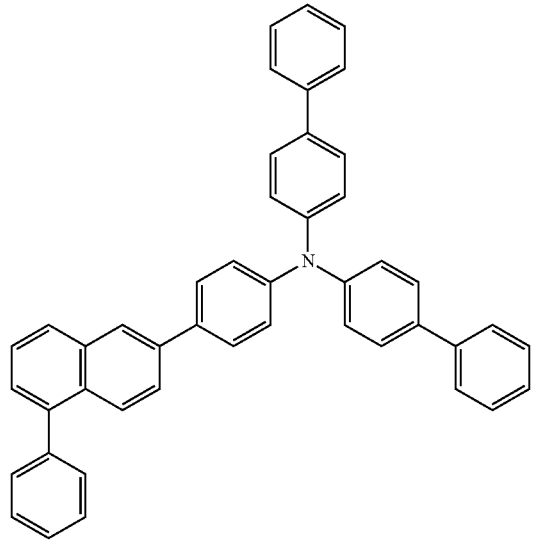
C60
D3
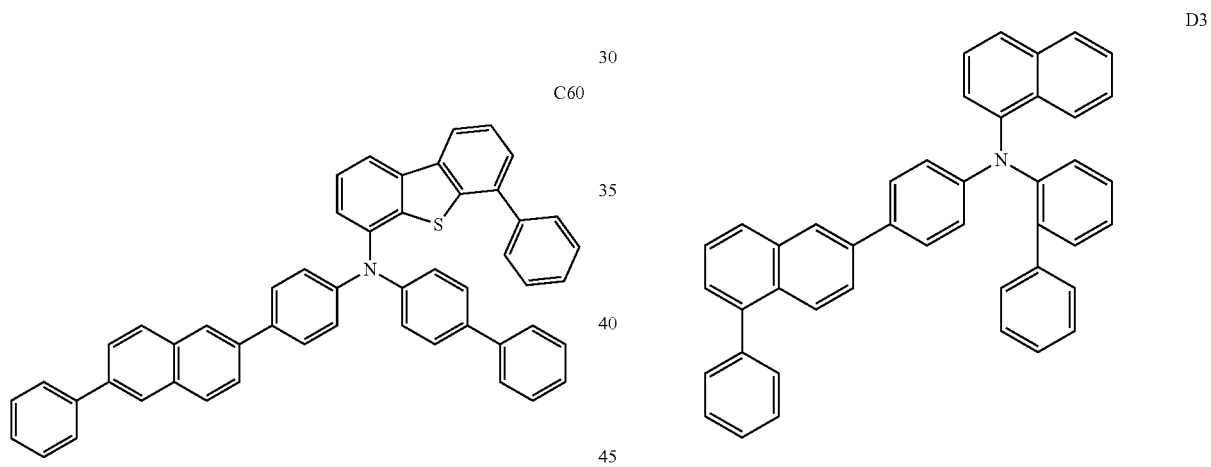
[Compound Group 4]
D1
D4
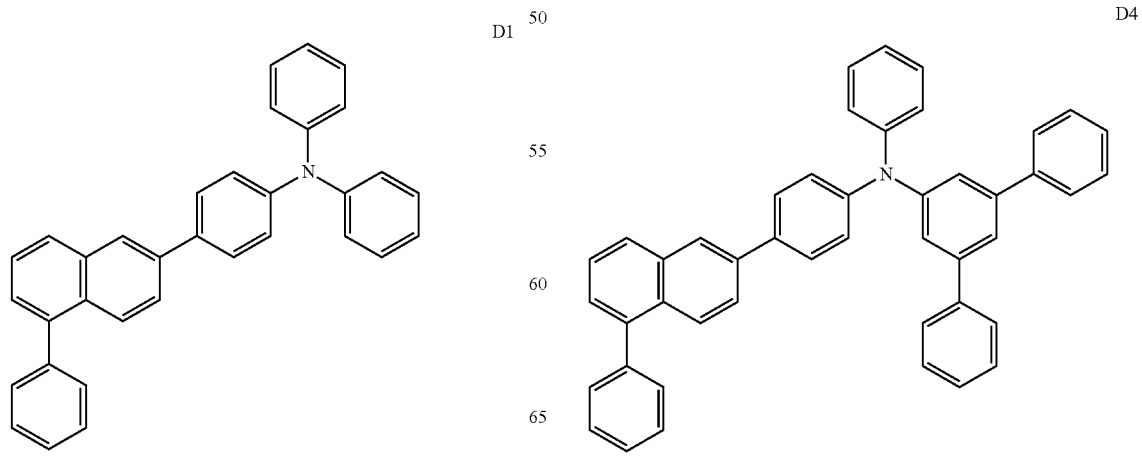

D5
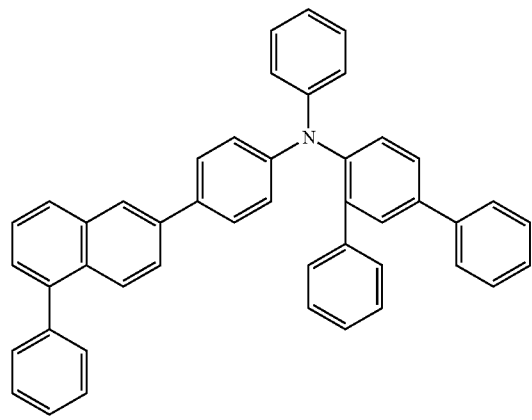
D6
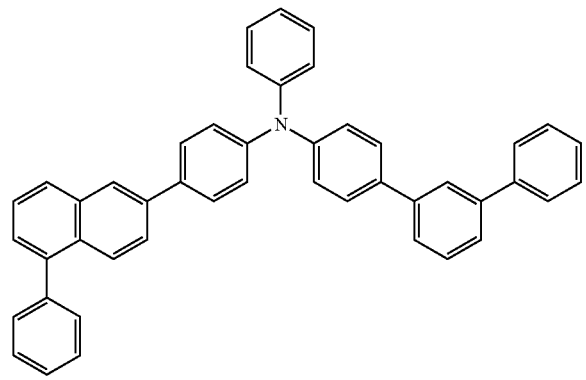
D7
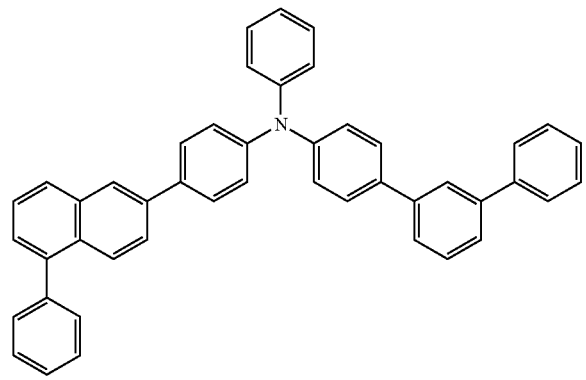
D8
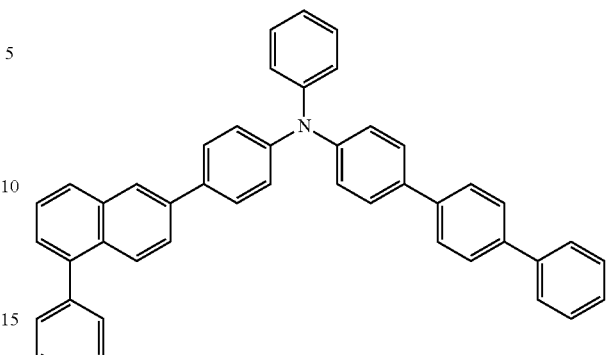
D9
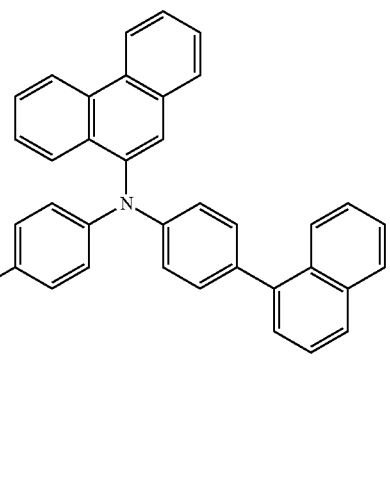
D10
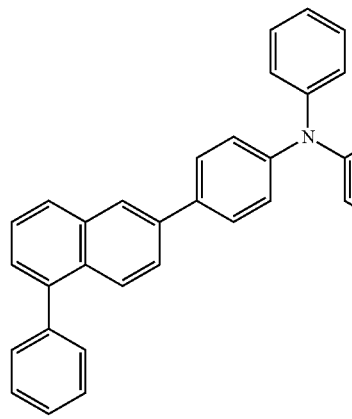

D11
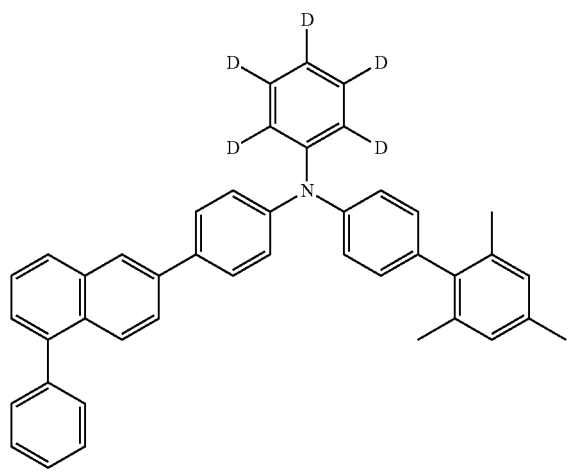
D12
D13
D14
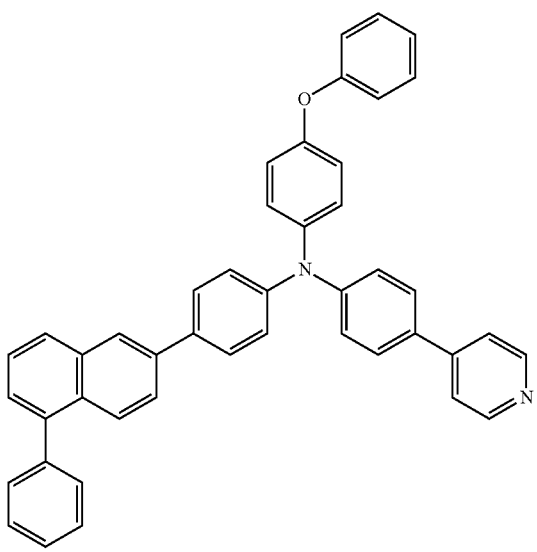
D15
D16
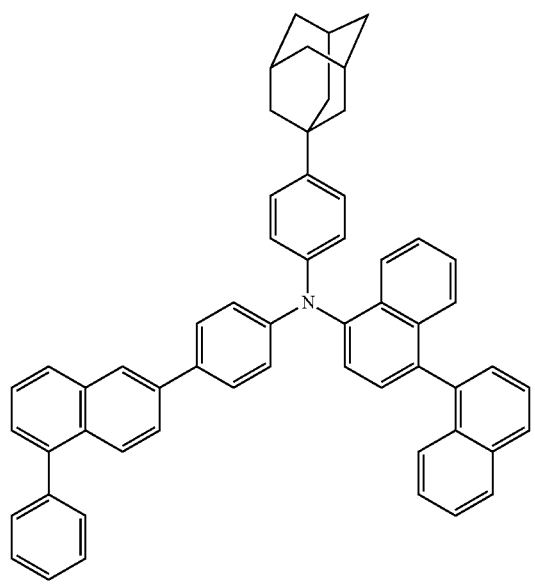
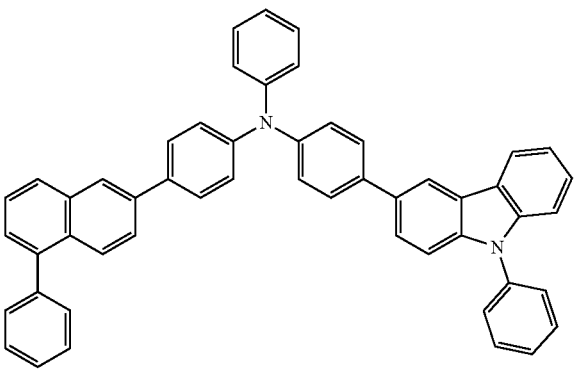

D17

D18

D19

D20

D21

D22

D23
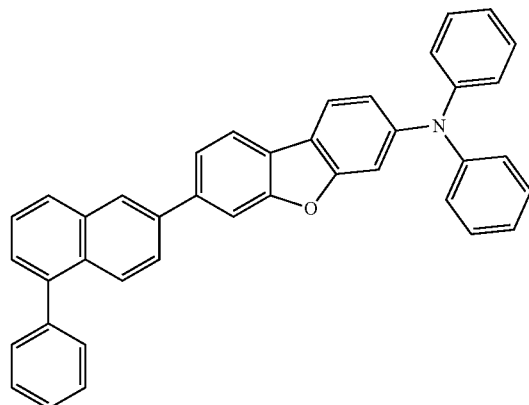
D24
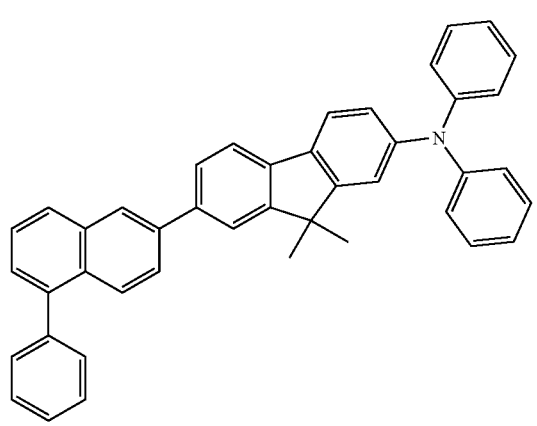
D25
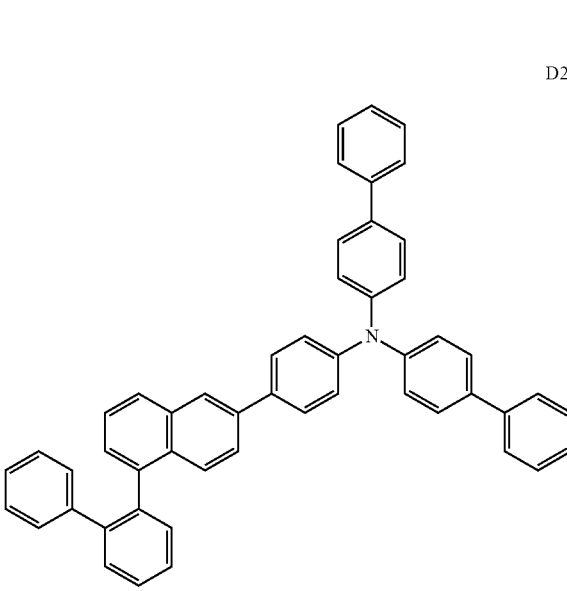
D26
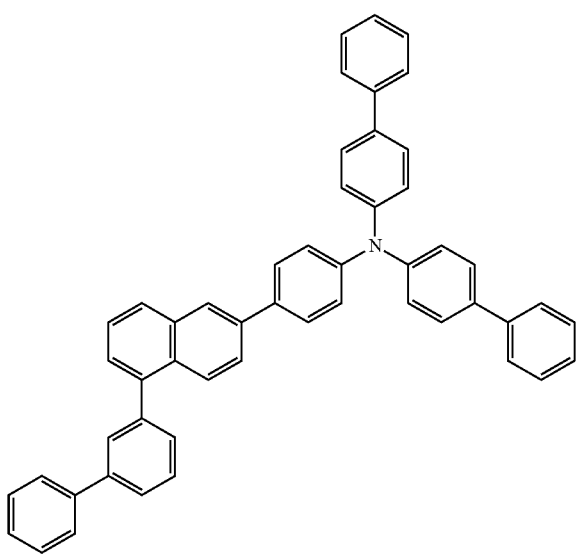
D27
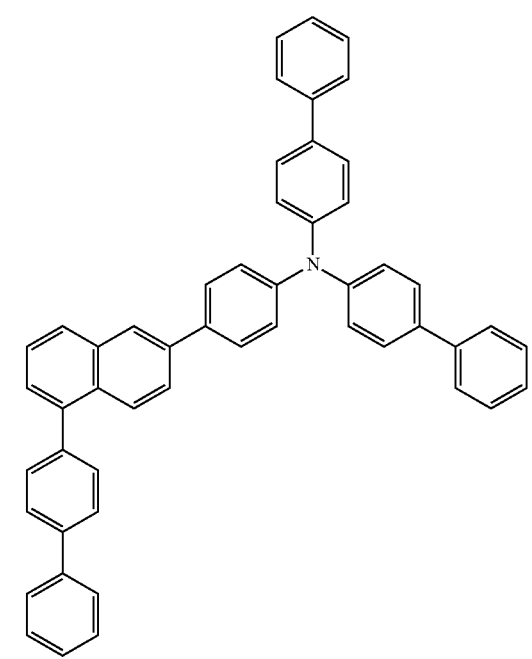

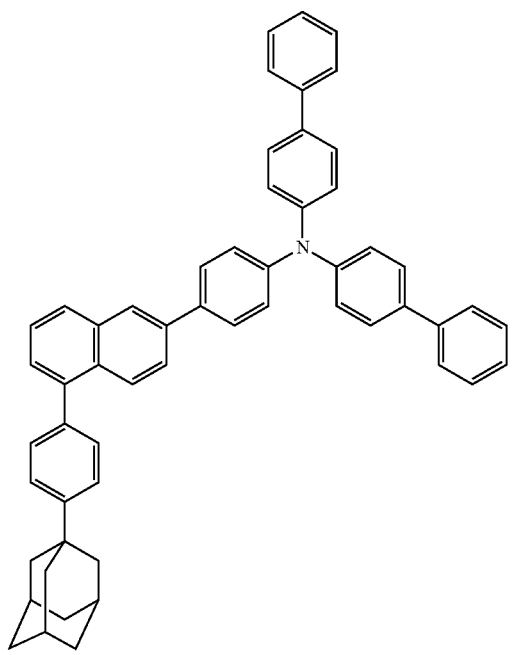
D28
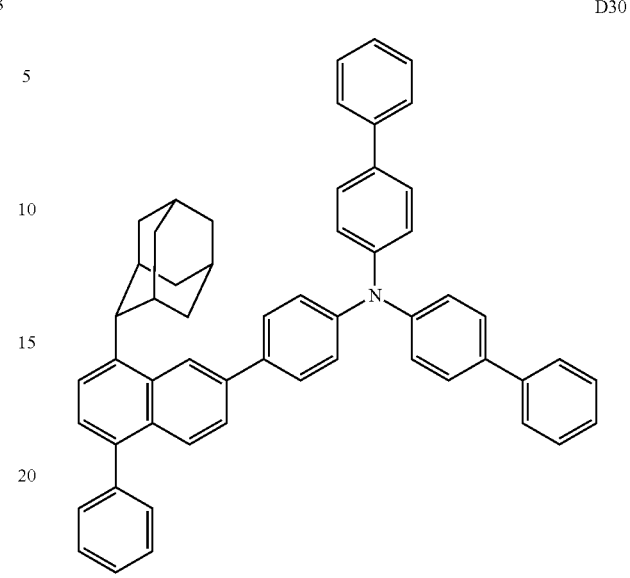
D30
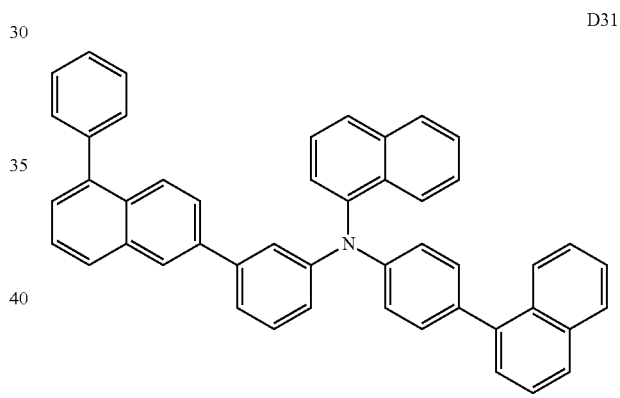
D31
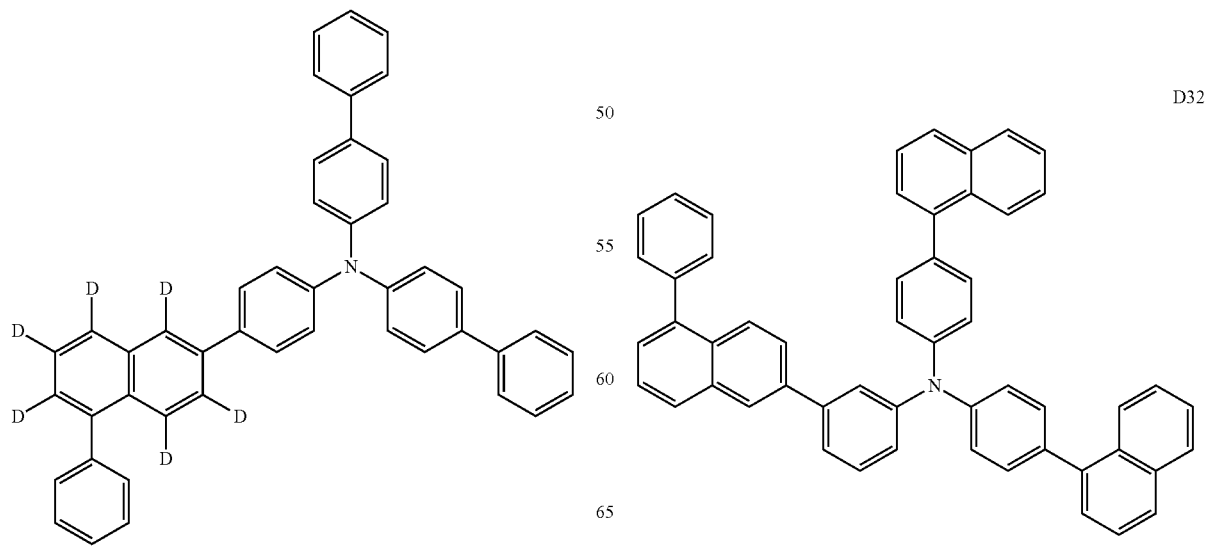
D29 D32

D33
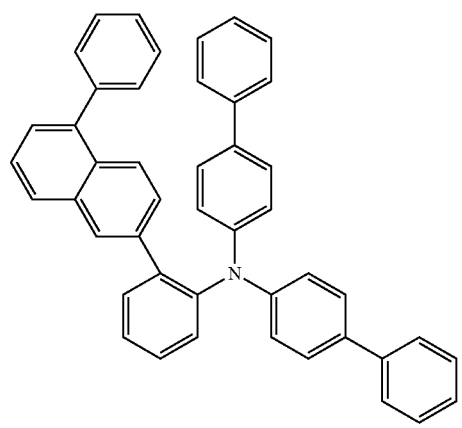
D36
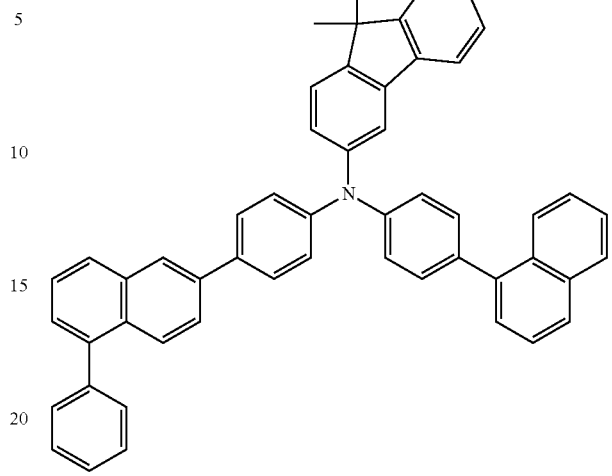
D34
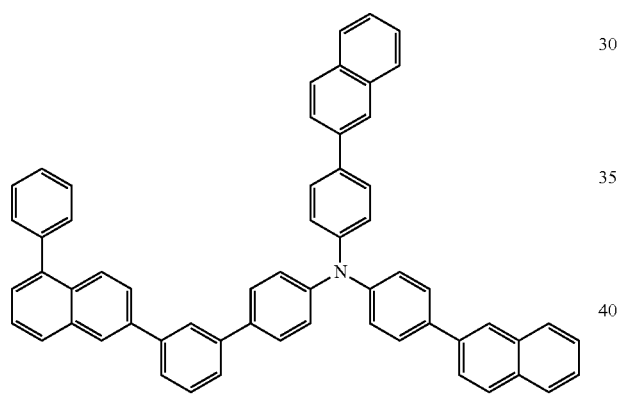
D37
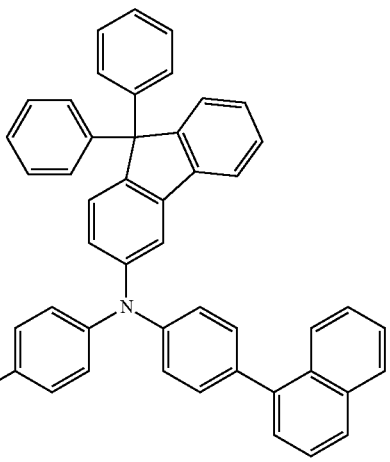
D35
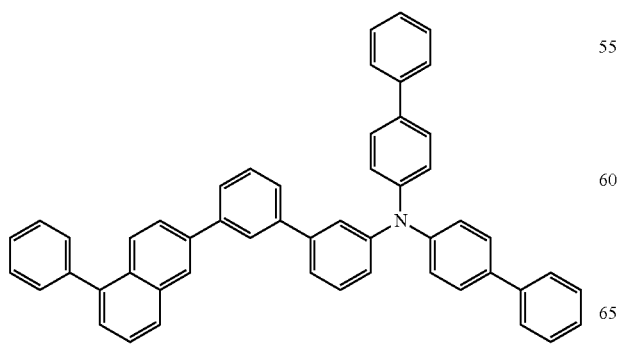

D38
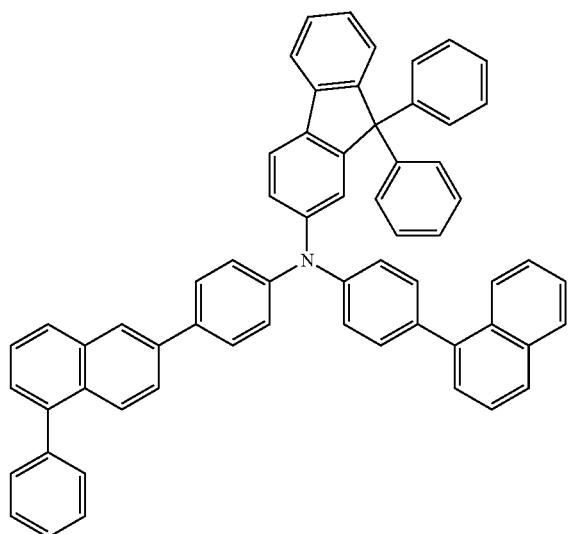
D39
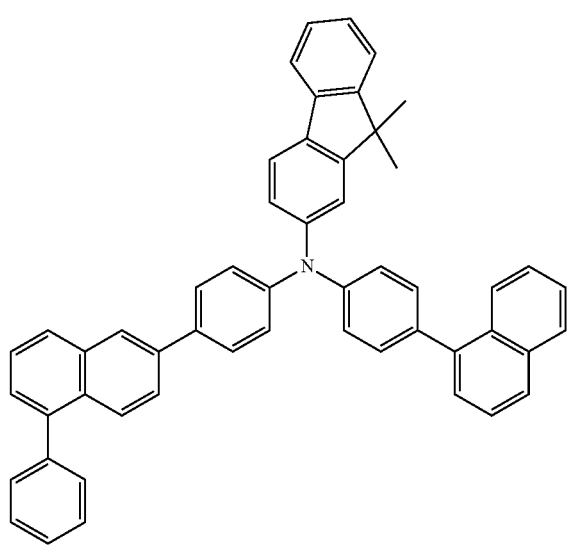
D41
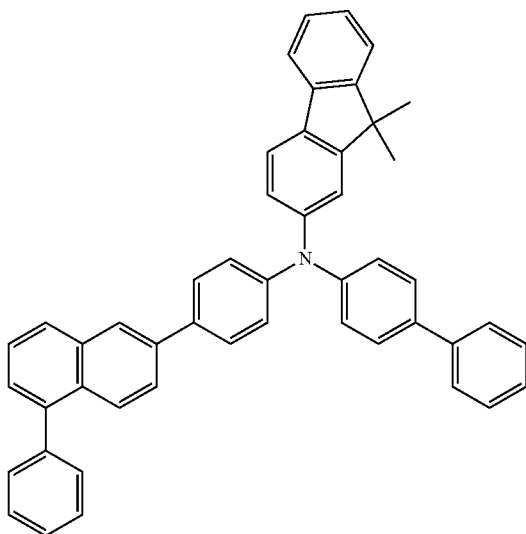
D42
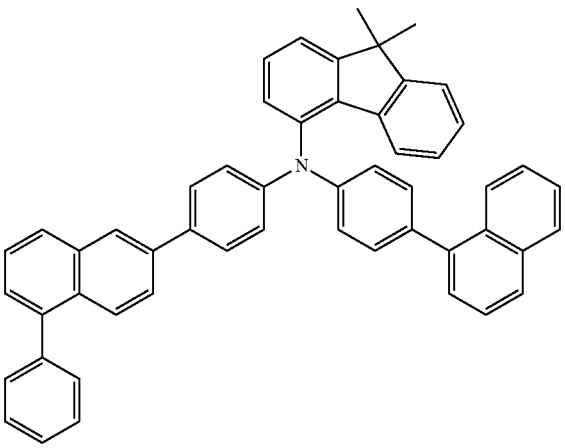
D40
D43
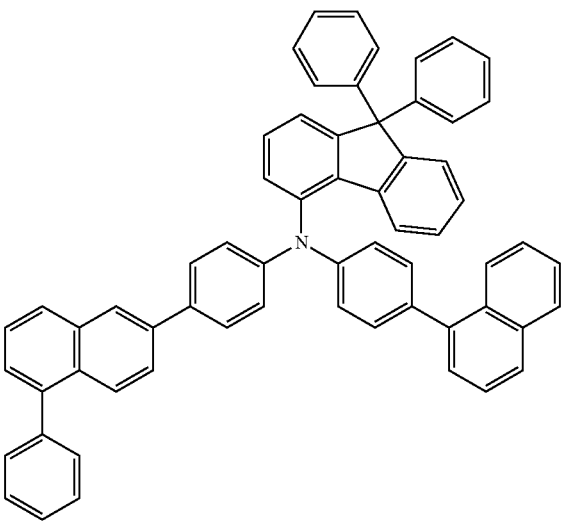

D44
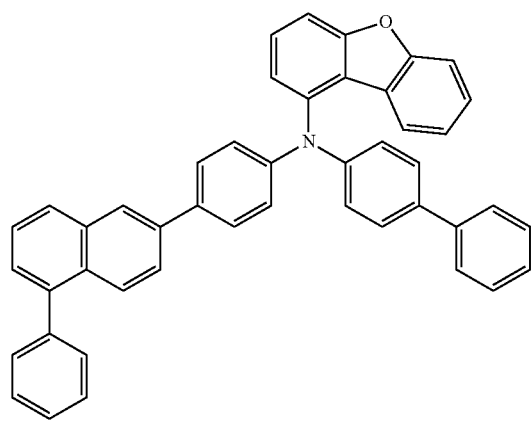
D45
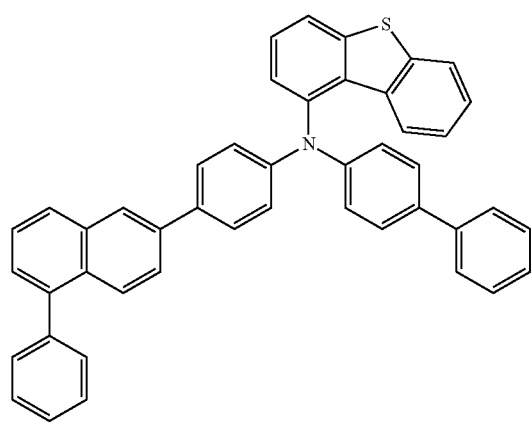
D46
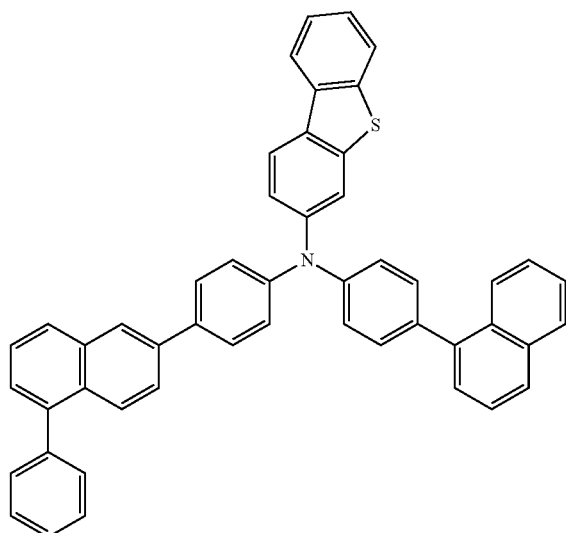
D47
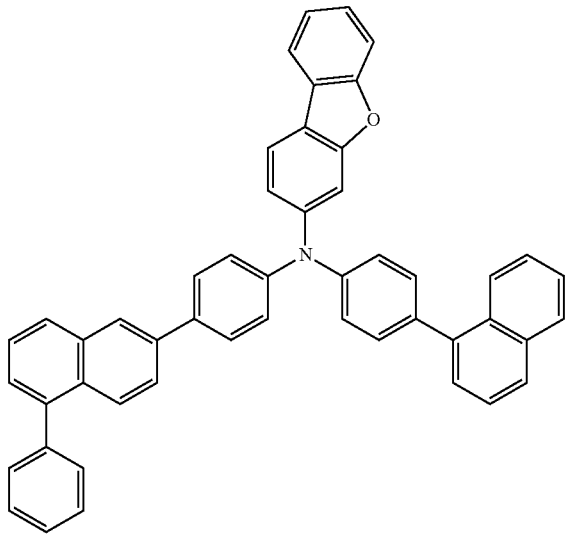
D48
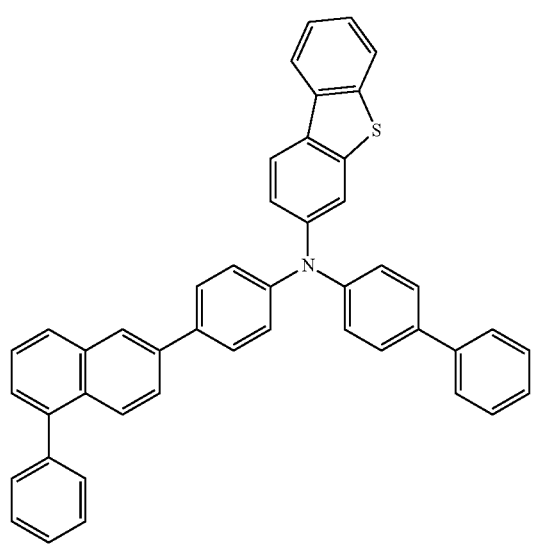
D49
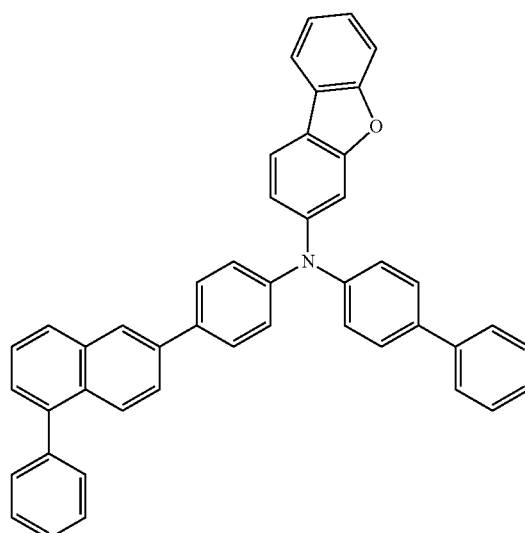

D50
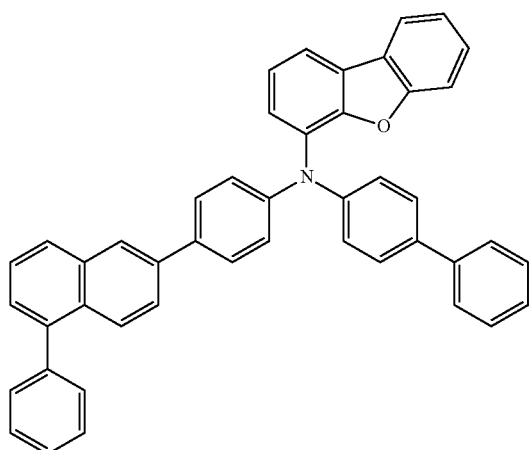
D51
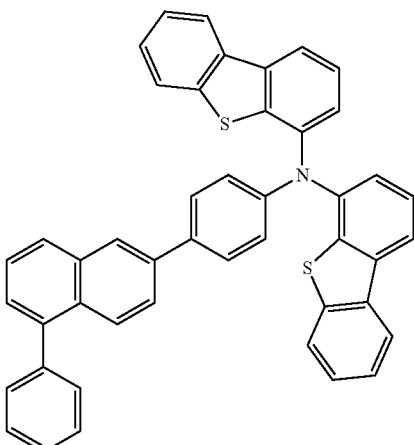
D53
D52
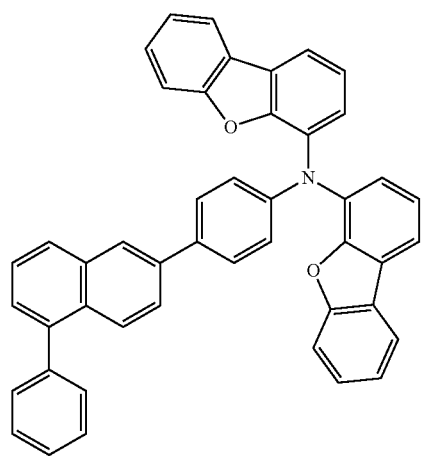
D54
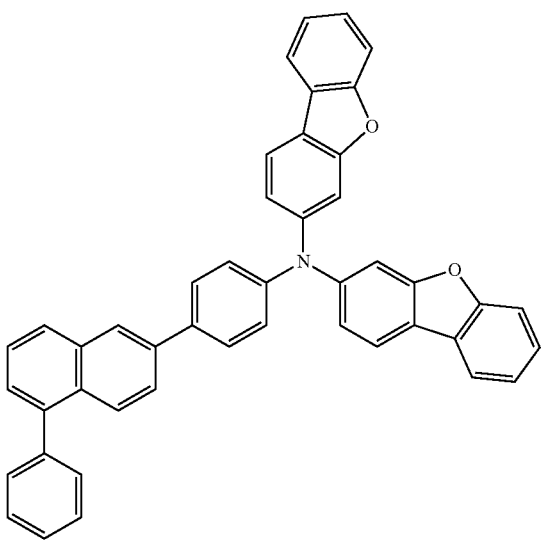
D55
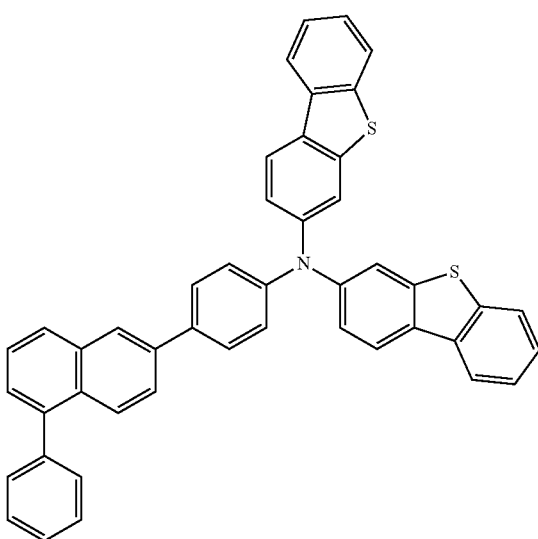

D56
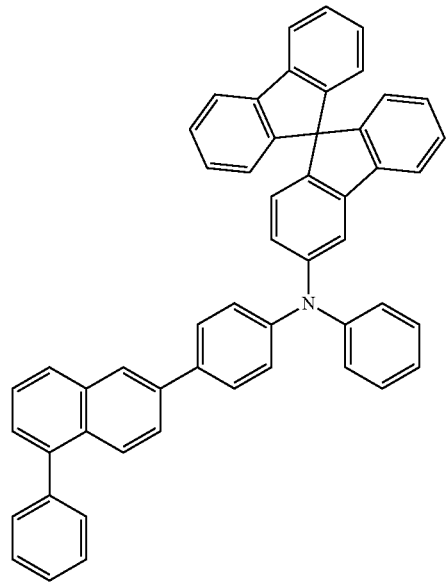
D57
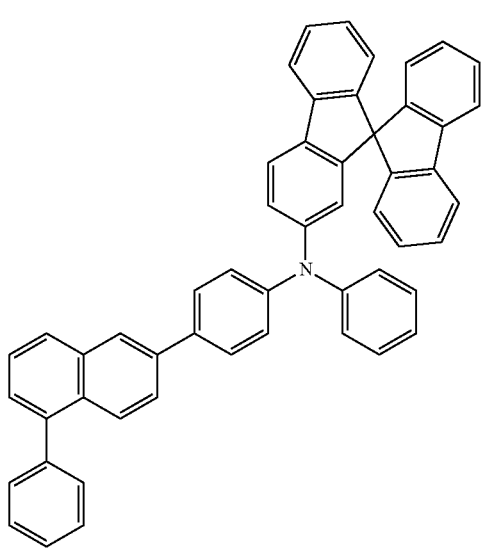
D58
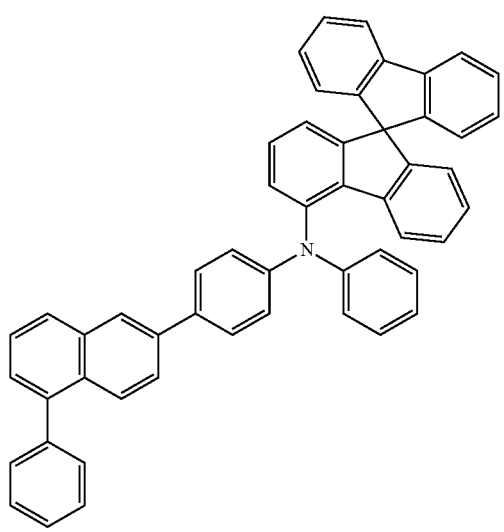
D59
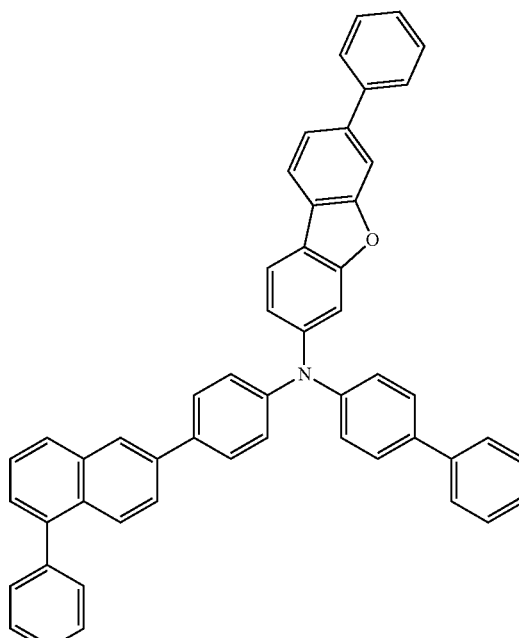
D60
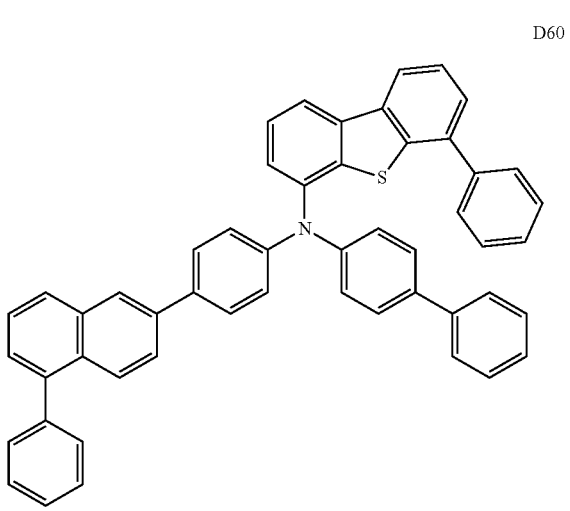

[Compound Group 5]
[Compound Group 6]
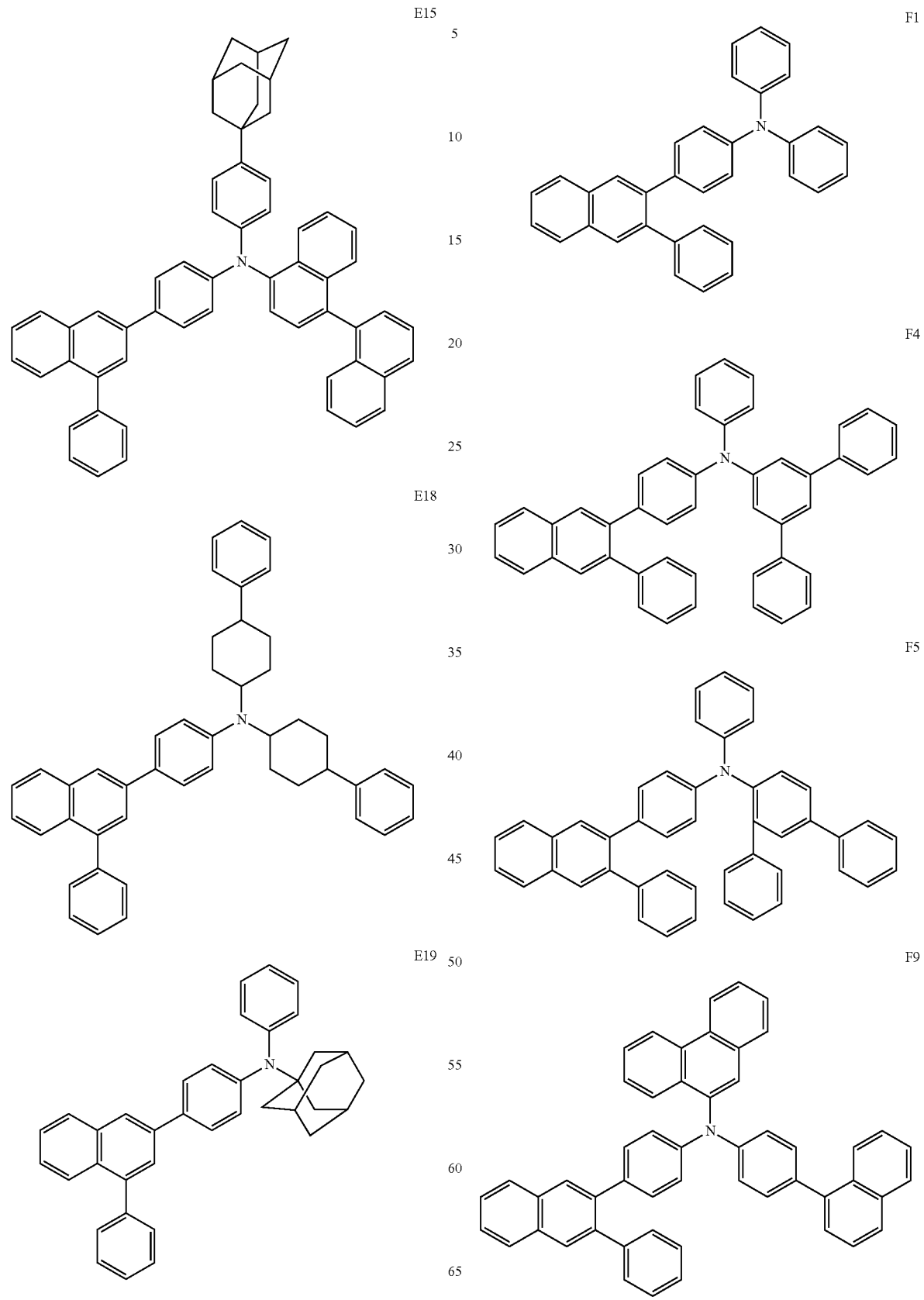

F10
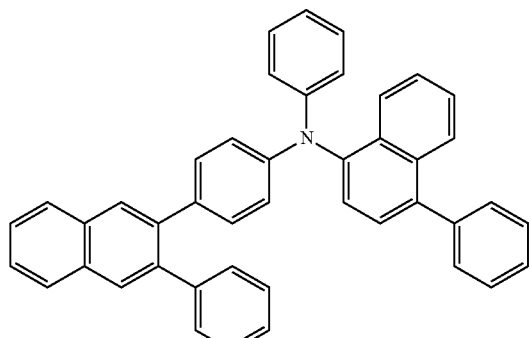
F12
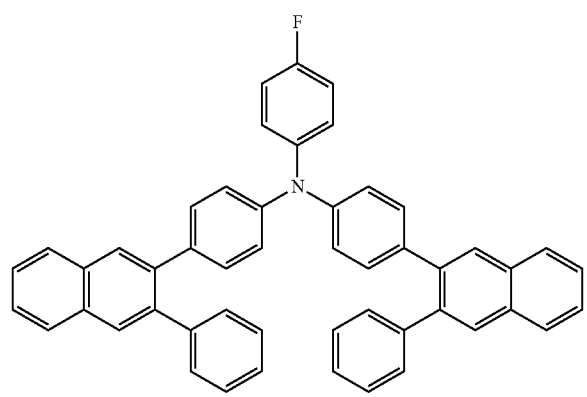
F13
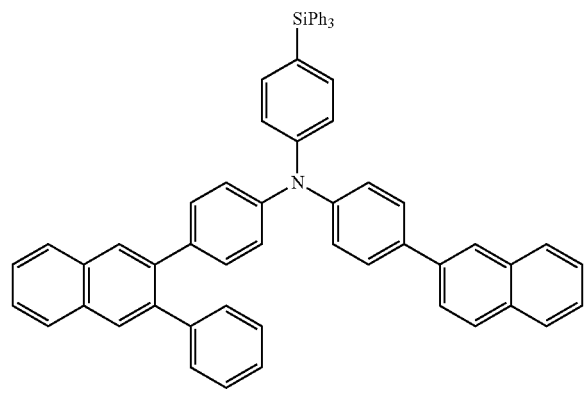
F14
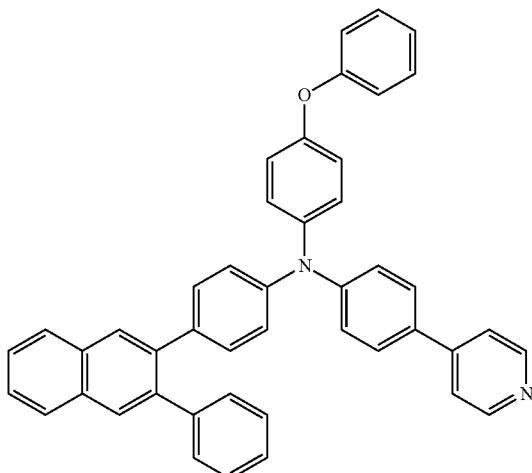
F15
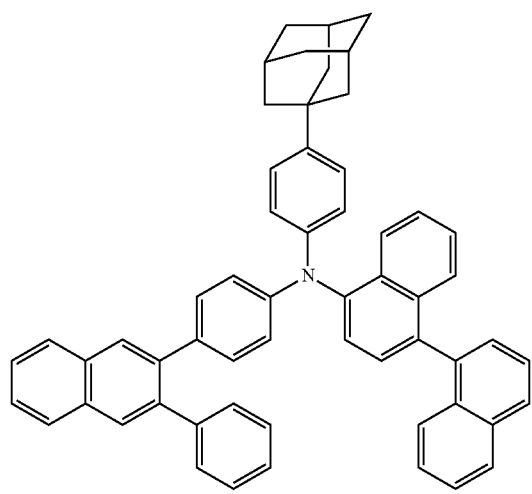
F16
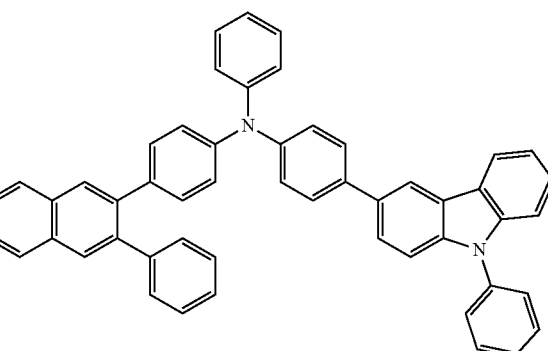

F18
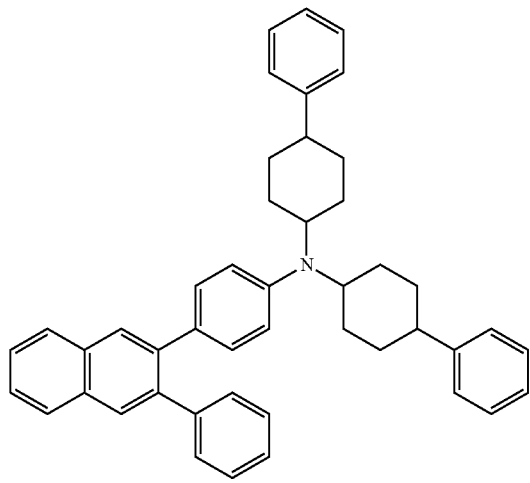
F19
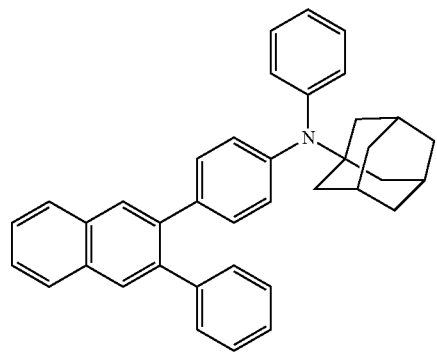
F20
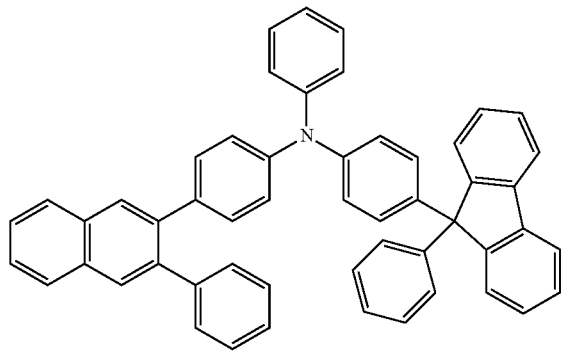
F31
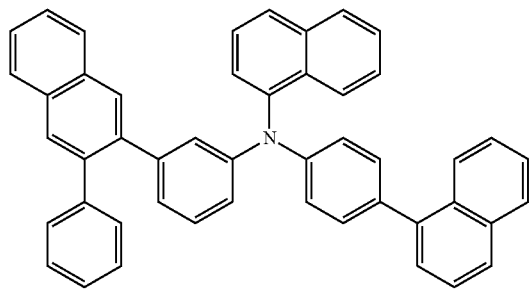
F32
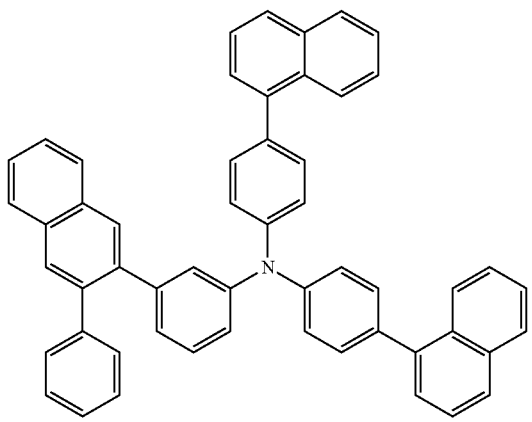
F34
[Compound Group 7]
G1
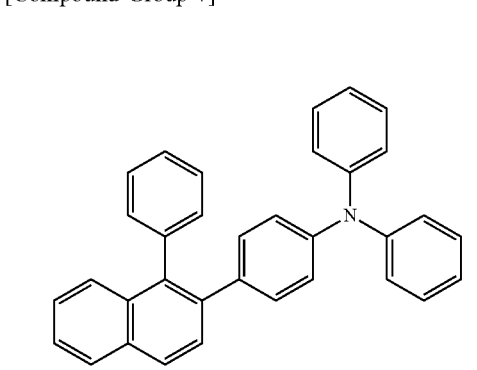
G4
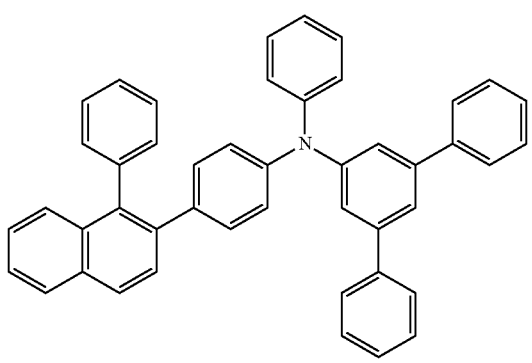

G5
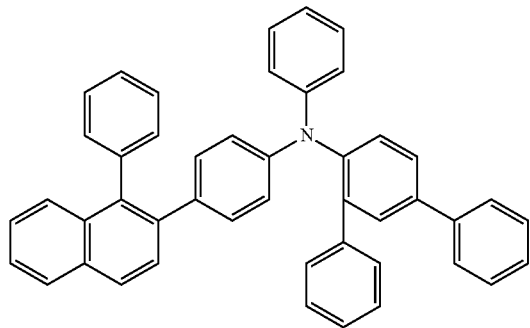
G9
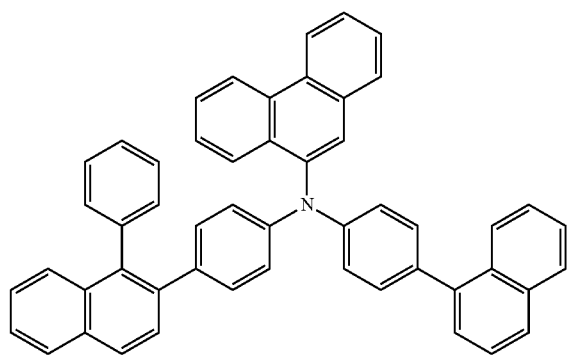
G10
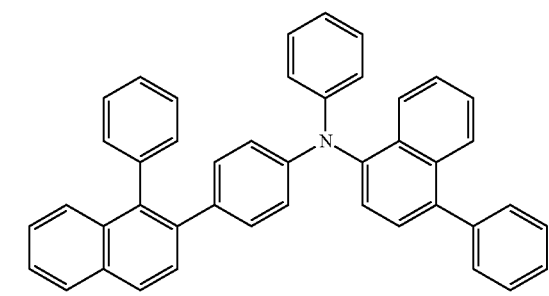
G12
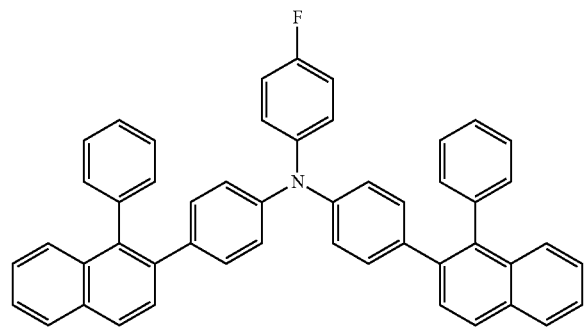
G13
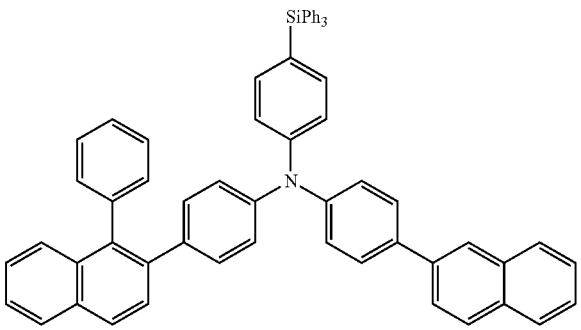
G14
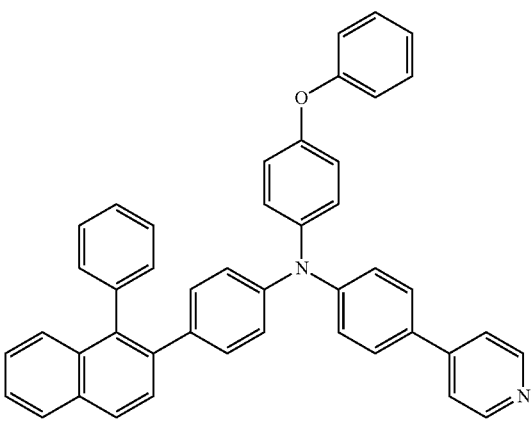
G15
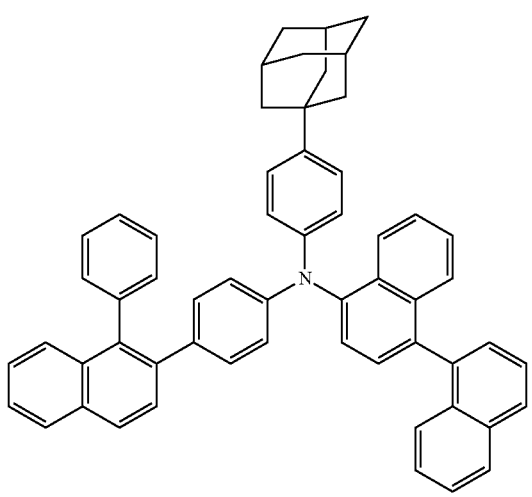

G16
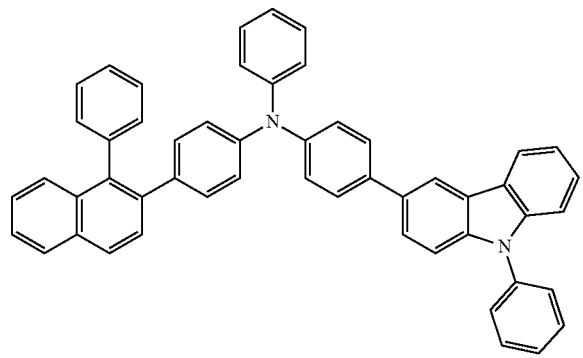
G18
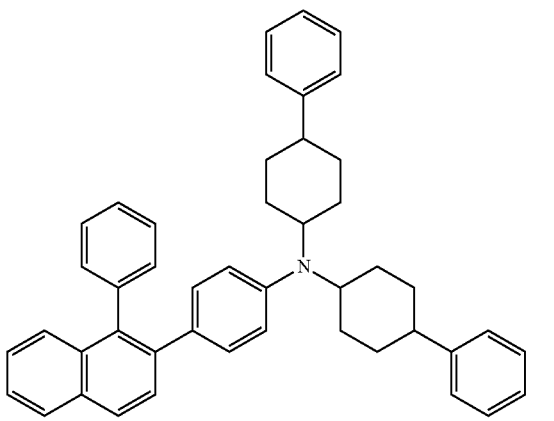
G19
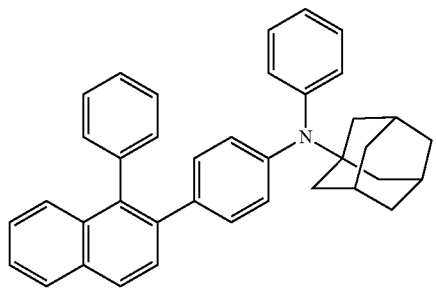
G20
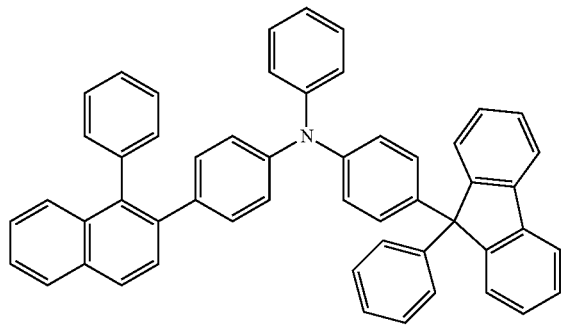
G31
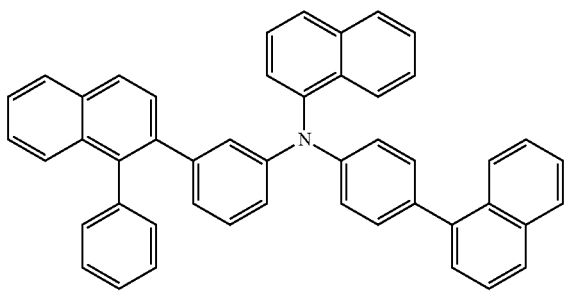
G32
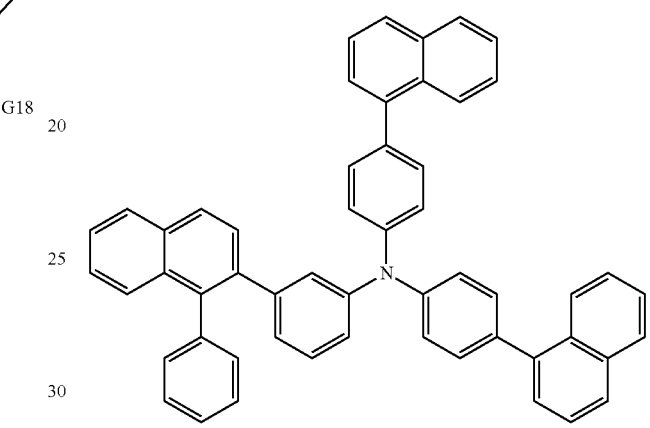
G34
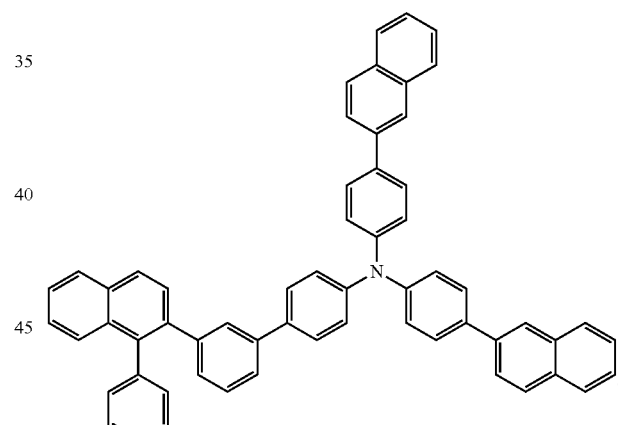
G35
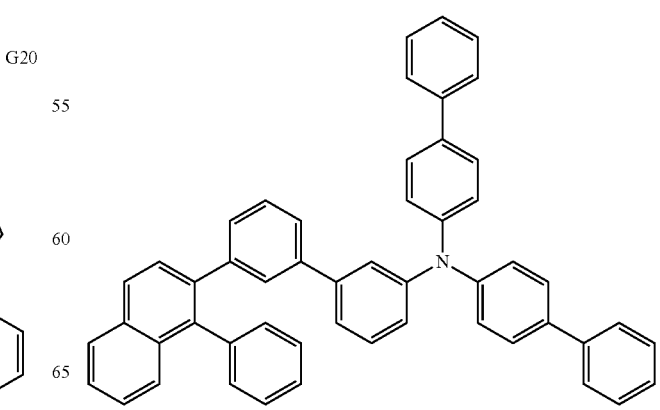

G36
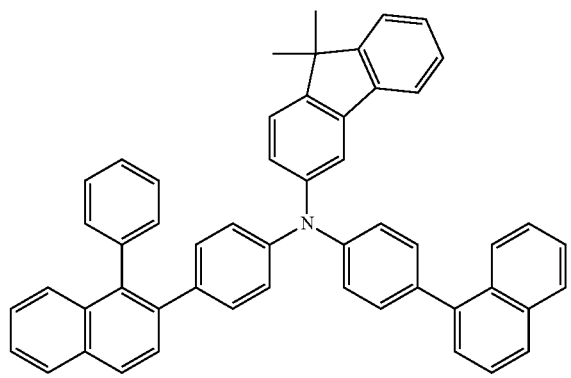
G37
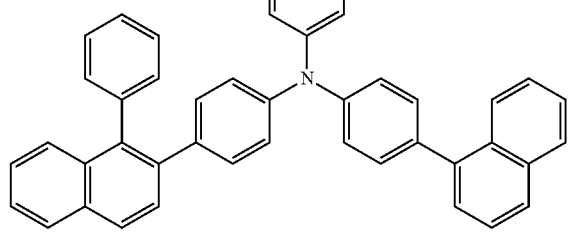
G38
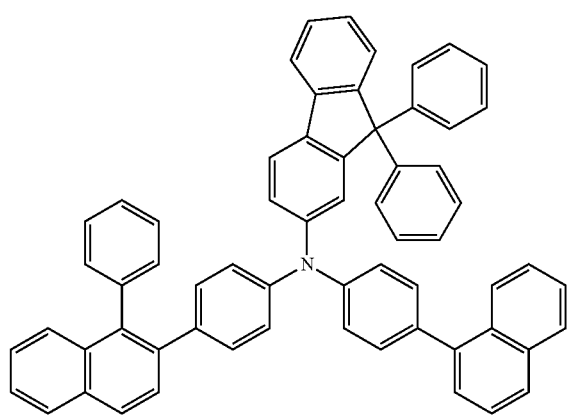
G39
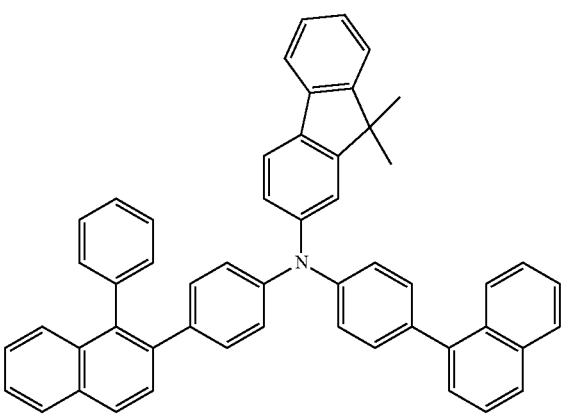
G40
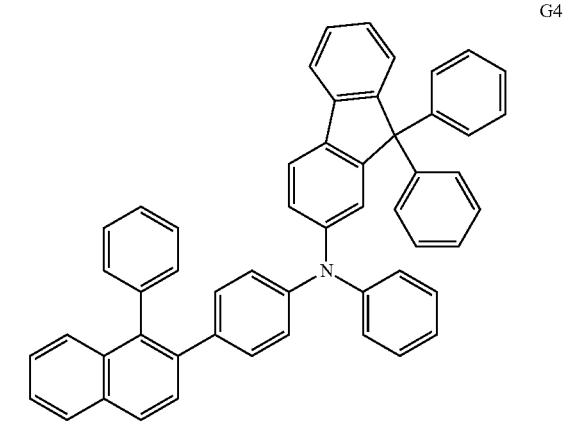
G41
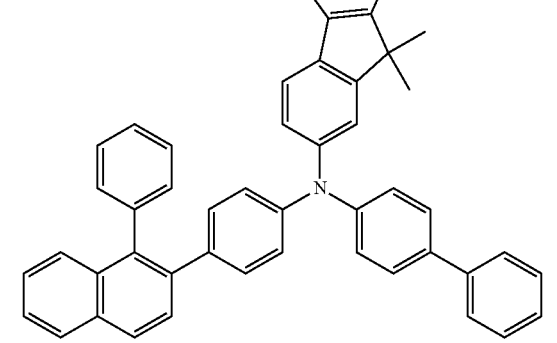
G42
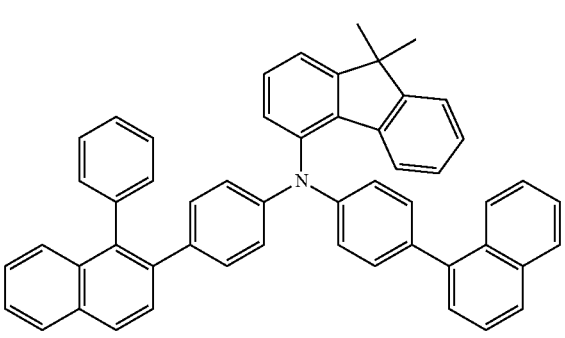

G43
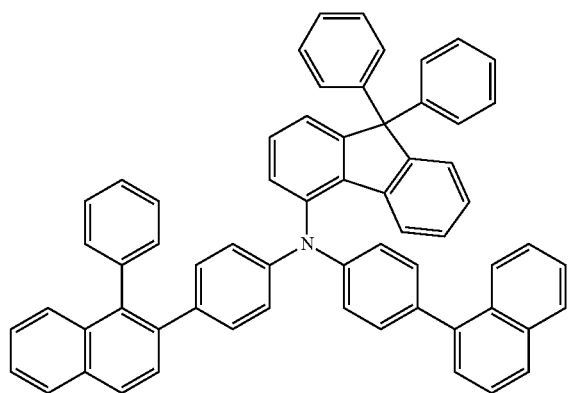
G44
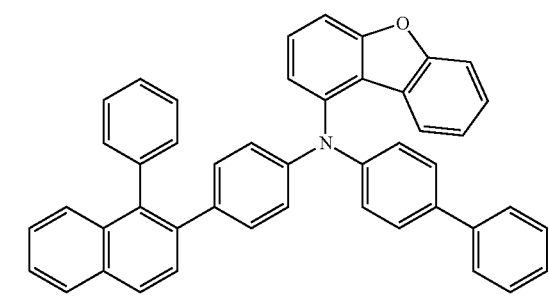
G45
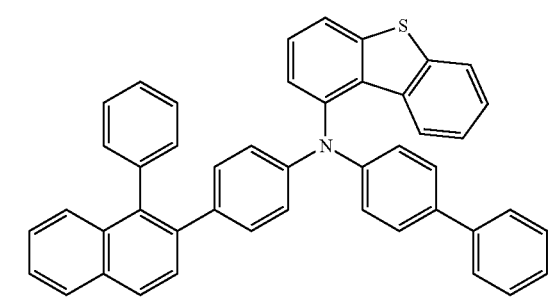
G46
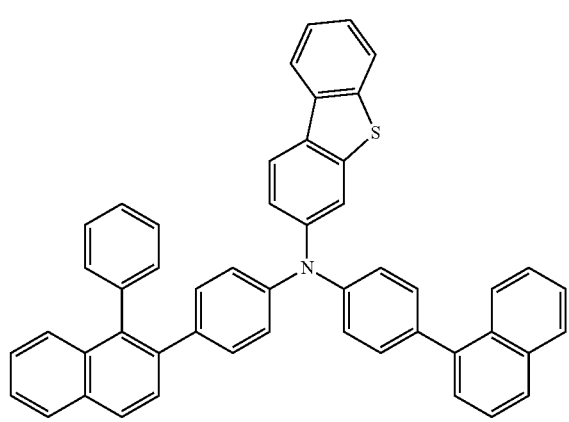
G47
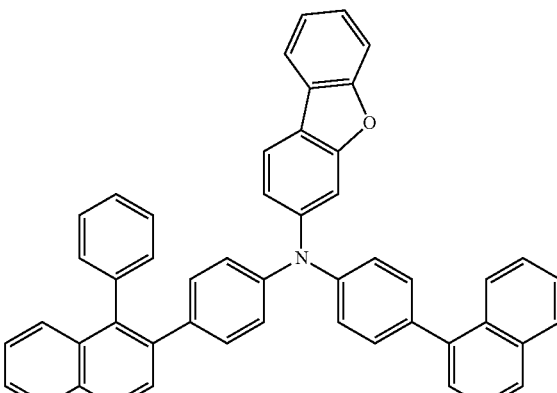
G48
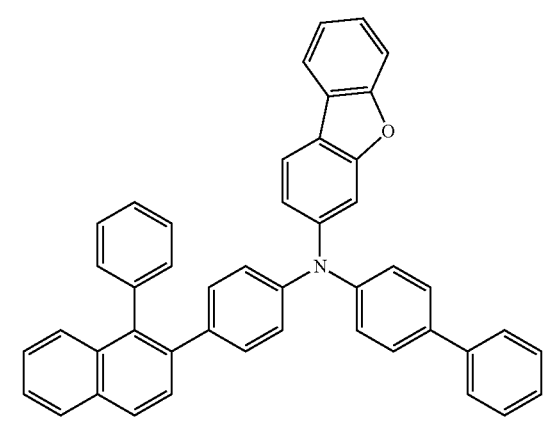
G49
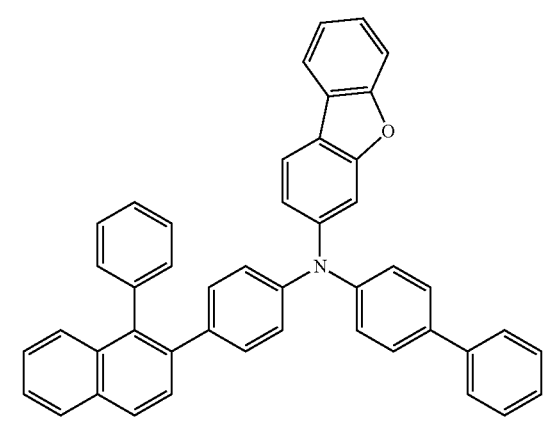
G50
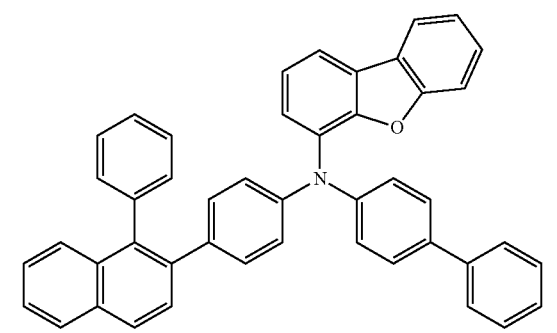

G51
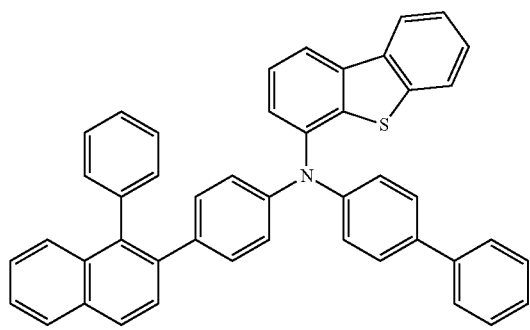
G52
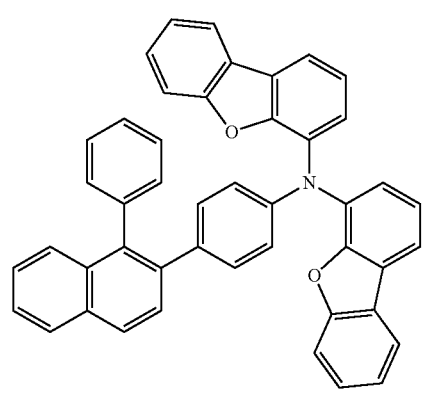
G53
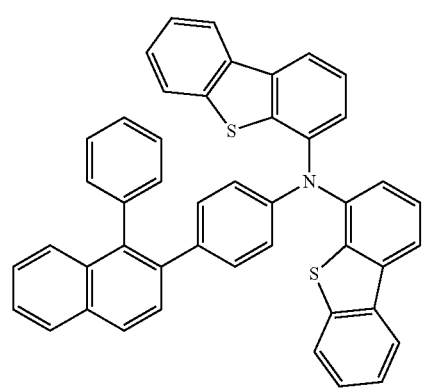
G54
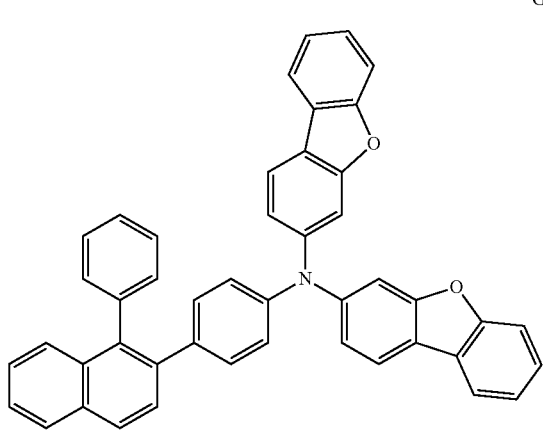
G55
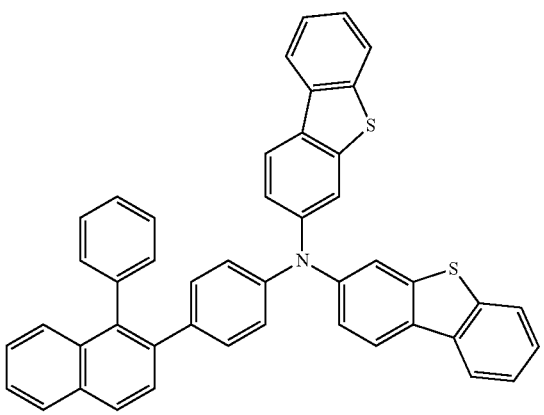
G56
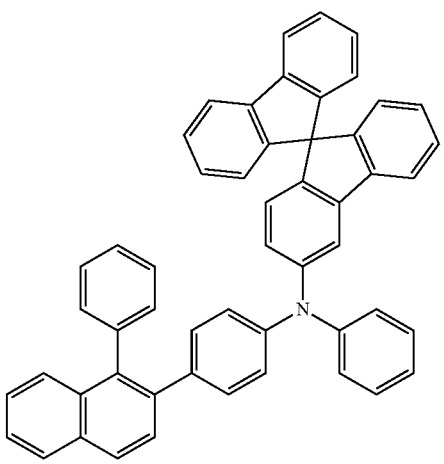
G57
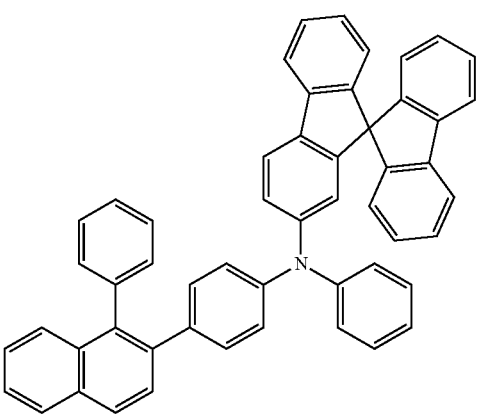

-continued
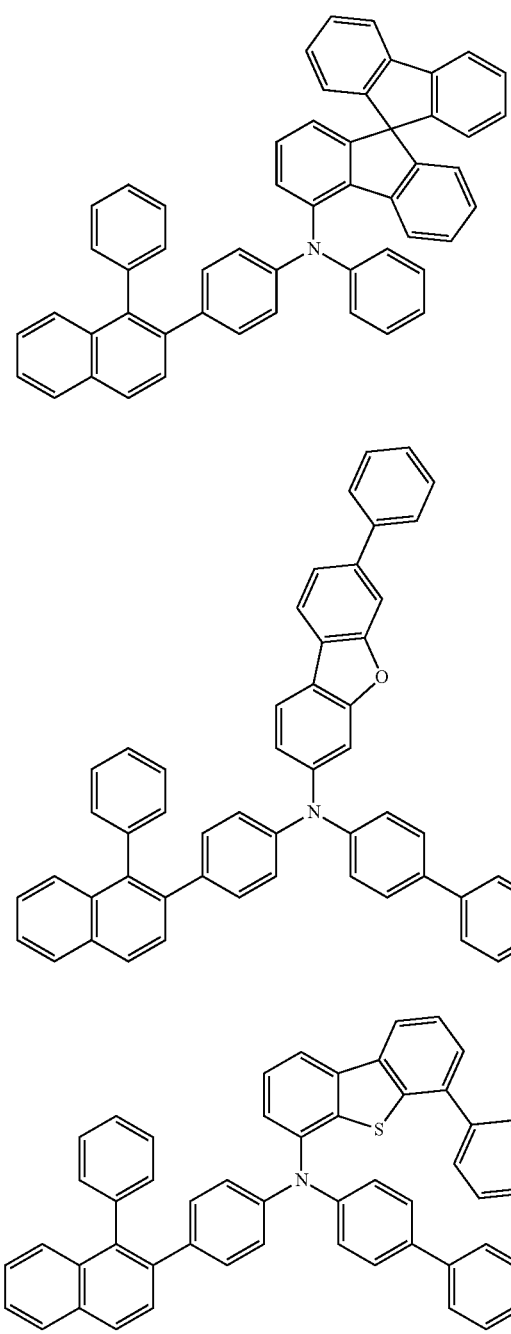
13. A monoamine compound represented by at least one of the following Formulae 2 to 8:
[Formula 2]
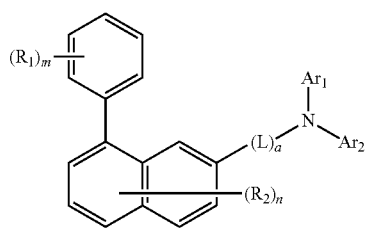
-continued
[Formula 3]
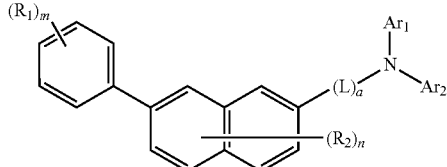
[Formula 4]
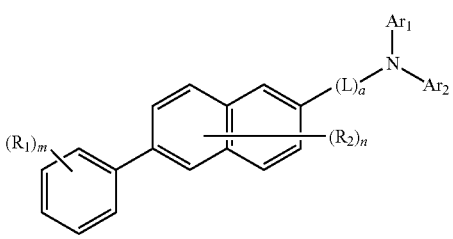
[Formula 5]
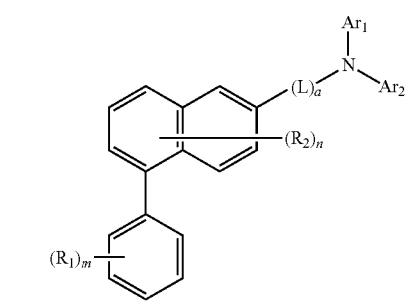
[Formula 6]
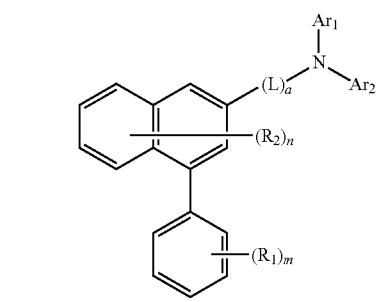
[Formula 7]
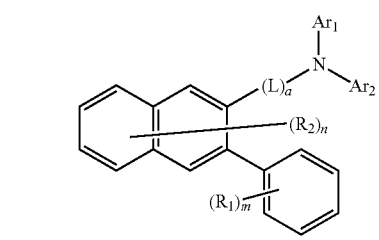
[Formula 8]
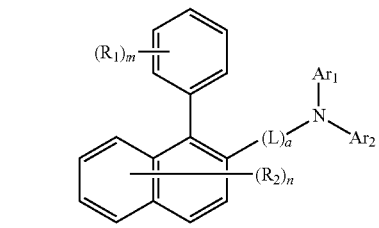
wherein in Formula 2 to 8,
$Ar_1$ and $Ar_2$ are each independently a substituted or unsubstituted alkyl group having 1 to 10 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 2 to 30 ring carbon atoms, provided that when any one of $Ar_1$ and $Ar_2$ is 3-dibenzofuranyl, the other one of $Ar_1$ and $Ar_2$ is not 9-phenanthryl, L is a substituted or unsubstituted arylene group having 6 to 30 ring carbon atoms, or a substituted or unsubstituted heteroarylene group having 2 to 30 ring carbon atoms, $R_1$ is a hydrogen atom, a deuterium atom, a halogen atom, a substituted or unsubstituted alkyl group having 1 to 20 carbon atoms, a substituted or unsubstituted cycloalkyl group having 3 to 20 ring carbon atoms, or a substituted or unsubstituted aryl group having 6 to 30 ring carbon atoms, $R_2$ is a hydrogen atom, a deuterium atom, a halogen atom, a substituted or unsubstituted alkyl group having 1 to 20 carbon atoms, or a substituted or unsubstituted cycloalkyl group having 3 to 20 ring carbon atoms, a is an integer of 0 to 3, m is an integer of 0 to 1, and n is an integer of 0 to 6, wherein in Formula 3, when one of $Ar_1$ and $Ar_2$ is a naphthalene group or a phenyl group substituted with a naphthalene group and the other one of $Ar_1$ and $Ar_2$ is a substituted or unsubstituted aryl group,
the naphthalene group in the one of $Ar_1$ and $Ar_2$ is unsubstituted, or
the substituted or unsubstituted aryl group of the one of $Ar_1$ and $Ar_2$ is a substituted or unsubstituted aryl group having 7 to 30 ring carbon atoms, wherein in Formula 4, a is an integer of 1 to 3, wherein in Formula 6, i) $Ar_1$ and $Ar_2$ are not dimethylfluorenyl groups, ii) when any one of $Ar_1$ and $Ar_2$ is a p-biphenyl group and the other one of $Ar_1$ and $Ar_2$ includes an aryl substituent, the number of ring carbon atoms in the aryl substituent is 13 to 30, iii) L is a phenylene group, a is an integer of 1 or more and 3 or less, and when L includes an m-phenylene group, $Ar_1$ and $Ar_2$ are not an unsubstituted or alkyl-substituted phenyl group, or an unsubstituted p-biphenyl group, and vi) when $Ar_1$ and $Ar_2$ are each a heteroaryl group comprising S, or one of $Ar_1$ or $Ar_2$ is a heteroaryl group comprising S, and an other one of $Ar_1$ or $Ar_2$ is a heteroaryl group comprising O, the heteroaryl group comprising S is a substituted or unsubstituted dibenzothiophene group, and the heteroaryl group comprising O is a substituted or unsubstituted dibenzofuran group, and wherein in Formula 7 and Formula 8, i) $Ar_1$ and $Ar_2$ are not an unsubstituted p-biphenyl group or an unsubstituted p-terphenyl group, ii) when $Ar_1$ and $Ar_2$ are a fluorene group or a fluorene derivative, $Ar_1$ and $Ar_2$ are substituents represented by Formula 7a;

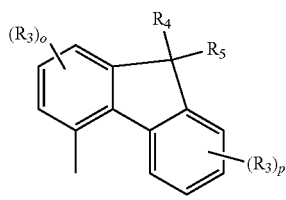

[Formula 7a]

wherein in Formula 7a, $R_3$ is a hydrogen atom, a deuterium atom, a halogen atom, a substituted or unsubstituted alkyl group having 1 to 20 carbon atoms, a substituted or unsubstituted cycloalkyl group having 3 to 20 ring carbon atoms, or a substituted or unsubstituted aryl group having 6 to 30 ring carbon atoms, $R_4$ and $R_5$ are each independently a hydrogen atom, a deuterium atom, a halogen atom, a substituted or unsubstituted cycloalkyl group having 3 to 20 ring carbon atoms, or a substituted or unsubstituted aryl group having 6 to 30 ring carbon atoms, or may combine with each other to form a ring, is an integer of 0 or more and 3 or less, p is an integer of 0 or more and 4 or less, iii) L is a substituted or unsubstituted phenylene group, and vi) when one of $Ar_1$ and $Ar_2$ is an unsubstituted 2-dibenzofuran group, an unsubstituted 2-dibenzothiophene group, an unsubstituted 3-dibenzofuran group, or an unsubstituted 3-dibenzothiophene group, the other one of $Ar_1$ and $Ar_2$ is a substituted or unsubstituted phenylnaphthyl group, a substituted or unsubstituted dibenzofuran group, or a substituted or unsubstituted dibenzothiophene group.

14. The monoamine compound as claimed in claim 13, wherein L is a substituted or unsubstituted phenylene group.

15. The monoamine compound as claimed in claim 13, wherein $Ar_1$ and $Ar_2$ are each independently a substituted or unsubstituted aryl group having 6 to 12 ring carbon atoms.

16. The monoamine compound as claimed in claim 13, wherein $Ar_1$ and $Ar_2$ are each independently a substituted or unsubstituted heteroaryl group having 5 to 12 ring carbon atoms.

17. The monoamine compound as claimed in claim 13, wherein $R_2$ is a hydrogen atom or a deuterium atom.

18. The monoamine compound as claimed in claim 14, wherein the monoamine compound is at least one selected from the group of compounds represented in the following Compound Groups 1 to 7:

[Compound Group 1]

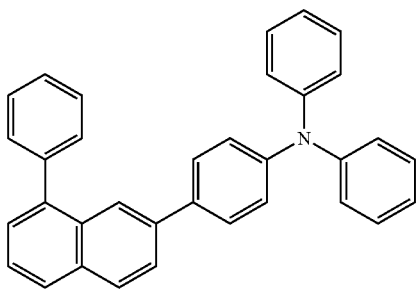

A1

A2
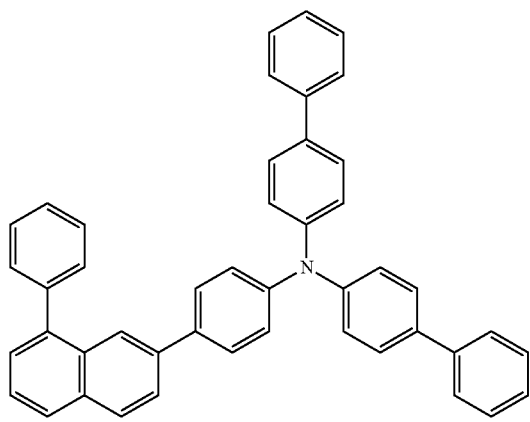
A3
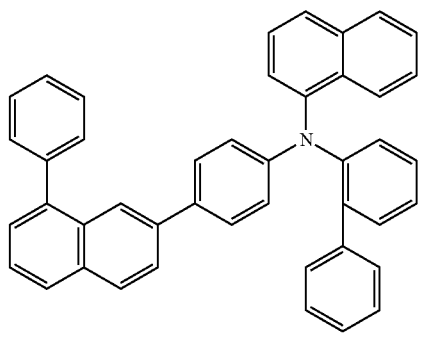
A4
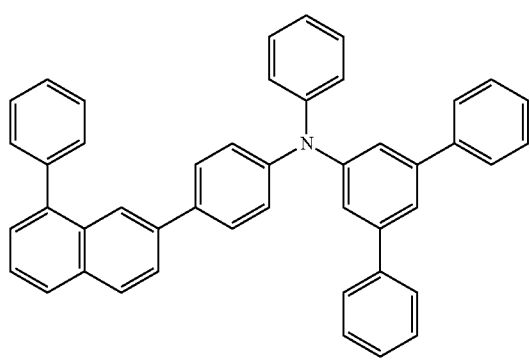
A5
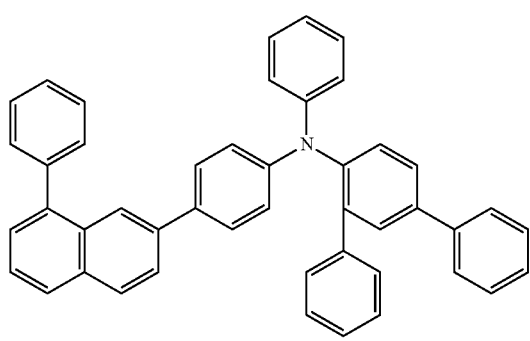
A6
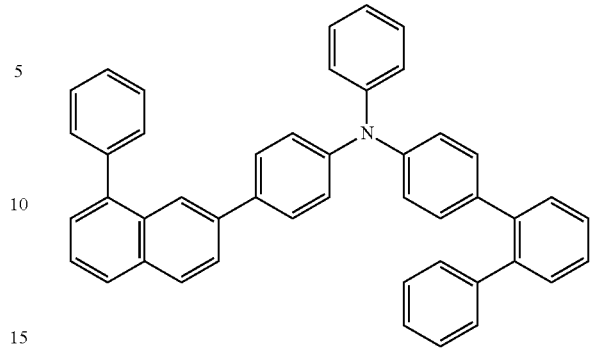
A7
A8
A9
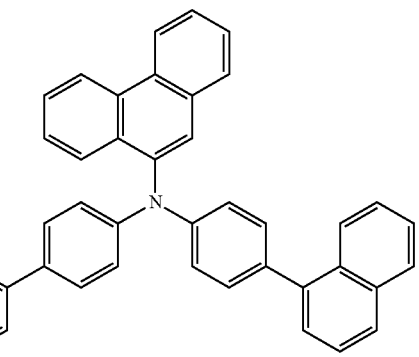

A10
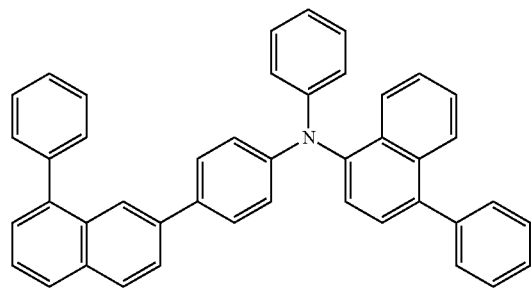
A11
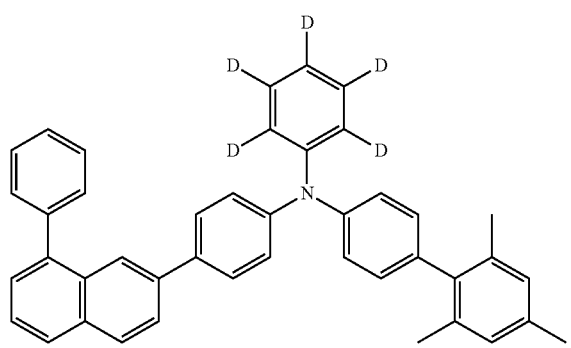
A12
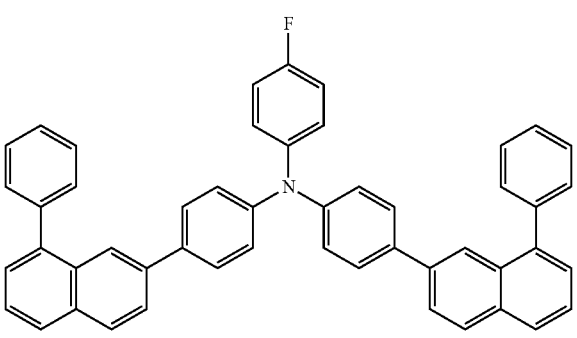
A13
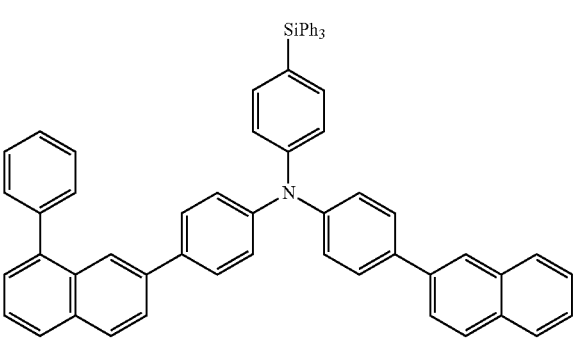
A14
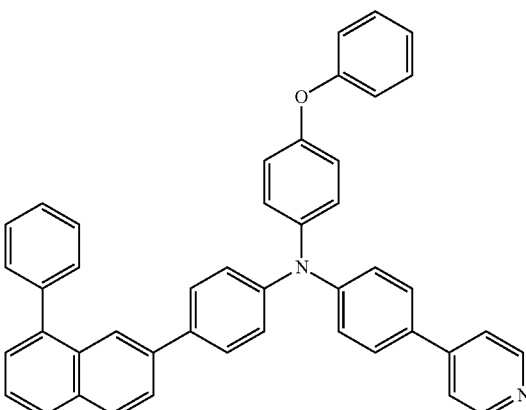
A15
A16
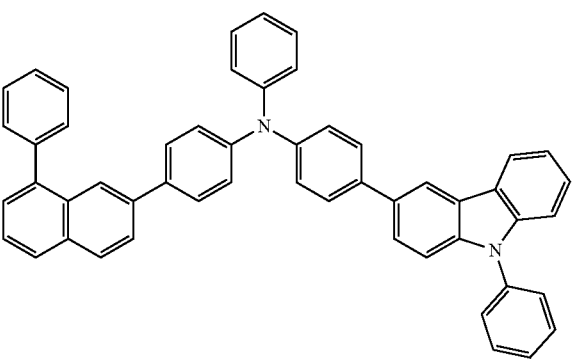

-continued
A17
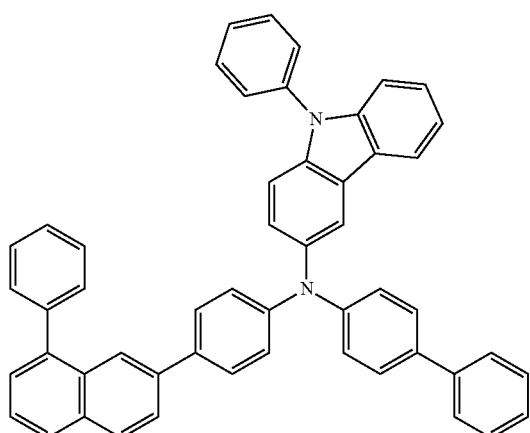
A18
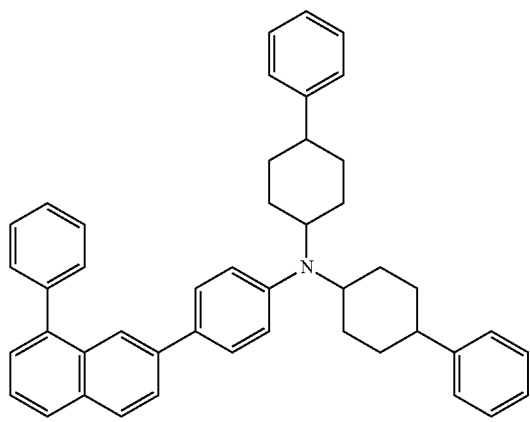
A19
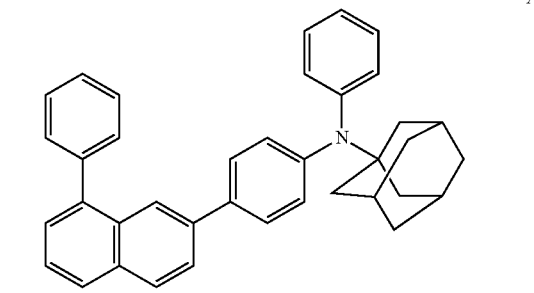
A20
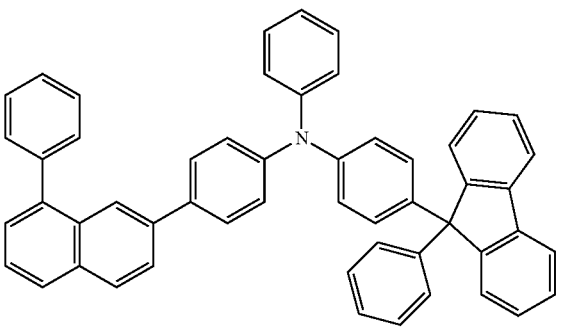
-continued
A21
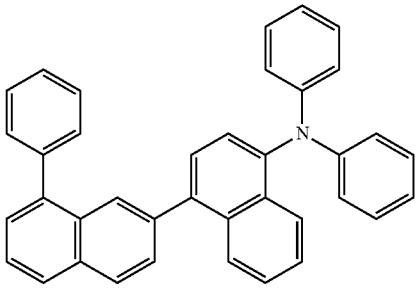
A22
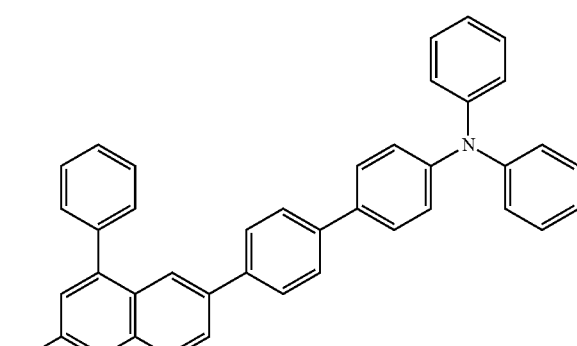
A23
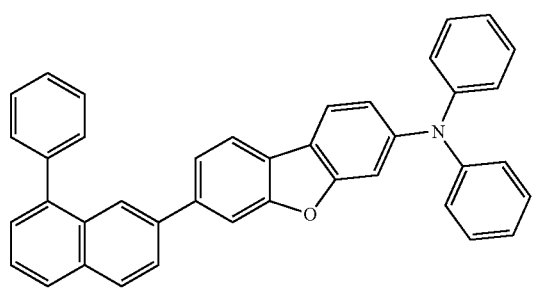
A24
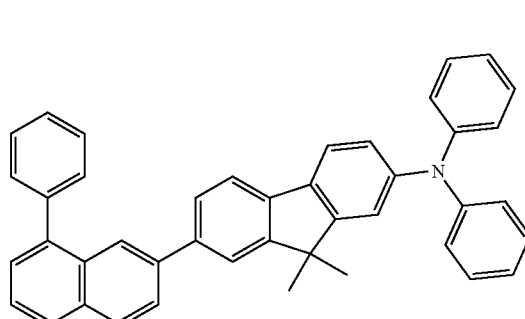

A25
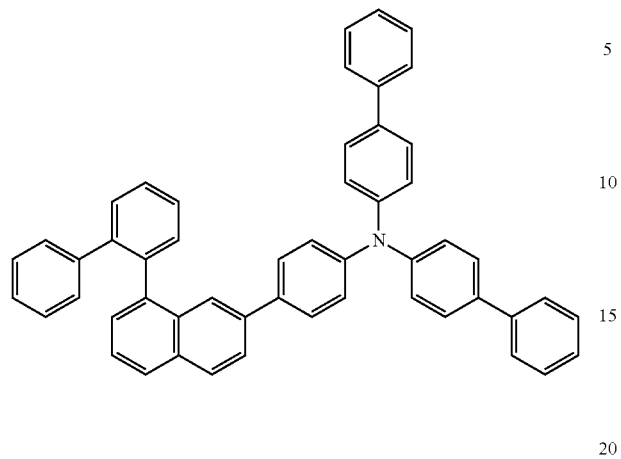
A28
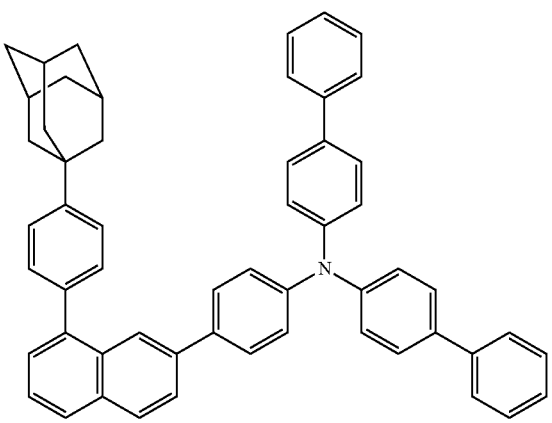
A26
A29
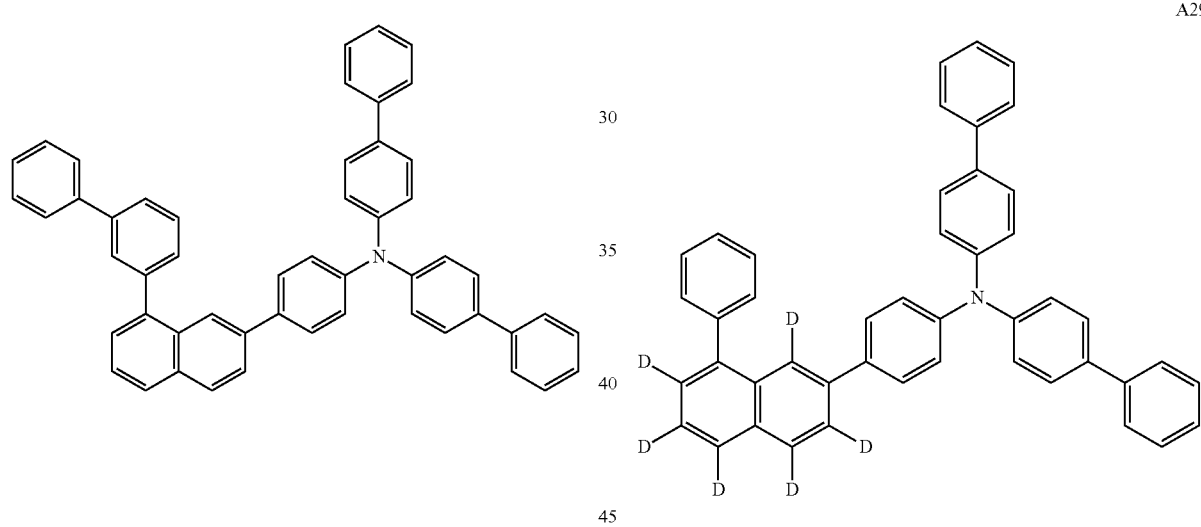
A27
A30
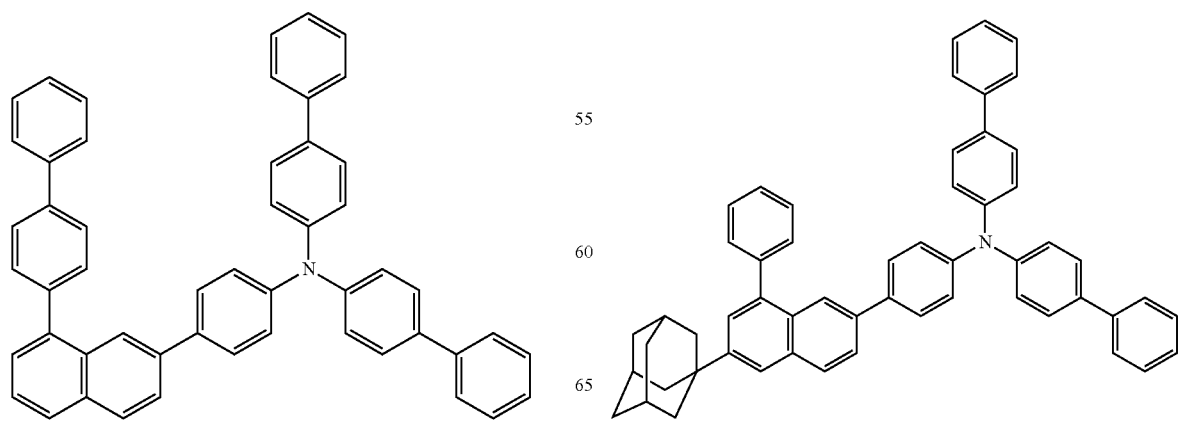

A31
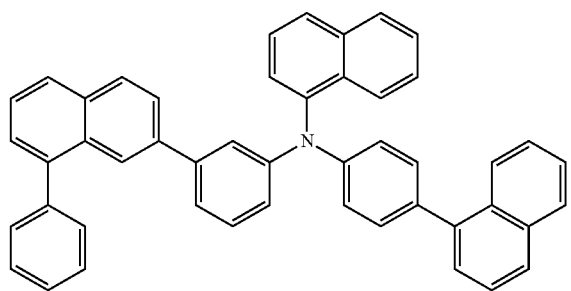
A32
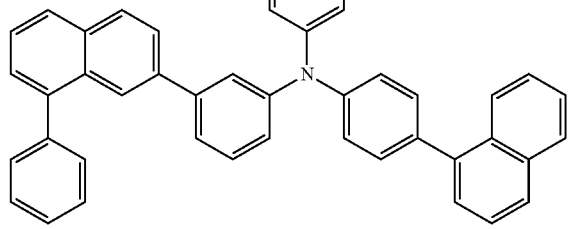
A33
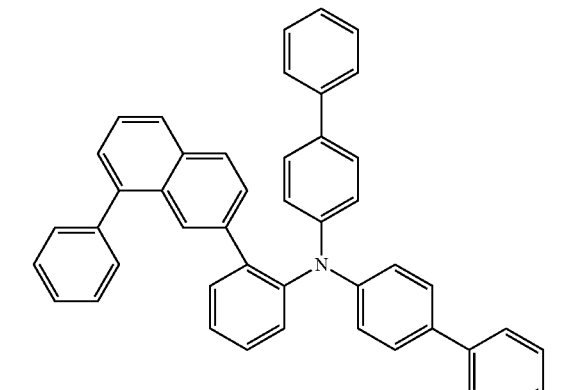
A34
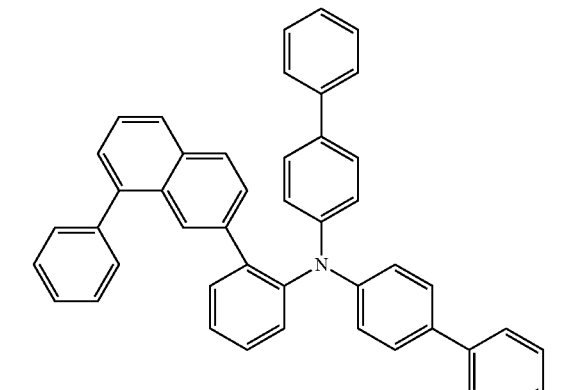
A35
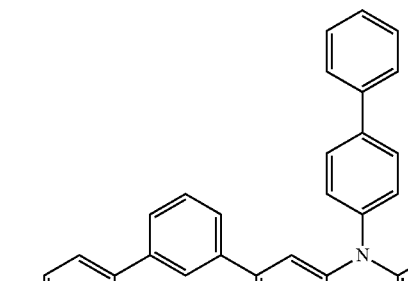
A36
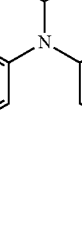
A37
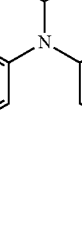

293                                                                 294
-continued                                                      -continued
A38
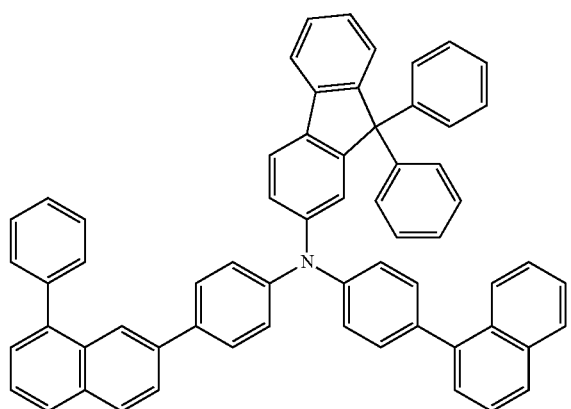
A39
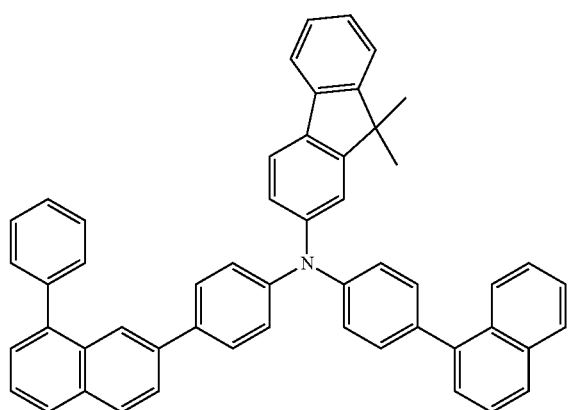
A40
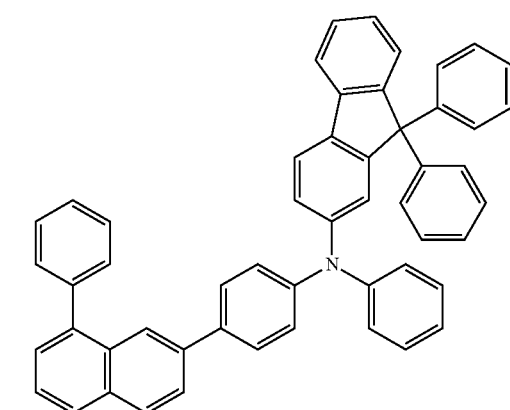
A41
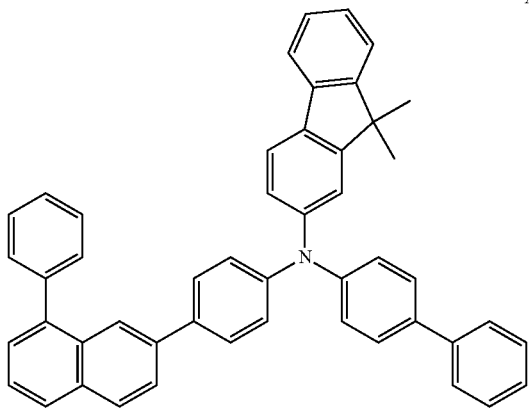
A42
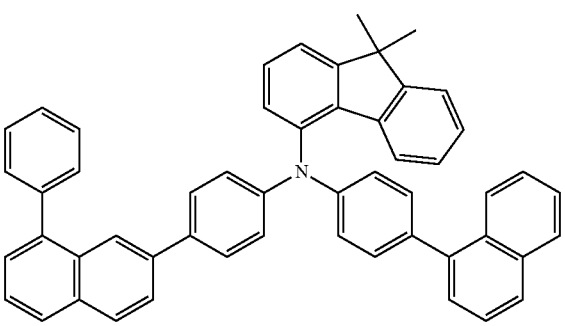
A43
A44
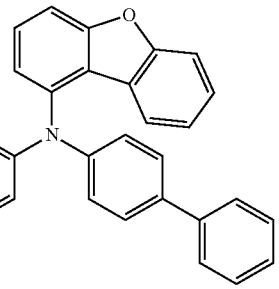

A45
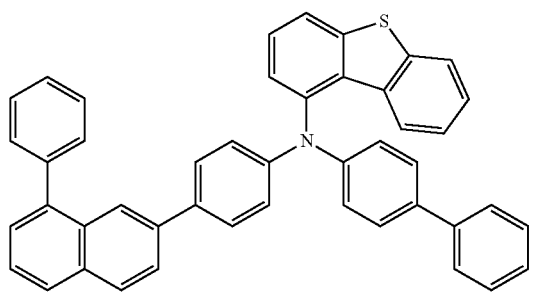
A46
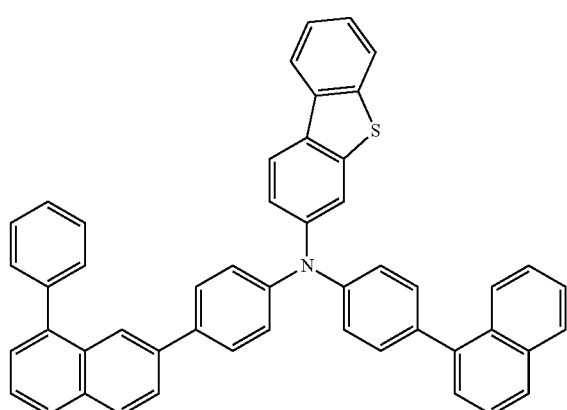
A47
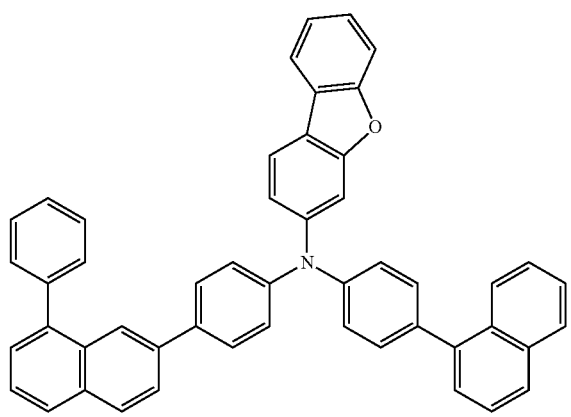
A48
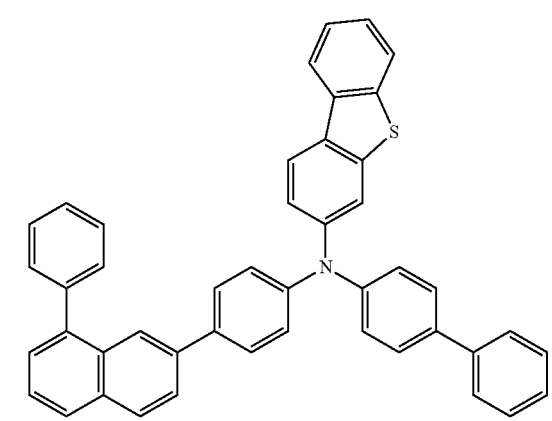
A49
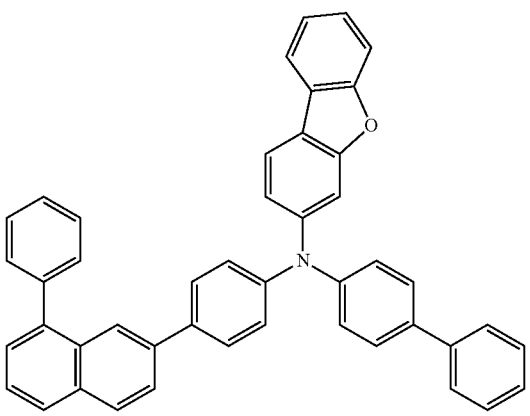
A50
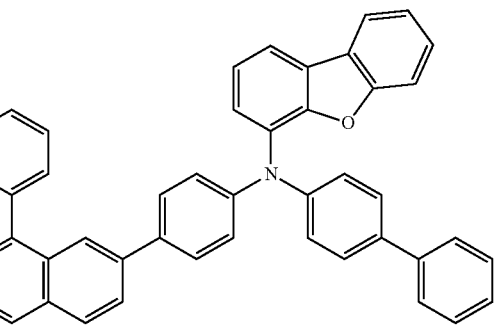
A51
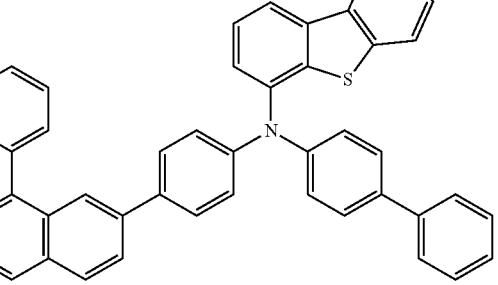
A52

A53
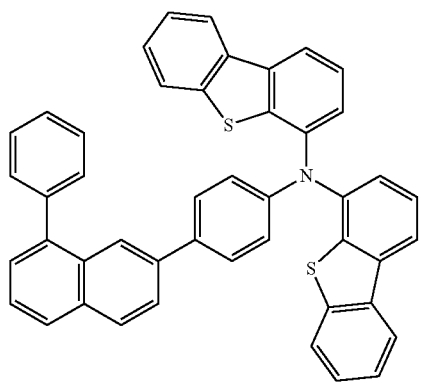
A56
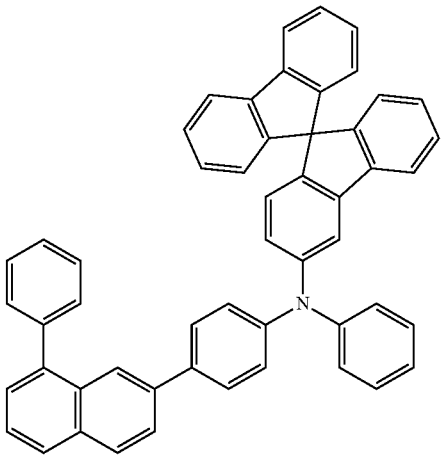
A54
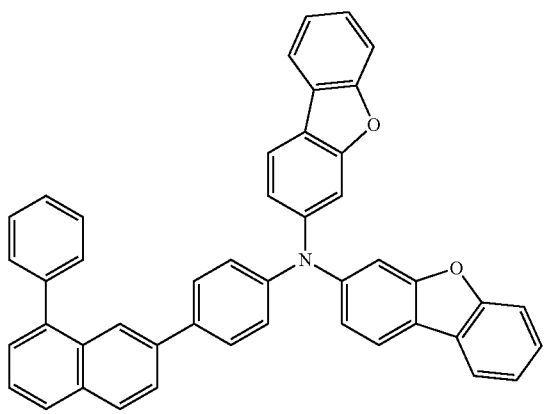
A57
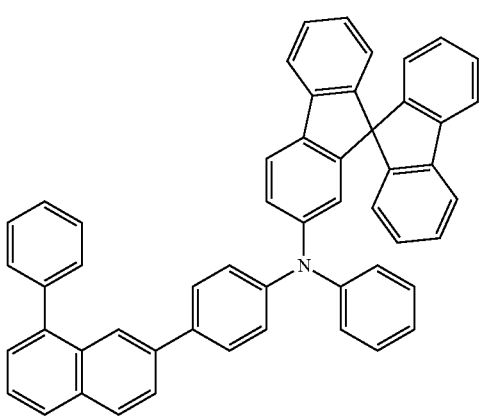
A55
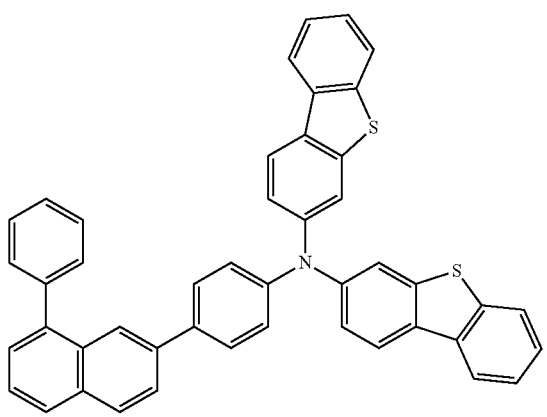
A58
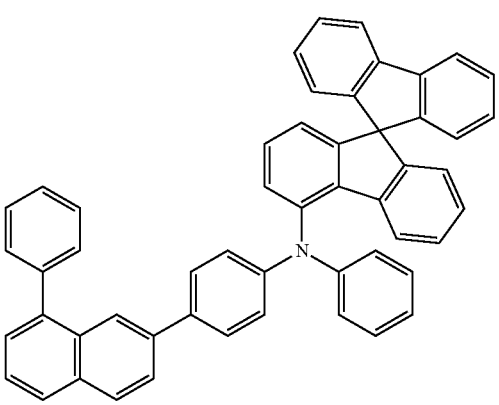

A59
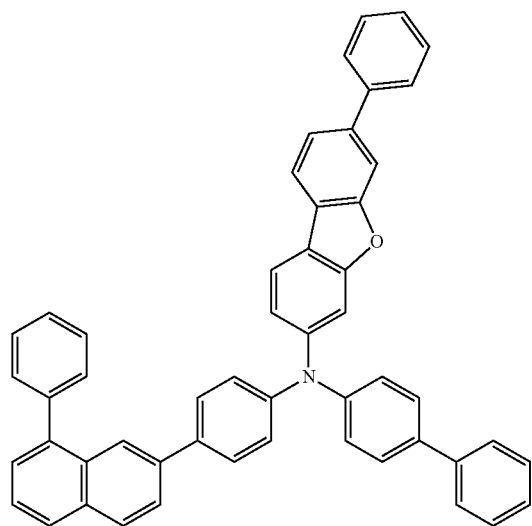
B2
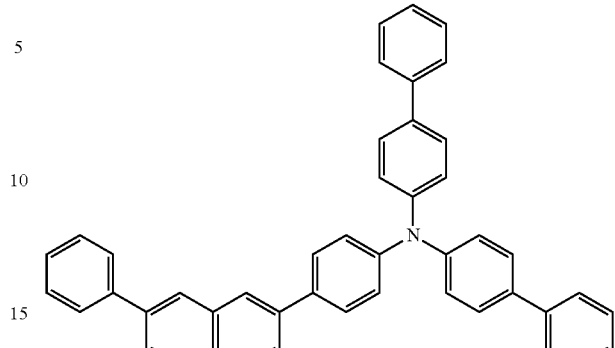
B3
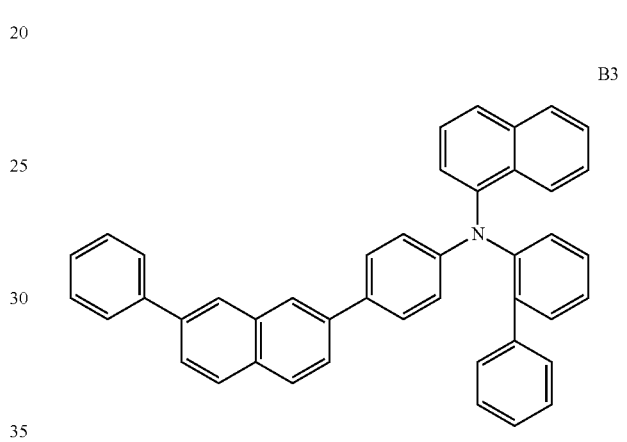
A60
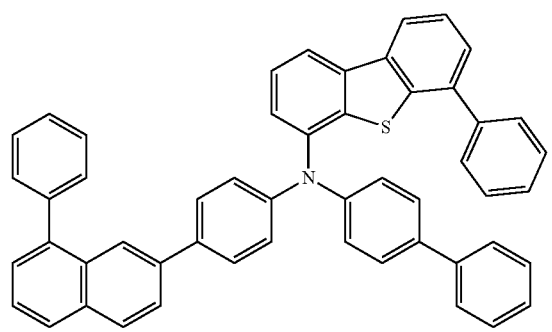
B4
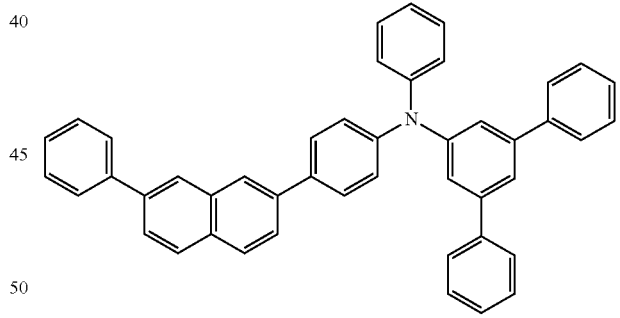
[Compound Group 2]
B1
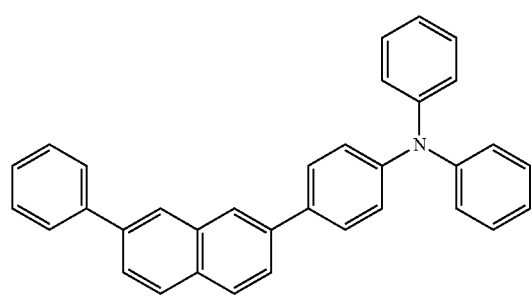
B5
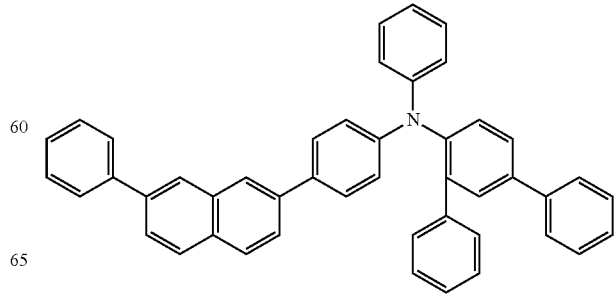

B6
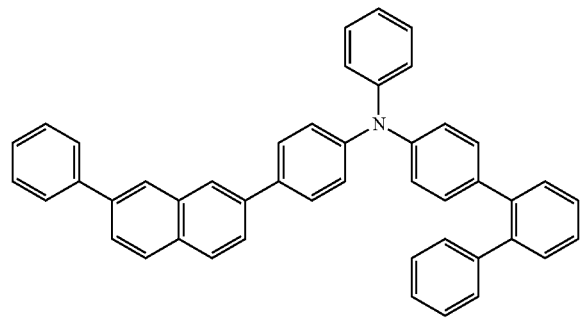
B7
B8
B9
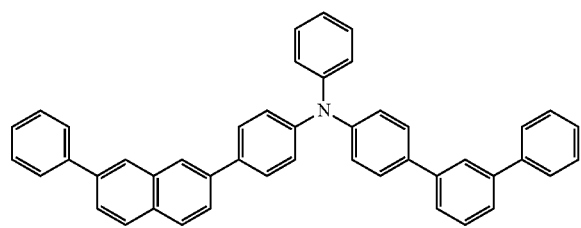
B10
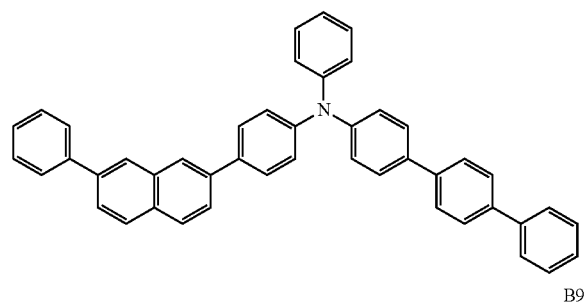
B11
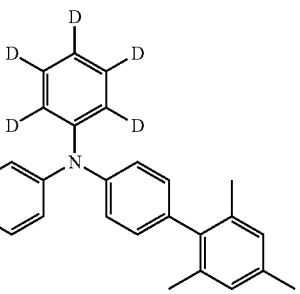
B13
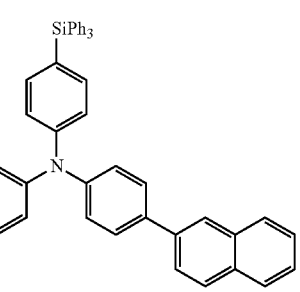
B14
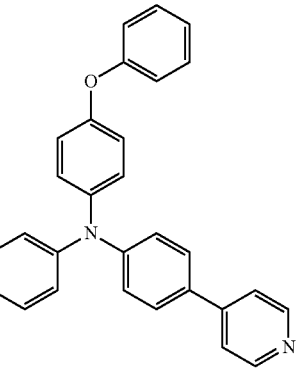
B16
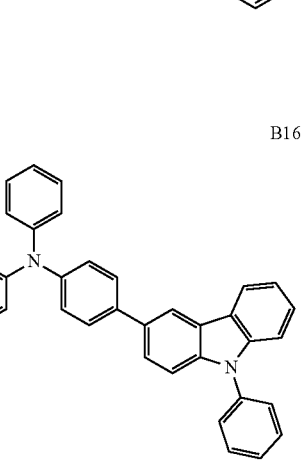

-continued

B17

B18

B19

B20

B21

B22

B23

B24

-continued

B25 B26 B27 B28 B29 B30 B31 B32

B33
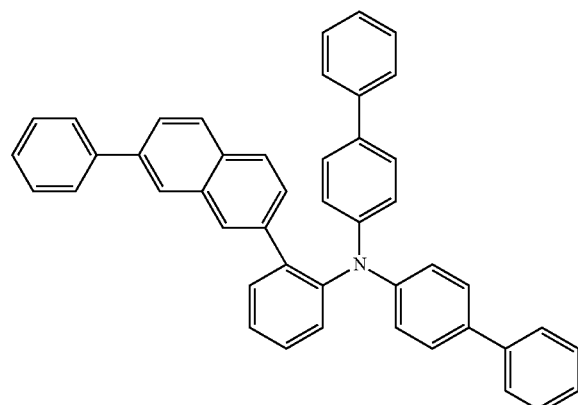
B34
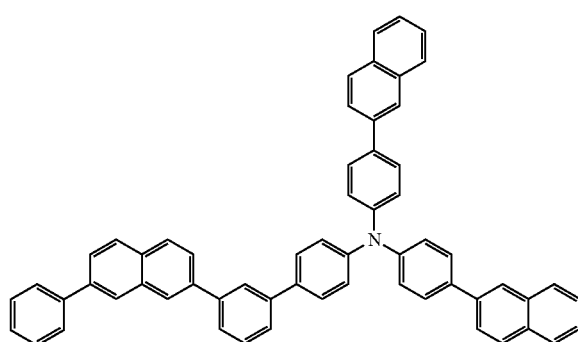
B35
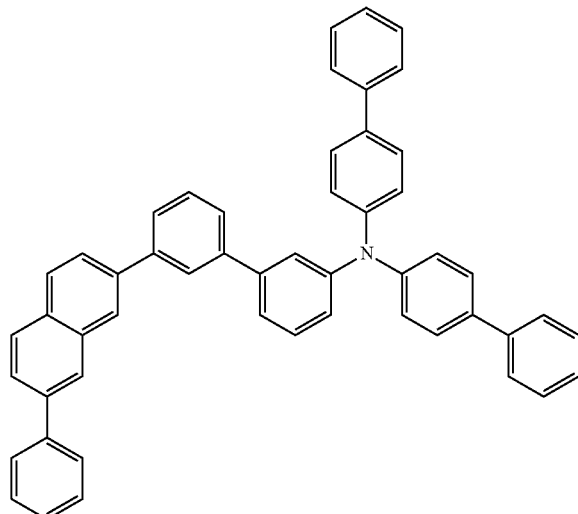
B36
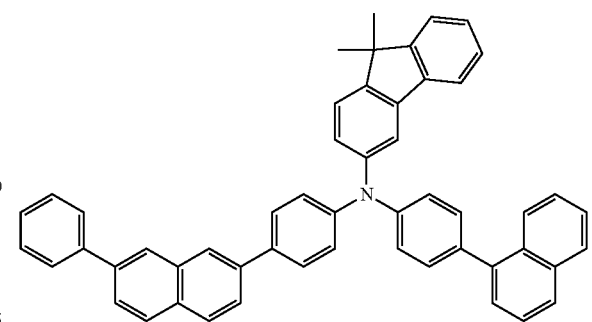
B37
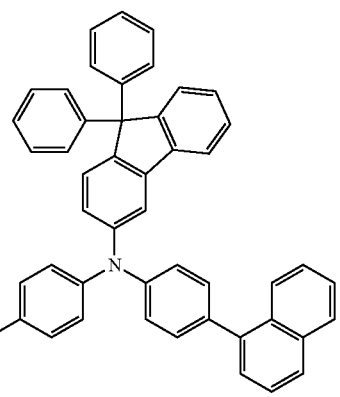
B38
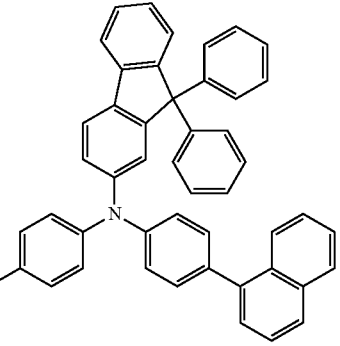
B39
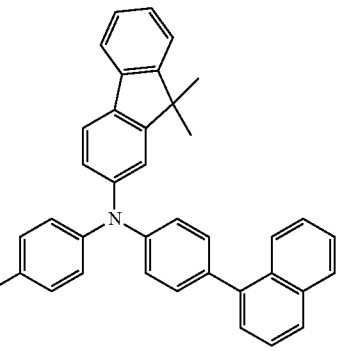

-continued
B40
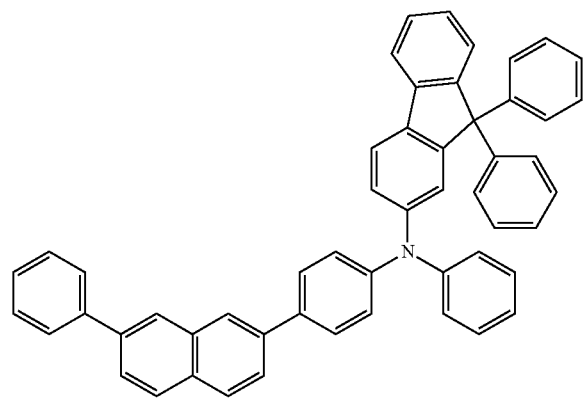
B41
B42
B43
B44
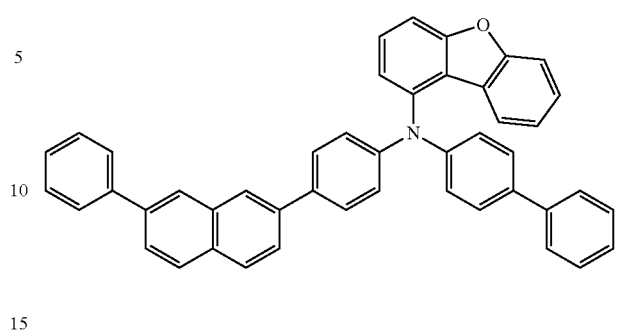
B45
B46
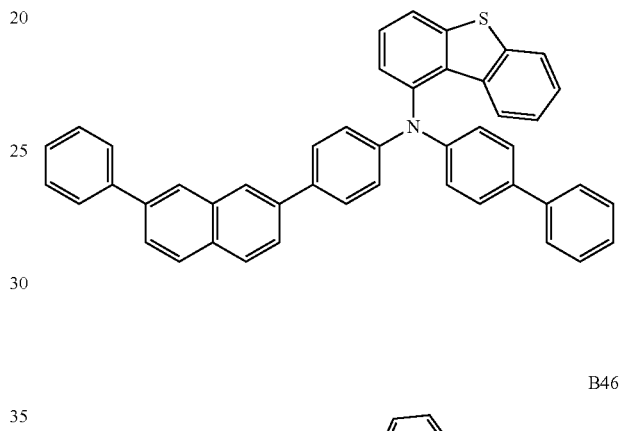
B47
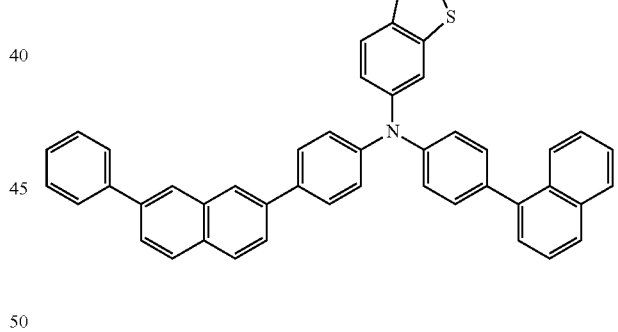
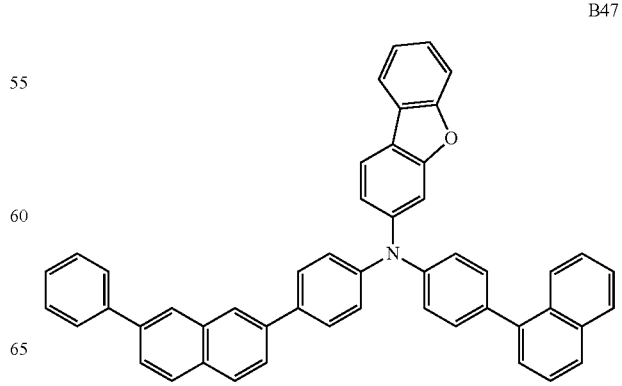

B48
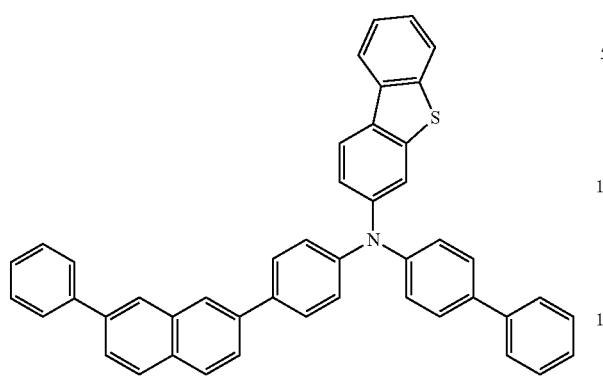
B49
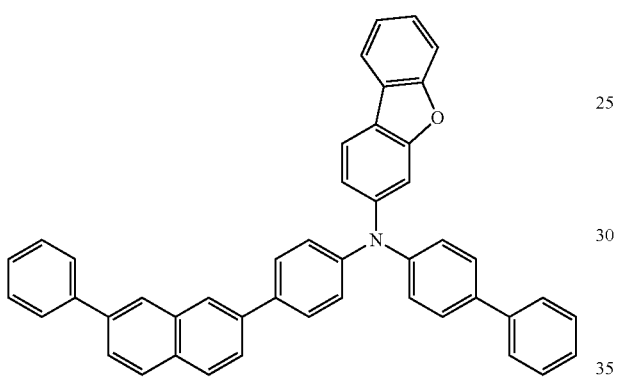
B50
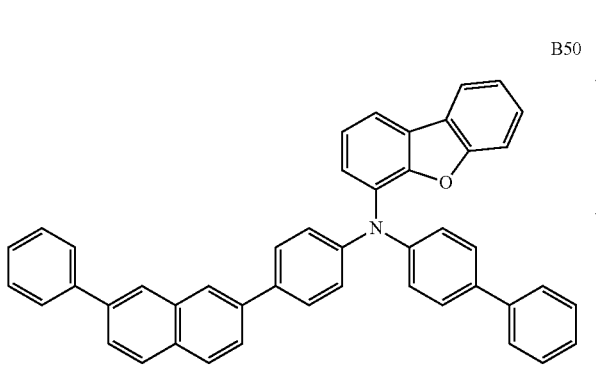
B51
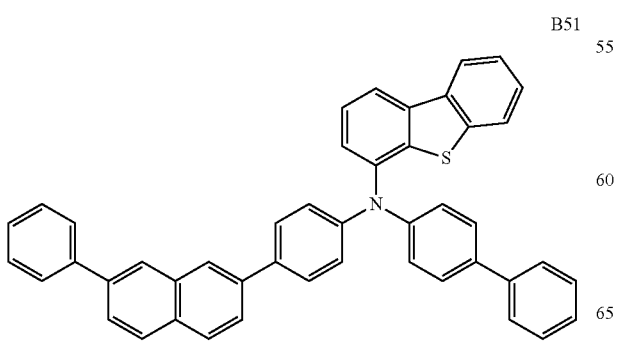
B52
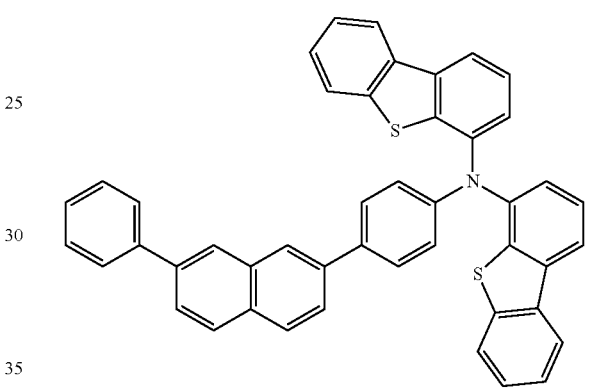
B53
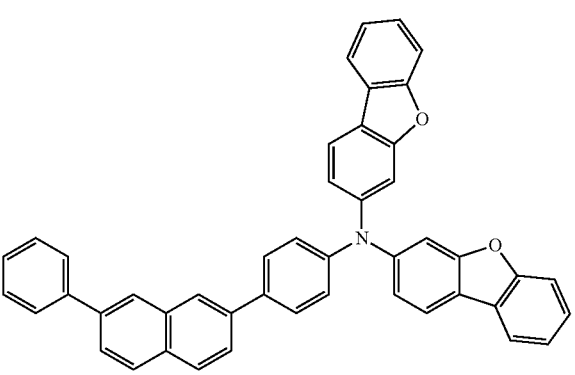
B54
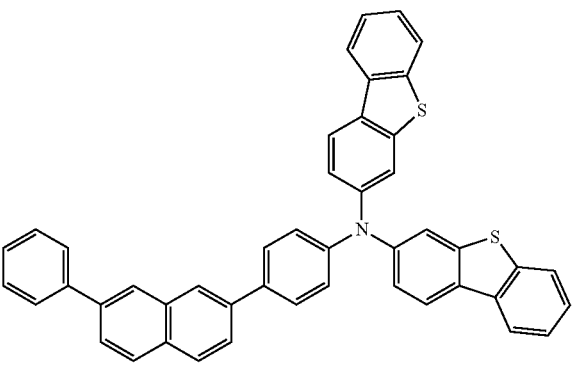
B55

B56
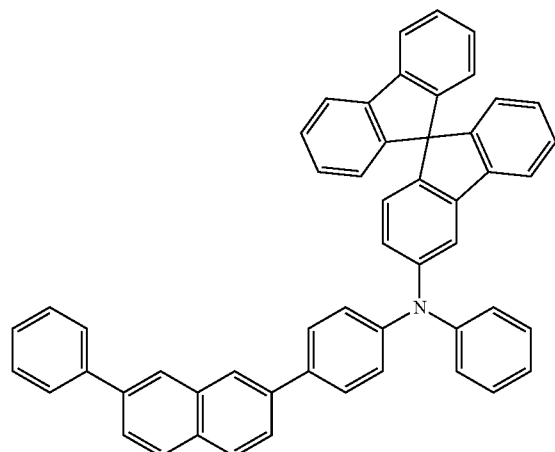
B57
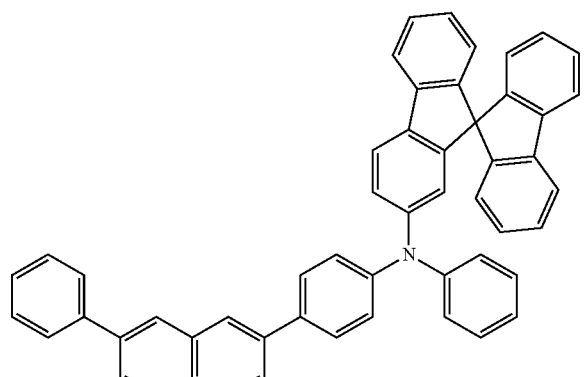
B58
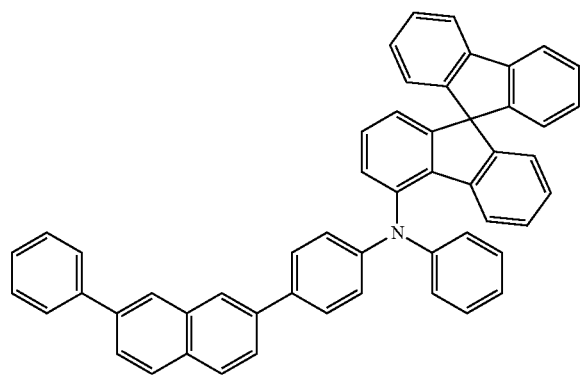
B59
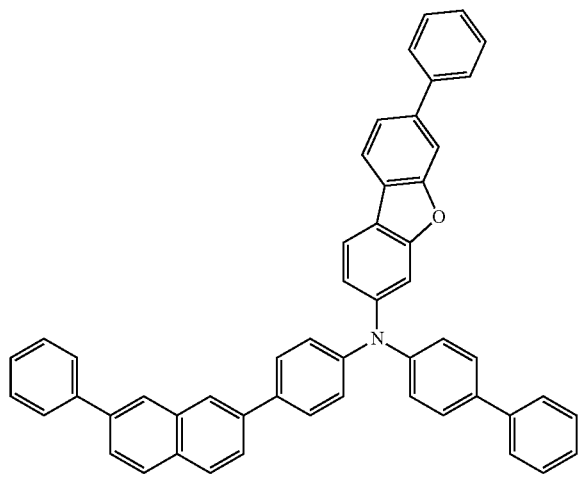
B60
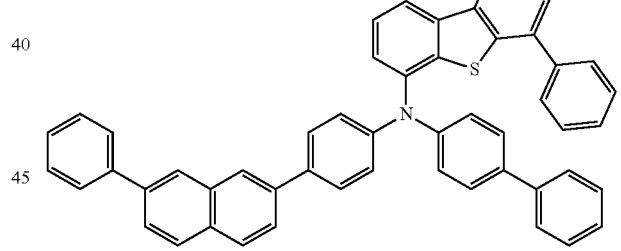
[Compound Group 3]
C1
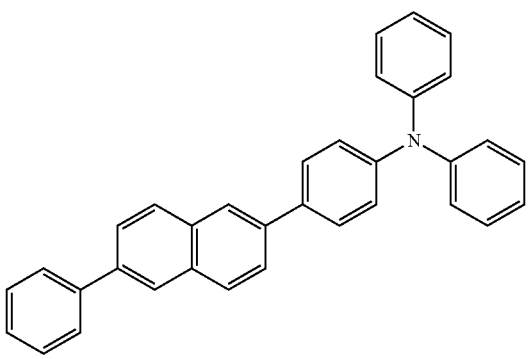

C2
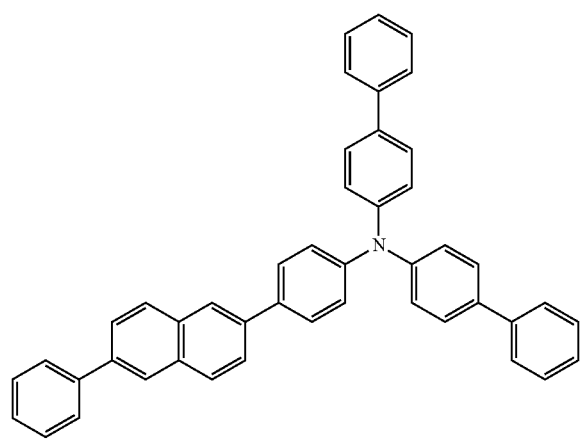
C3
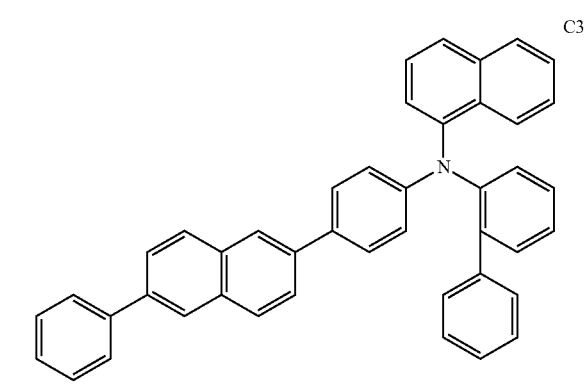
C4
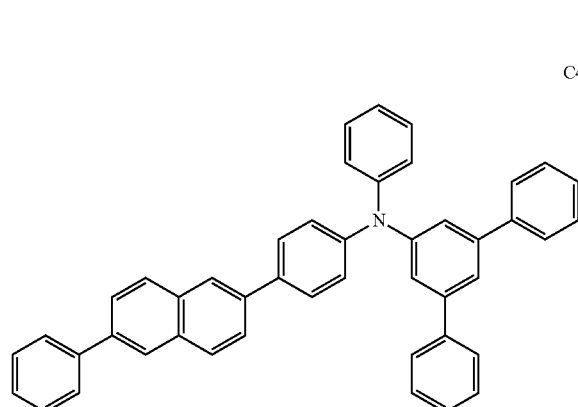
C5
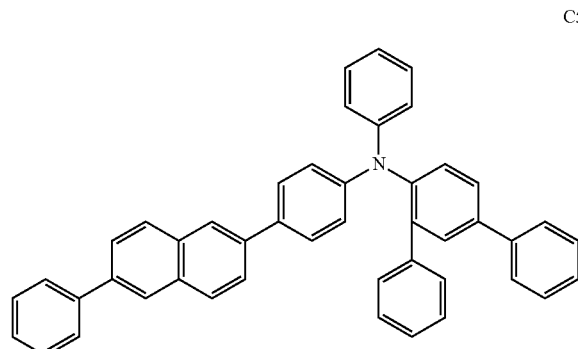
C6
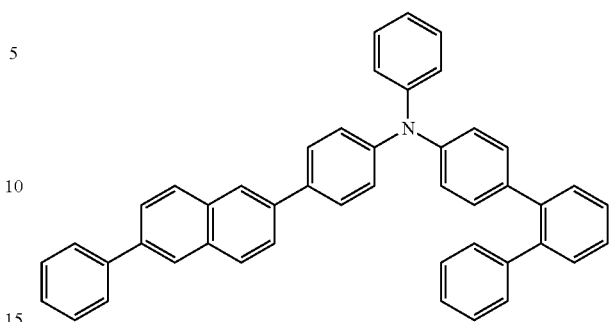
C7
C8
C9
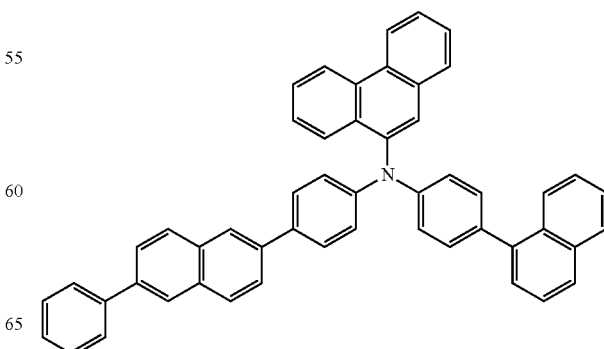

317
-continued
C10
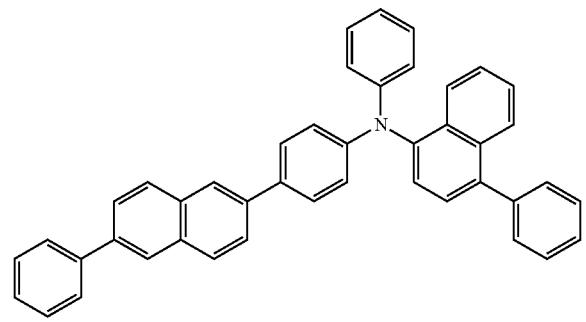
C11
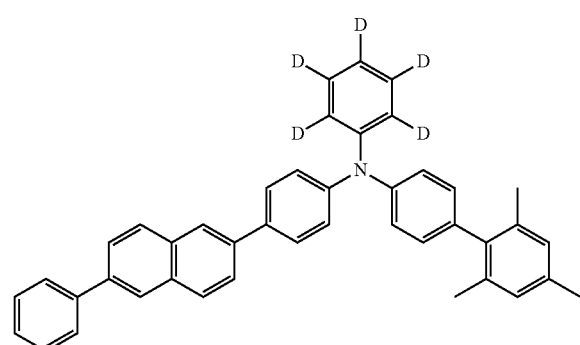
C12
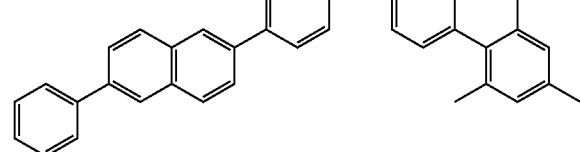
C13
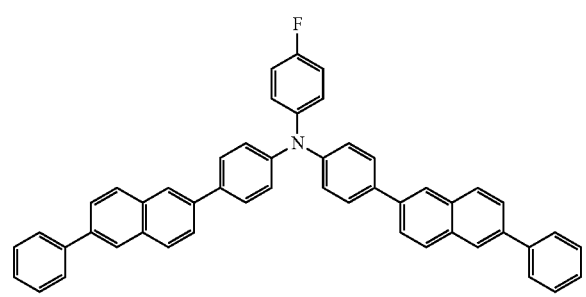
318
-continued
C14
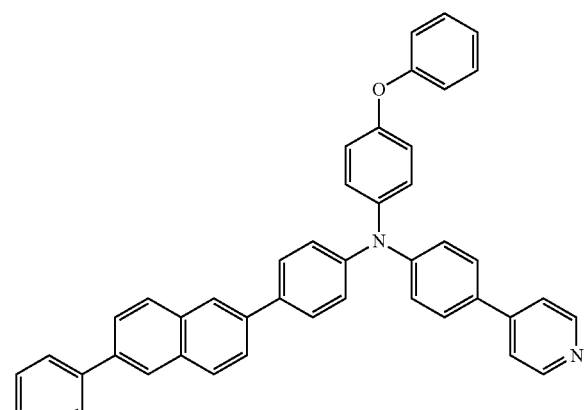
C15
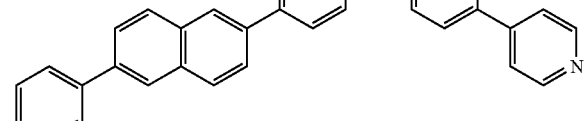
C16
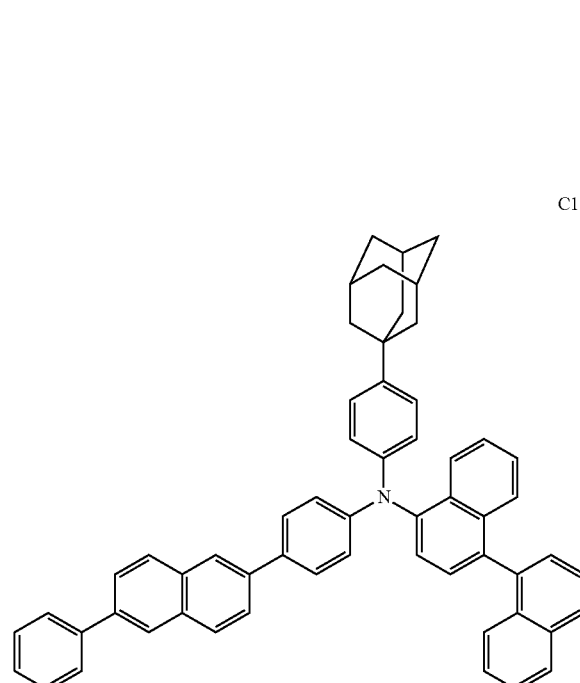

-continued
C17
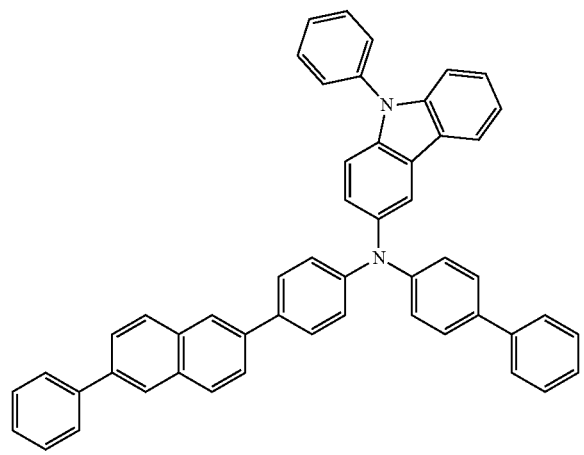
C18
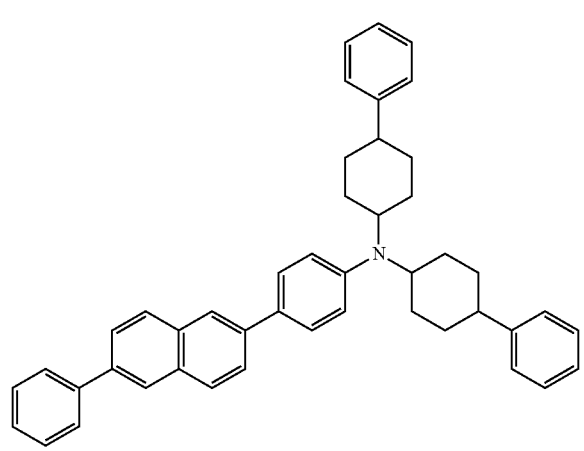
C19
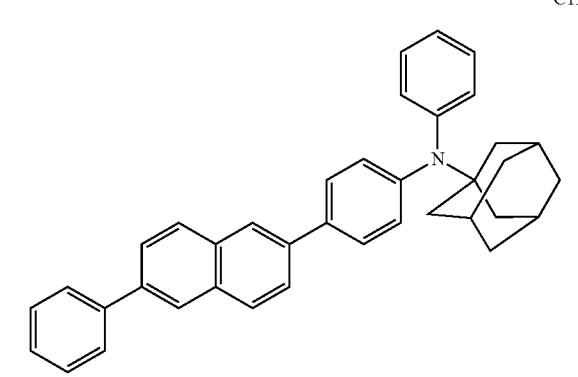
C20
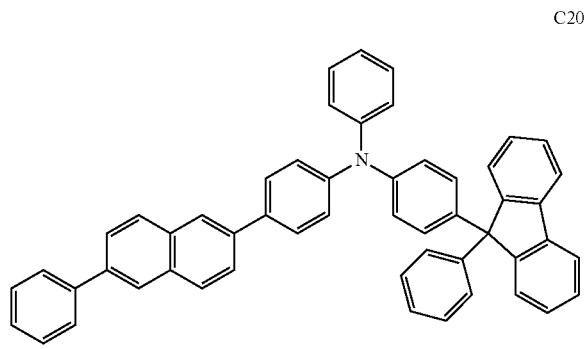
-continued
C21
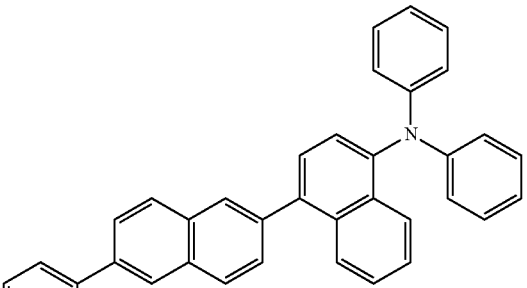
C22
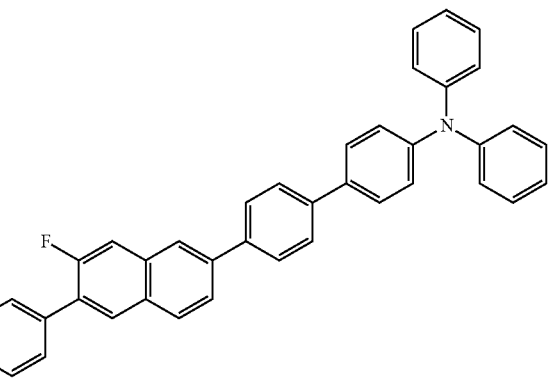
C23
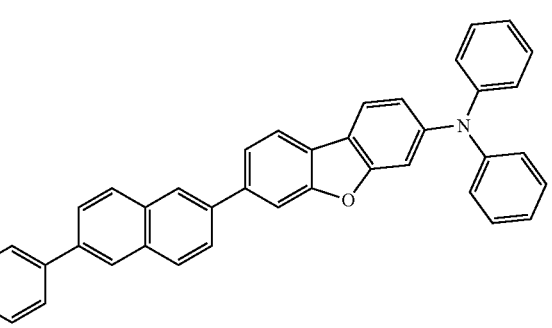
C24
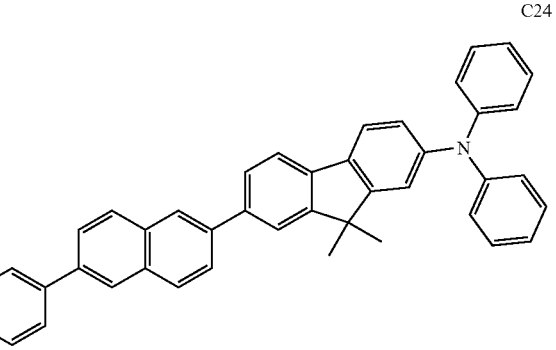

-continued
C25
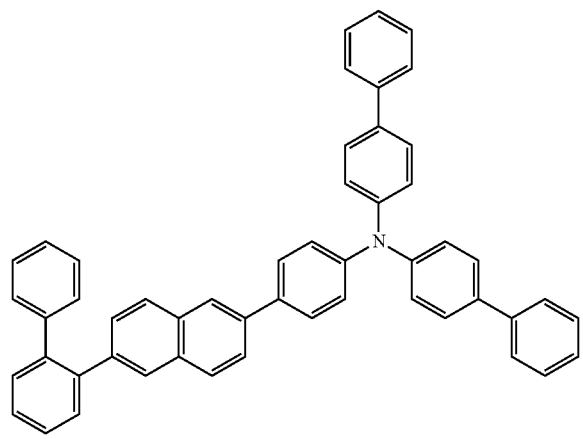
C26
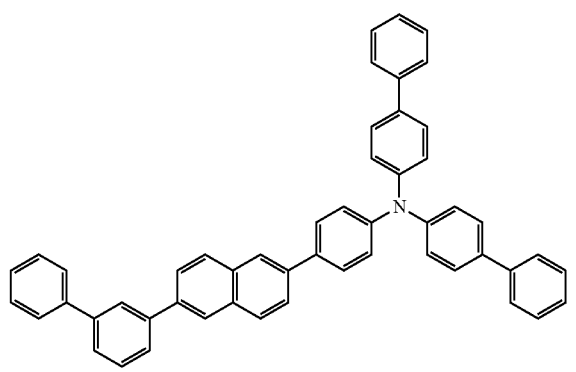
C27
C28
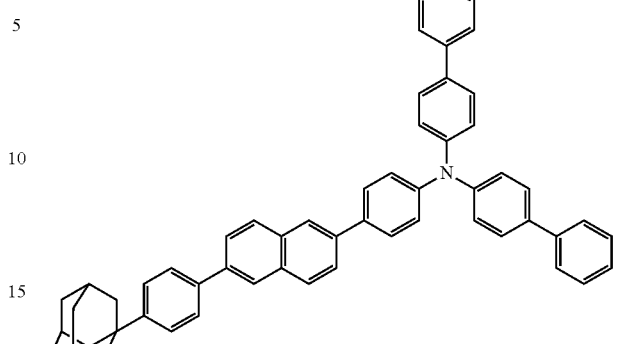
C29
C30
C31
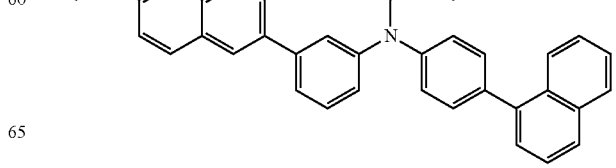

C32
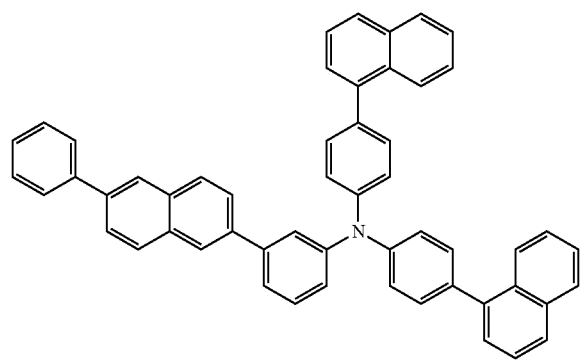
C36
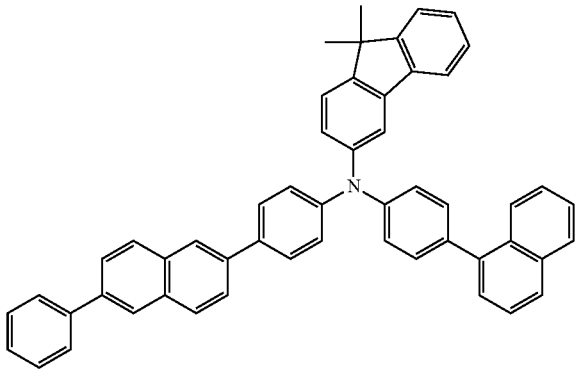
C33
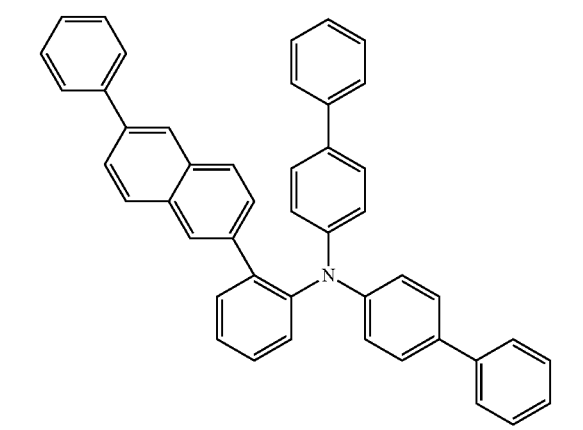
C37
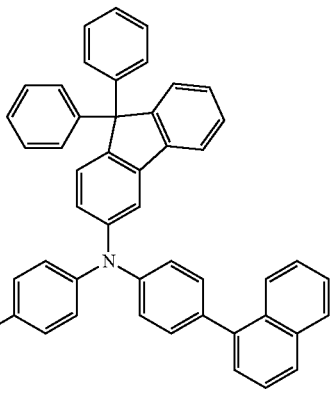
C34
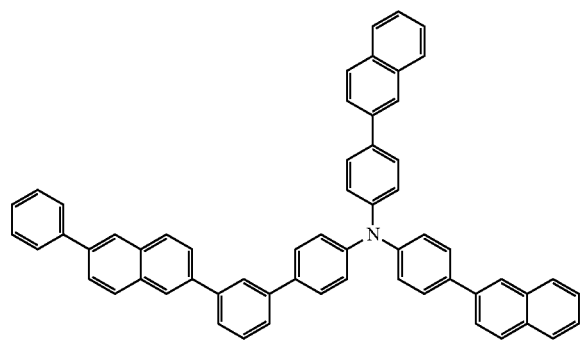
C35
C38
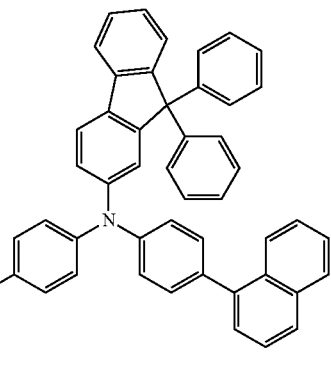

C39
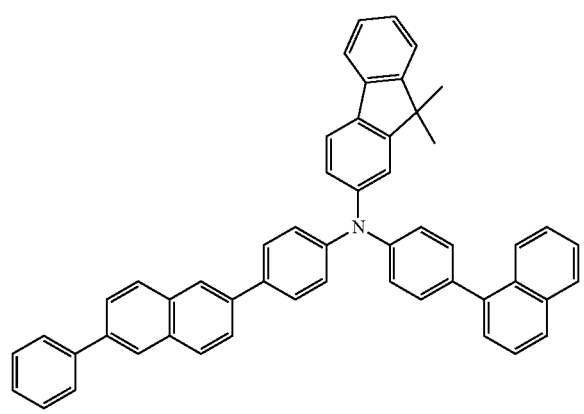
C40
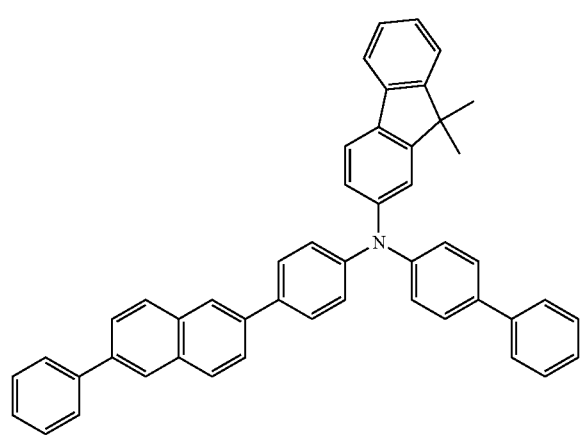
C41
C42
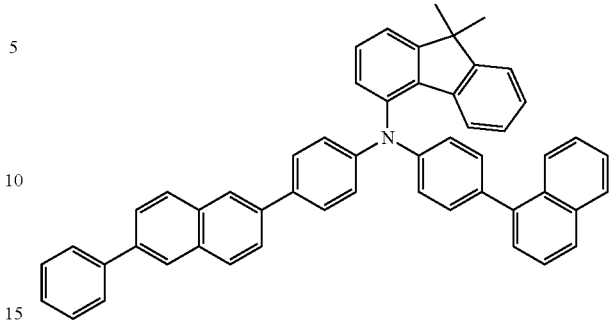
C43
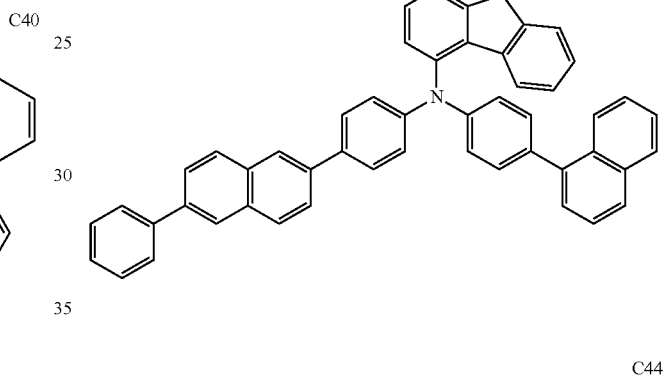
C44
C45
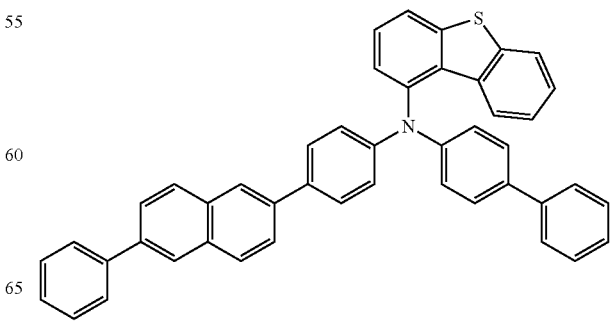

-continued
C46
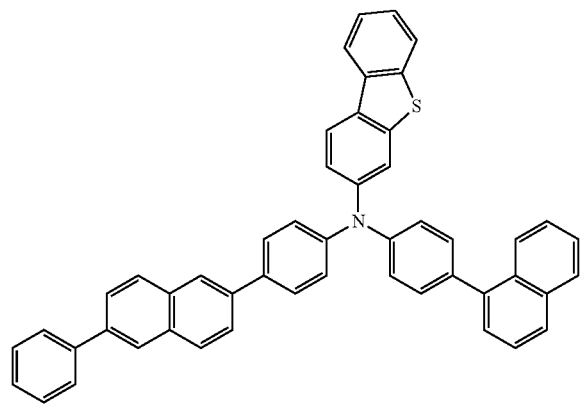
C47
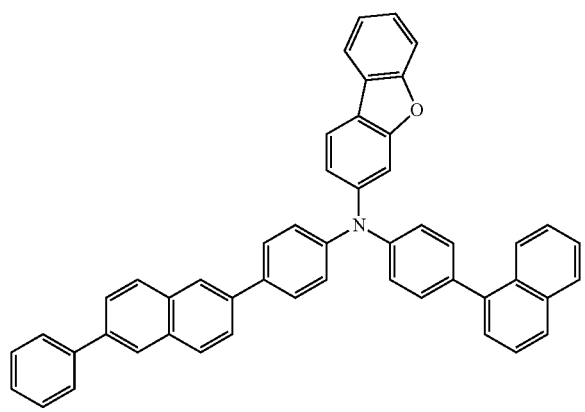
C48
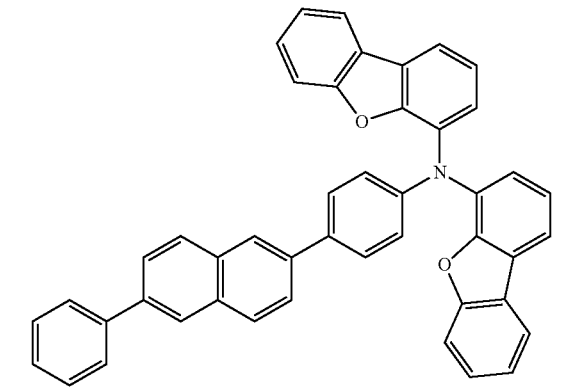
-continued
C49
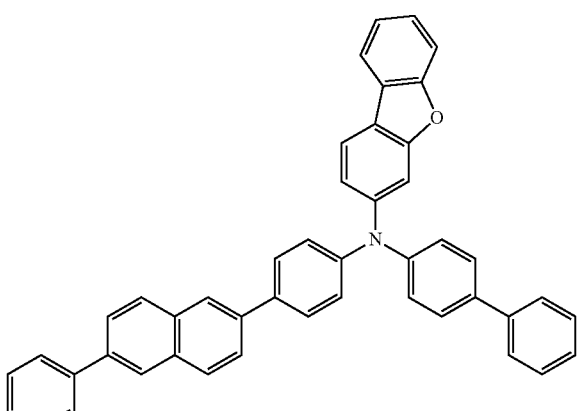
C50
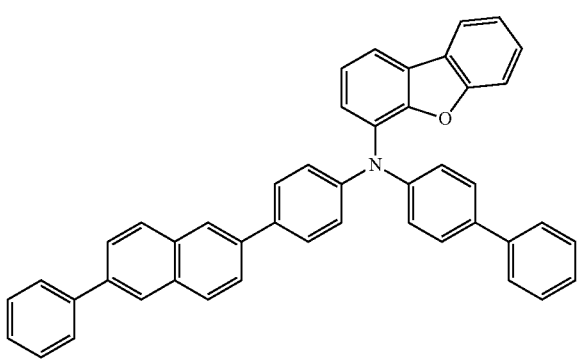
C51
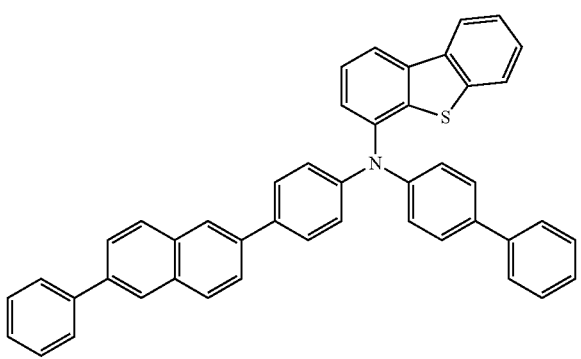
C52
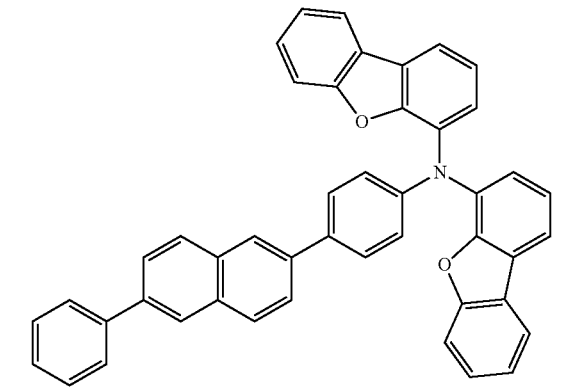

C53
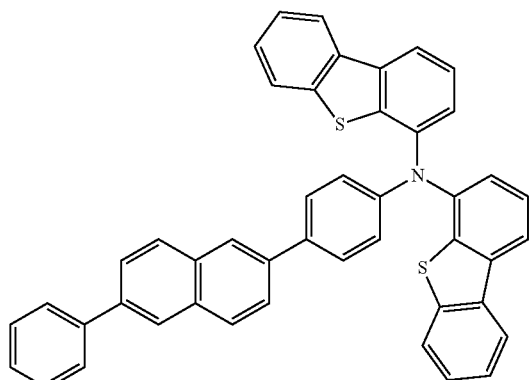
C54
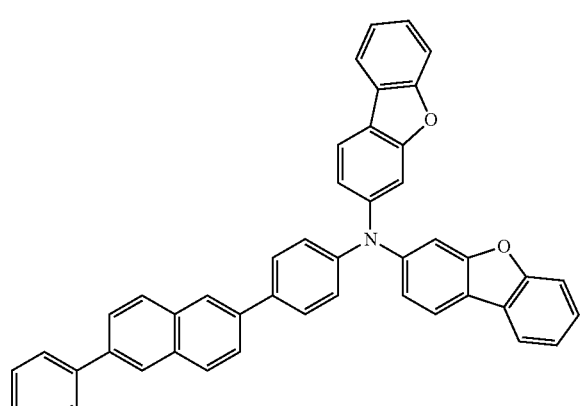
C55
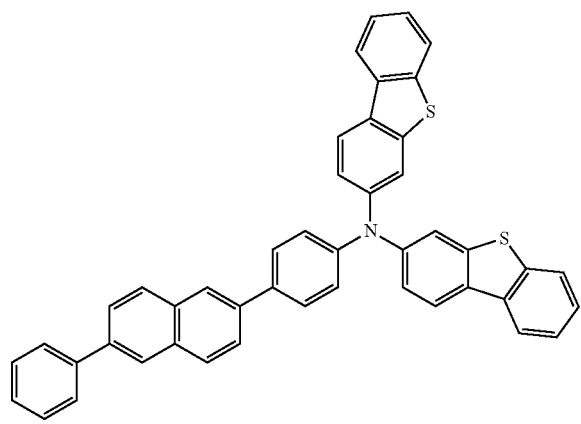
C56
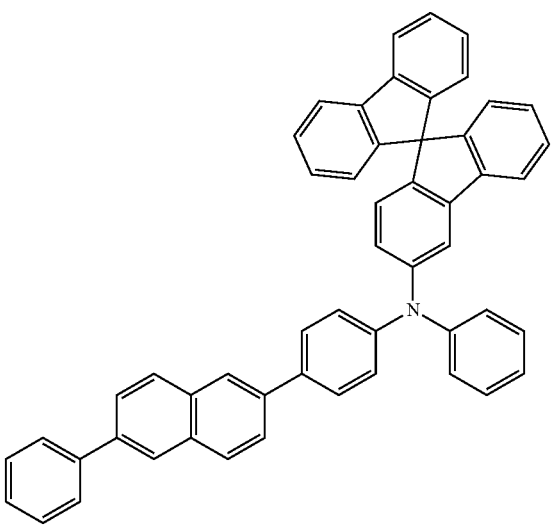
C57
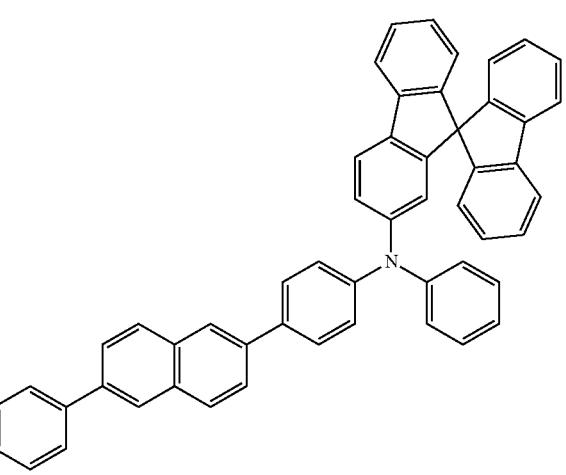
C58
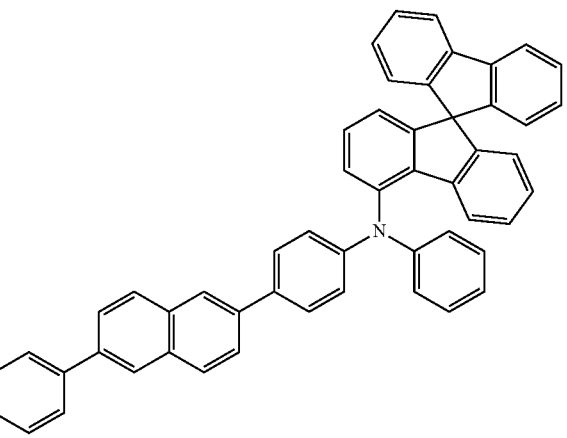

-continued
C59
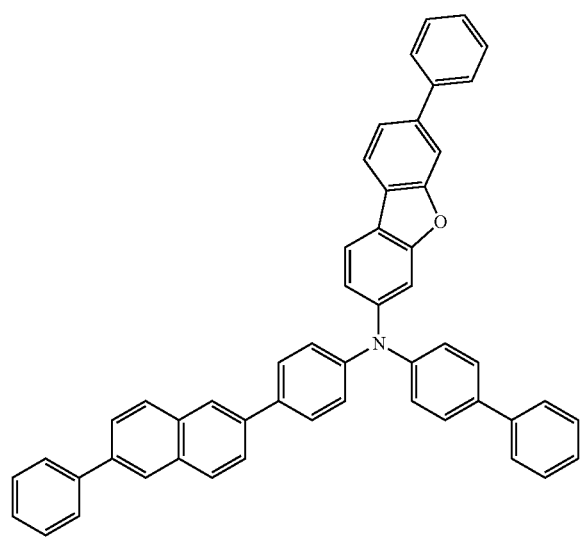
C60
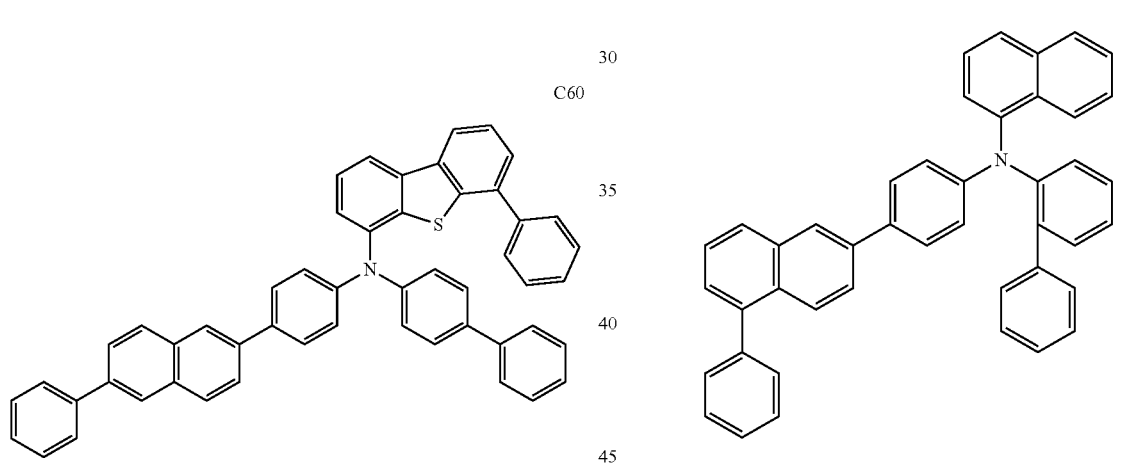
[Compound Group 4]
-continued
D2
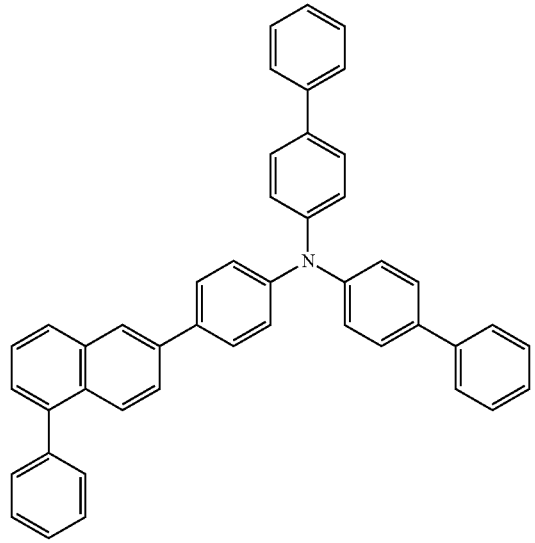
D3
D1
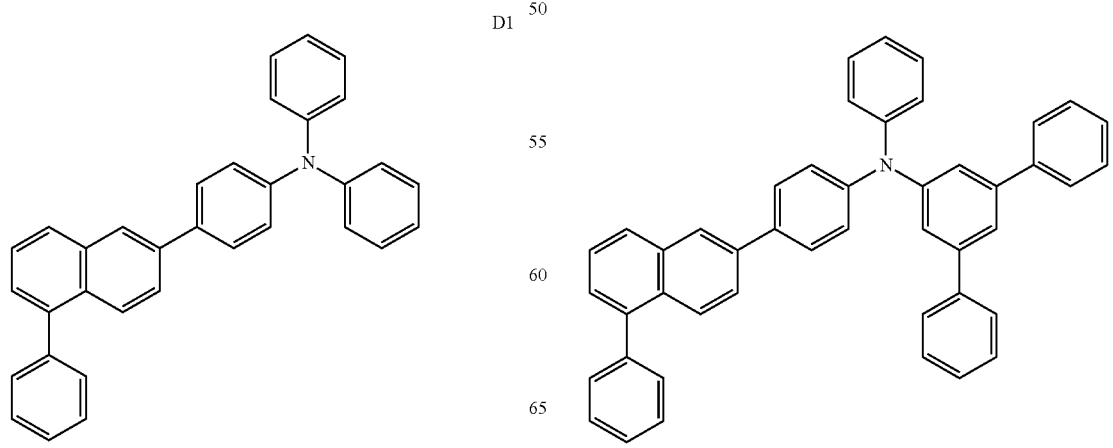
D4

D5
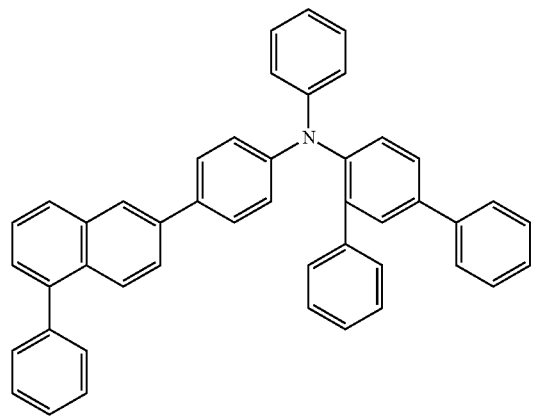
D6
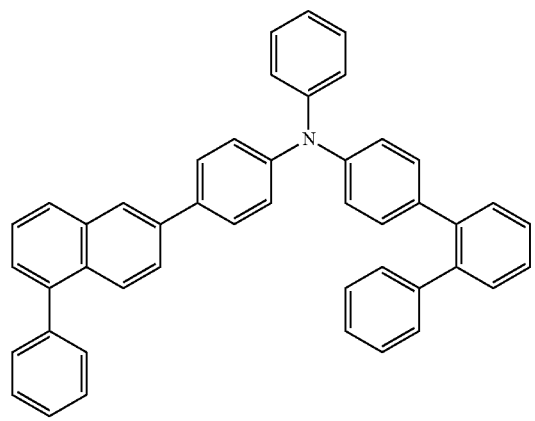
D7
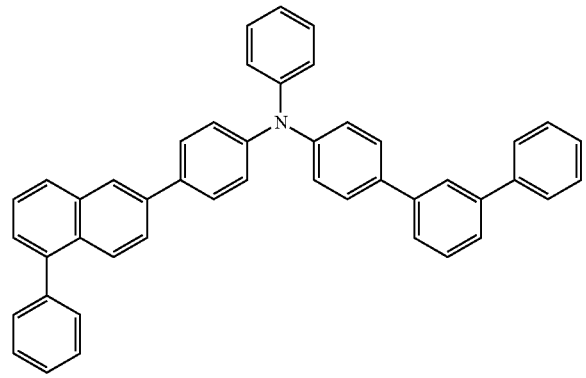
D8
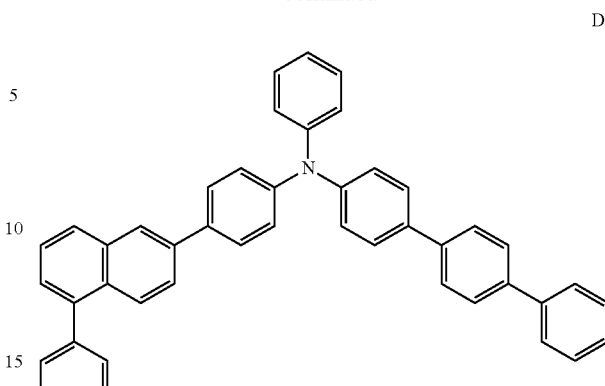
D9
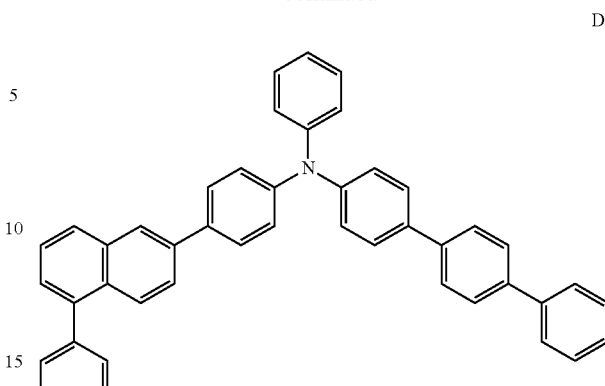
D10
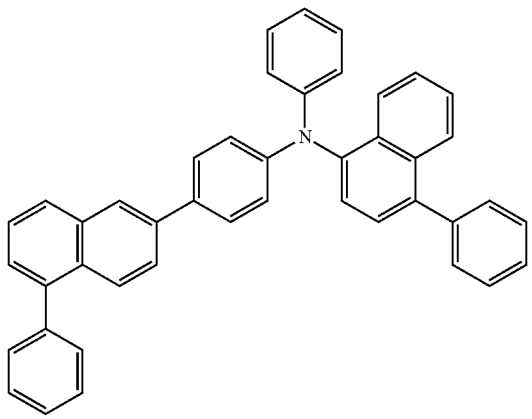

-continued
D11
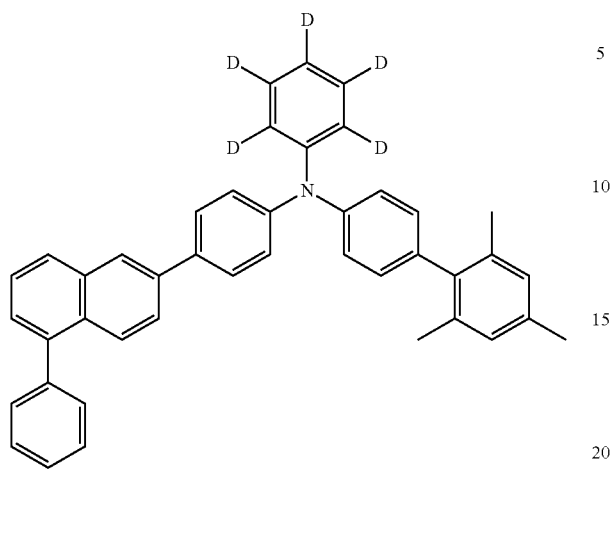
D12
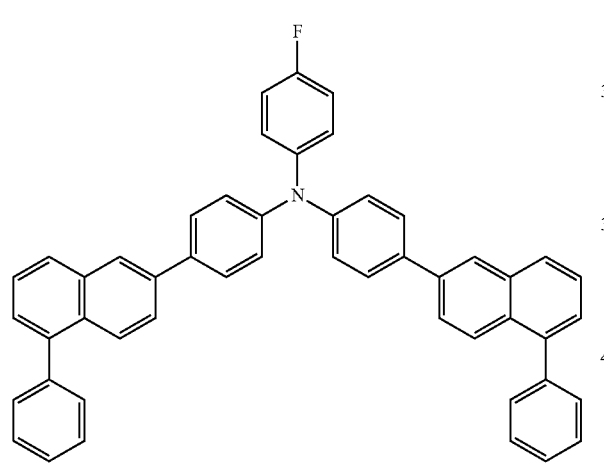
D13
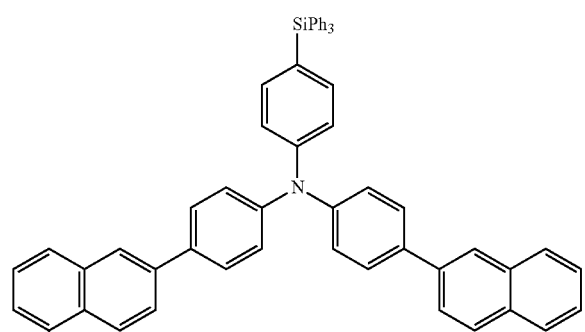
D14
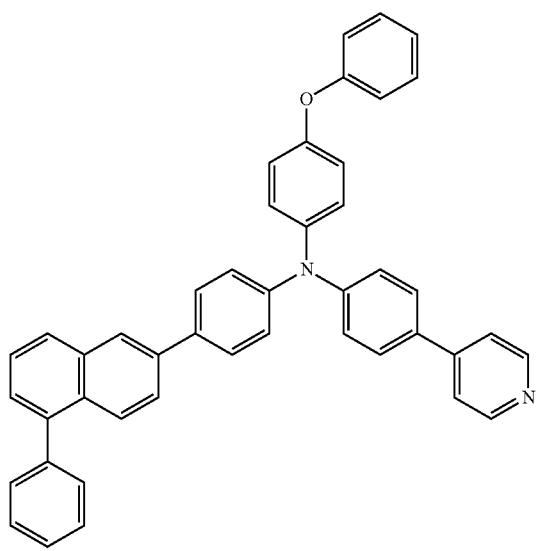
D15
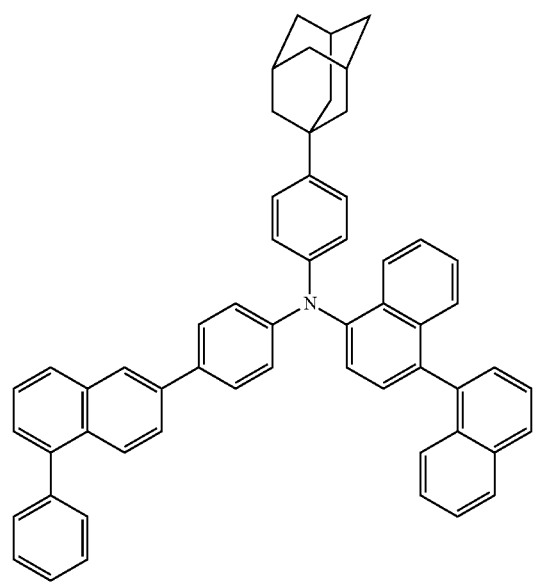
D16
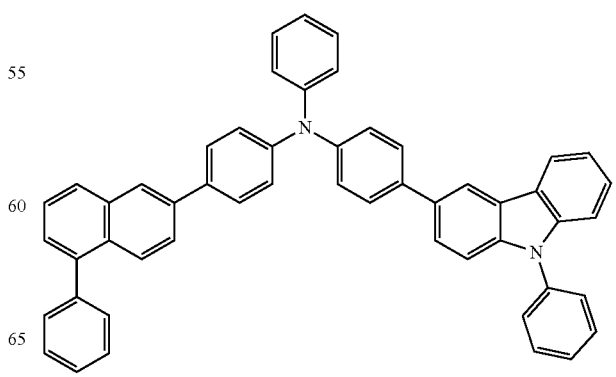

D17
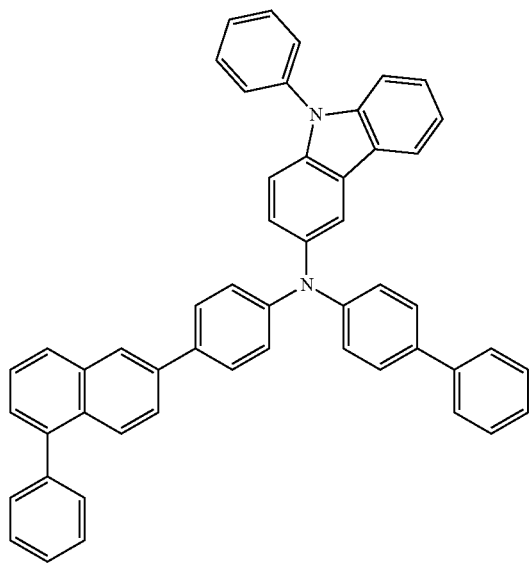
D18
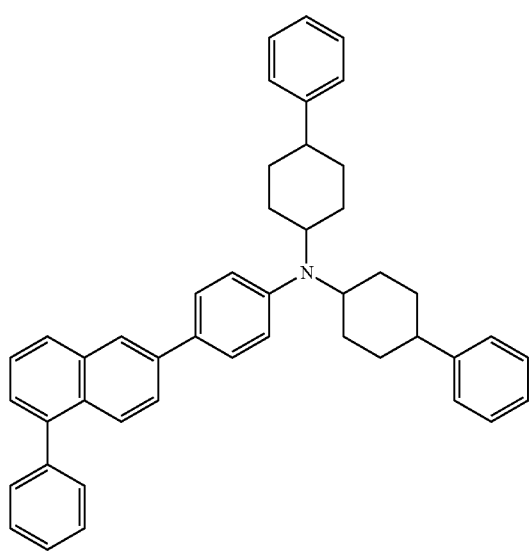
D19
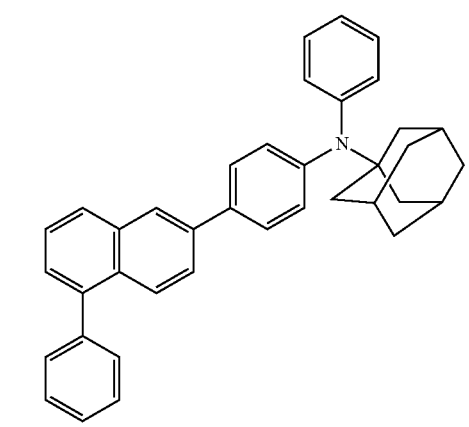
D20
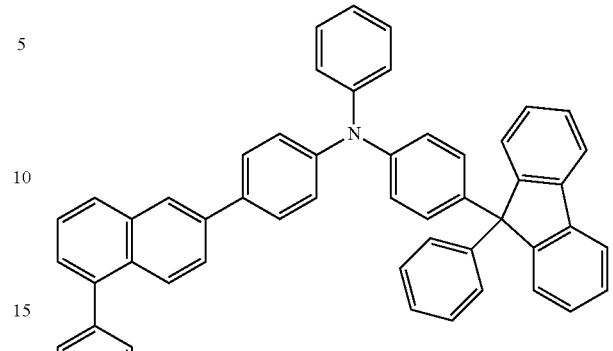
D21
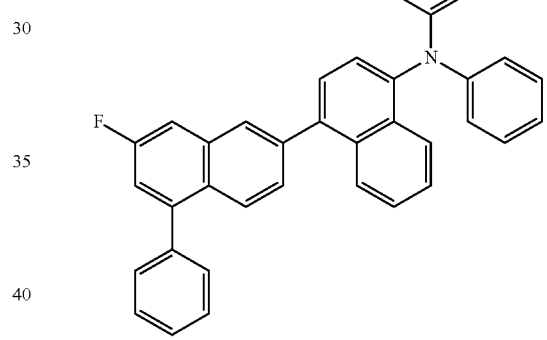
D22
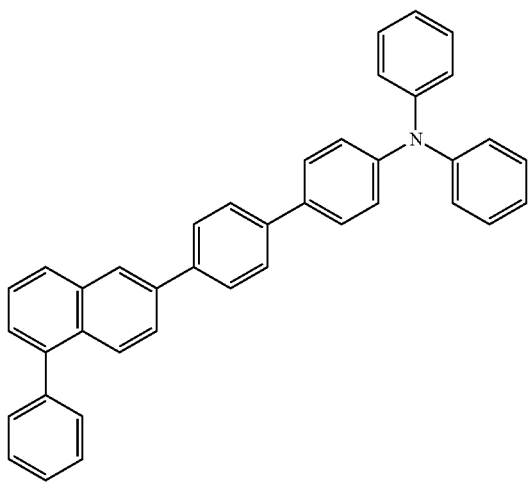

-continued
D23
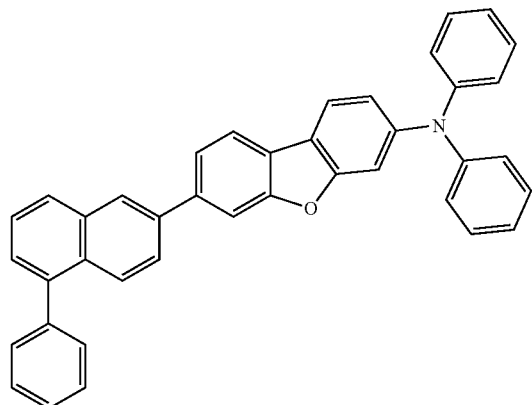
D24
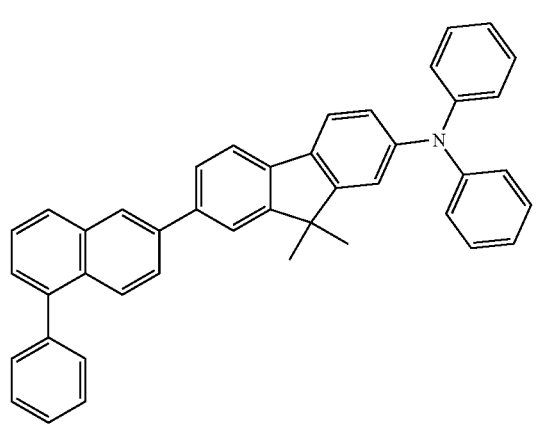
D25
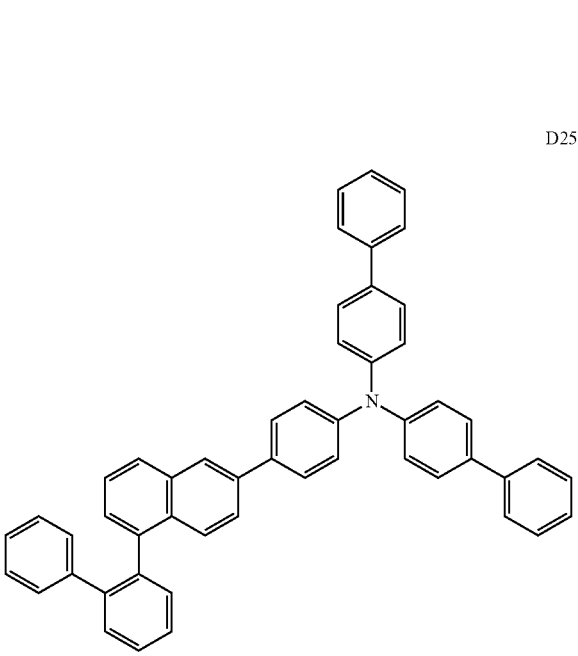
D26
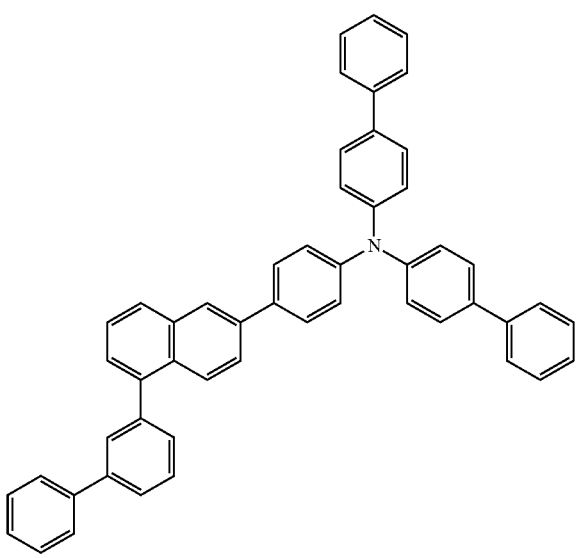
D27
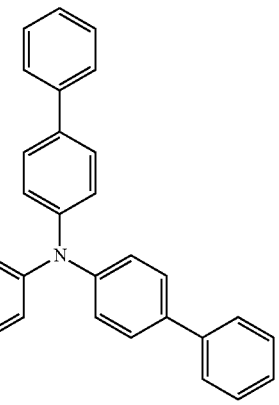

D28
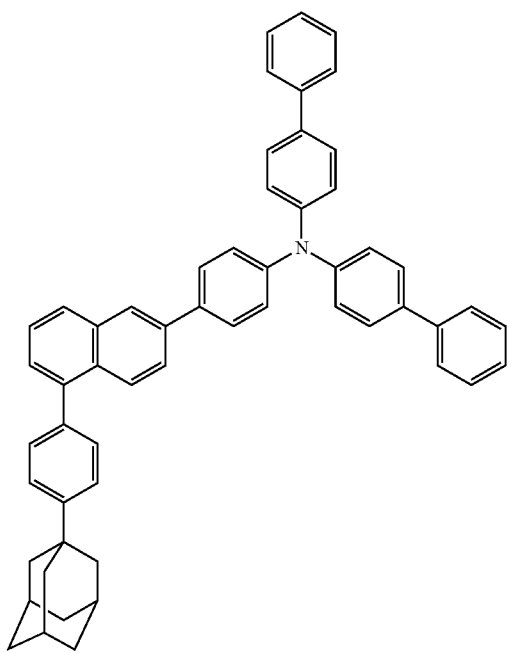
D30
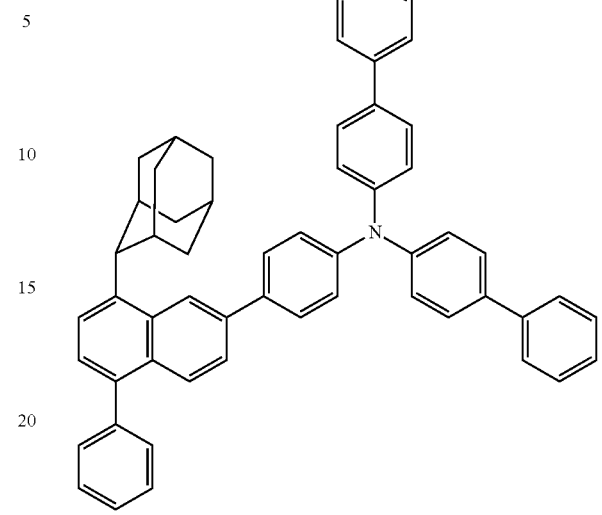
D31
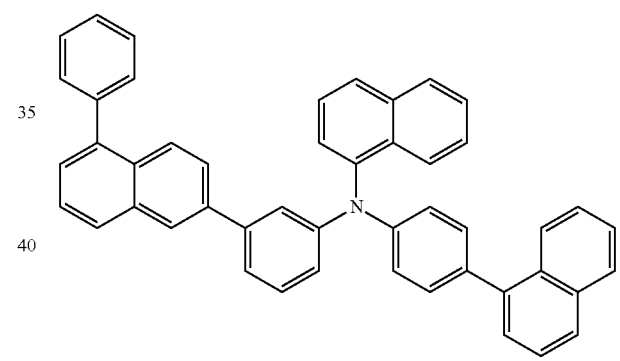
D29
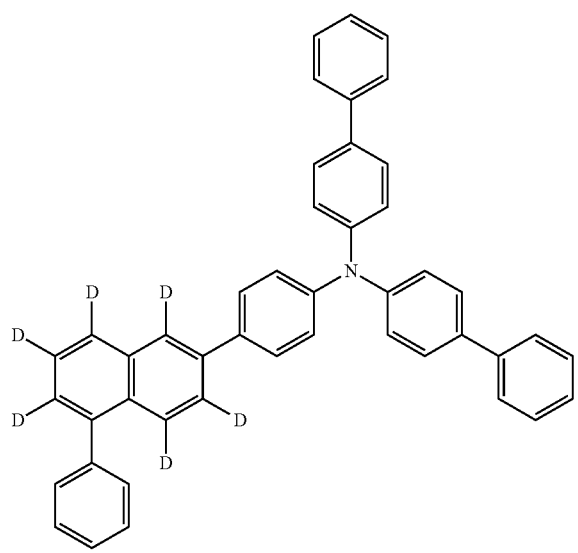
D32
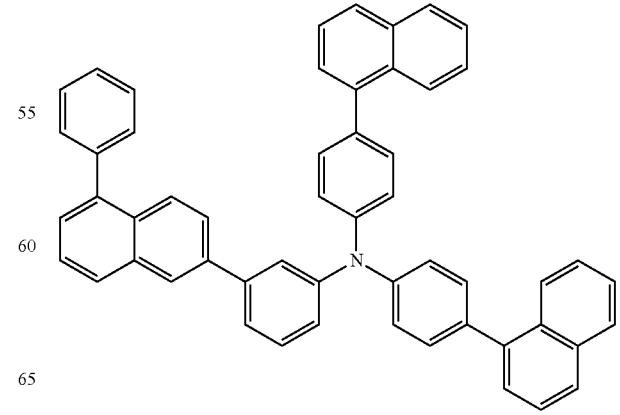

D33
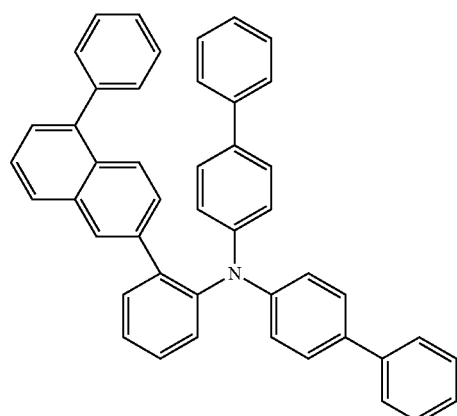
D36
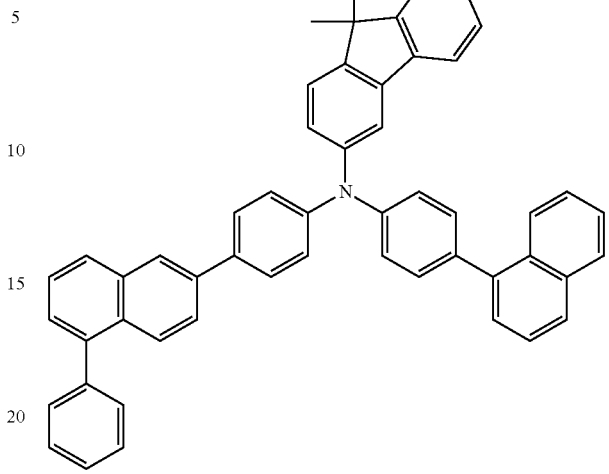
D34
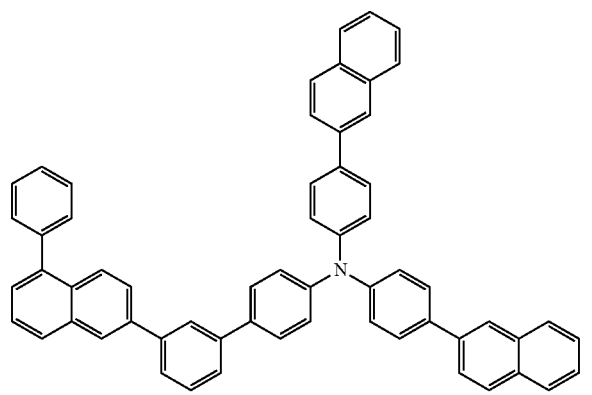
D35
D37
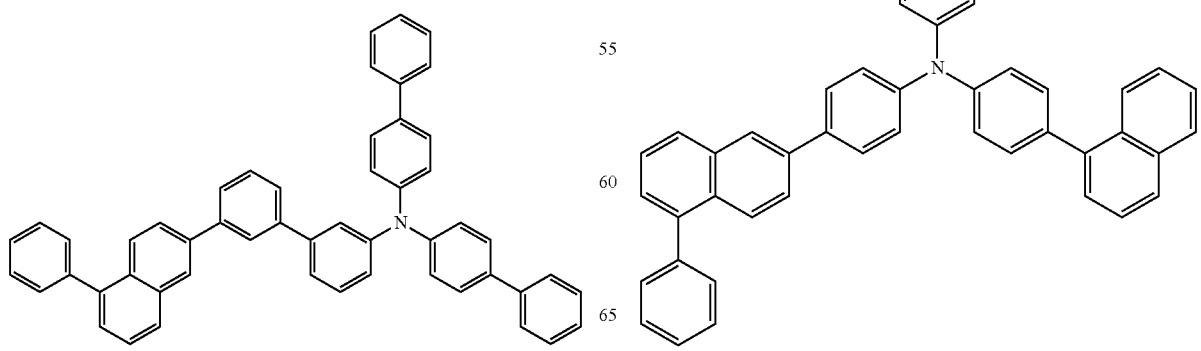

D38
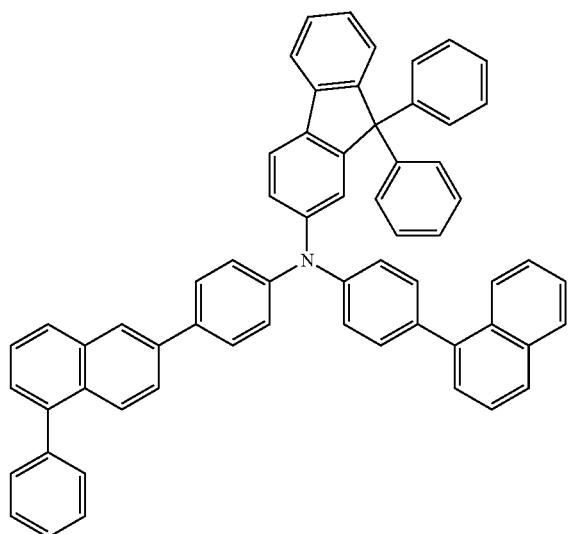
D39
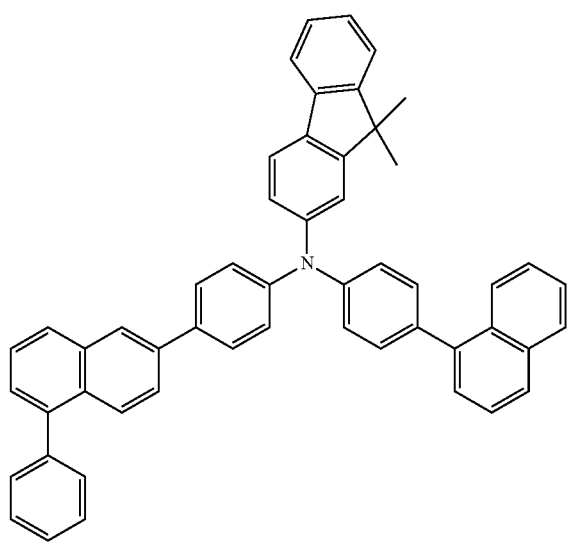
D40
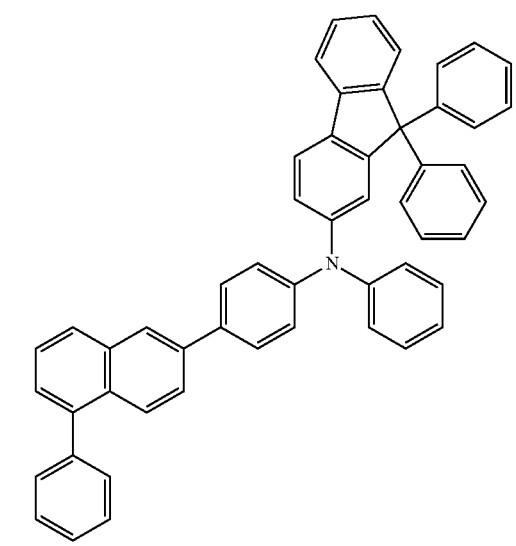
D41
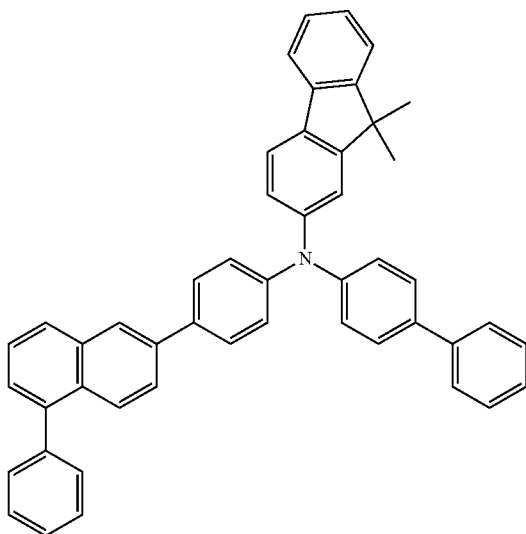
D42
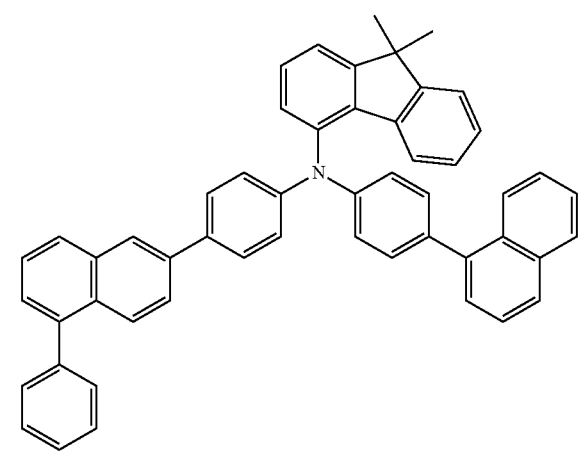
D43
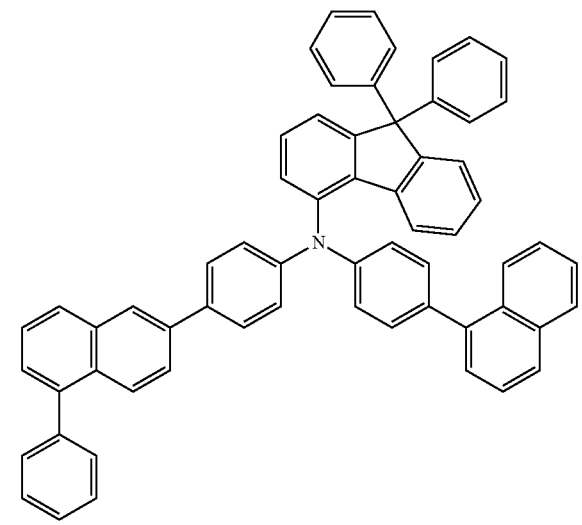

-continued
D44
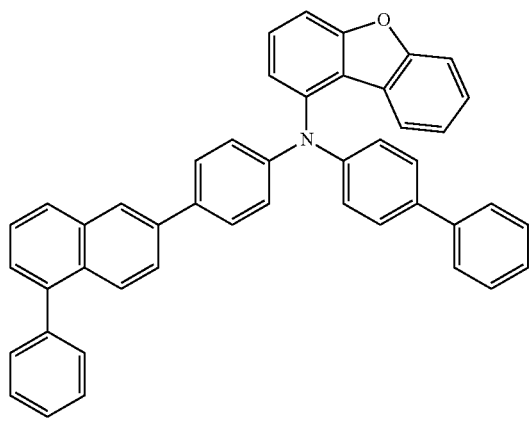
D45
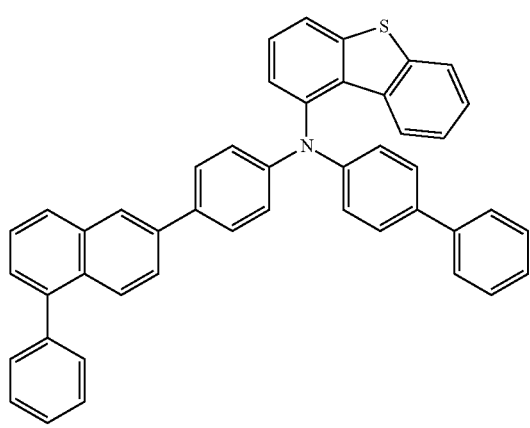
D46
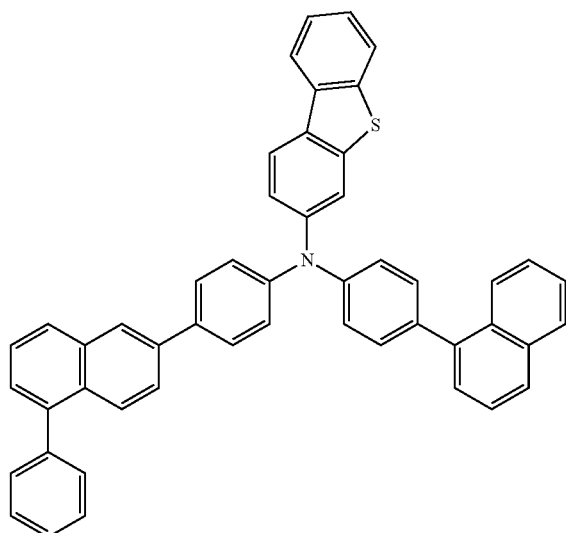
-continued
D47
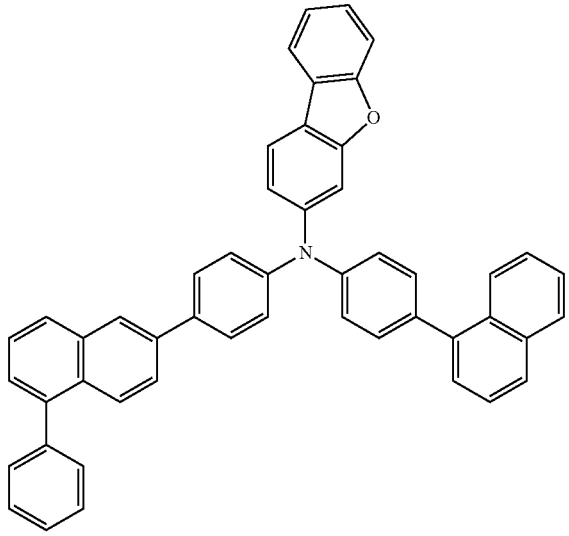
D48
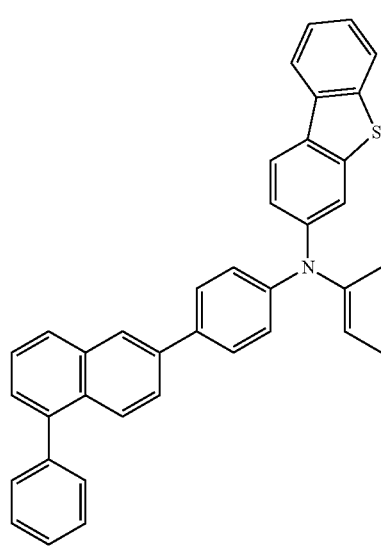
D49
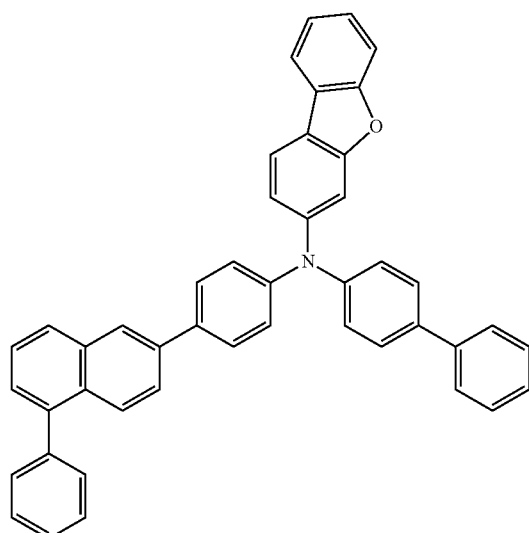

-continued
D50
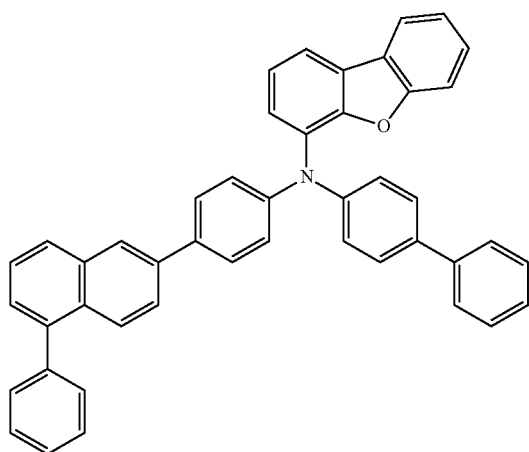
D53
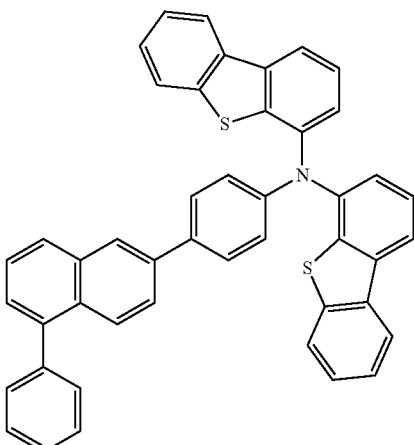
D51
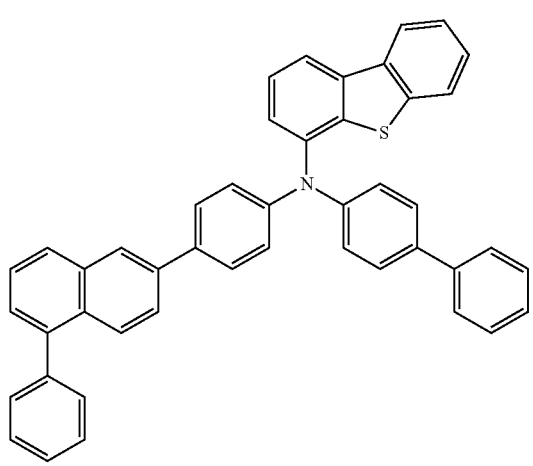
D54
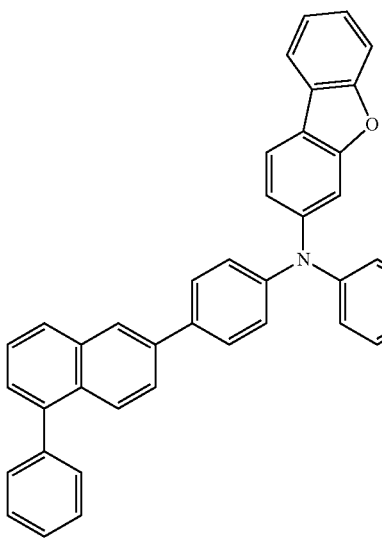
D52
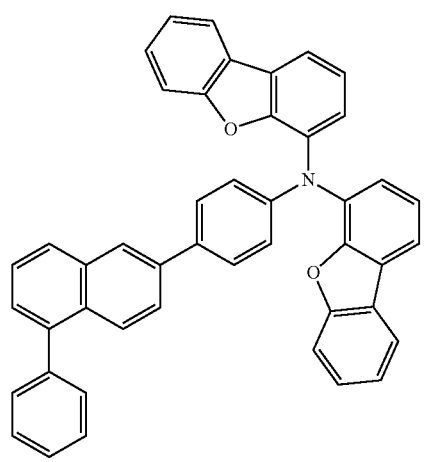
D55
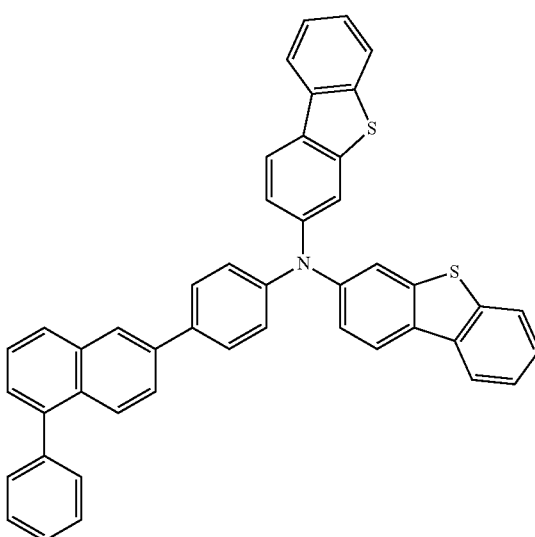

-continued
D56
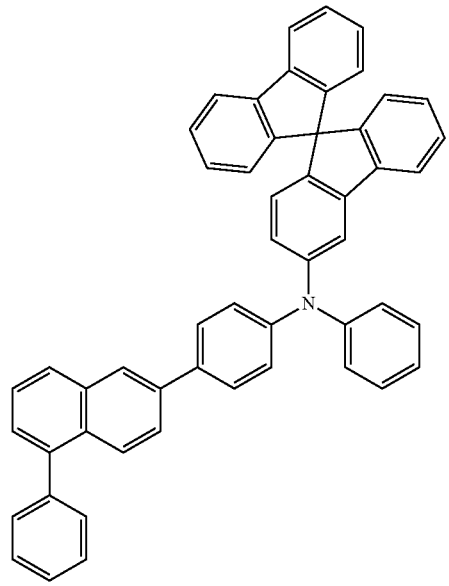
D57
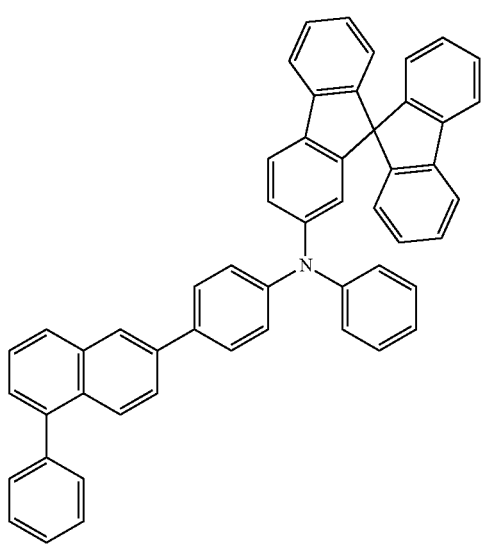
D58
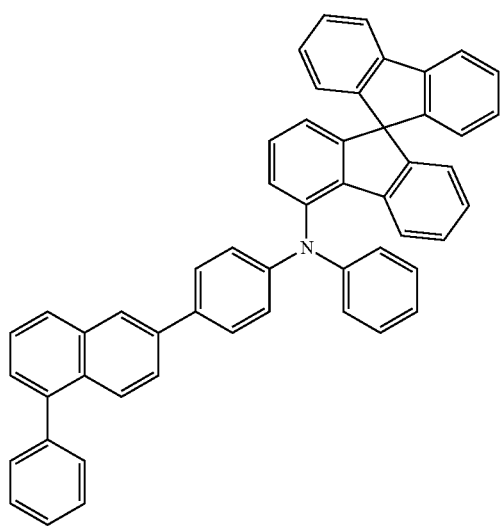
-continued
D59
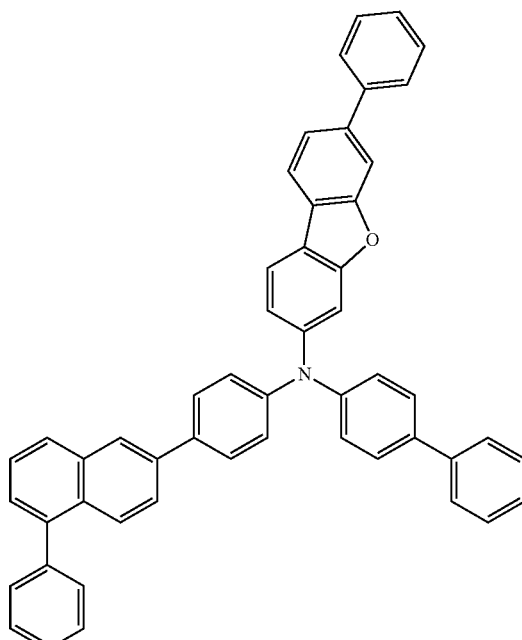
D60
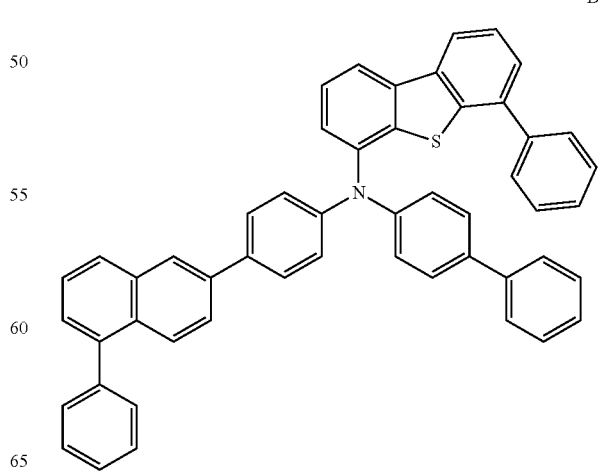

[Compound Group 5]
[Compound Group 6]
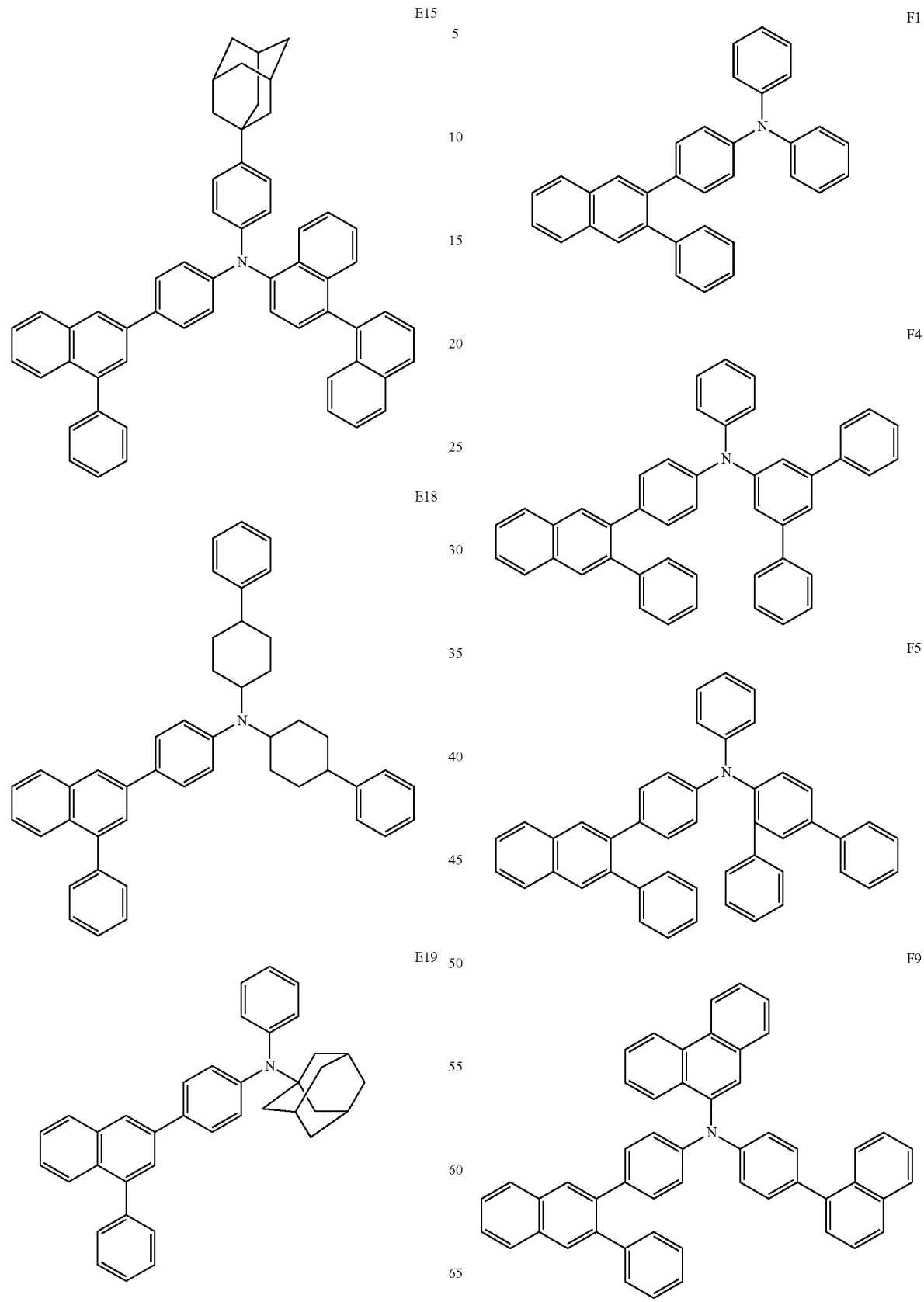

F10
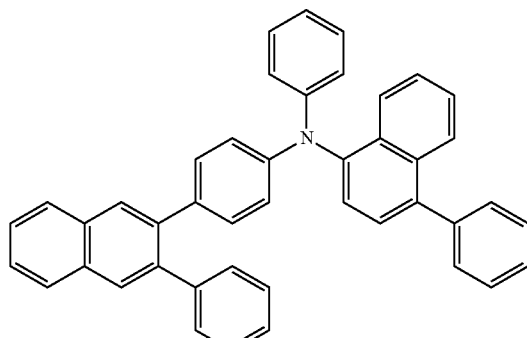
F12
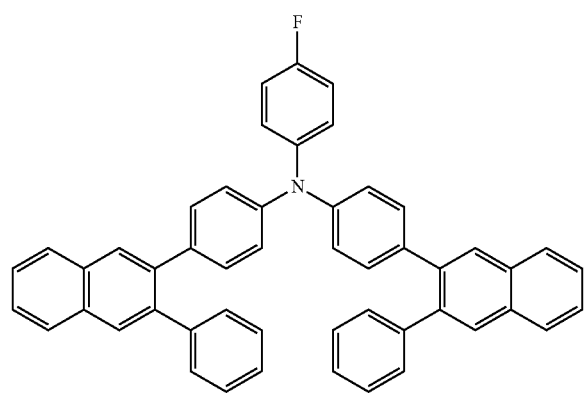
F13
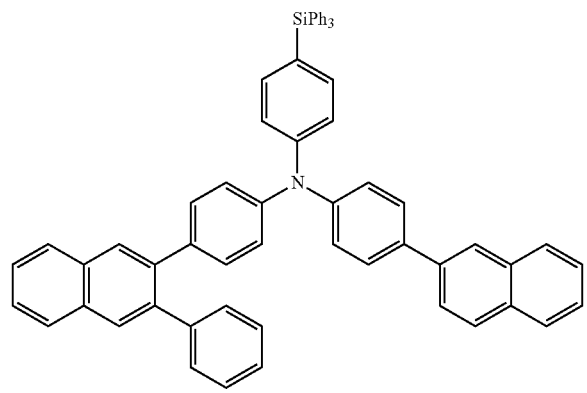
F14
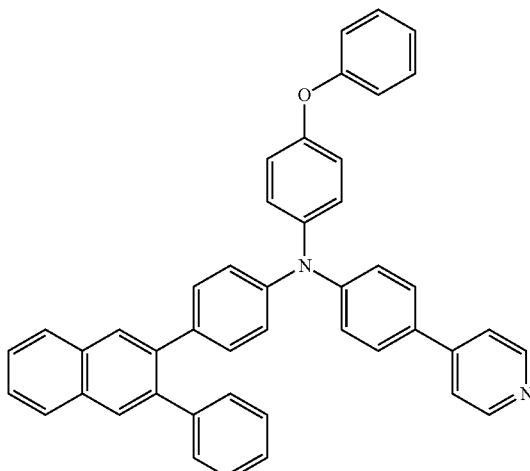
F15
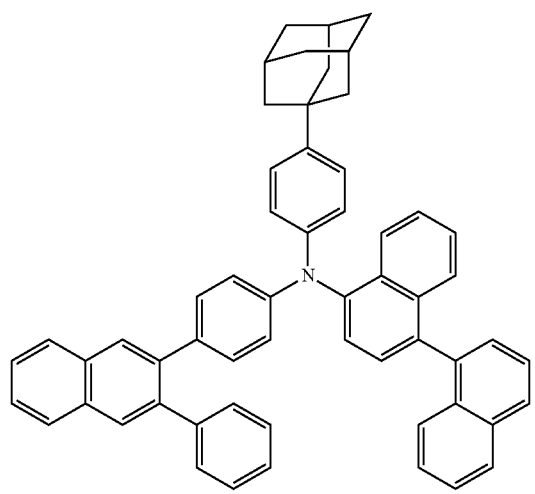
F16
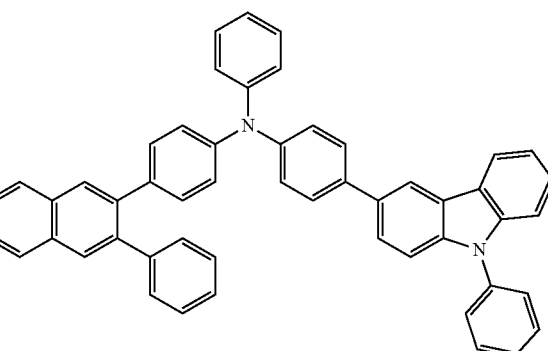

F18
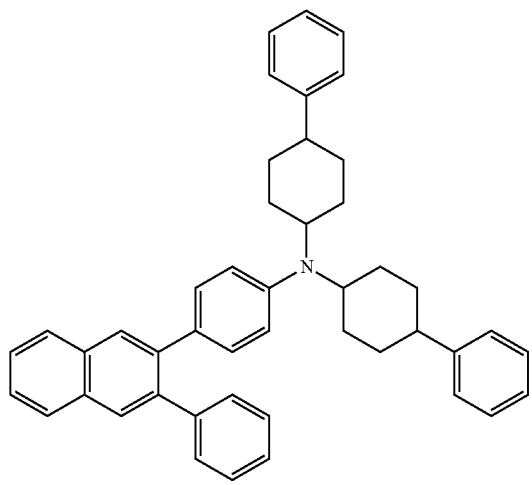
F32
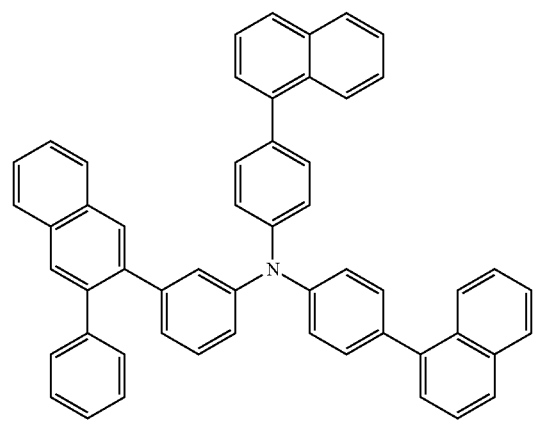
F19
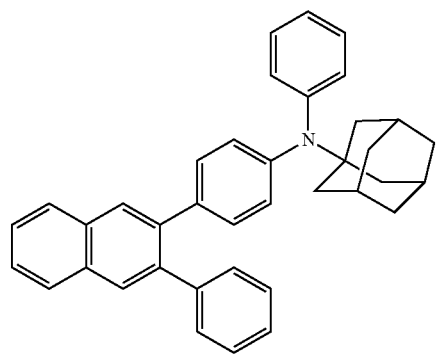
F34
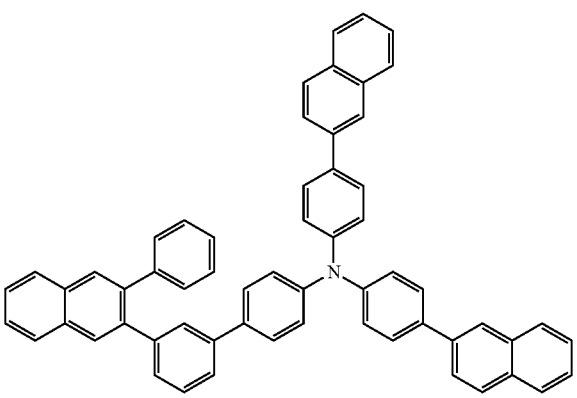
[Compound Group 7]
F20
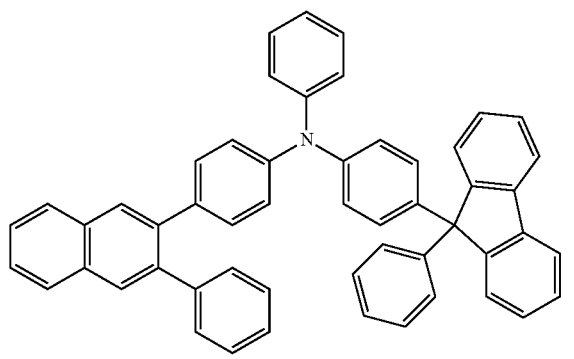
G1
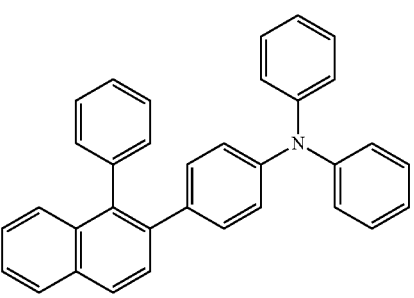
F31
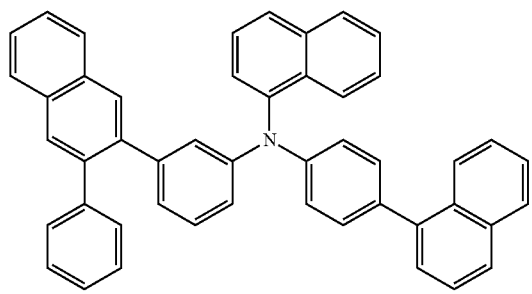
G4
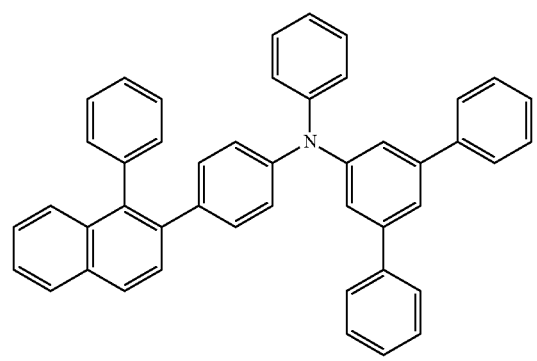

G5
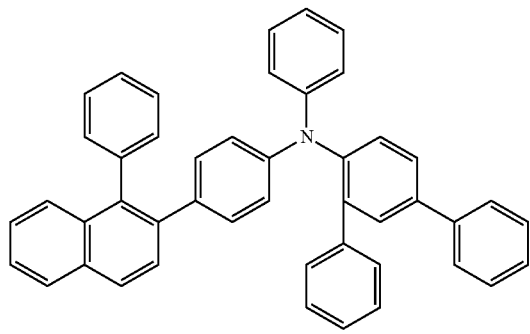
G9
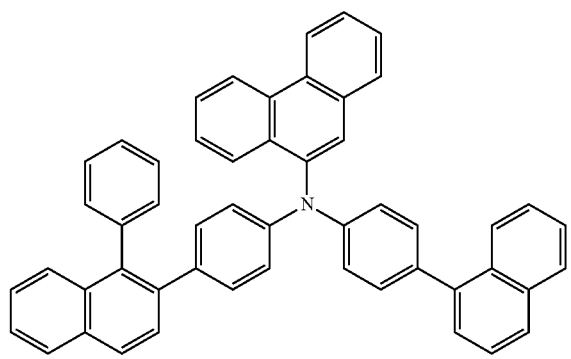
G10
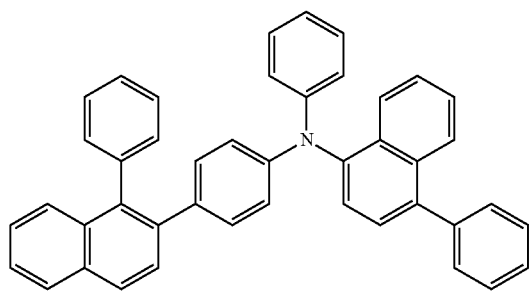
G12
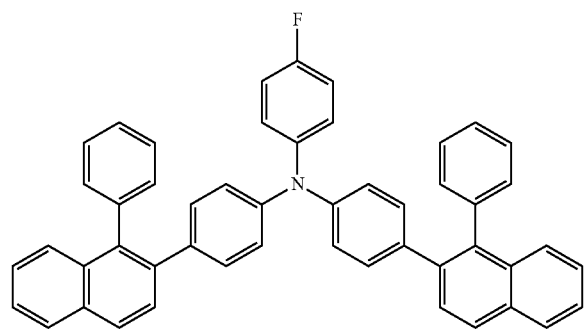
G13
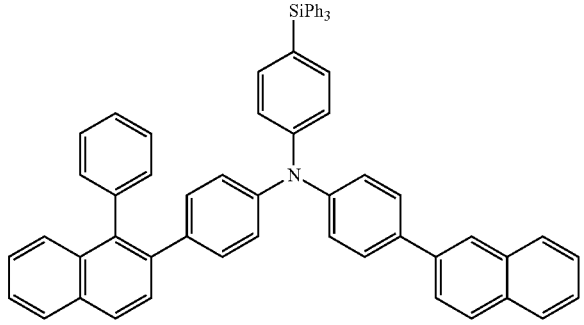
G14
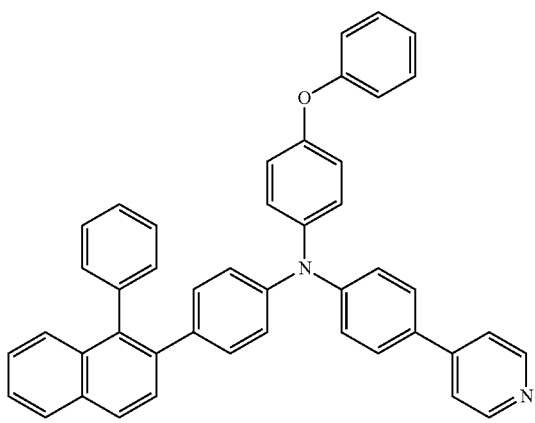
G15
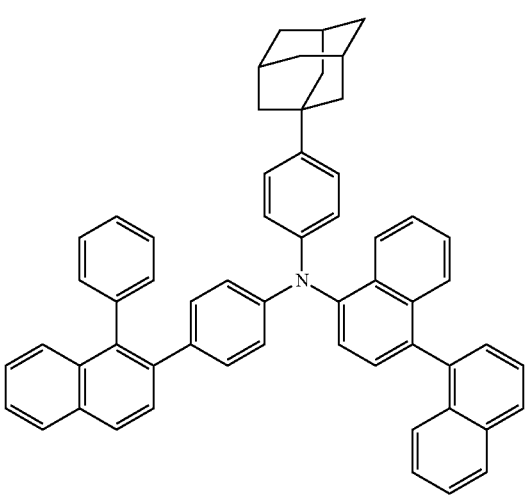

G16
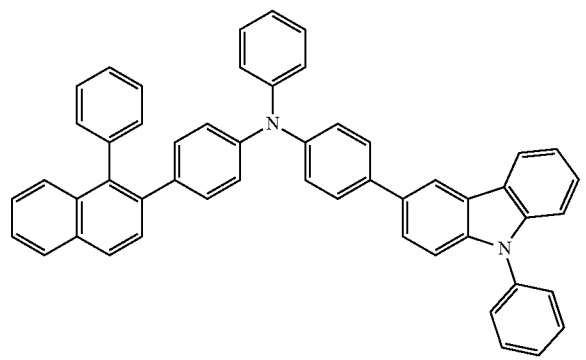
G18
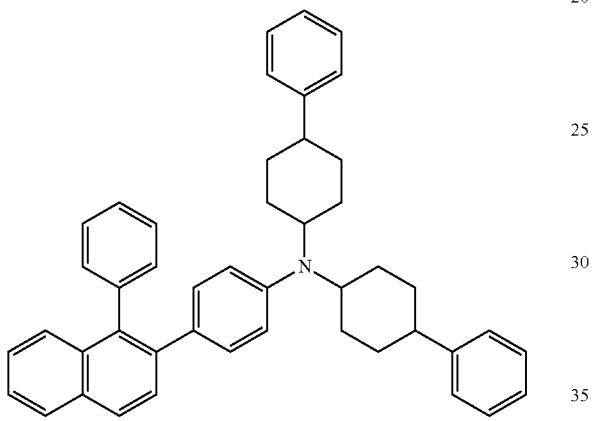
G19
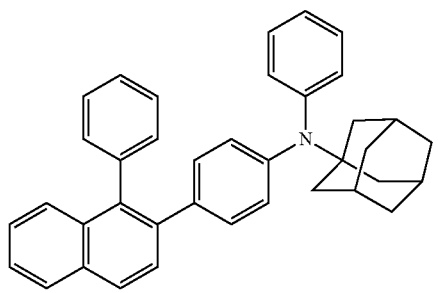
G20
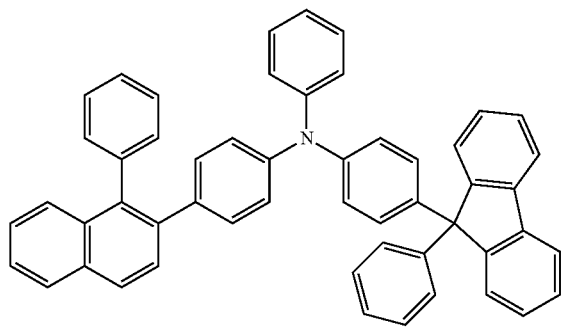
G31
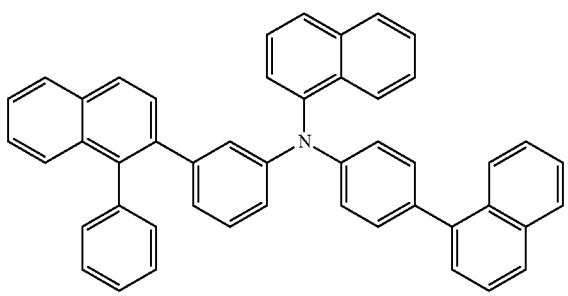
G32
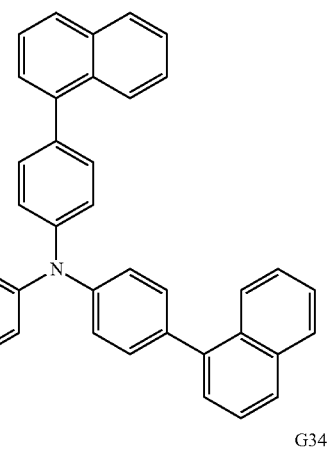
G34
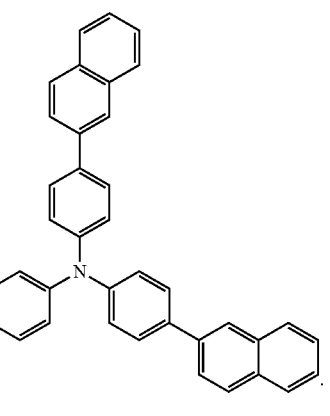
G35
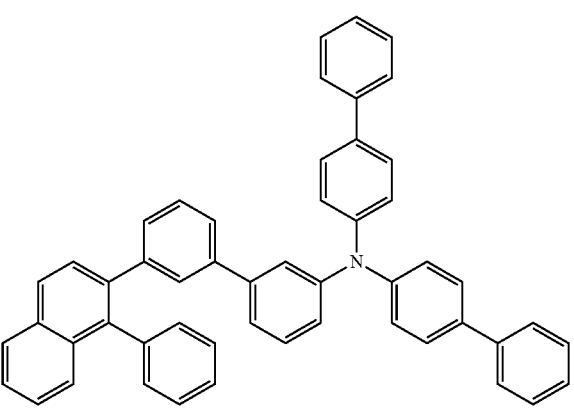

G36
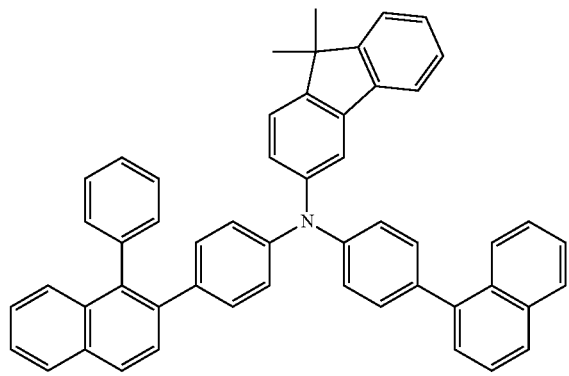
G39
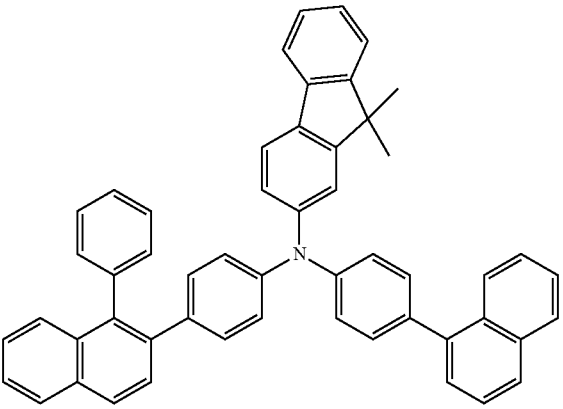
G37
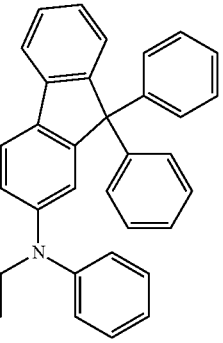
G40
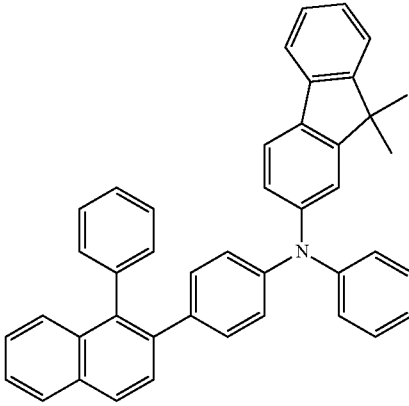
G41
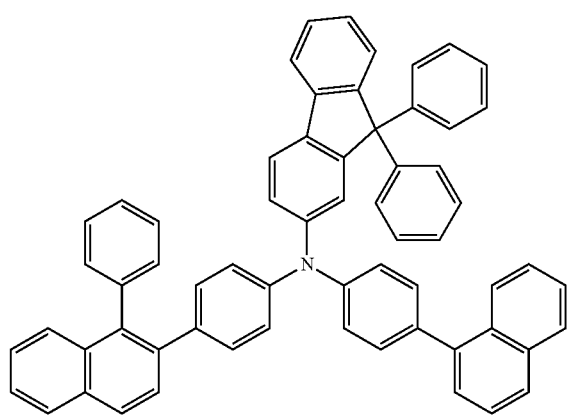
G38
G42
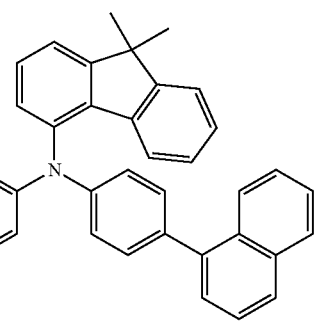

G43
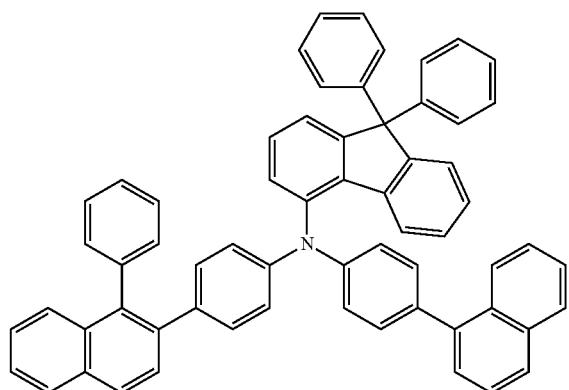
G44
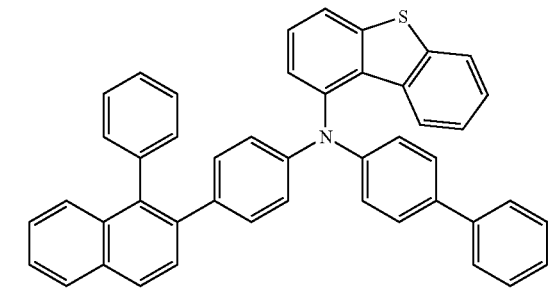
G45
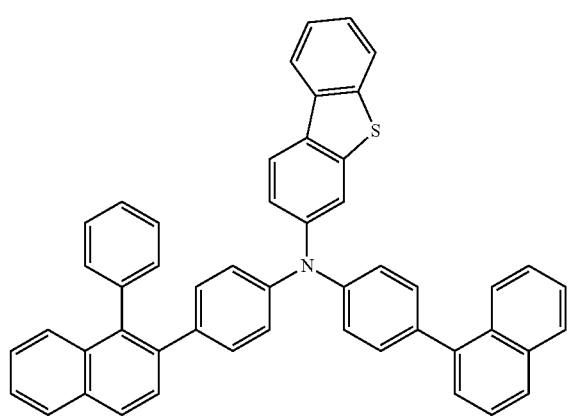
G46
G47
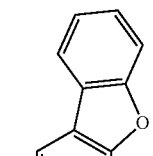
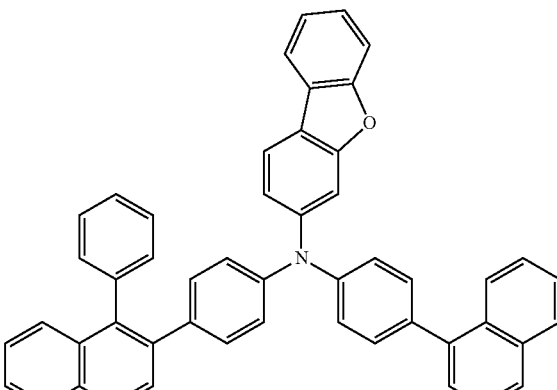
G48
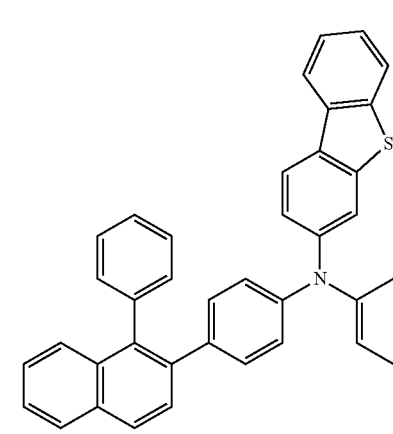
G49
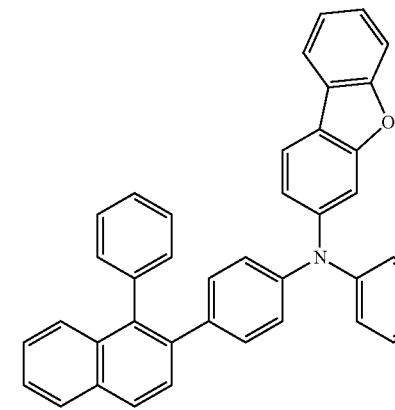
G50
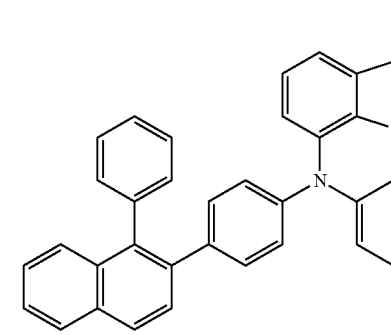

G51
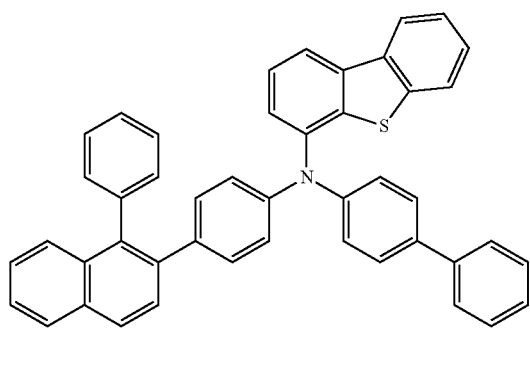
G52
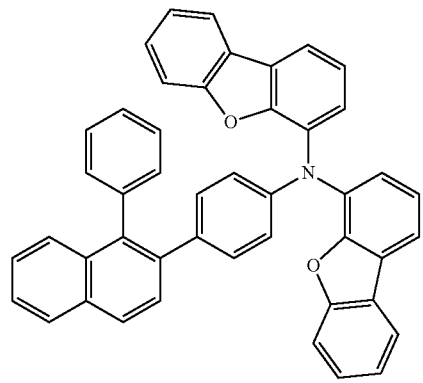
G53
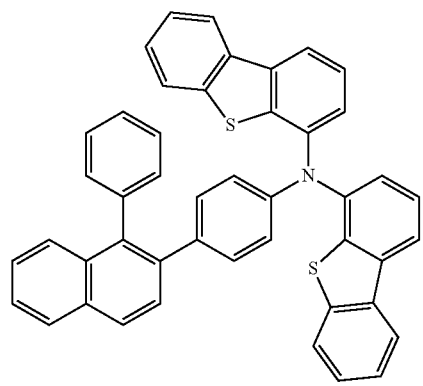
G54
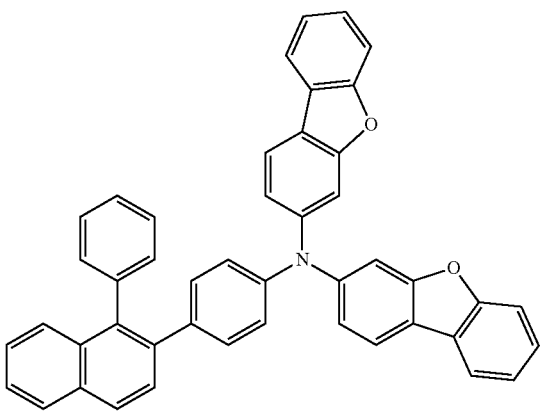
G55
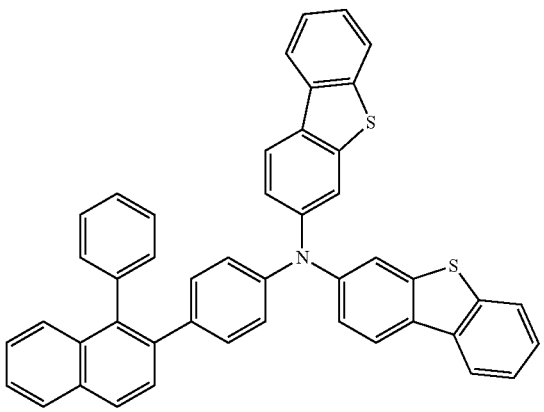
G56
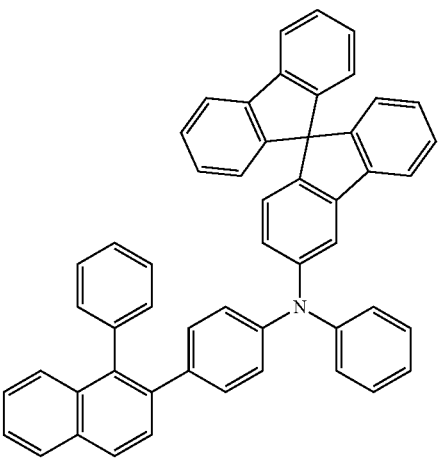

-continued
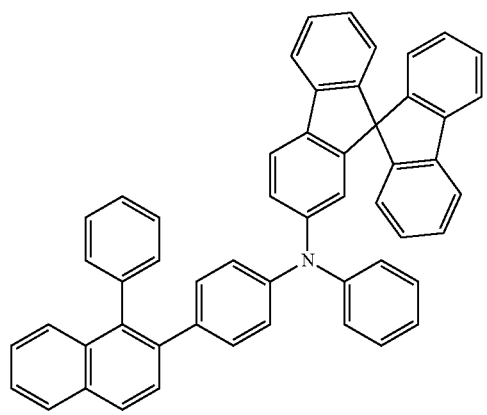
G57
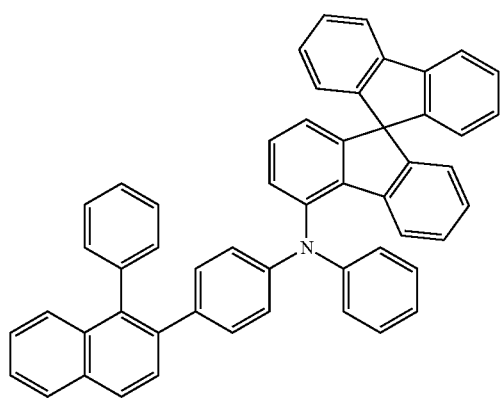
G58
-continued
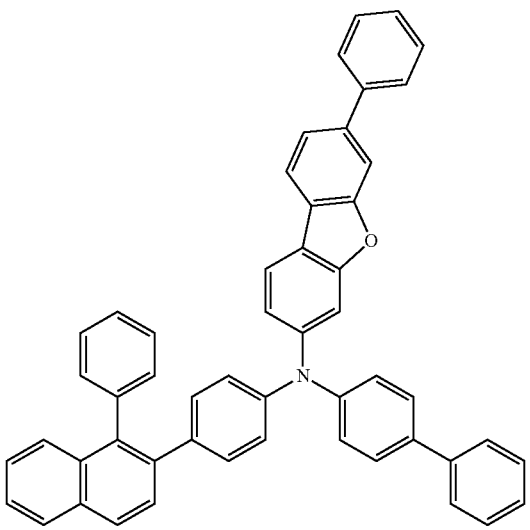
G59
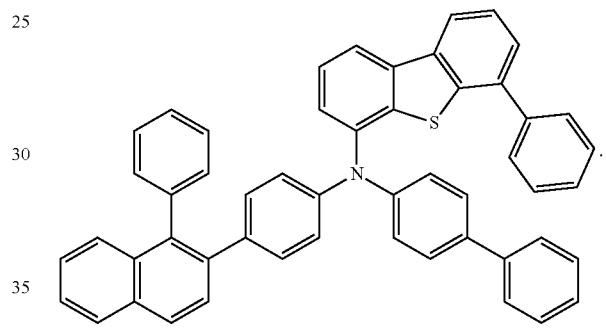
G60
* * * * *

UNITED STATES PATENT AND TRADEMARK OFFICE
CERTIFICATE OF CORRECTION

PATENT NO. : 11,871,656 B2
APPLICATION NO. : 16/256225
DATED : January 9, 2024
INVENTOR(S) : Hideo Miyake et al.

Page 1 of 6

It is certified that error appears in the above-identified patent and that said Letters Patent is hereby corrected as shown below:

In the Claims

In Column 191, Line 46, in Claim 1, before "is" insert -- o --.

In Column 272, Lines 50-65, Column 273, Lines 3-66, Column 274, Lines 3-66, Column 275, Lines 3-66, Column 276, Lines 3-66, Column 277, Lines 3-66, Column 278, Lines 3-66, Column 279, Lines 3-52, in Claim 12, below " 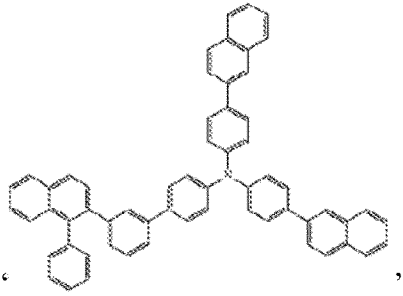 " delete

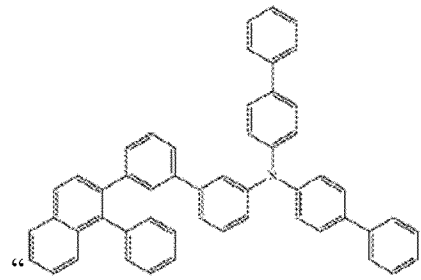

Signed and Sealed this
Eleventh Day of June, 2024

Katherine Kelly Vidal
*Director of the United States Patent and Trademark Office*

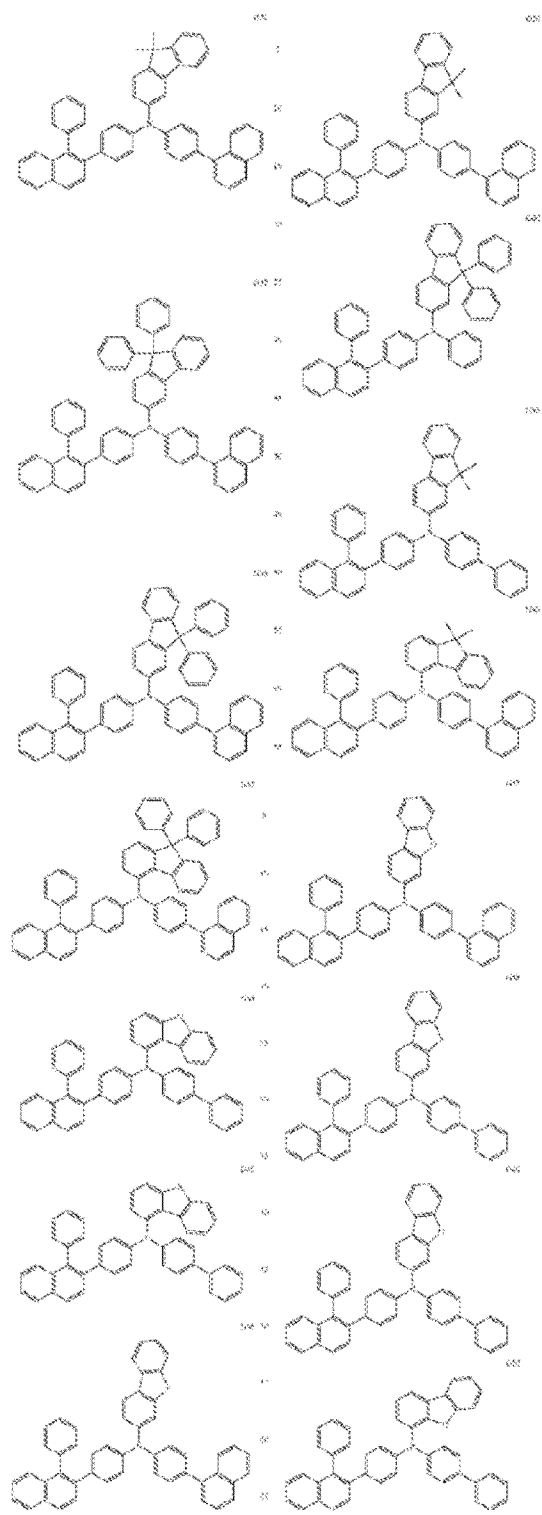

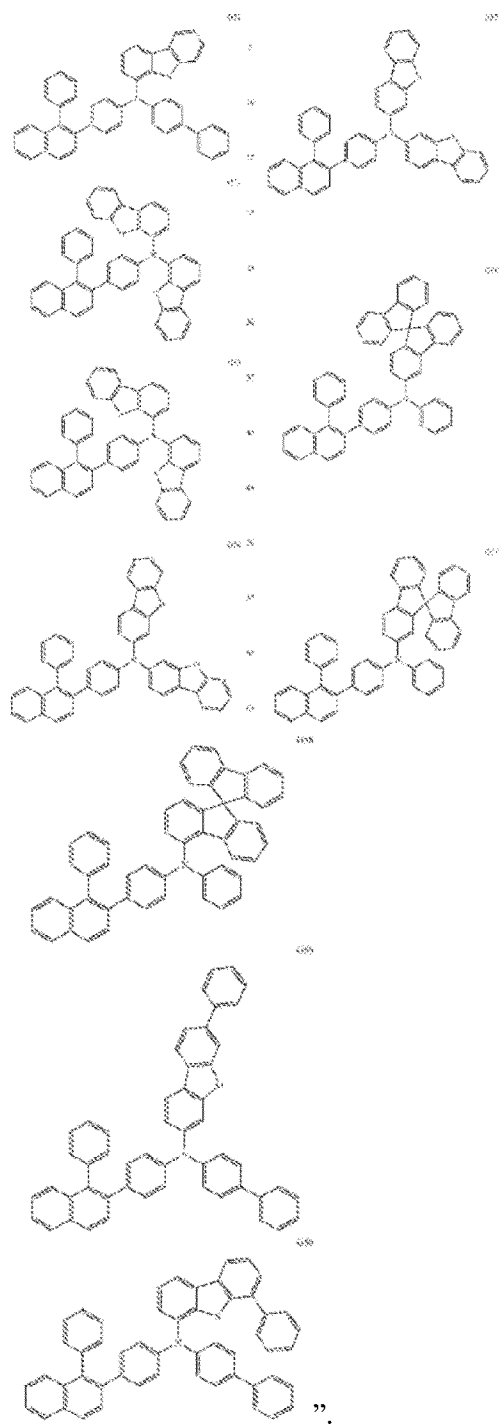
”.
In Column 282, Line 17, in Claim 13, before "is" insert -- o --.
In Column 282, Line 47, in Claim 18, delete "14," and insert -- 13, --.

CERTIFICATE OF CORRECTION (continued)
U.S. Pat. No. 11,871,656 B2

Page 4 of 6

In Column 362, Lines 50-66, Column 363, Lines 3-66, Column 364, Lines 3-66, Column 365, Lines 3-66, Column 366, Lines 3-66, Column 367, Lines 3-66, Column 368, Lines 3-66, Column 369, Lines 3-37, Column 370, Lines 3-37, in Claim 18, below

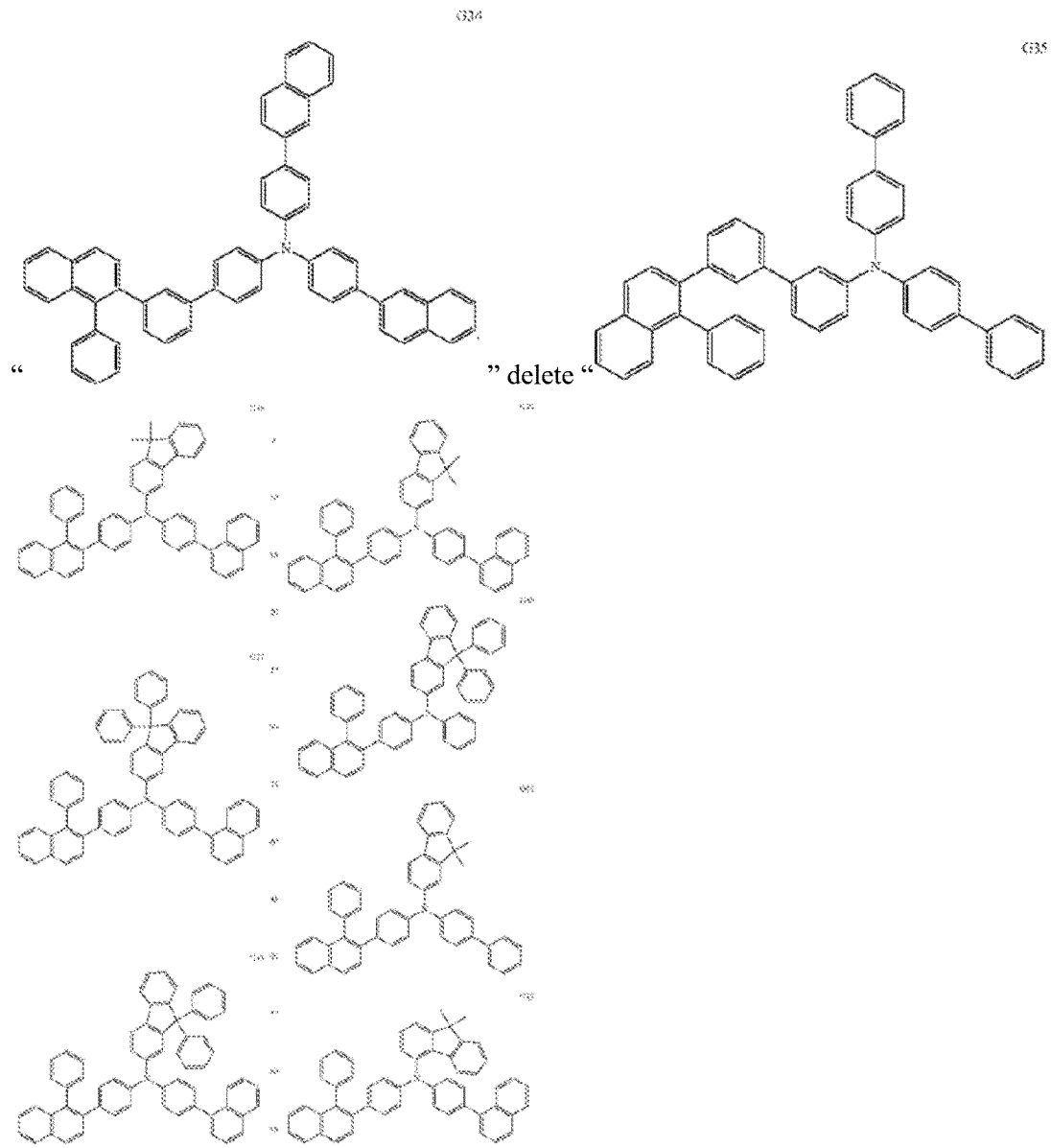

" delete "